US012752011B2

(12) United States Patent
Guo et al.

(10) Patent No.: US 12,752,011 B2
(45) Date of Patent: Oct. 6, 2026

(54) BENZOHETEROCYCLE SUBSTITUTED TETRAHYDROISOQUINOLINE COMPOUND

(71) Applicants: SHANGHAI JEYOU PHARMACEUTICAL CO., LTD., Shanghai (CN); JIANGXI JEMINCARE GROUP CO., LTD, Nanchang (CN)

(72) Inventors: Shuchun Guo, Shanghai (CN); Jun Fan, Shanghai (CN); Nan Wu, Shanghai (CN); Zhihua Fang, Shanghai (CN); Wenqiang Shi, Shanghai (CN); Yang Liu, Shanghai (CN); Jianbiao Peng, Shanghai (CN); Haibing Guo, Shanghai (CN)

(73) Assignees: SHANGHAI JEYOU PHARMACEUTICAL CO., LTD, Shanghai (CN); JIANGXI JEMINCARE GROUP CO., LTD, Nanchang (CN)

( * ) Notice: Subject to any disclaimer, the term of this patent is extended or adjusted under 35 U.S.C. 154(b) by 502 days.

(21) Appl. No.: 18/257,922

(22) PCT Filed: Dec. 17, 2021

(86) PCT No.: PCT/CN2021/139314
§ 371 (c)(1),
(2) Date: Jun. 16, 2023

(87) PCT Pub. No.: WO2022/127917
PCT Pub. Date: Jun. 23, 2022

(65) Prior Publication Data

US 2024/0082406 A1 Mar. 14, 2024

(30) Foreign Application Priority Data

Dec. 18, 2020 (CN) ......................... 202011508096.4
Mar. 11, 2021 (CN) ......................... 202110266745.2
Dec. 13, 2021 (CN) ......................... 202111523273.0

(51) Int. Cl.
*A61K 47/55* (2017.01)
*A61K 47/54* (2017.01)

(52) U.S. Cl.
CPC ............ *A61K 47/55* (2017.08); *A61K 47/545* (2017.08)

(58) Field of Classification Search
None
See application file for complete search history.

(56) References Cited

U.S. PATENT DOCUMENTS 8,541,448 B2 * 9/2013 Charmot .............. C07D 217/04 546/144
11,147,884 B2 * 10/2021 Dotsenko .................. A61P 9/12
2012/0263670 A1 10/2012 Charmot et al.
2013/0274285 A1 10/2013 Bell et al.
2015/0299131 A1 10/2015 Bell et al.
2017/0210736 A1 7/2017 Kuroda et al.
2019/0275028 A1 9/2019 Carreras et al.
2019/0374649 A1 12/2019 Dotsenko et al.

FOREIGN PATENT DOCUMENTS

CN 1617856 A 5/2005
CN 101723980 6/2010
CN 102333759 A 1/2012
CN 101573344 3/2013
CN 103819403 A 5/2014
CN 104837503 A 8/2015
CN 110291082 A 9/2019
EP 1453810 B1 * 3/2009 .............. A61P 43/00
JP 2008506711 A 3/2008
WO 1999002524 1/1999
WO 2006020049 A 2/2006
WO 2008082198 7/2008
(Continued)

OTHER PUBLICATIONS

Written Opinion of the International Searching Authority in PCT/CN2021/139314, dated Mar. 16, 2022 with WIPO translation.
International Search Report in PCT/CN2021/139314, dated Mar. 16, 2022 with WIPO translation.
Mar. 16, 2022 International Search Report issued in International Patent Application No. PCT/CN2021/139314.
Mar. 16, 2022 Written Opinion of the International Searching Authority issued in International Patent Application No. PCT/CN2021/139314.
Mar. 29, 2023 First Office Action issued in Chinese Patent Application No. 2021115527544.
Nov. 14, 2022 First Office Action issued in Taiwanese Patent Application No. 110147593.
(Continued)

*Primary Examiner* — Clinton A Brooks
*Assistant Examiner* — Nicola Maria Bauer
(74) *Attorney, Agent, or Firm* — Pilloff Passino & Cosenza LLP; Rachel Pilloff; Sean Passino

(57) ABSTRACT

The present invention provides a benzoheterocycle substituted tetrahydroisoquinoline compound, and in particular, relates to a compound shown in formula (I) and a pharmaceutically acceptable salt thereof, and the compound for the treatment of chronic kidney disease.

(I)

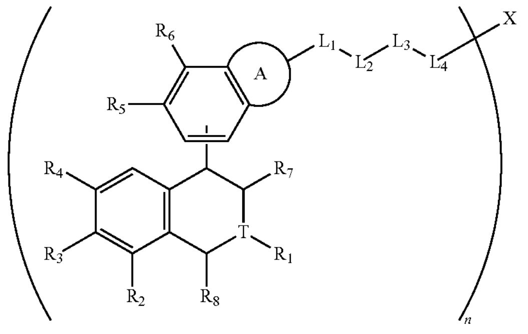

19 Claims, 5 Drawing Sheets

(56) References Cited

FOREIGN PATENT DOCUMENTS

| | | | | | |
|---|---|---|---|---|---|
| WO | 2012177725 | | | 12/2012 | |
| WO | WO-2014029984 | A1 | * | 2/2014 | .............. A61P 31/12 |
| WO | 2018129556 | A1 | | 7/2018 | |

OTHER PUBLICATIONS

Mar. 29, 2023 Search Report issued in Chinese Patent Application No. 2021115527544.

Nov. 14, 2022 Search Report issued in Taiwanese Patent Application No. 110147593.

Nov. 11, 2024, European Search Report issued in European Patent Application No. 21905840.1.

First Office Action issued in Korean Patent Application No. 10-2023-7023999, mailed Feb. 2, 2026.

Jul. 23, 2024 First Office Action issued in Japanese Patent Application No. 2023537062.

May 21, 2026 First Office Action issued in Indian Patent Application No. 202347047585.

Eric D. Labonté, et al., Gastrointestinal Inhibition of Sodium-Hydrogen Exchanger 3 Reduces Phosphorus Absorption and Protects against Vascular Calcification in CKD. J Am Soc Nephrol. May 2015;26(5):1138-49. doi: 10.1681/ASN.2014030317. Epub Nov. 17, 2014. PMID: 25404658. PMCID: PMC4413764.

* cited by examiner

BENZOHETEROCYCLE SUBSTITUTED TETRAHYDROISOQUINOLINE COMPOUND

The present application claims the right of the following priorities:

application number: CN202011508096.4, filed on Dec. 18, 2020;

application number: CN202110266745.2, filed on Mar. 11, 2021;

application number: CN202111523273.0, filed on Dec. 13, 2021.

TECHNICAL FIELD

The present disclosure relates to the field of medicinal chemistry, and in particular, relates to benzoheterocycle substituted tetrahydroisoquinoline compounds, preparation methods thereof and use thereof.

BACKGROUND

Phosphate is an important mineral that regulates various metabolic processes including signal transduction, energy production, and mineral metabolism, and is primarily absorbed in the small intestine and filtered by the kidneys, and subsequently reabsorbed or excreted via the renal tubules. Thus, serum phosphate concentrations remain within a physiological range despite differences in daily phosphate intake. In patients with advanced chronic kidney disease (CKD), the renal phosphorus metabolism function is basically lost, which leads to hyperphosphatemia. Studies have shown that hyperphosphatemia is associated with multiple adverse clinical outcomes in CKD patients, including: induction of vascular calcification, increased incidence and risk of death of cardiovascular disease, secondary hyperparathyroidism, metabolic bone disease or ectopic calcification resulted from renal osteodystrophy, promotion of renal failure and progression of cardiovascular disease.

Currently, the main treatment measures for hyperphosphatemia are low phosphate diet, hemodialysis treatment and taking phosphate binder drugs with meals. Clinical experience shows that it is difficult to control phosphate intake through diet; the efficiency of hemodialysis is limited; therefore, the use of phosphate binder drugs is an important treatment method for lowering serum phosphorus currently. At present, there are two main kinds of phosphate binder drugs commonly used in clinic: phosphate binders containing metal ions (calcium/magnesium/iron/lanthanum) and ion-exchange resin-type binders (sevelamer or sevelamer carbonate). For the former phosphate binders containing metal ions, patients need to strengthen the management of metal ions in the drug, and the drug is affected by pH and has a weak phosphorus binding effect, which is prone to cause diarrhea and is not tolerated by patients. The latter binding phosphorus through ion exchange is not absorbed by the gastrointestinal tract which can reduce accumulation, and has fewer side effects than the former. However, the dosage of the two kinds of drugs is large and the price of which is high, the patient's compliance is poor.

It is known that there are two main ways for the intestinal tract to absorb phosphate: passive cell bypass transport and active transport dependent on transfer proteins, and passive cell bypass phosphate transport is considered to be the main reason of phosphate absorption in humans. The cell bypass phosphate transport is primarily driven by a concentration gradient of phosphate, which is absorbed by tight junction complex formed between cells, and it has been shown in the literature that such tight conjunction complex has permeability specificity for specific ions through the regulation of signal transduction. Sodium-hydrogen antiporter 3 (NHE3/SLC9A3) is a kind of gastrointestinal transfer protein expressed in the apical part of intestinal epithelial cells and mainly responsible for maintaining sodium ion balance, which can affect sodium absorption in the intestinal tract by inhibiting NHE3 activity in the intestinal tract, thus altering the concentration of hydrogen ions in the intestinal epithelial cells and thus affecting the change of local pH; decrease the permeability of the tight junction complex formed between cells to phosphate and reduce phosphate absorption by cell bypass. In clinical practice, the need for serum phosphorus control in patients with advanced CKD has not been met, so it is necessary to further develop drugs with different mechanisms to lower serum phosphorus.

Among the drugs marketed in our country, the diagnostic method for hyperphosphatemia in CKD patients is relatively single; therefore, it is necessary to further develop more effective and safer drugs to lower serum phosphorus levels.

CONTENT OF THE PRESENT INVENTION

In one aspect of the present disclosure, the present disclosure provides a compound represented by formula (I), an optical isomer thereof and a pharmaceutically acceptable salt thereof, (I)

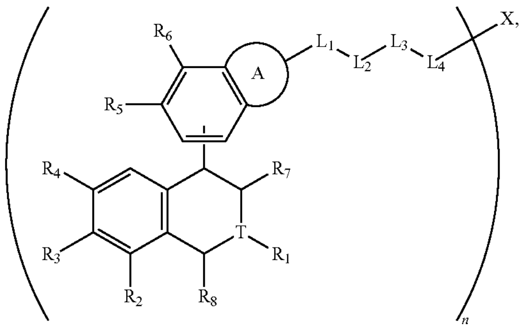

wherein, $R_1$ is selected from H, $C_{1-6}$ alkyl, $C_{3-6}$ cycloalkyl and 4-6 membered heterocycloalkyl, and the $C_{1-6}$ alkyl, $C_{3-6}$ cycloalkyl or 4-6 membered heterocycloalkyl is optionally substituted with 1, 2 or 3 R;

$R_2$, $R_3$, $R_4$, $R_5$, $R_6$ are each independently selected from H, halogen, OH, $NH_2$, CN, $C_{1-6}$ alkyl and $C_{1-6}$ heteroalkyl, and the $C_{1-6}$ alkyl or $C_{1-6}$ heteroalkyl is optionally substituted with 1, 2 or 3 R;

$R_7$, $R_8$ are each independently selected from H;

or, $R_7$ and $R_1$ are attached to form a 5-6 membered ring;

or, $R_8$ and $R_1$ are attached to form a 5-6 membered ring;

T is selected from N and CH;

ring A is selected from 5-6 membered heterocycloalkyl, 5-6 membered heterocycloalkenyl and 5-6 membered heteroaryl, and the 5-6 membered heterocycloalkyl, 5-6 membered heterocycloalkenyl or 5-6 membered heteroaryl is optionally substituted with 1, 2 or 3 R;

n is selected from 2 and 3;

$L_1$ is selected from $$-(CH_2)_{1-6}-,$$

and the

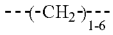

is optionally substituted with 1, 2 or 3 R;

$L_2$ is selected from

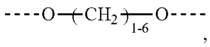

and the

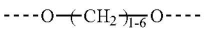

is optionally substituted with 1, 2 or 3 R;

$L_3$ is selected from a single bond,

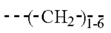 and 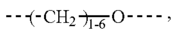

and the

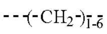 or 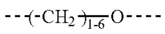

is optionally substituted with 1, 2 or 3 R;

$L_4$ is selected from

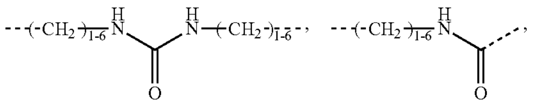

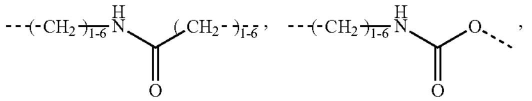

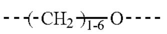 and

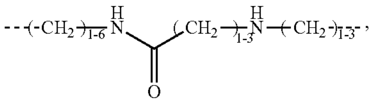

and the

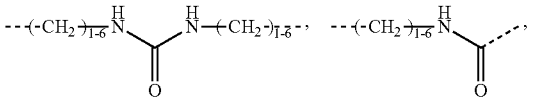

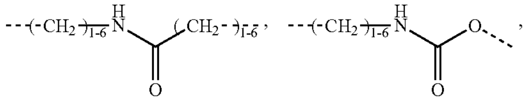

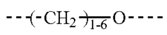 or

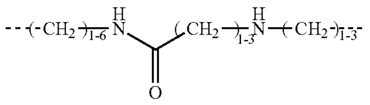

is optionally substituted with 1, 2 or 3 R;

X is selected from a single bond, O, N, NH, $C_{3-8}$ cycloalkyl, 5-10 membered heterocycloalkyl, $C_{1-6}$ alkyl, $C_{5-10}$ spirocyclyl, 5-10 membered spiroheterocyclyl, $C_{5-10}$ fused cyclyl, 5-10 membered fused heterocyclyl, $C_{5-10}$ aryl and 5-12 membered heteroaryl, and the $C_{3-8}$ cycloalkyl, 5-10 membered heterocycloalkyl, $C_{1-6}$ alkyl, $C_{5-10}$ spirocyclyl, 5-10 membered spiroheterocyclyl, $C_{5-10}$ fused cyclyl, 5-10 membered fused heterocyclyl, $C_{5-10}$ aryl or 5-12 membered heteroaryl is optionally substituted with 1, 2 or 3 $R_X$;

$R_X$ is each independently selected from OH, $NH_2$, $C_{1-6}$ alkyl, $C_{1-6}$ alkoxy, $C_{1-6}$ alkylthio, $C_{1-6}$ alkylamino, 5-6 membered heterocycloalkyl, —NHC(═O)N($C_{1-6}$ alkyl)$_2$, —NHC(═O)NH$C_{1-6}$ alkyl and —NHC(═O)$C_{1-6}$ alkyl-O—$C_{1-6}$ alkyl, and the $C_{1-6}$ alkyl, $C_{1-6}$ alkoxy, $C_{1-6}$ alkylthio, $C_{1-6}$ alkylamino, 5-6 membered heterocycloalkyl, —NHC(═O)N($C_{1-6}$ alkyl)$_2$, —NHC(═O)NH$C_{1-6}$ alkyl or —NHC(═O)$C_{1-6}$ alkyl-O—$C_{1-3}$ alkyl is optionally substituted with 1, 2, 3, 4 or 5 R;

R is each independently selected from H, halogen, OH, $NH_2$, CN,

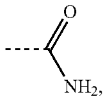

$C_{1-6}$ alkyl, $C_{1-6}$ alkoxy, $C_{1-6}$ alkylthio, $C_{1-6}$ alkylamino and 5-6 membered heterocycloalkyl, and the $NH_2$, $C_{1-6}$ alkyl, $C_{1-6}$ alkoxy, $C_{1-6}$ alkylthio, $C_{1-6}$ alkylamino or 5-6 membered heterocycloalkyl is optionally substituted with 1, 2 or 3 R';

R' is selected from F, Cl, Br, I, OH, $NH_2$, $CH_3$ and COOH;

the 4-6 membered heterocycloalkyl, $C_{1-6}$ heteroalkyl, 5-6 membered heterocycloalkyl, 5-6 membered heterocycloalkenyl, 5-6 membered heteroaryl, 6-12 membered heteroaromatic ring, 5-10 membered spiroheterocyclyl and 5-10 membered fused heterocyclyl contains 1, 2 or 3 heteroatoms or heteroatomic groups independently selected from 0, NH, S, C(═O), C(═O)O, S(═O), S(═O)$_2$ and N.

In some embodiments of the present disclosure, the above R is selected from H, F, Cl, Br, I, OH, $NH_2$, COOH,

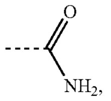

Me, $CF_3$

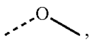, 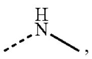, 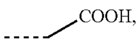, 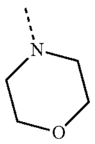, and

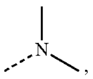

and other variables are as defined in the present disclosure.

In some embodiments of the present disclosure, the above $R_1$ is selected from H, $CH_3$,

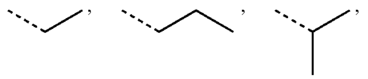

piperidinyl and tetrahydropyrrolyl, and the $CH_3$,

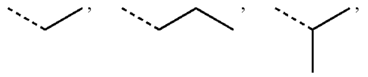

piperidinyl or tetrahydropyrrolyl is optionally substituted with 1, 2 or 3 R, and other variables are as defined in the present disclosure.

In some embodiments of the present disclosure, the above $R_1$ is selected from H, $CH_3$,

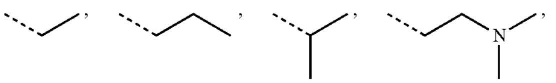

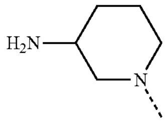

and

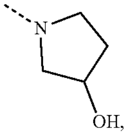

and other variables are as defined in the present disclosure.

In some embodiments of the present disclosure, the above $R_2$, $R_3$, $R_4$, $R_5$, $R_6$ are each independently selected from H, F, Cl, Br, OH, $NH_2$, CN, $CH_3$,

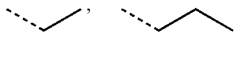

and

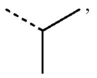

and other variables are as defined in the present disclosure.

In some embodiments of the present disclosure, the above ring A is selected from pyrrolidin-2-one group, isothiazolidine-1,1-dioxide group, 1,2-thiazine-1,1-dioxide group, piperidin-2-one group, 3,4-dihydropyridin-2(1H)-one group, 5,6-dihydro-2H-1,2-thiazine-1,1-dioxide group, pyridinyl group and pyrazolyl group, and the pyrrolidin-2-one group, isothiazolidine-1,1-dioxide group, 1,2-thiazine-1,1-dioxide group, piperidin-2-one group, 3,4-dihydropyridin-2(1H)-one group, 5,6-dihydro-2H-1,2-thiazine-1,1-dioxide group, pyridinyl group or pyrazolyl group is optionally substituted with 1, 2 or 3 R, and other variables are as defined in the present disclosure.

In some embodiments of the present disclosure, the above structural unit

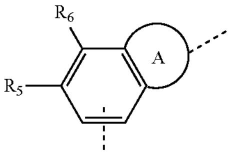

is selected from

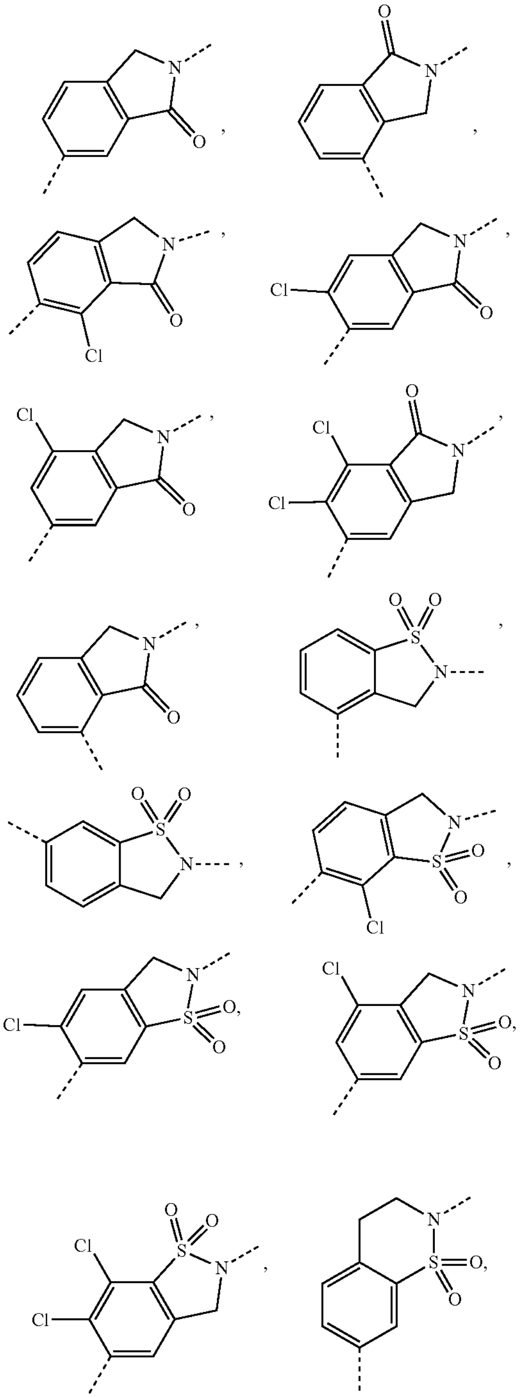

-continued

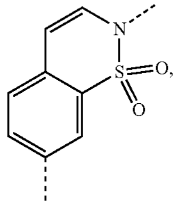 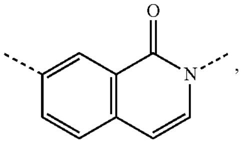

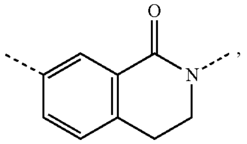 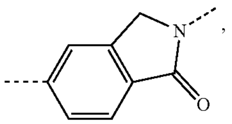

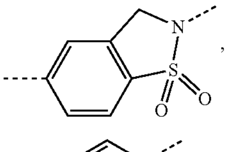 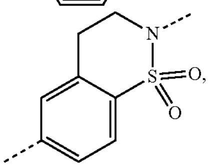

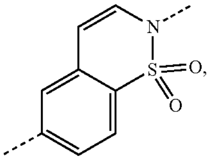 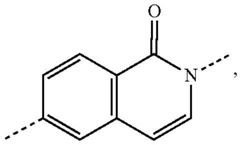

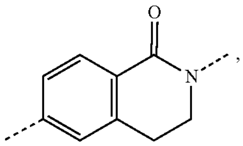 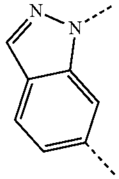 and

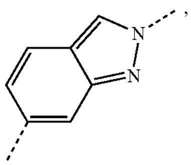

and other variables are as defined in the present disclosure.

In some embodiments of the present disclosure, the above $L_1$ is selected from

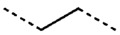 and 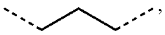

and other variables are as defined in the present disclosure.

In some embodiments of the present disclosure, the above $L_2$ is selected from

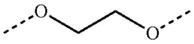 and 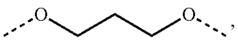

and other variables are as defined in the present disclosure.

In some embodiments of the present disclosure, the above $L_3$ is selected from a single bond,

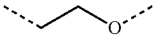 and 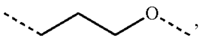

and other variables are as defined in the present disclosure.

In some embodiments of the present disclosure, the above $L_4$ is selected from

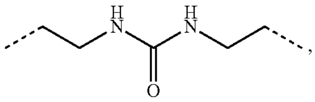

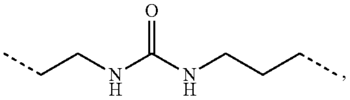

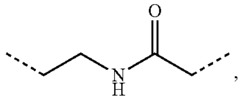 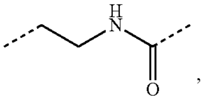

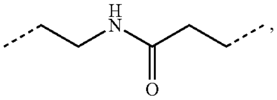 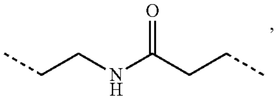

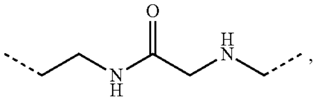

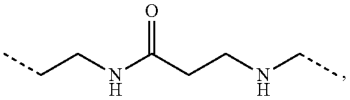

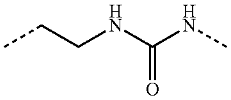 and

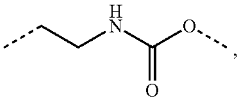 and the

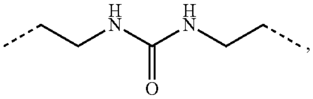 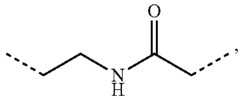

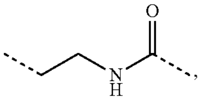 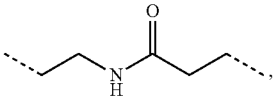

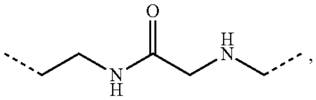

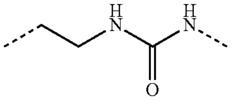 or 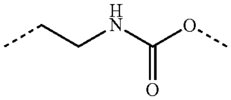

is optionally substituted with 1, 2 or 3 R, and other variables are as defined in the present disclosure.

In some embodiments of the present disclosure, the above $L_4$ is selected from

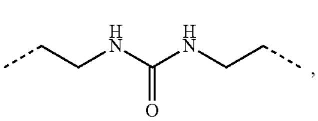

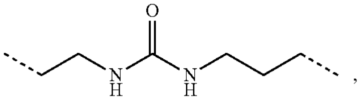

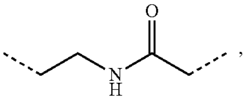 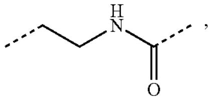

-continued

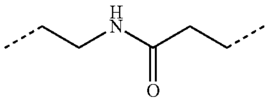
,
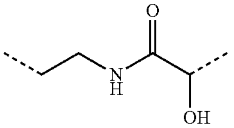
,
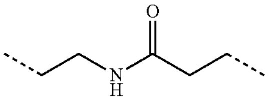
,
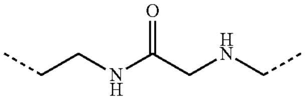
,
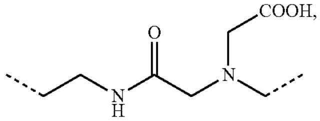
,
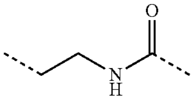
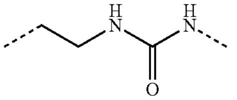
,
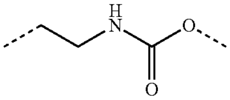
and
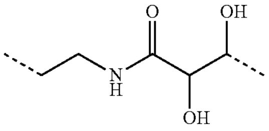
, and other variables are as defined in the present disclosure.

In some embodiments of the present disclosure, the above structural unit is

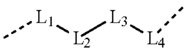

selected from

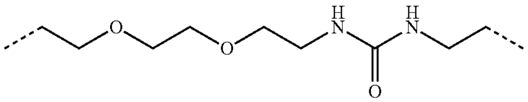
,
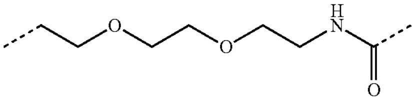
,
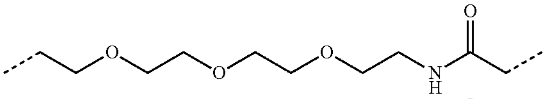
,
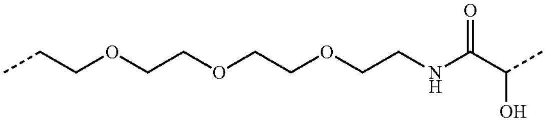
,
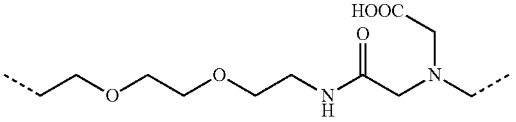
,
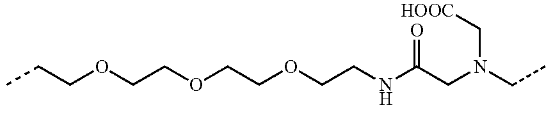
,

-continued

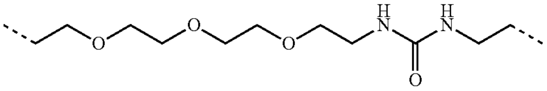
,
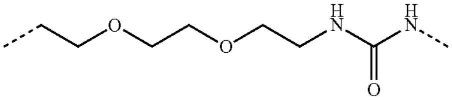
,
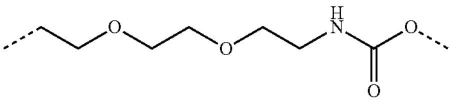
,
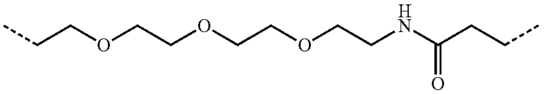
,
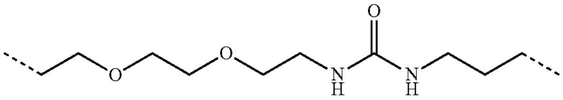
,
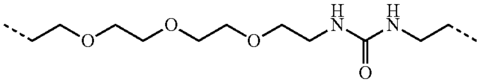
and
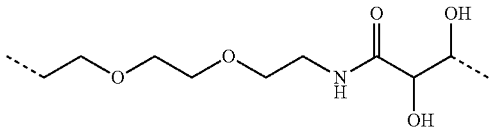
, and other variables are as defined in the present disclosure.

In some embodiments of the present disclosure, the above X is selected from a single bond, N, NH, O, $C_{1-6}$ alkyl, $C_{3-6}$ cycloalkyl, $C_{5-8}$ spirocyclyl, 5-8 membered spiroheterocyclyl, $C_{5-8}$ fused cyclyl, 5-8 membered fused heterocyclyl, phenyl and 5-6 membered heteroaryl, and the $C_{1-6}$ alkyl, $C_{3-6}$ cycloalkyl, $C_{5-8}$ spirocyclyl, 5-8 membered spiroheterocyclyl, $C_{5-10}$ fused cyclyl, 5-8 membered fused heterocyclyl, phenyl and 5-6 membered heteroaryl are optionally substituted with 1, 2 or 3 $R_X$, and other variables are as defined in the present disclosure.

In some embodiments of the present disclosure, the above X is selected from a single bond, N, NH, O, $C_{1-6}$ alkyl, $C_{3-6}$ cycloalkyl, 5-6 membered heterocycloalkyl, $C_{5-8}$ spirocyclyl, 5-8 membered spiroheterocyclyl, $C_5$-8 bridged heterocyclyl, 5-8 membered bridged heterocyclyl, $C_{5-8}$ fused cyclyl, 5-8 membered fused heterocyclyl, phenyl and 5-6 membered heteroaryl, and the $C_{1-6}$ alkyl, $C_{3-6}$ cycloalkyl, 5-6 membered heterocycloalkyl, $C_{5-8}$ spirocyclyl, 5-8 membered spiroheterocyclyl, $C_{5-8}$ bridged heterocyclyl, 5-8 membered bridged heterocyclyl, $C_{5-8}$ fused cyclyl, 5-8 membered fused heterocyclyl, phenyl and 5-6 membered heteroaryl are optionally substituted with 1, 2 or 3 $R_X$, and other variables are as defined in the present disclosure.

In some embodiments of the present disclosure, the above X is selected from a single bond, N, NH, O, $C_{1-6}$ alkyl, $C_{3-8}$ cycloalkyl, 5-8 membered heterocycloalkyl, phenyl and 5-6 membered heteroaryl, and the $C_{1-6}$ alkyl, $C_{3-8}$ cycloalkyl, 5-8 membered heterocycloalkyl, phenyl and 5-6 membered heteroaryl are optionally substituted with 1, 2 or 3 $R_X$, and other variables are as defined in the present disclosure.

In some embodiments of the present disclosure, the above $R_X$ is selected from OH, $NH_2$,

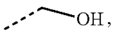,
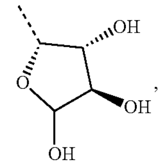,
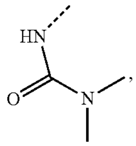,
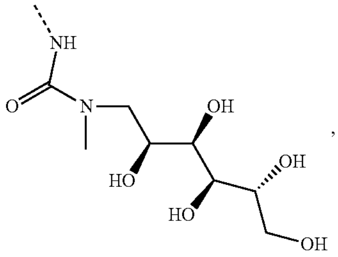,
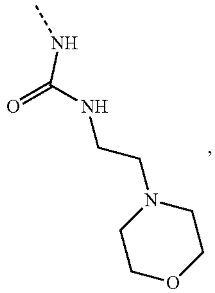,
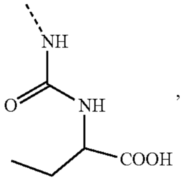,
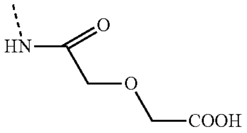
and
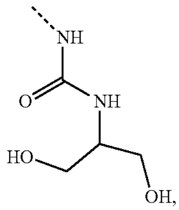

and other variables are as defined in the present disclosure.

In some embodiments of the present disclosure, the above X is selected from a single bond, N,

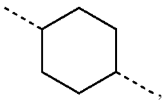,
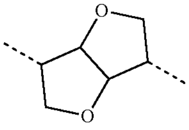,
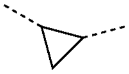,
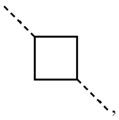,
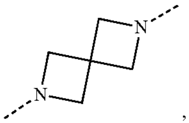,
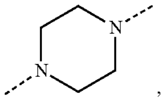,

-continued

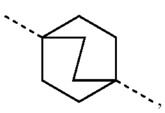,
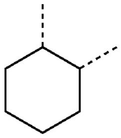,
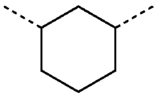,
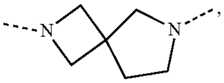,
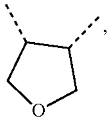,
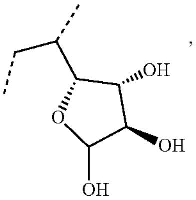,
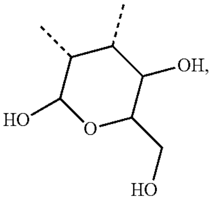
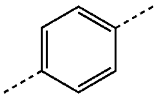,
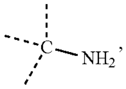
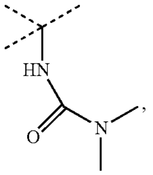
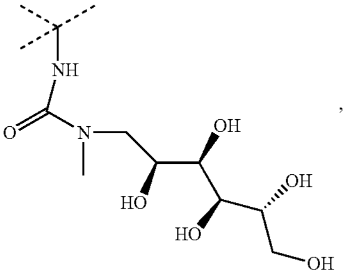,
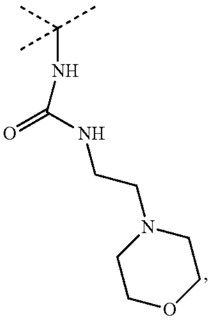
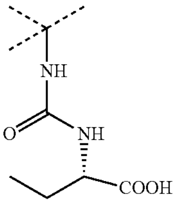,
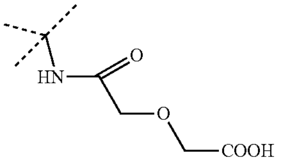
and
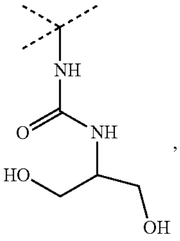, and other variables are as defined in the present disclosure.

In another aspect of the present disclosure, the present disclosure also provides a compound represented by the following formula, an optical isomer thereof and a pharmaceutically acceptable salt thereof, selected from:

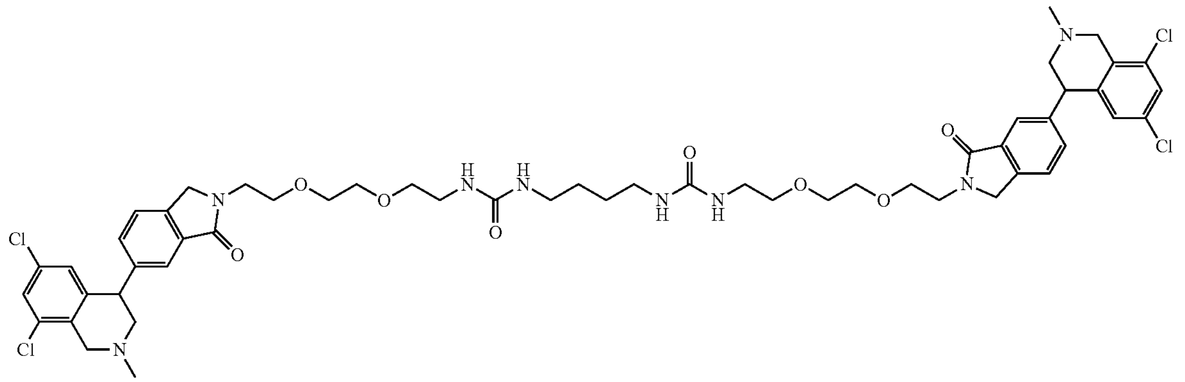
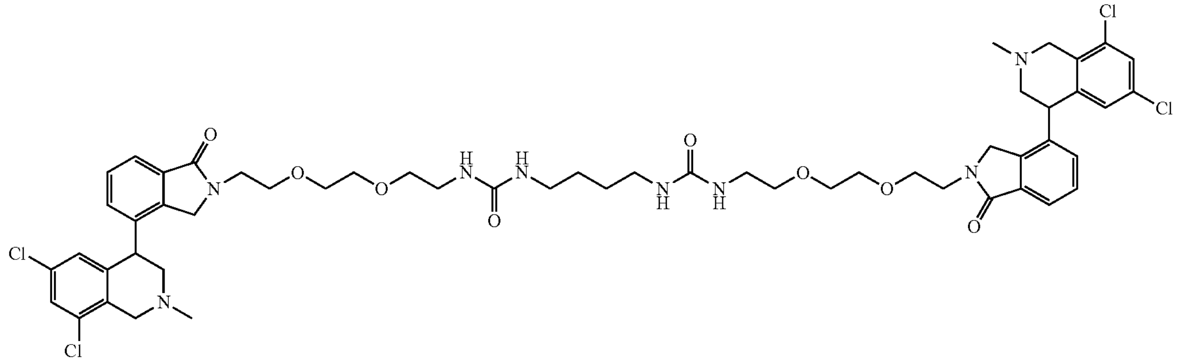
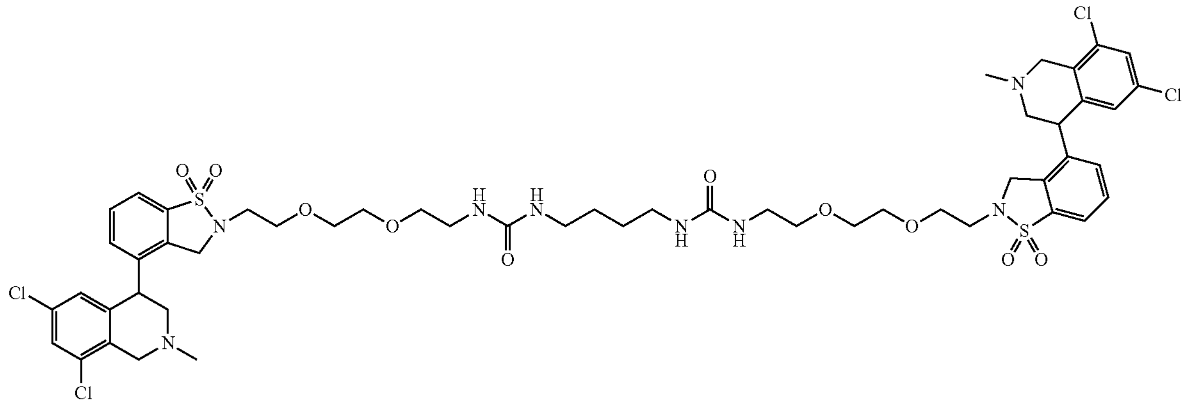
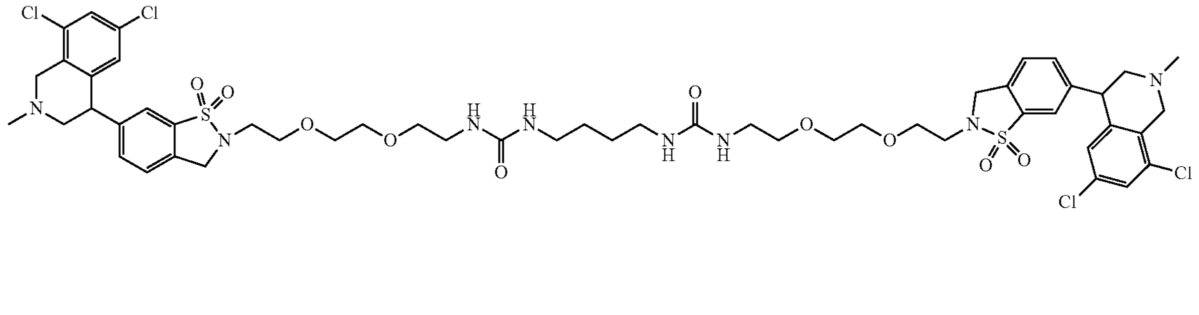

-continued
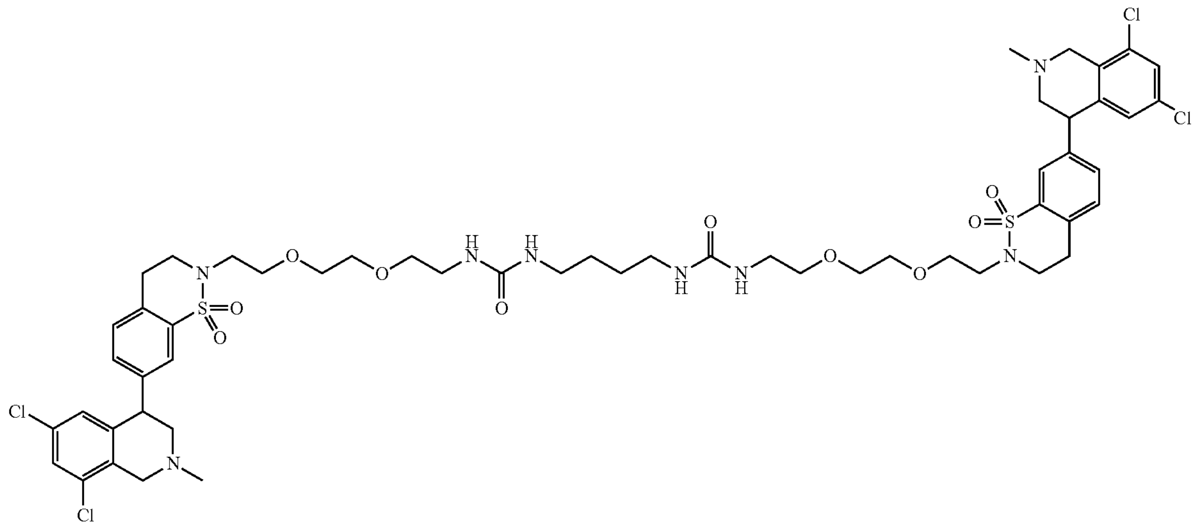
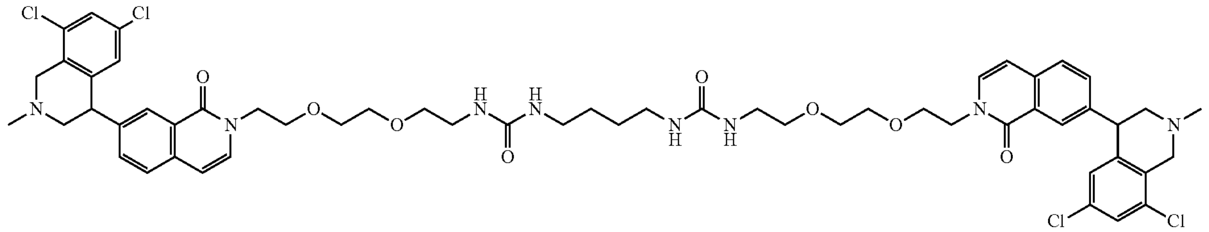
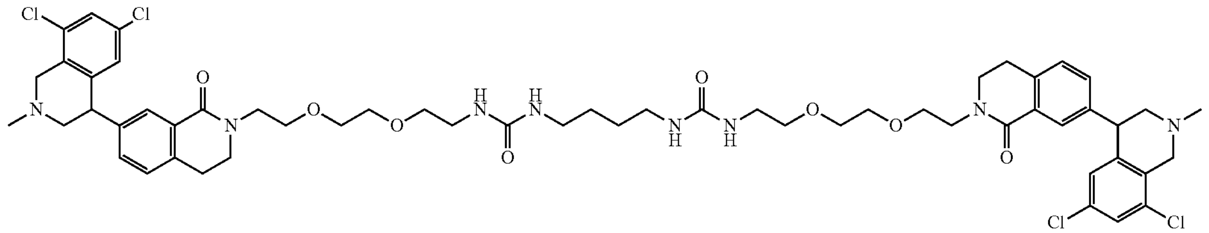
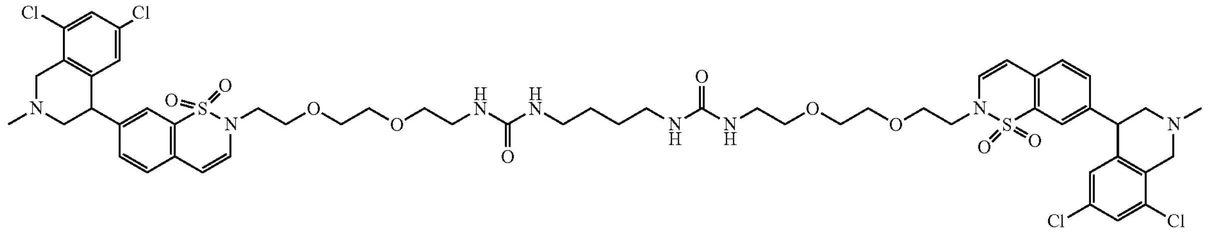
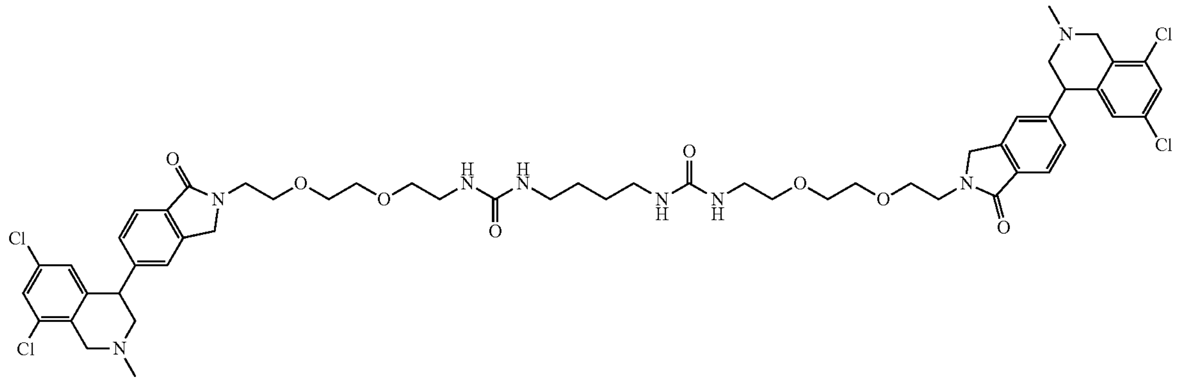

-continued
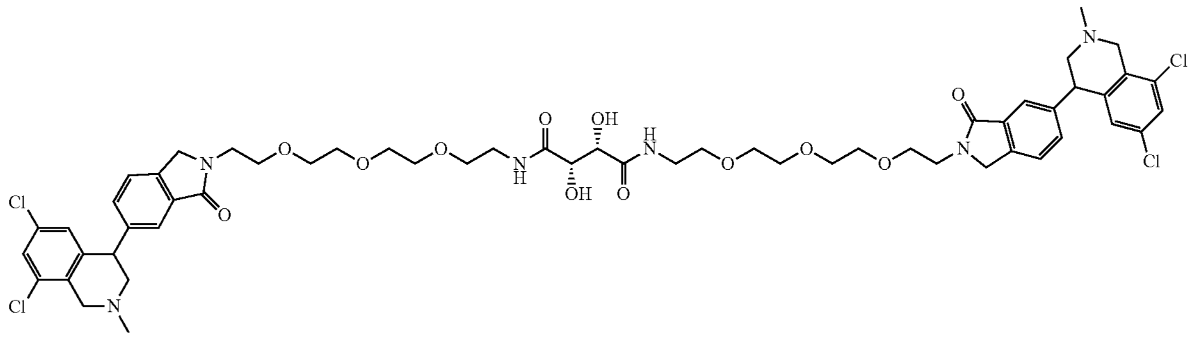
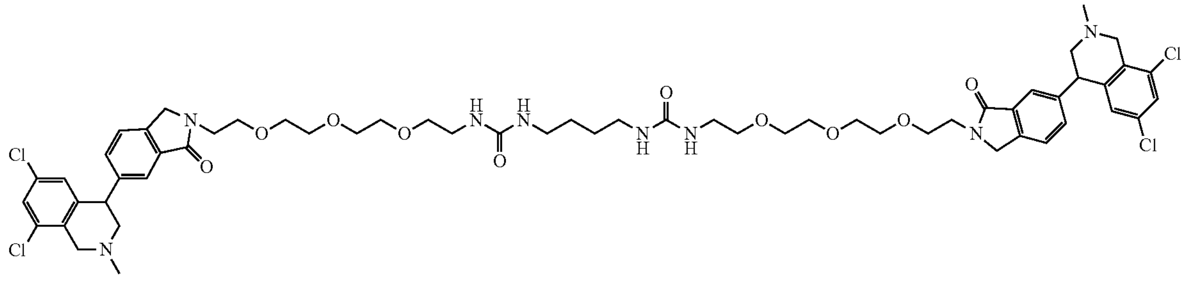
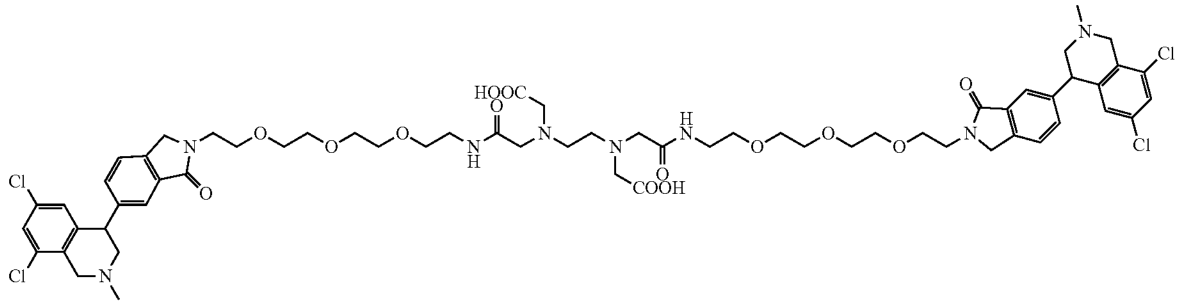
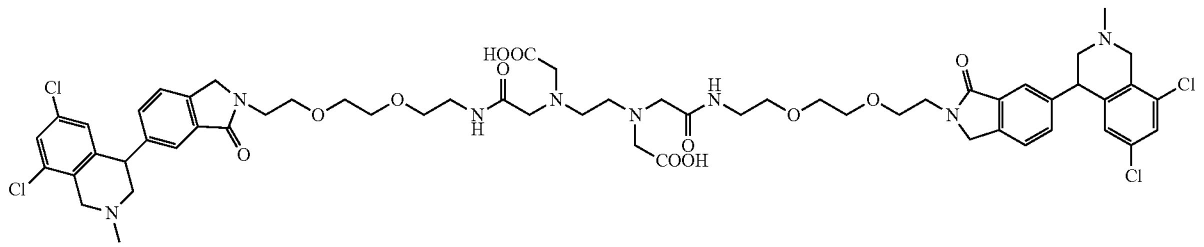
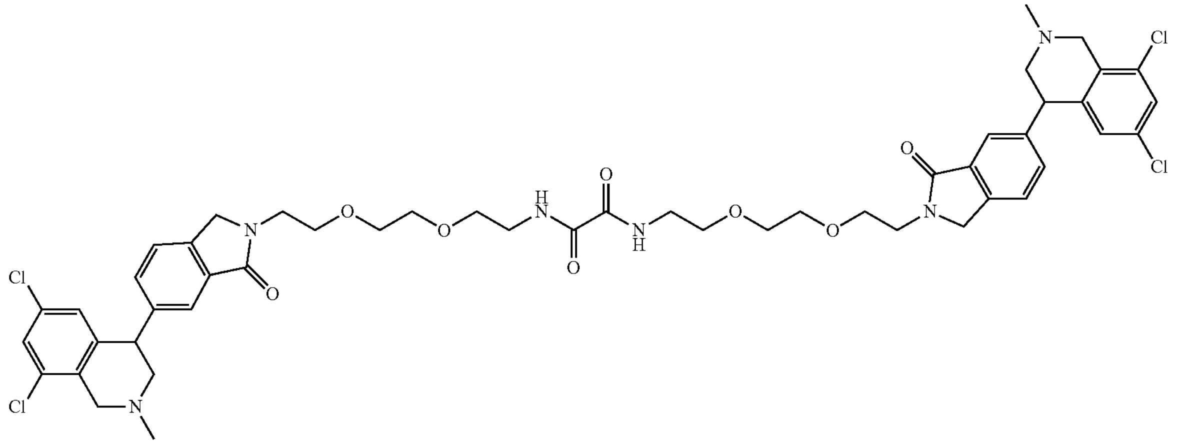

-continued
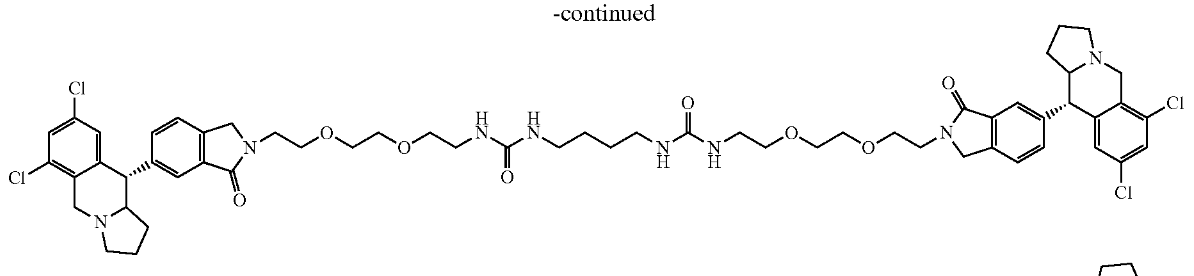
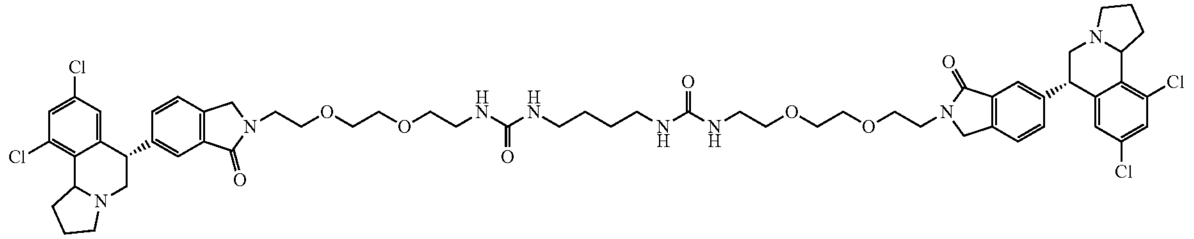
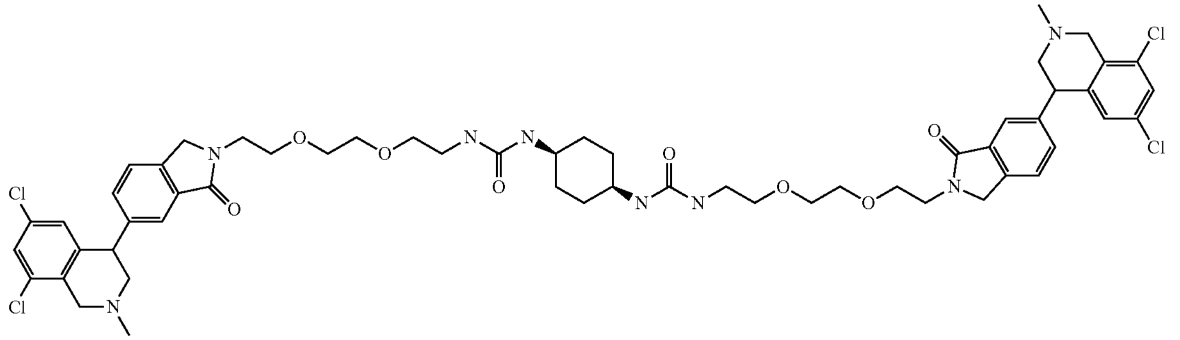
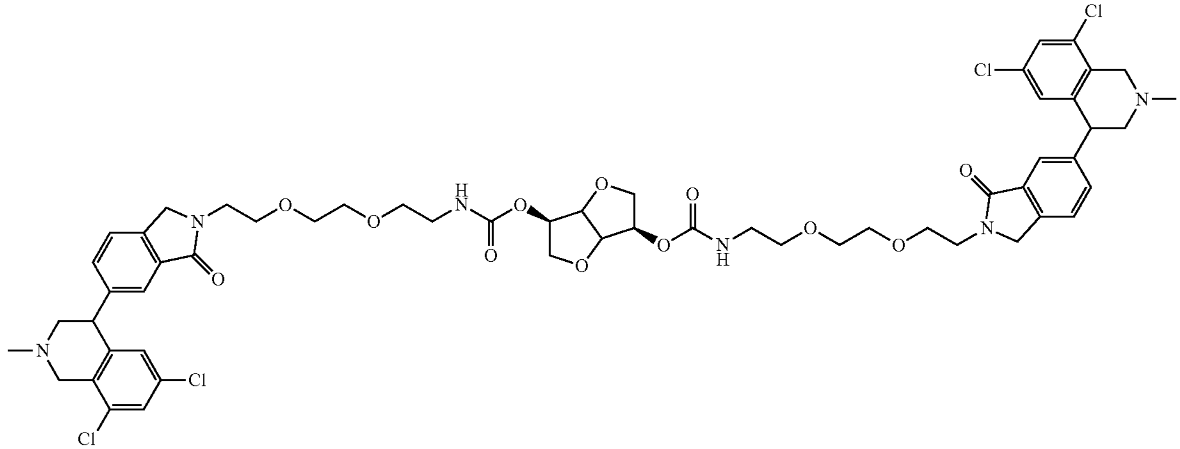
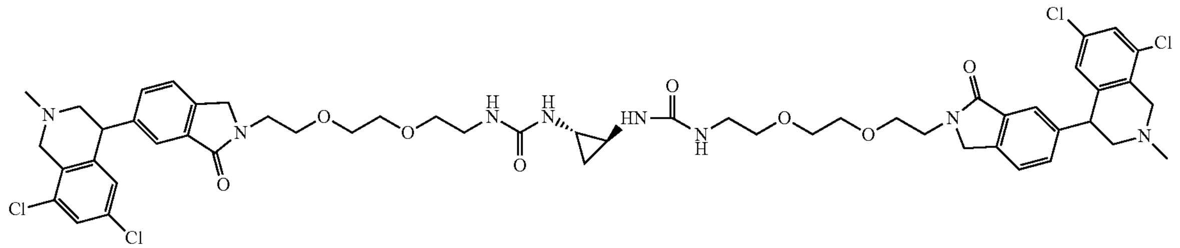
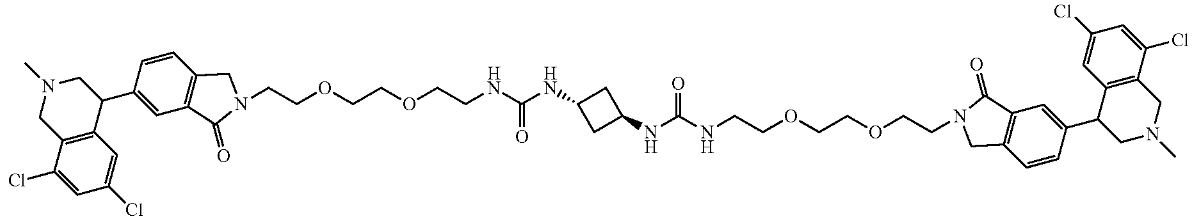

-continued
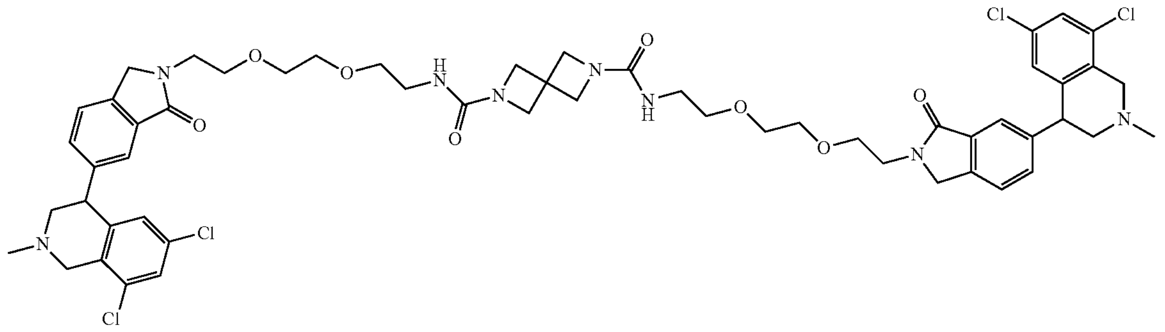
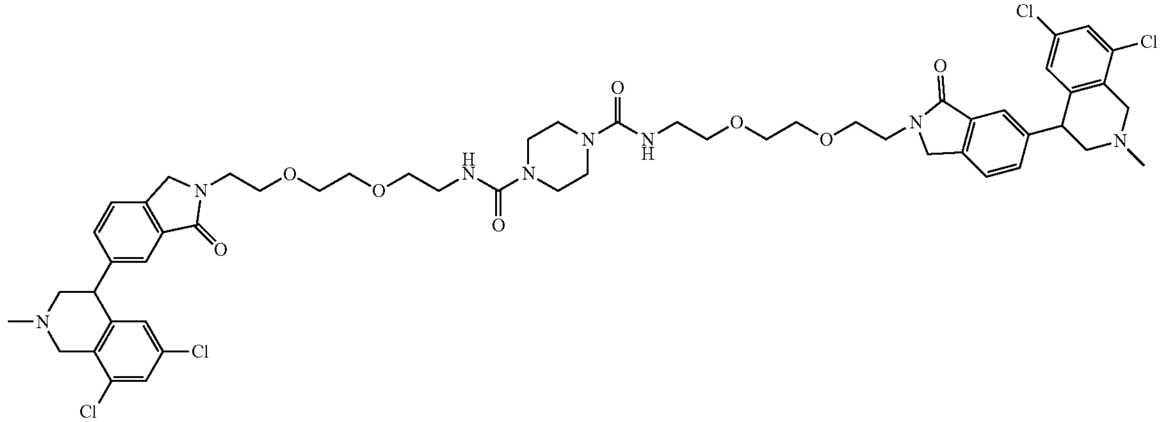
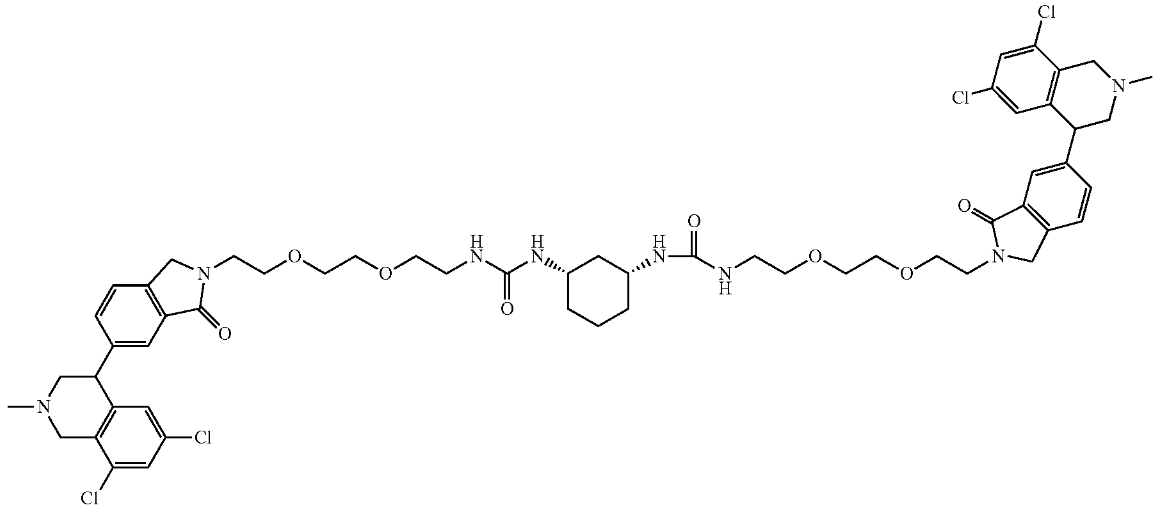
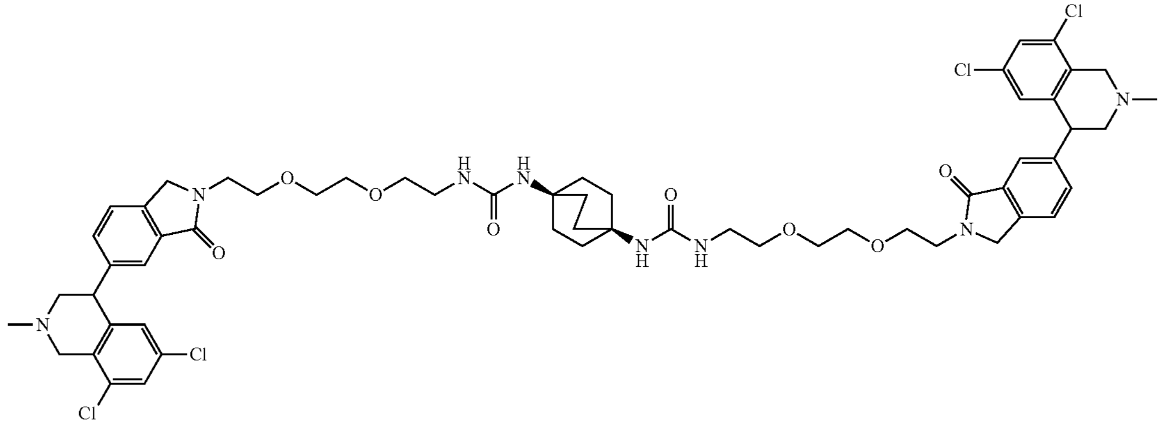

-continued
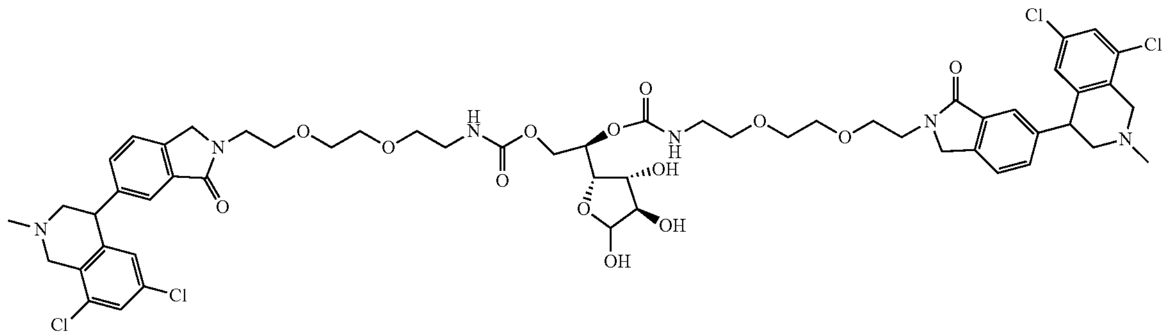
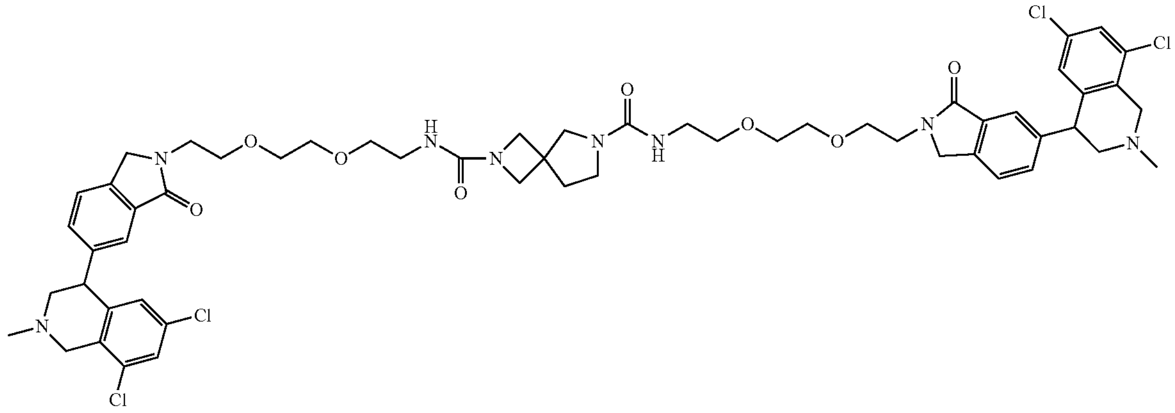
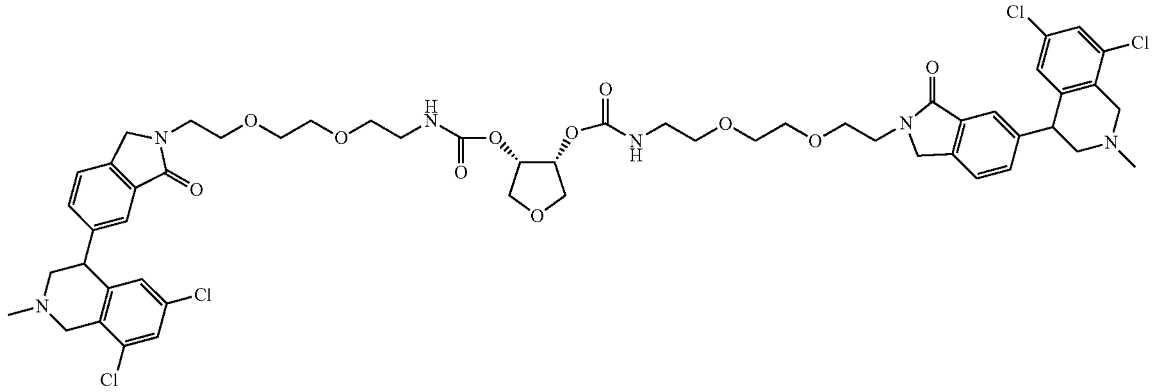
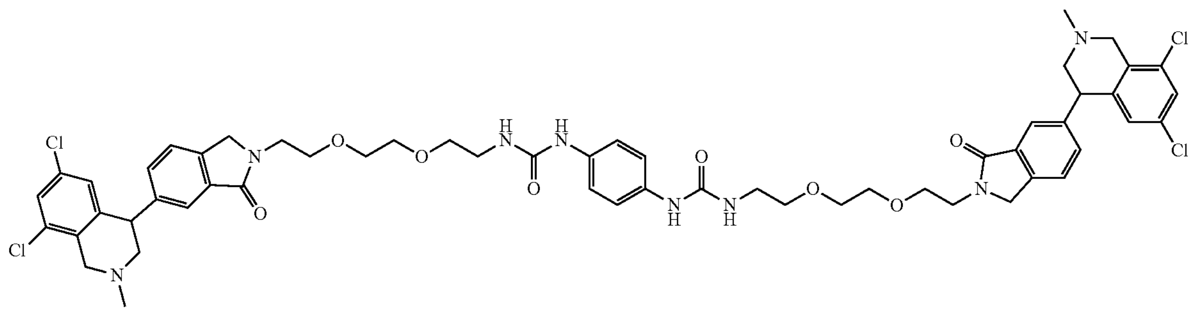

-continued
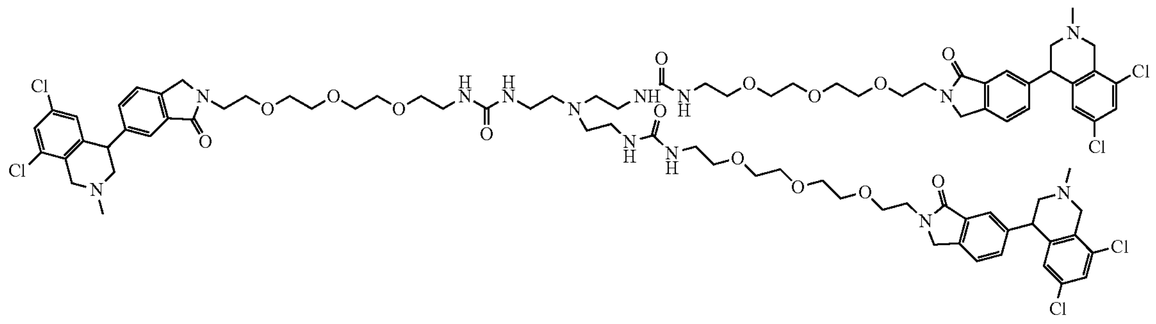
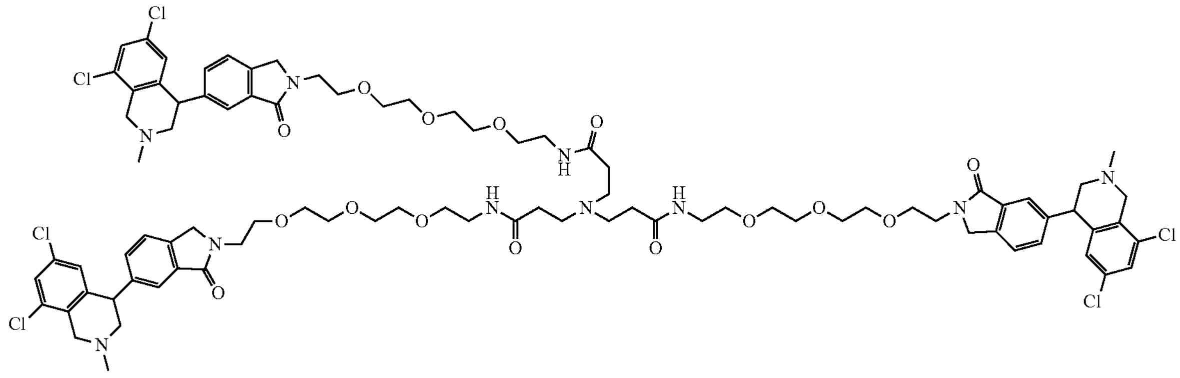
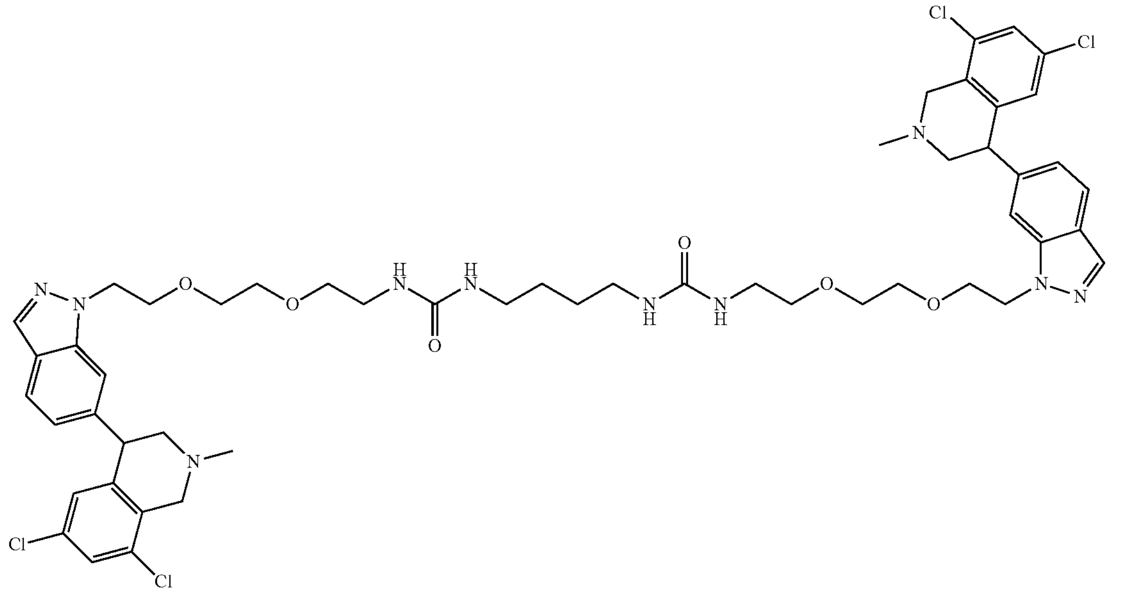
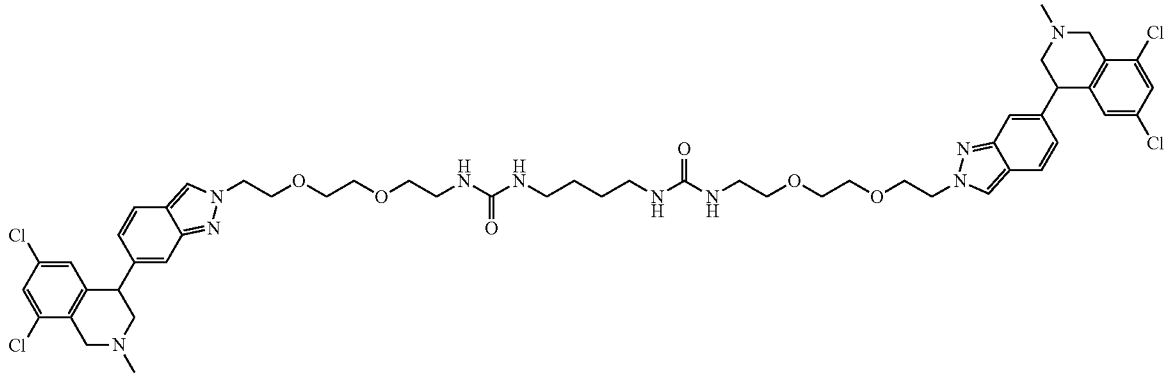

-continued
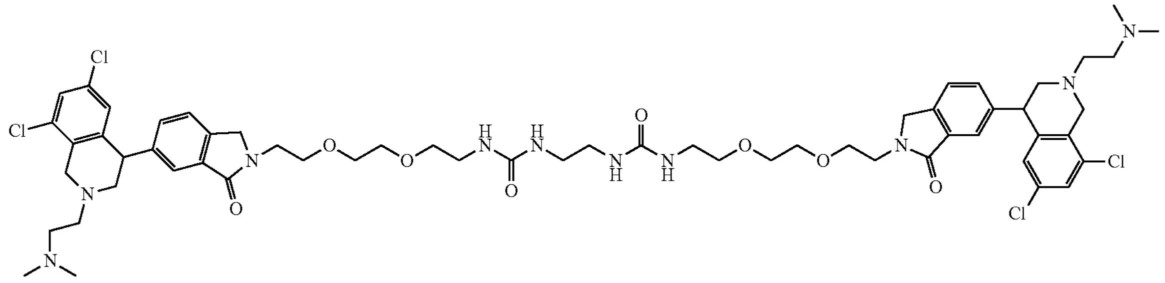
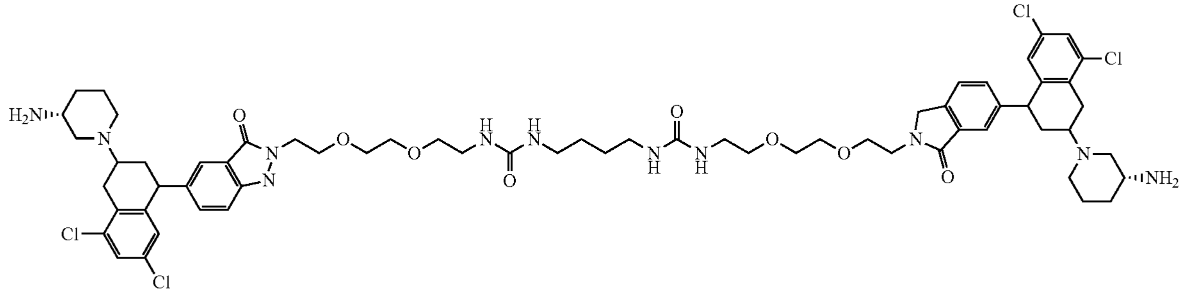
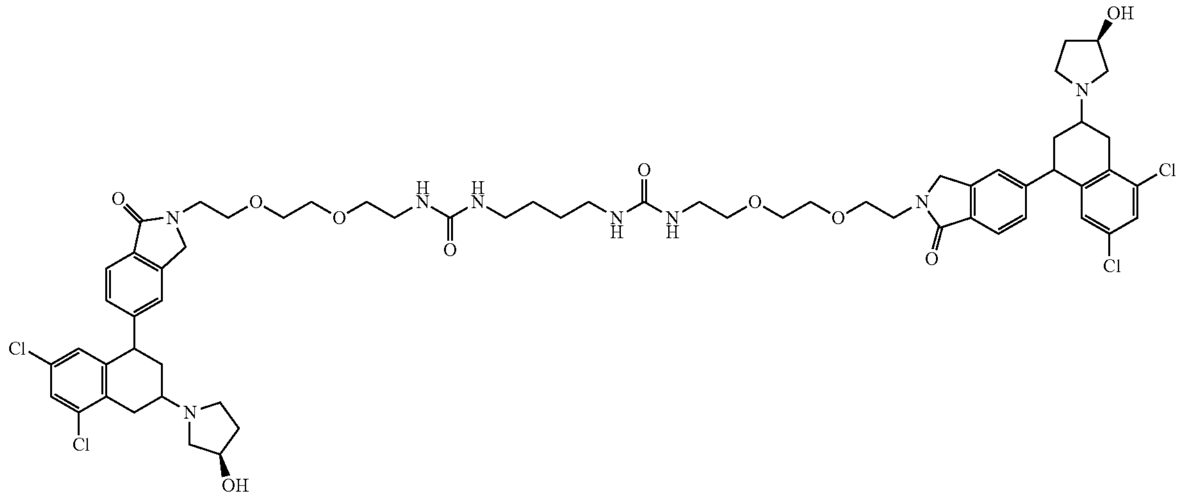
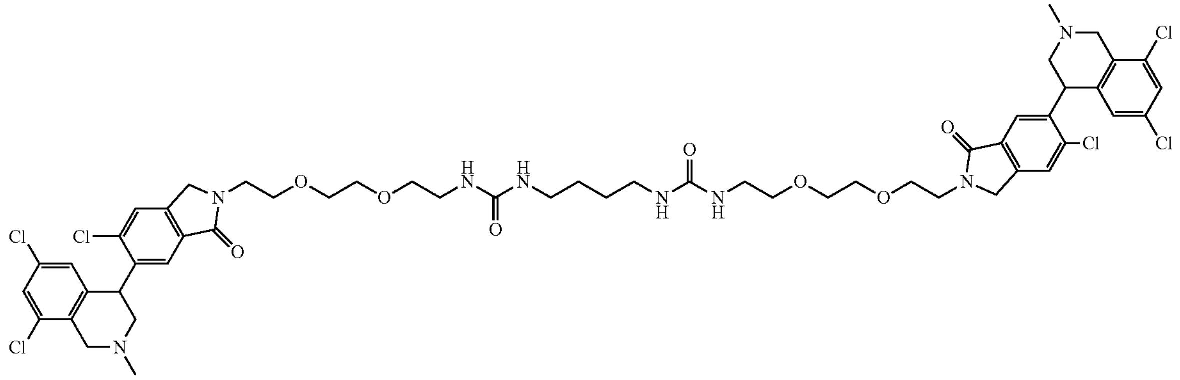

-continued
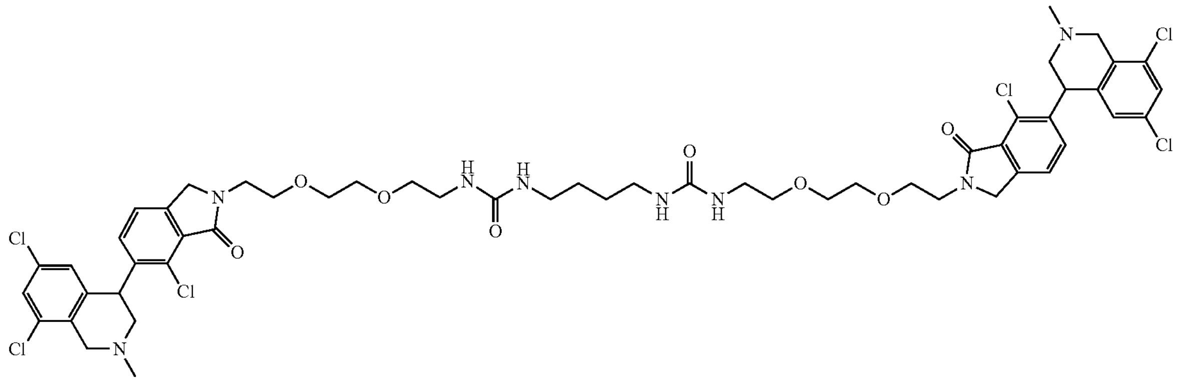
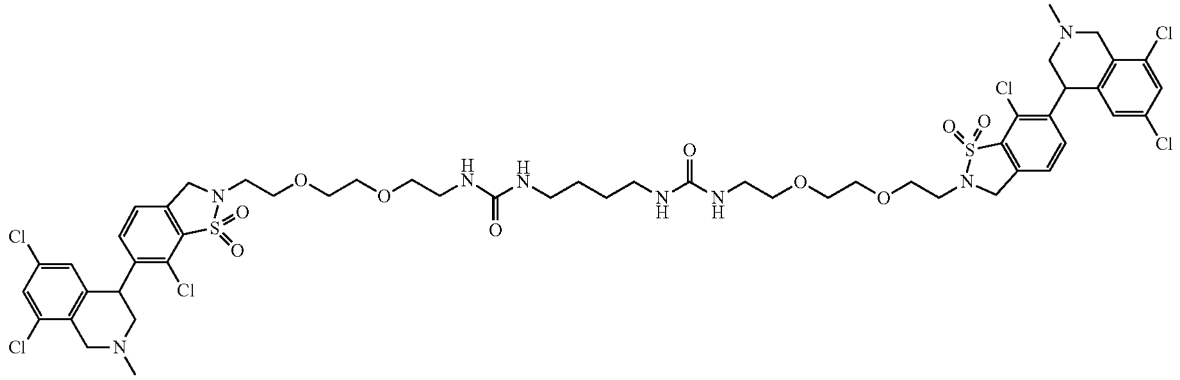
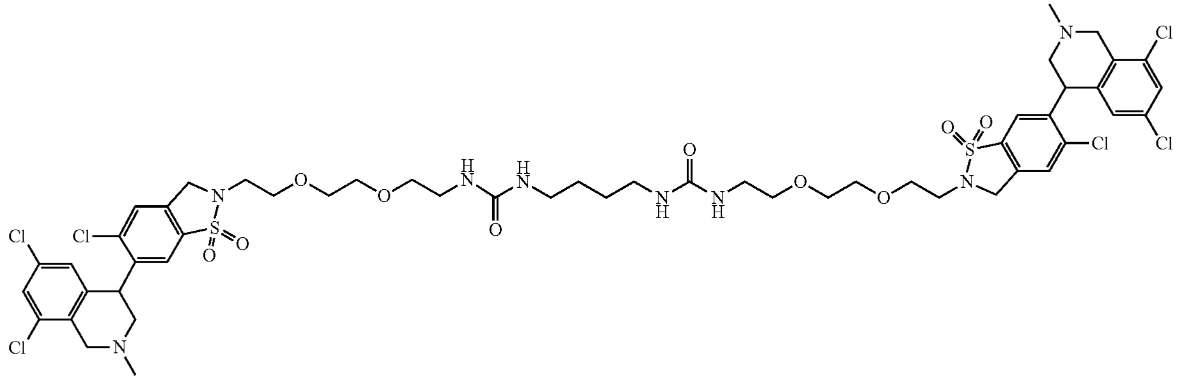
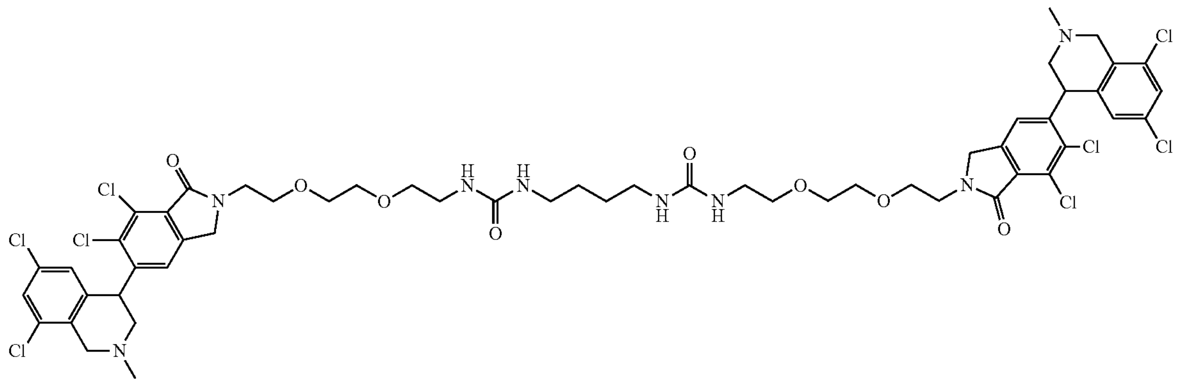

-continued
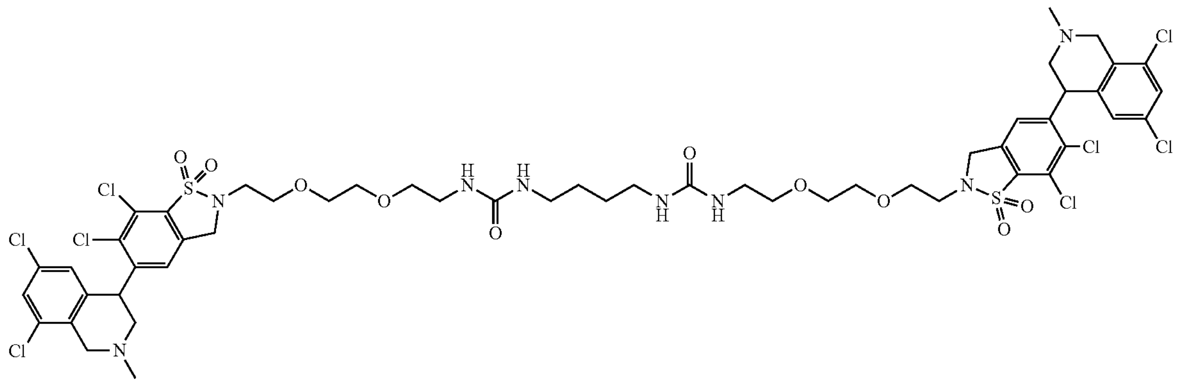
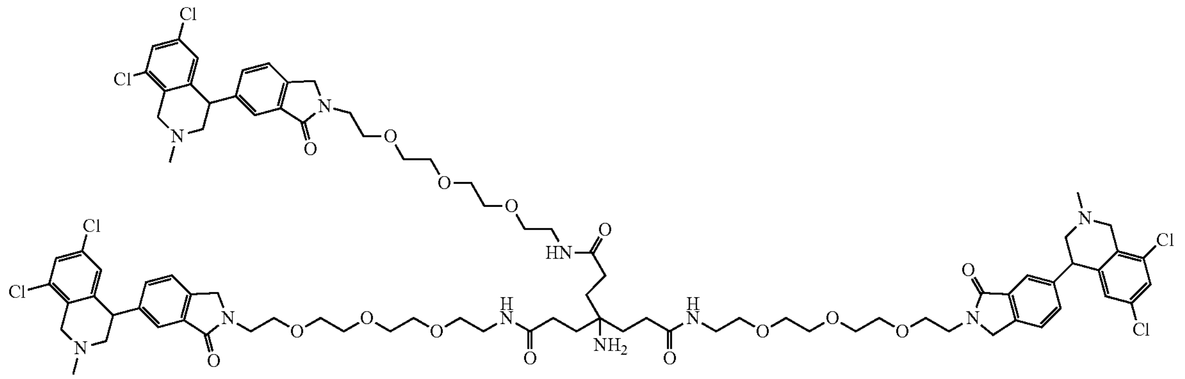
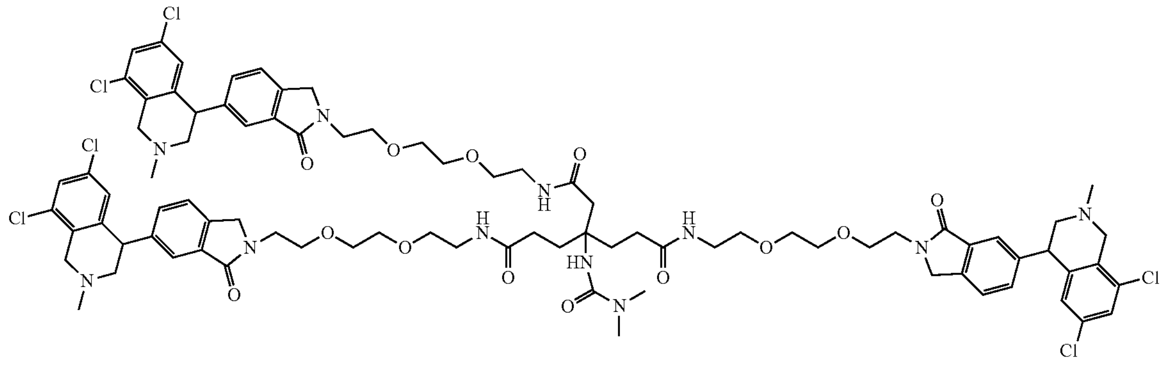
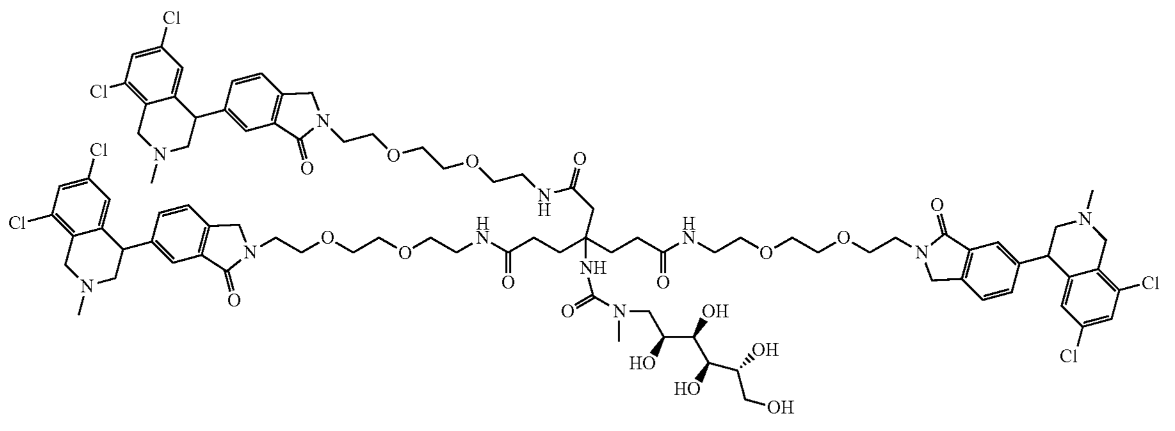

-continued
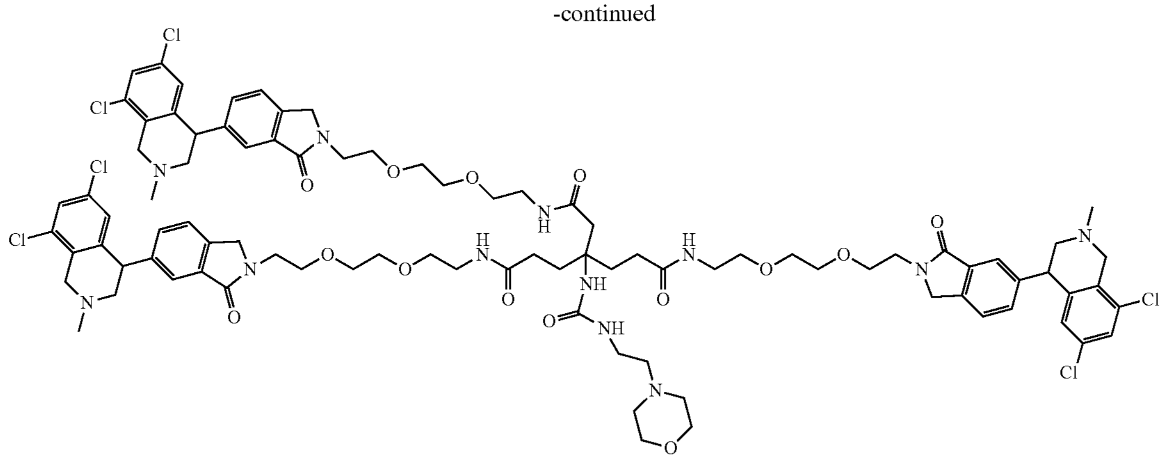
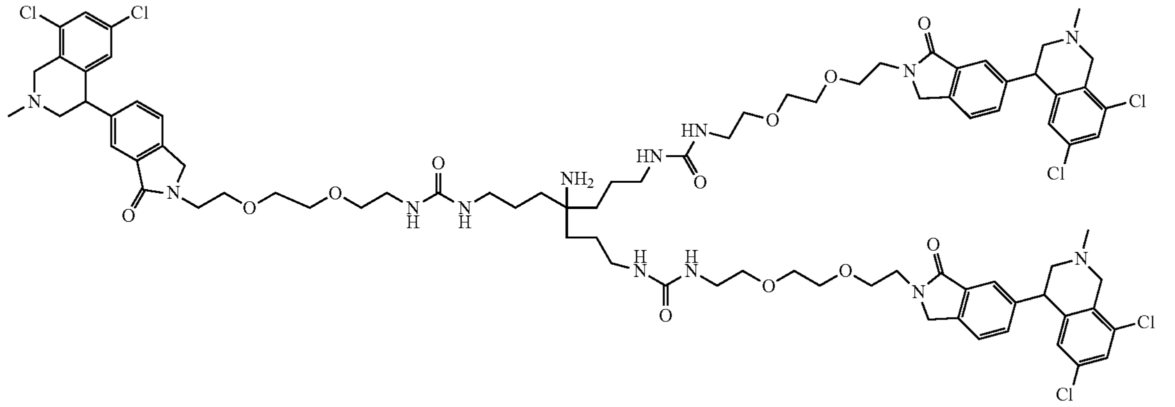
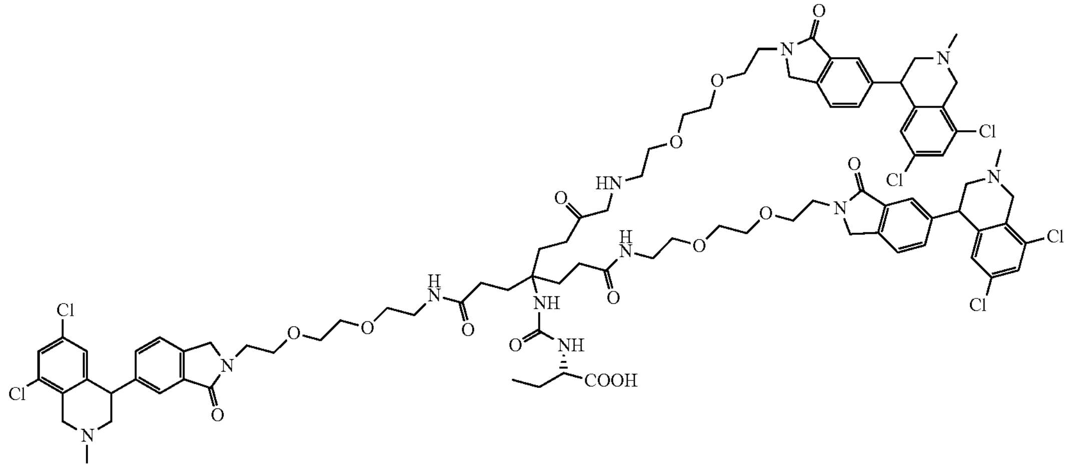
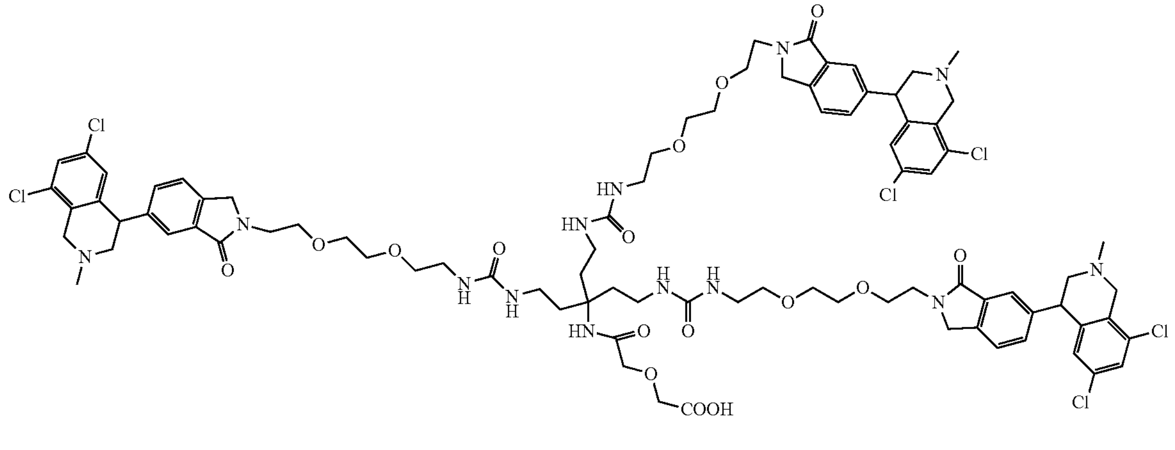

-continued
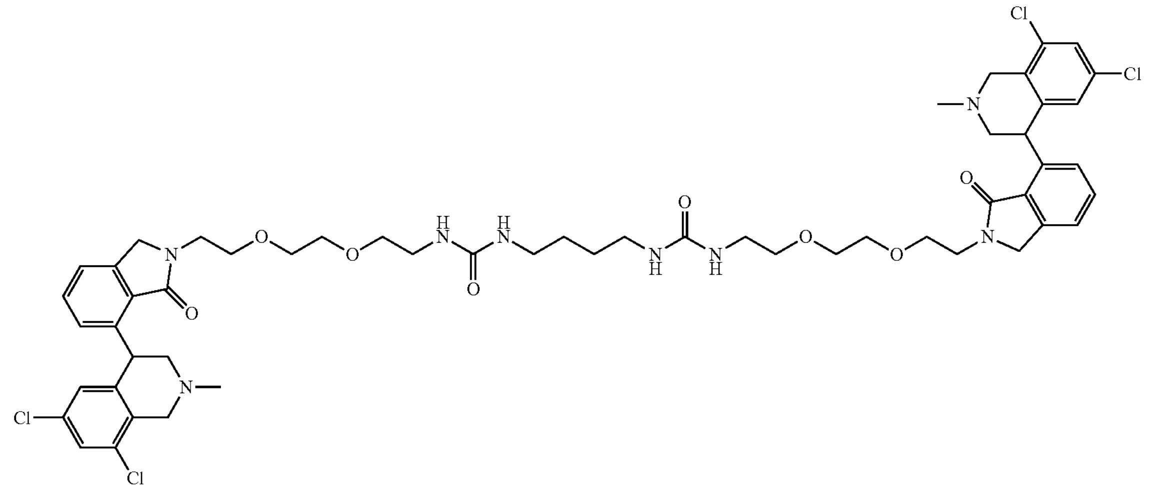
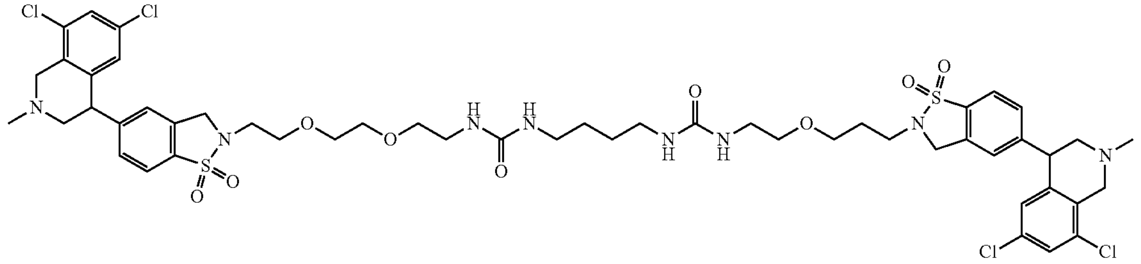
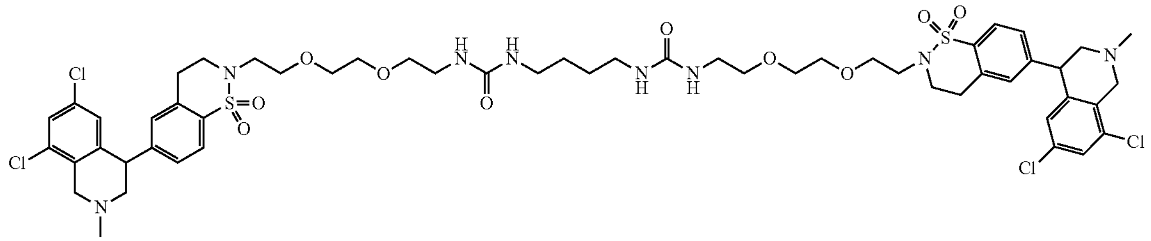
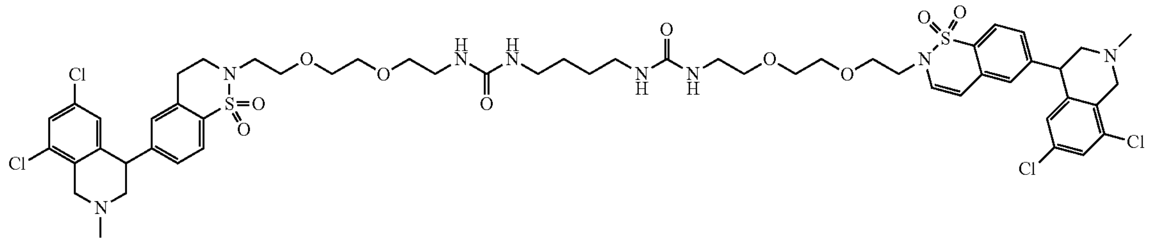
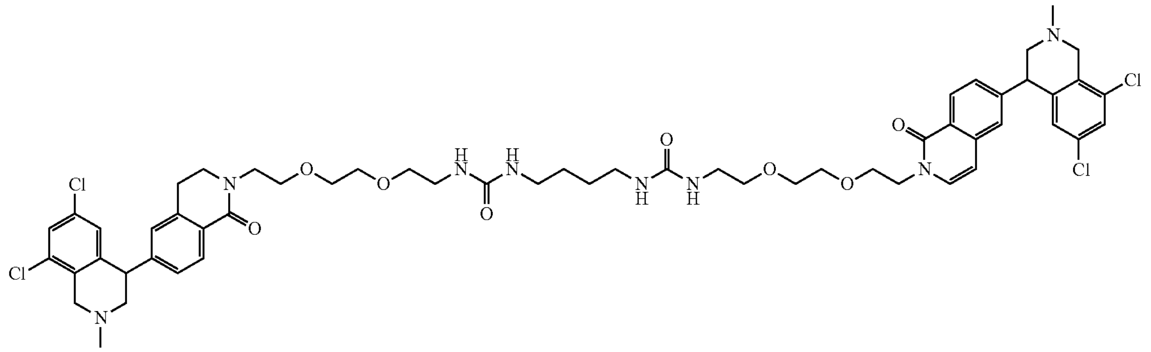

-continued
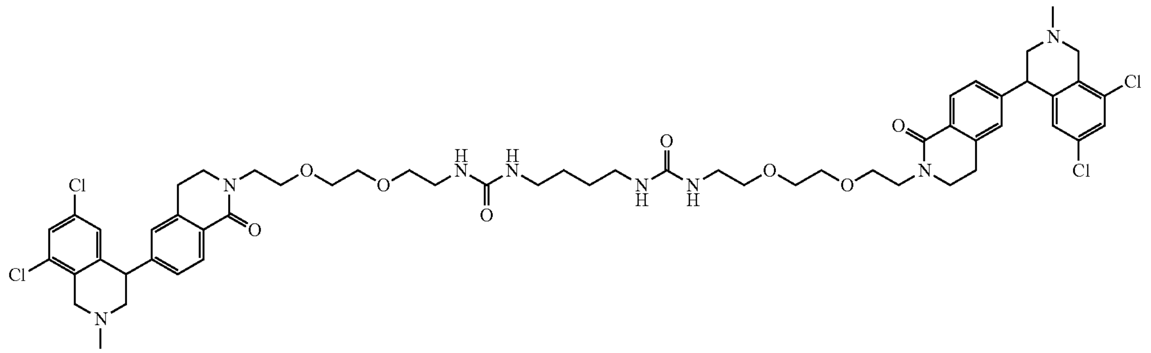
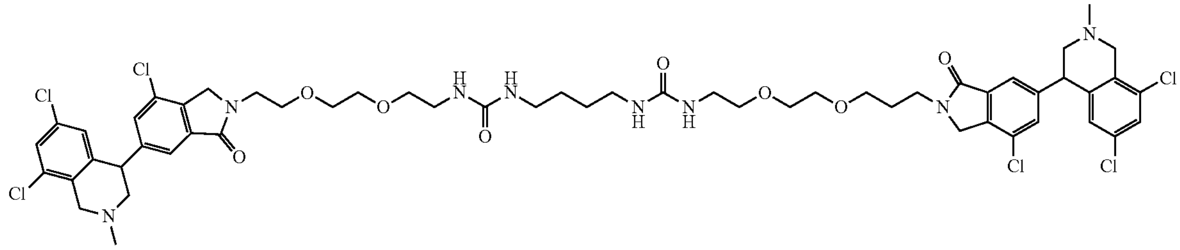
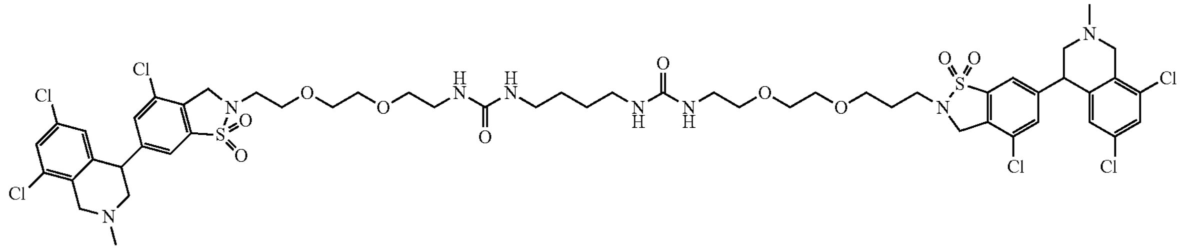
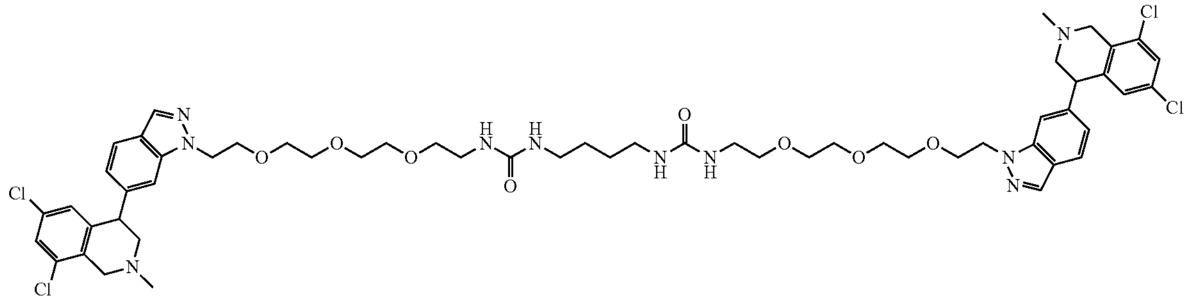
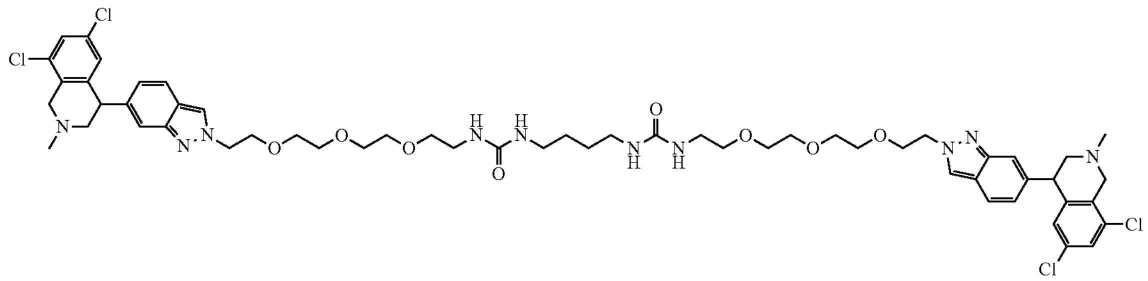
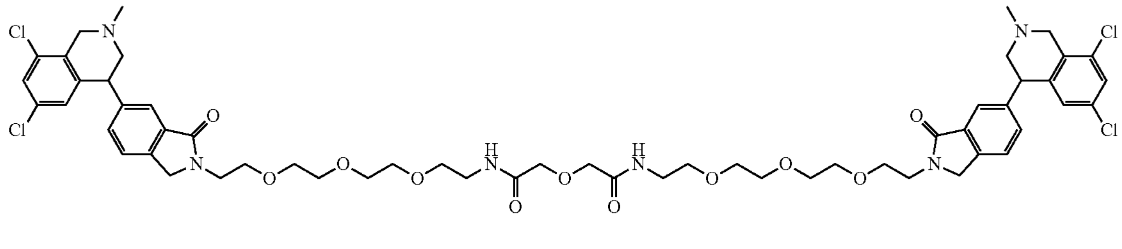

-continued

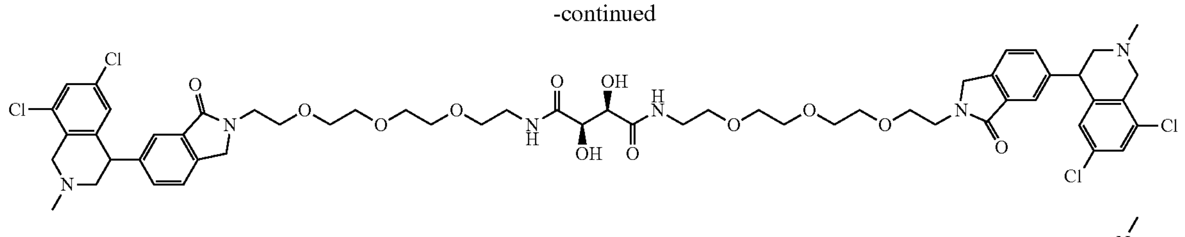

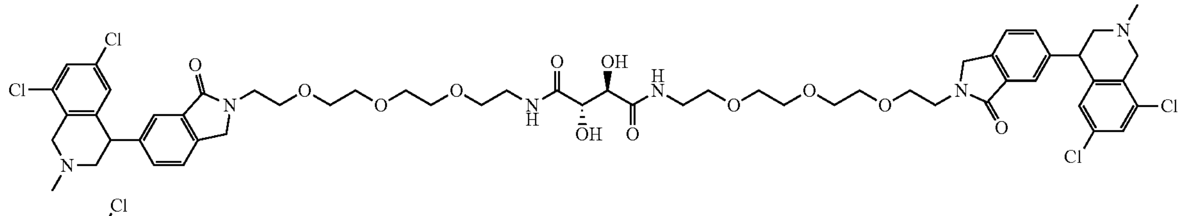

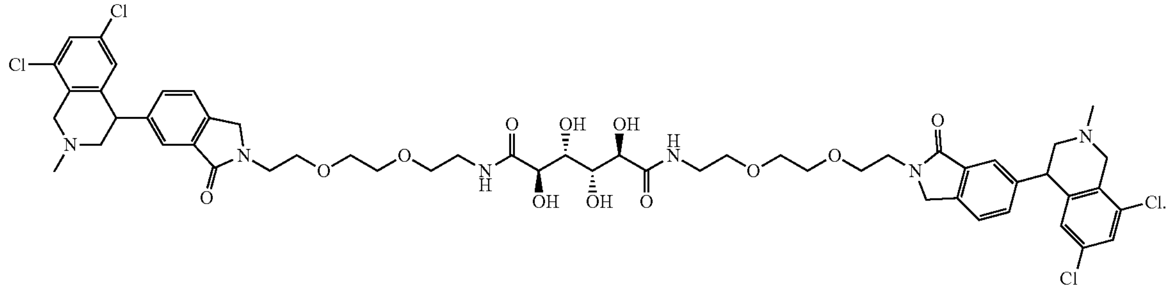

In another aspect of the present disclosure, the present disclosure also provides a use of the above compound, an optical isomer thereof and a pharmaceutically acceptable salt thereof in the preparation of a medicament for inhibiting NHE-mediated reverse transport of sodium or hydrogen ions.

In another aspect of the present disclosure, the present disclosure also provides a use of the above compound, an optical isomer thereof and a pharmaceutically acceptable salt thereof in the preparation of a medicament for treating irritable bowel syndrome, heart failure, chronic kidney disease, end-stage renal disease or liver disease.

Definition and Description

Unless otherwise specified, the following terms and phrases used herein have the following meanings. A specific term or phrase should not be considered indefinite or unclear in the absence of a particular definition, but should be understood according to the common meaning. When a trade name appears herein, it is intended to refer to its corresponding commercial product or active ingredient thereof.

The term "pharmaceutically acceptable" is used herein in terms of those compounds, materials, compositions, and/or dosage forms, which are suitable for use in contact with human and animal tissues within the scope of reliable medical judgment, without excessive toxicity, irritation, anaphylactic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the neutral form of the compound into contact with a sufficient amount of acid in a solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, trifluoroacetic acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereoisomers, (D)-isomers, (L)-isomers, and racemic and other mixtures thereof, such as enantiomers or diastereomer enriched mixtures, all of which are within the scope of the present disclosure. Additional asymmetric carbon atoms may be present in substituents such as alkyl. All these isomers and their mixtures are encompassed within the scope of the present disclosure.

The compounds of the present disclosure may exist in specific. Unless otherwise specified, the term “tautomer” or “tautomeric form” means that at room temperature, the isomers of different functional groups are in dynamic equilibrium and can be transformed into each other quickly. If tautomers possibly exist (such as in solution), the chemical equilibrium of tautomers can be reached. For example, proton tautomer (also called prototropic tautomer) includes interconversion through proton migration, such as keto-enol isomerization and imine-enamine isomerization. Valence tautomer includes some recombination of bonding electrons for mutual transformation. A specific example of keto-enol tautomerization is the tautomerism between two tautomers of pentane-2,4-dione and 4-hydroxypent-3-en-2-one.

The compound of the present disclosure may contain an unnatural proportion of atomic isotope at one or more than one atom(s) that constitute the compound. For example, the compound can be radiolabeled with a radioactive isotope, such as tritium ($^{3}H$), iodine-125 ($^{125}I$) or C-14 ($^{14}C$). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure. The term “optional” or “optionally” means that the subsequently described event or circumstance may, but does not necessarily, occur, and the description includes instances where the event or circumstance occurs and the event or circumstance where it does not.

The term “substituted” refers to one or more than one hydrogen atom(s) on a specific atom are substituted by the substituent, including deuterium and hydrogen variables, as long as the valence of the specific atom is normal and the substituted compound is stable. The term “optionally substituted” means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound. For example,

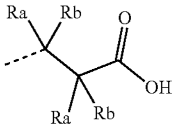

can be selected from

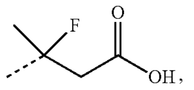 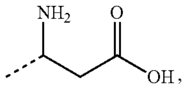

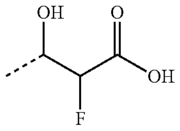 and 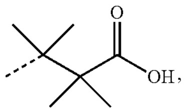

and the like.

A dash (“–”) that is not between two letters or symbols indicates the connection site of the substituent. For example, $C_{1-6}$ alkylcarbonyl- refers to a $C_{1-6}$ alkyl that is attached to the rest of the molecule through a carbonyl. However, when the connection site of the substituent is obvious to those skilled in the art, for example, a halogen substituent, the “–” may be omitted.

Unless otherwise indicated, when the valence bond of a group is marked with a dashed line “ ⁄ ”, for example, in

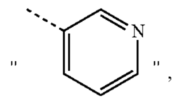

the dashed line indicates the connection site between the group and the other part of the molecule.

When one of the variables is selected from a single bond, it means that the two groups connected are directly connected, for example, when $L_1$ in

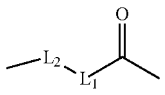

represents a single bond, it means that the structure is actually

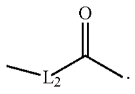

When the enumerative substituent does not indicate by which atom it is linked to the group to be substituted, such substituent can be bonded by any atom thereof, for example, when pyridyl acts as a substituent, it can be linked to the group to be substituted by any carbon atom on the pyridine ring.

When the enumerative linking group does not indicate the direction for linking, the direction for linking is arbitrary, for example, the linking group L in

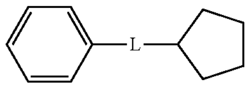 is 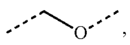

then

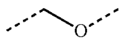

can link phenyl and cyclopentyl to form

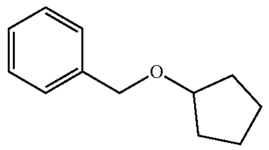 [SMILES: c1ccc(COC2CCCC2)cc1]

in the direction same as left-to-right reading order, and can also link phenyl and cyclopentyl to form

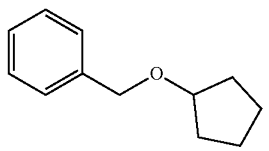 [SMILES: c1ccc(COC2CCCC2)cc1]

in the direction contrary to left-to-right reading order. A combination of the linking groups, substituents and/or variables thereof is allowed only when such combination can result in a stable compound.

Unless otherwise specified, the number of atoms in a ring is generally defined as the number of ring members, for example, "4-6 membered ring" refers to a "ring" in which 4 to 6 atoms are arranged around.

Unless otherwise specified, the term "$C_{1-6}$ alkyl" refers to a linear or branched saturated hydrocarbon group consisting of 1 to 6 carbon atoms. The $C_{1-6}$ alkyl includes $C_{1-5}$, $C_{1-4,\ 2-6}$ alkyl, etc.; it can be monovalent (such as methyl), divalent (such as methylene) or multivalent (such as methine). Examples of $C_{1-5}$ alkyl include but are not limited to methyl (Me), ethyl (Et), propyl such as n-propyl (n-Pr) or isopropyl (i-Pr), butyl such as n-butyl (n-Bu), isobutyl (i-Bu), sec-butyl (s-Bu), and t-butyl (tert-Bu), pentyl, hexyl, etc.

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$ and $C_{2-3}$ alkyl, etc.; it can be monovalent (such as methyl), divalent (such as methylene) or multivalent (such as methine). Examples of $C_{1-3}$ alkyl include but are not limited to methyl (Me), ethyl (Et), propyl (including n- and isopropyl) and the like.

Unless otherwise specified, "$C_{2-6}$ alkenyl" refers to a linear or branched hydrocarbon group consisting of 2 to 6 carbon atoms containing at least one carbon-carbon double bond, and the carbon-carbon double bond may be located at any position of the group. The $C_{2-6}$ alkenyl includes $C_{2-4}$, $C_{2-3}$, $C_4$, $C_3$ and $C_2$ alkenyl, etc.; it can be monovalent, divalent or multivalent. Examples of $C_{2-6}$ alkenyl include, but are not limited to, ethenyl, propenyl, butenyl, pentenyl, hexenyl, butadienyl, pentadienyl, hexadienyl, etc.

Unless otherwise specified, "$C_{2-3}$ alkenyl" refers to a linear or branched hydrocarbon group consisting of 2 to 3 carbon atoms containing at least one carbon-carbon double bond, and the carbon-carbon double bond may be located at any position of the group. The $C_{2-3}$ alkenyl includes $C_3$ and $C_2$ alkenyl; the $C_{2-3}$ alkenyl can be monovalent, divalent or multivalent. Examples of $C_{2-3}$ alkenyl include, but are not limited to, ethenyl, propenyl, etc.

The term "heteroalkyl" by itself or in combination with another term, refers to a stable straight or branched alkyl atomic group or a composition thereof, consisting of a certain number of carbon atoms and at least one heteroatom or heteroatomic group. In some embodiments, the heteroatom is selected from B, O, N, and S, wherein nitrogen and sulfur atoms are optionally oxidized, and nitrogen heteroatom is optionally quaternized. In other embodiments, the heteroatomic group is selected from $-C(=O)O-$, $-C(=O)-$, $-C(=S)-$, $-S(=O)$, $-S(=O)_2-$, $-C(=O)N(H)-$, $-N(H)-$, $-C(=NH)-$, $-S(=O)_2N(H)-$ and $-S(=O)N(H)-$. In some embodiments, the heteroalkyl is $C_{1-6}$ heteroalkyl; in other embodiments, the heteroalkyl is $C_{1-3}$ heteroalkyl. The heteroatom or heteroatomic group may be located at any internal position of a heteroalkyl, including the position where the alkyl is attached to the rest of the molecule, but the term "alkoxy" is customary expressions referring to those alkyl groups that are attached to the rest of the molecule by an oxygen atom. Examples of heteroalkyl include, but are not limited to, $-OCH_3$, $-OCH_2CH_3$, $-OCH_2CH_2CH_3$, $-OCH_2(CH_3)_2$, $-CH_2-CH_2-O-CH_3$, $-NHCH_3$, $-N(CH_3)_2$, $-NHCH_2CH_3$, $-N(CH_3)(CH_2CH_3)$, $-CH_2-CH_2-NH-CH_3$, $-CH_2-CH_2-N(CH_3)-CH_3$, $-SCH_3$, $-SCH_2CH_3$, $-SCH_2CH_2CH_3$, $-SCH_2(CH_3)_2$, $-CH_2-S-CH_2-CH_3$, $-CH_2-CH_2$, $-S(=O)-CH_3$, $-CH_2-CH_2-S(=O)_2-CH_3$, and up to two heteroatoms can be consecutive, such as $-CH_2-NH-OCH_3$.

Unless otherwise specified, the term "$C_{1-6}$ alkoxy" refers to an alkyl group containing 1 to 6 carbon atoms that are connected to the rest of the molecule through an oxygen atom. The $C_{1-6}$ alkoxy includes $C_{1-4}$, $C_{1-3}$, $C_{1-2}$, $C_{2-6}$, $C_{2-4}$, $C_6$, $C_5$, $C_4$ and $C_3$ alkoxy, etc. Examples of $C_{1-6}$ alkoxy include, but are not limited to, methoxy, ethoxy, propoxy (including n-propoxy and isopropoxy), butoxy (including n-butoxy, isobutoxy, s-butoxy, and t-butoxy), pentyloxy (including n-pentyloxy, isopentyloxy, and neopentyloxy), and hexyloxy, etc.

Unless otherwise specified, the term "$C_{1-4}$ alkoxy" refers to an alkyl group containing 1 to 4 carbon atoms that are connected to the rest of the molecule through an oxygen atom. The $C_{1-4}$ alkoxy includes $C_{1-3}$, $C_{1-2}$, $C_{2-4}$, $C_4$ and $C_3$ alkoxy, etc. Examples of $C_{1-6}$ alkoxy include, but are not limited to, methoxy, ethoxy, propoxy (including n-propoxy and isopropoxy), butoxy (including n-butoxy, isobutoxy, s-butoxy, and t-butoxy), pentyloxy (including n-pentyloxy, isopentyloxy, and neopentyloxy), and hexyloxy, etc.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-2}$, $C_{2-3}$, $C_3$ and $C_2$ alkoxy, etc. Examples of $C_{1-3}$ alkoxy include, but are not limited to, methoxy, ethoxy, propoxy (including n-propoxy and isopropoxy), etc.

Unless otherwise specified, the term "$C_{1-6}$ alkylamino" refers to an alkyl group containing 1 to 6 carbon atoms that are connected to the rest of the molecule through an amino group. The $C_{1-6}$ alkylamino includes $C_{1-4}$, $C_{1-3}$, $C_{1-2}$, $C_{2-6}$, $C_{2-4}$, $C_6$, $C_5$, $C_4$, $C_3$ and $C_2$ alkylamino, etc. Examples of $C_{1-6}$ alkylamino include, but are not limited to, $-NHCH_3$, $-N(CH_3)_2$, $-NHCH_2CH_3$, $-N(CH_3)CH_2CH_3$, $-N(CH_2CH_3)(CH_2CH_3)$, $-NHCH_2CH_2CH_3$, $-NHCH_2(CH_3)_2$, $-NHCH_2CH_2CH_2CH_3$, etc.

Unless otherwise specified, the term "$C_{1-4}$ alkylamino" refers to an alkyl group containing 1 to 4 carbon atoms that are connected to the rest of the molecule through an amino group. The $C_{1-4}$ alkylamino includes $C_{1-3}$, $C_{1-2}$, $C_{2-4}$, $C_4$, $C_3$ and $C_2$ alkylamino, etc. Examples of $C_{1-4}$ alkylamino include, but are not limited to, $—NHCH_3$, $—N(CH_3)_2$, $—NHCH_2CH_3$, $—N(CH_3)CH_2CH_3$, $—N(CH_2CH_3)(CH_2CH_3)$, $—NHCH_2CH_2CH_3$, $—NHCH_2(CH_3)_2$, $—NHCH_2CH_2CH_2CH_3$, etc.

Unless otherwise specified, the term "$C_{1-3}$ alkylamino" refers to an alkyl group containing 1 to 3 carbon atoms that are connected to the rest of the molecule through an amino group. The $C_{1-3}$ alkylamino includes $C_{1-2}$, $C_3$ and $C_2$ alkylamino, etc. Examples of $C_1$_3 alkylamino include, but are not limited to, $—NHCH_3$, $—N(CH_3)_2$, $—NHCH_2CH_3$, $—N(CH_3)CH_2CH_3$, $—NHCH_2CH_2CH_3$, $—NHCH_2(CH_3)_2$, etc.

Unless otherwise specified, the term "$C_{1-6}$ alkylthio" refers to an alkyl group containing 1 to 6 carbon atoms that are connected to the rest of the molecule by a sulfur atom. The $C_{1-6}$ alkylthio includes $C_{1-4}$, $C_{1-3}$, $C_{1-2}$, $C_{2-6}$, $C_{2-4}$, $C_6$, $C_5$, $C_4$, $C_3$ and $C_2$ alkylthio, etc. Examples of $C_{1-6}$ alkylthio include, but are not limited to, $—SCH_3$, $—SCH_2CH_3$, $—SCH_2CH_2CH_3$, $—SCH_2(CH_3)_2$, etc.

Unless otherwise specified, the term "$C_{1-4}$ alkylthio" refers to an alkyl group containing 1 to 4 carbon atoms that are connected to the rest of the molecule by a sulfur atom. The $C_{1-4}$ alkylthio includes $C_{1-3}$, $C_{1-2}$, $C_{2-4}$, $C_4$, $C_3$ and $C_2$ alkylthio, etc. Examples of $C_{1-4}$ alkylthio include, but are not limited to, $—SCH_3$, $—SCH_2CH_3$, $—SCH_2CH_2CH_3$, $—SCH_2(CH_3)_2$, etc.

Unless otherwise specified, the term "$C_{1-3}$ alkylthio" refers to an alkyl group containing 1 to 3 carbon atoms that are connected to the rest of the molecule by a sulfur atom. The $C_{1-3}$ alkylthio includes $C_{1-3}$, $C_{1-2}$ and $C_3$ alkylthio, etc. Examples of $C_{1-3}$ alkylthio include, but are not limited to, $—SCH_3$, $—SCH_2CH_3$, $—SCH_2CH_2CH_3$, $—SCH_2(CH_3)_2$, etc.

Unless otherwise specified, the term "cycloalkyl" refers to a saturated or partially unsaturated monocyclic or polycyclic hydrocarbon substituent, and the cycloalkyl contains 3 to 20 carbon atoms, preferably contains 3 to 12 carbon atoms (it can be a specific point or an interval between any two points, such as 3, 4, 5, 6 ring atoms, 4 to 11 ring atoms, 6 to 12 ring atoms, etc.), more preferably contains 3 to 8 carbon atoms, most preferably contains 3 to 6 (such as 3, 4, 5 or 6) carbon atoms. Non-limiting examples of the monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, etc., preferably cycloalkyl; the polycyclic cycloalkyl includes cycloalkyl of spiro ring, fused ring and bridged ring.

Unless otherwise specified, "$C_{3-9}$ cycloalkyl" refers to a saturated monovalent monocyclic or bicyclic hydrocarbon group having 3-9 ring carbon atoms, such as having 3-8 ring carbon atoms, such as having 3-6 ring carbon atoms, such as 3-4 ring carbon atoms. For example, "$C_{3-9}$ cycloalkyl" means a cycloalkyl group with 3-9 ring carbon atoms. Similarly, "$C_{3-8}$ cycloalkyl" means a cycloalkyl group with 3-8 ring carbon atoms; "$C_{3-6}$ cycloalkyl" means a cycloalkyl group with 3-6 ring carbon atoms; "$C_{3-4}$ cycloalkyl" means a cycloalkyl group with 3-4 ring carbon atoms. Examples of cycloalkyl include, but are not limited to, cyclopropyl, cyclobutyl, cyclopentyl, cyclohexyl, cycloheptyl and cyclooctyl, etc.

Unless otherwise specified, "$C_{4-6}$ cycloalkyl" refers to a saturated cyclic hydrocarbon group consisting of 4 to 6 carbon atoms, which is a monocyclic and bicyclic system, and the $C_{4-6}$ cycloalkyl includes $C_{4-5}$, $C_{5-6}$, $C_4$, $C_5$ and $C_6$ cycloalkyl, etc.; it can be monovalent, divalent or multivalent. Examples of $C_{4-6}$ cycloalkyl include, but are not limited to, cyclobutyl, cyclopentyl, cyclohexyl, etc.

Unless otherwise specified, the term "$C_{5-10}$ spirocyclyl" refers to a 5 to 10 membered polycyclic group that shares one carbon atom (called a spiro atom) between monocyclic rings, which may contain one or more double bonds, but none of the rings has a fully conjugated π-electron system. Preferably 7 to 10 membered. Spirocycloalkyl is divided into monospirocycloalkyl, bispirocycloalkyl or multispirocycloalkyl according to the number of spiro atoms shared between rings, preferably monospirocycloalkyl and bispirocycloalkyl.

More preferably 4/4, 4/5, 4/6, 5/5 or 5/6 membered monospirocycloalkyl. Non-limiting examples of the spirocycloalkyl include:

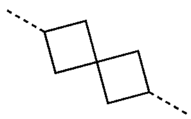
and
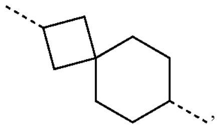
, etc.

Unless otherwise specified, the term "$C_{5-10}$ fused cyclyl" refers to a 5 to 10 membered, full-carbon polycyclic group in which any two rings share two non-directly attached carbon atoms, and which may contain one or more double bonds, but none of the rings has a fully conjugated π-electron system. Preferably 7 to 10 membered. According to the number of rings, it can be divided into bicyclic, tricyclic, tetracyclic or polycyclic bridged cycloalkyl, preferably bicyclic, tricyclic or tetracyclic, and more preferably bicyclic or tricyclic. Non-limiting examples of "$C_{5-10}$ fused ring" include:

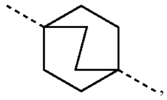
, etc.

Unless otherwise specified, the term "bridged cycloalkyl" refers to a 5 to 10 membered, full-carbon polycyclic group, in which any two rings share two non-directly attached carbon atoms, and which may contain one or more double bonds, but none of the rings has a fully conjugated π-electron system. Preferably 6 to 10 membered, more preferably 7 to 10 membered. According to the number of rings, it can be divided into bicyclic, tricyclic, tetracyclic or polycyclic bridged cycloalkyl groups, preferably bicyclic, tricyclic or tetracyclic, and more preferably bicyclic or tricyclic. Non-limiting examples of the bridged cycloalkyl include:

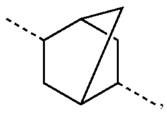
, etc.

Unless otherwise specified, the term "heterocycloalkyl" refers to a saturated or partially unsaturated monocyclic or polycyclic hydrocarbon substituent containing 3 to 20 ring atoms, one or more of which are heteroatoms selected from nitrogen, oxygen or S(O)m (where m is an integer 0 to 2), but excluding ring portion of —O—O—, —O—S— or —S—S—, with the remaining ring atoms being carbon. Preferably, it contains 3 to 12 ring atoms (it can be a specific point or an interval between any two points, such as 3, 4, 5, 6 ring atoms, 4 to 11 ring atoms, 6 to 12 ring atoms, etc.), 1 to 4 of which are heteroatoms; more preferably, it contains 3 to 8 ring atoms, 1 to 3 of which are heteroatoms; most preferably, it contains 3 to 6 ring atoms, 1 to 3 of which are heteroatoms. Non-limiting examples of monocyclic heterocyclyl include azetidinyl, pyrrolidinyl, imidazolidinyl, tetrahydrofuryl, tetrahydropyranyl, tetrahydrothienyl, dihydroimidazolyl, dihydrofuryl, dihydropyrazolyl, dihydropyrrolyl, piperidinyl, piperazinyl, morpholinyl, thiomorpholinyl, homopiperazinyl, etc., preferably tetrahydropyranyl, piperidinyl, pyrrolidinyl. Polycyclic heterocyclyl includes spiro, fused and bridged heterocyclyl.

Unless otherwise specified, the term “3-6 membered heterocycloalkyl” by itself or in combination with other terms refers to a saturated cyclic group consisting of 3 to 6 ring atoms, wherein 1, 2, 3 or 4 ring atoms are heteroatoms independently selected from O, S and N, and the rest are carbon atoms, wherein nitrogen atoms are optionally quaternized, and nitrogen and sulfur heteroatoms can be optionally oxidized (i.e., NO and $S(O)_p$, p is 1 or 2). It includes monocyclic and bicyclic systems, wherein the bicyclic systems include spiro ring, fused ring and bridged ring. In addition, with regard to the “3-6 membered heterocycloalkyl”, the heteroatom may occupy the connection position of the heterocycloalkyl with the rest of the molecule. The 3-6 membered heterocycloalkyl includes 5-6 membered, 4 membered, 5 membered and 6 membered heterocycloalkyl, etc. Examples of 4-6 membered heterocycloalkyl include, but are not limited to, azetidinyl, oxetanyl, thietanyl, pyrrolidinyl, pyrazolidinyl, imidazolidinyl, tetrahydrothienyl (including tetrahydrothiophen-2-yl and tetrahydrothiophen-3-yl, etc.), tetrahydrofuranyl (including tetrahydrofuran-2-yl, etc.), tetrahydropyranyl, piperidinyl (including 1-piperidinyl, 2-piperidinyl and 3-piperidinyl, etc.), piperazinyl (including 1-piperazinyl and 2-piperazinyl, etc.), morpholinyl (including 3-morpholinyl and 4-morpholinyl, etc.), dioxinyl, dithianyl, isoxazolidinyl, isothiazolidinyl, 1,2-oxazinyl, 1,2-thiazinyl, hexahydropyridazinyl, homopiperazinyl or homopiperidinyl, etc.

Unless otherwise specified, the term “5-10 membered spiroheterocyclyl” refers to a 5 to 10 membered polycyclic heterocyclic group that shares one atom (called a spiro atom) between monocyclic rings, wherein one or more ring atoms are heteroatoms selected from nitrogen, oxygen or $S(O)_m$ (where m is an integer 0 to 2) and the remaining ring atoms are carbon. It may contain one or more double bonds, but none of the rings has a fully conjugated π-electron system. Preferably 7 to 10 membered. The spiroheterocyclyl is divided into monospiroheterocyclyl, bispiroheterocyclyl or multispiroheterocyclyl according to the number of spiro atoms shared between rings, preferably monospiroheterocyclyl and bispiroheterocyclyl.

More preferably 4/4, 4/5, 4/6, 5/5 or 5/6 membered monospiroheterocyclyl. Non-limiting examples of the spiro heterocyclyl include:

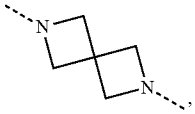,
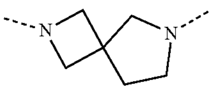
and

-continued

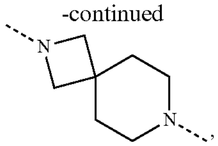, etc.

Unless otherwise specified, the term “5-10 membered fused heterocyclyl” refers to a 5 to 10 membered, polycyclic heterocyclic group, in which each ring shares an adjacent pair of atoms with other rings in the system, one or more rings can contain one or more double bonds, but none of the rings has a fully conjugated π-electron system, wherein one or more ring atoms are heteroatoms selected from nitrogen, oxygen or $S(O)_m$ (where m is an integer of 0 to 2) and the remaining ring atoms are carbon. Preferably 6 to 10 membered, more preferably 7 to 10 membered. According to the number of rings, it can be divided into bicyclic, tricyclic, tetracyclic or polycyclic fused heterocyclyl, preferably bicyclic or tricyclic, and more preferably 5/5 or 5/6 membered bicyclic fused heterocyclyl. Non-limiting examples of the fused heterocyclyl include:

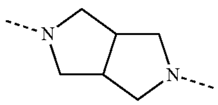
and
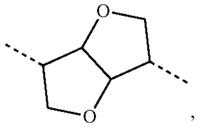, etc.

Unless otherwise specified, the term “bridged heterocyclyl” refers to a 5 to 10 membered, polycyclic heterocyclic group, in which any two rings share two atoms that are not directly connected, which may contain one or more double bonds, but none of the rings has a fully conjugated π-electron system, in which one or more ring atoms are heteroatoms selected from nitrogen, oxygen or $S(O)_m$ (where m is an integer of 0 to 2) and the remaining ring atoms are carbon. Preferably 6 to 10 membered, more preferably 7 to 10 membered. According to the number of rings, it can be divided into bicyclic, tricyclic, tetracyclic or polycyclic bridged heterocyclyl, preferably bicyclic, tricyclic or tetracyclic, and more preferably bicyclic or tricyclic. Non-limiting examples of bridged heterocyclyl include:

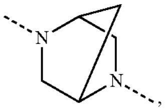, etc.

Unless otherwise specified, the term “cycloalkenyl” in the present disclosure refers to a cyclic alkenyl group. The “$C_{3-7}$ cycloalkenyl” includes $C_3$, $C_4$, $C_5$, $C_6$ and $C_7$ alkenyl, etc. Examples of cycloalkenyl include, but are not limited to, cyclobutenyl, cyclopentenyl and cyclohexenyl.

Unless otherwise specified, the term “heterocycloalkenyl” in the present disclosure refers to a cycloalkenyl group containing several heteroatoms. “5-6 membered heterocycloalkenyl” by itself or in combination with other terms refers to an unsaturated cyclic group consisting of 5 to 6 ring atoms, wherein 1, 2, 3 or 4 ring atoms are heteroatoms independently selected from O, S and N, and the rest are carbon atoms, wherein nitrogen atoms are optionally quaternized, and nitrogen and sulfur heteroatoms can be optionally oxidized (i.e., NO and $S(O)_p$, p is 1 or 2). Examples of heterocycloalkenyl include, but are not limited to

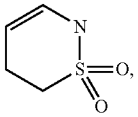

etc.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$, etc.; similarly, n membered to n+m membered means that the number of atoms on the ring is from n to n+m, for example, 3 to 12 membered ring includes 3 membered ring, 4 membered ring, 5 membered ring, 6 membered ring, 7 membered ring, 8 membered ring, 9 membered ring, 10 membered ring, 11 membered ring, and 12 membered ring, and any range from n to n+m is also included, for example, 3 to 12 membered ring includes 3 to 6 membered ring, 3 to 9 membered ring, 5 to 6 membered ring, 5 to 7 membered ring, 6 to 7 membered ring, 6 to 8 membered ring, and 6 to 10 membered ring, etc.

Unless otherwise specified, the term "heteroaryl" refers to a heteroaromatic system containing 1 to 4 heteroatoms, 5 to 20 ring atoms, wherein the heteroatoms are selected from oxygen, sulfur and nitrogen. The heteroaryl is preferably 5 to 10 membered, containing 1 to 3 heteroatoms; more preferably 5 or 6 membered, containing 1 to 3 heteroatoms; non-limiting examples are pyrazolyl, imidazolyl, furyl, thienyl, thiazolyl, oxazolyl, pyrrolyl, triazolyl, tetrazolyl, pyridinyl, pyrimidinyl, thiadiazole, pyrazinyl, etc. The heteroaryl ring may be fused to an aryl, heterocyclyl, or cycloalkyl ring, wherein the ring attached to the parent structure is a heteroaryl ring, non-limiting examples of which include:

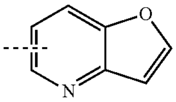

and

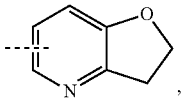

, etc.

The heteroaryl may be optionally substituted or unsubstituted, and when substituted, the substituents are preferably one or more of the following groups independently selected from one or more of alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkoxy, heterocycloalkoxy, cycloalkylthio and heterocycloalkylthio.

Those skilled in the art should understand that some compounds of the formula (I) may have one or more chiral centers, so there are two or more stereoisomers. Therefore, the compounds of the present disclosure may exist in the form of a single stereoisomer (e.g., enantiomers, diastereomers) and mixtures thereof in any ratios such as racemate, and in an appropriate situation, may exist in the form of tautomer and geometric isomer thereof.

The term "stereoisomer" used herein refers to the compound with the same chemical composition but different in the spatial arrangement of atoms or groups. Stereoisomers include enantiomers, diastereomers and conformational isomers.

The term "enantiomer" used herein refers to two stereoisomers of compound that are non-superimposable mirror images of each other.

The term "diastereomer" used herein refers to stereoisomers with two or more chiral centers and the molecules are not mirror images of each other. Diastereomers have different physical properties, such as melting point, boiling point, spectral properties or biological activity. Mixtures of diastereomers can be separated by high-resolution analytical methods such as electrophoresis and chromatography such as HPLC.

The definition and practice of stereochemistry can be followed in S. P. Parker, McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active form, that is, they have the ability to rotate the plane of plane-polarized light. When describing optically active compounds, the prefixes D and L or R and S are used to indicate the absolute configuration of the molecule with respect to its chiral center. The prefixes d and 1 or (+) and (−) are used to refer to the symbol of the compound rotating plane-polarized light, where (−) or 1 refers to that the compound is levorotatory. Compounds prefixed with (+) or D are dextral. For a given chemical structure, the stereoisomers are the same except that they mirror each other. Specific stereoisomers can also be called enantiomers, and mixtures of such isomers are usually called enantiomer mixtures. The 50:50 mixture of enantiomers is called racemic mixture or racemate, which can occur in the absence of stereoselectivity or stereospecificity in chemical reactions or methods. The terms "racemic mixture" and "racemate" refer to an equimolar mixture of two enantiomers that do not have optical activity.

Racemic mixtures can be used in their own form or split into individual isomers. Through resolution, stereochemically pure compounds or mixtures enriched in one or more isomers can be obtained. Methods for separating isomers are well known (see Allinger n. L. and Eliel E. L., "topics in stereochemistry", Vol. 6, Wiley Interscience, 1971), including physical methods, such as chromatography using chiral adsorbents. Individual isomers in chiral form may be prepared from chiral precursors. Alternatively, the individual isomer may be obtained by chemical separation from the mixture of diastereoisomeric salts formed by chiral acids (e.g., single enantiomer of 10-camphorsulfonic acid, camphoric acid, α-bromocamphoric acid, tartaric acid, diacetyltartaric acid, malic acid, pyrrolidone-5-carboxylic acid, etc.), crystallizing the salt in stages, and then freeing one or two by the separated bases, optionally repeating the process, thereby obtaining one or two isomers substantially free of the other isomer, i.e., the desired stereoisomer with an optical purity of, for example, at least 91%, 92%, 93%, 94%, 95%, 96%, 97%, 98%, 99% or 99.5% by weight. Alternatively, as well known to those skilled in the art, the racemate can be covalently attached to a chiral compound (auxiliary) to obtain diastereomers.

The term "tautomer" or "tautomeric form" used herein refers to structural isomers of different energies that can be transformed into each other through low-energy barriers. For example, proton tautomers (also known as proton transfer tautomers) include interconversion by proton migration, such as keto-enol and imino-enamine isomerization. Valence tautomer includes interconversion through the recombination of some bonded electrons.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The technical and scientific terms used herein that are not specifically defined have the meanings commonly understood by those skilled in the art to which the present disclosure belongs.

DETAILED DESCRIPTION OF THE PREFERRED EMBODIMENT

Figure 1:
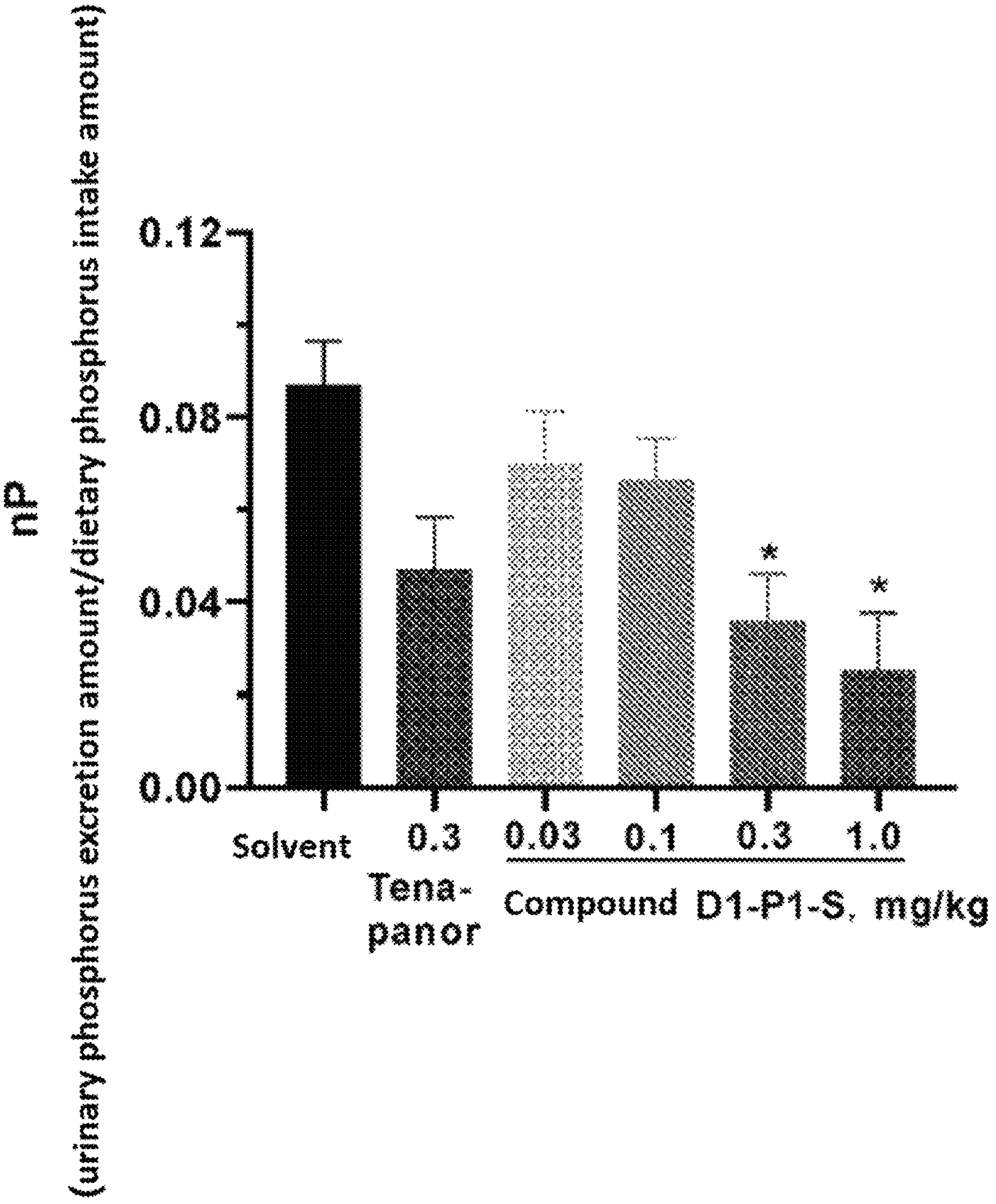
FIG. 1 is a standardized correction value (nP) of urinary phosphorus excretion amount against dietary phosphorus intake amount according to embodiments of the present disclosure.

The present application is described in detail by the embodiments below, but it does not mean that there are any adverse restrictions on the present application. The present application has been described in detail herein, wherein specific embodiments thereof are also disclosed, and it will be apparent to those skilled in the art that various variations and improvements can be made to specific embodiments of the present application without departing from the spirit and scope of the present application.

Synthesis of Embodiment A1

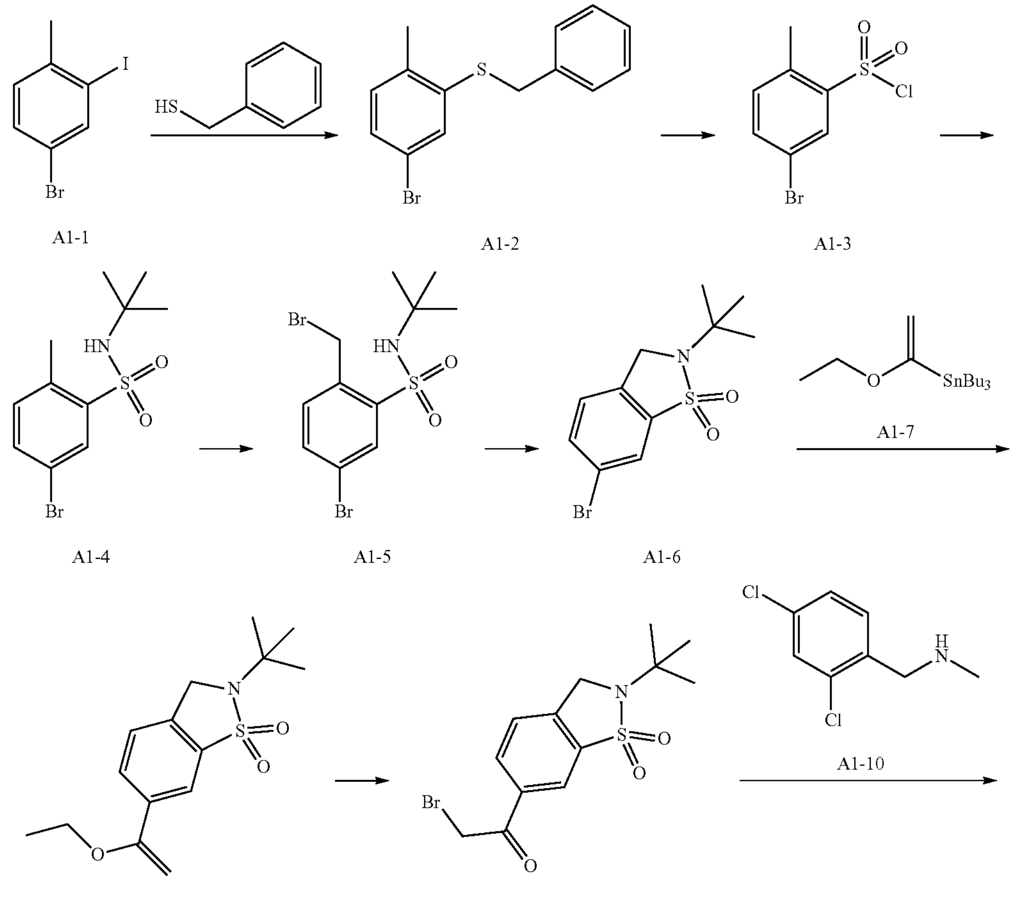

A1-1 A1-2 A1-3
A1-4 A1-5 A1-6
A1-8 A1-9

-continued
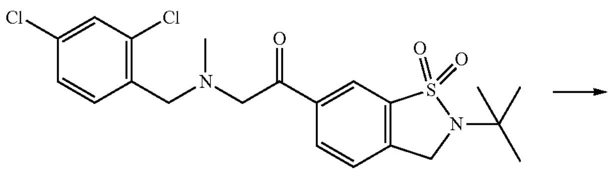
A1-11
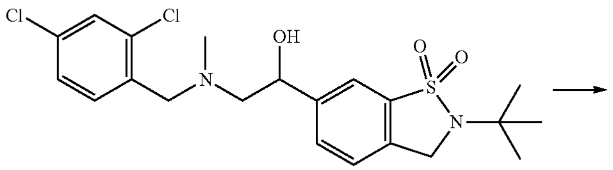
A1-12
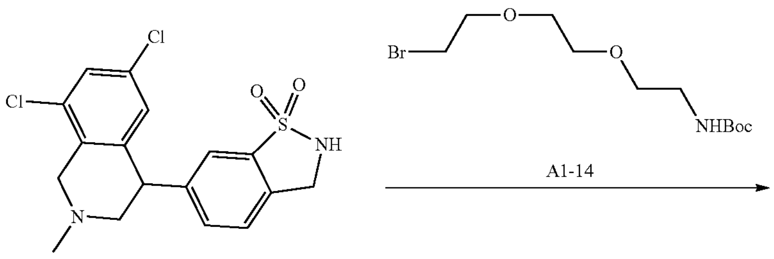
A1-13
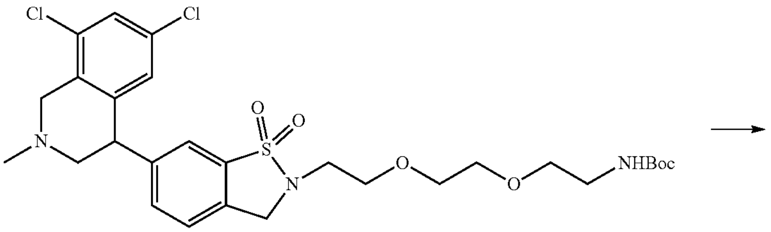
A1-15
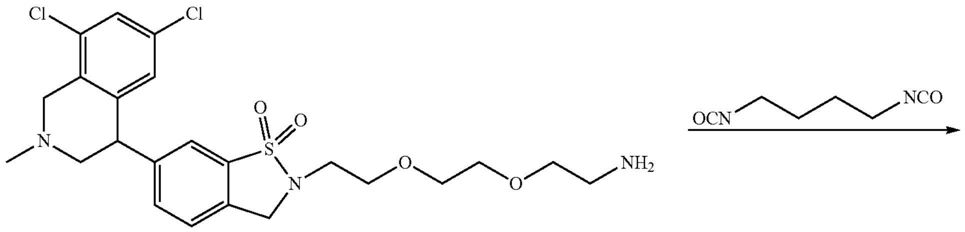
A1-16
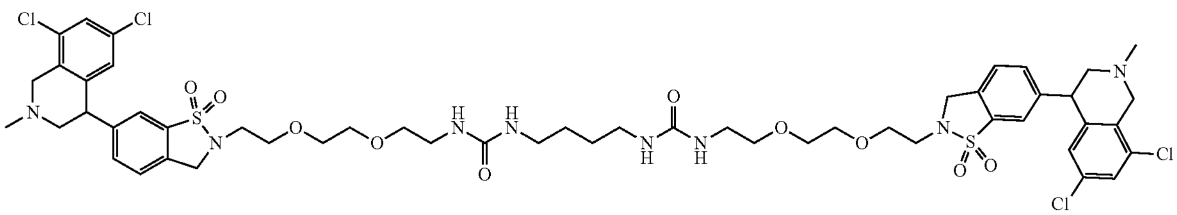
A1

Step 1: Preparation of Compound A1-2

Compound A1-1 (6.53 g, 22.0 mmol), tris(dibenzylideneacetone)dipalladium (700 mg, 0.76 mmol), xantphos (700 mg, 1.21 mmol), N,N-diisopropylethylamine (3.87 g, 30.0 mmol) were dissolved in 1,4-dioxane (50 mL) solution, then the system was heated under nitrogen atmosphere to 70° C., and the compound benzyl mercaptan (2.48 g, 20.0 mmol) was added dropwise to the reaction system, after the dropwise addition, the system was stirred at 70° C. for 3 hours. The reaction mixture was cooled to room temperature (25° C.), filtered with celite, and the filtrate was concentrated under vacuum to obtain the crude product, which was purified by silica gel column chromatography (ethyl acetate/petroleum ether (v/v)=0-6%) to obtain compound A1-2.

$^1$H NMR (400 MHz, DMSO-$d_6$) δ 7.44 (d, J=2.0 Hz, 1H), 7.41-7.36 (m, 2H), 7.35-7.29 (m, 2H), 7.29-7.23 (m, 2H), 7.13 (dd, J=8.0, 0.9 Hz, 1H), 4.27 (s, 2H), 2.18 (s, 3H).

Step 2: Preparation of Compound A1-3

Compound A1-2 (12.9 g, 43.87 mmol) was dissolved in a mixed solution of acetic acid (120 mL) and water (30 mL), to which N-chlorosuccinimide (23.30 g, 175.5 mmol) was added in batches at room temperature (25° C.), after the addition, the system was stirred at room temperature (25° C.) for 2 hours. The reaction mixture was concentrated under vacuum at low temperature (<30° C.) to obtain compound A1-3, which was directly used in the next step without further purification.

Step 3: Preparation of Compound A1-4

Tert-butylamine (6.3 g, 86 mmol) and triethylamine (13 g, 129 mmol) were dissolved in anhydrous dichloromethane (100 mL), then the system was cooled to 0° C., to which compound A1-3 was slowly added. After the addition, the system was heated to room temperature (25° C.) and reacted for 2 hours. Water (100 mL) was added to the reaction mixture, followed by liquid separation. The aqueous phase was extracted with dichloromethane (80 mL×2). The organic phases were combined, washed with saturated aqueous sodium chloride solution (100 mL), dried over anhydrous sodium sulfate, filtered, the filtrate was concentrated under vacuum to obtain the crude product. The crude product was purified by silica gel column chromatography (ethyl acetate/petroleum ether (v/v)=0-10%) to obtain compound A1-4.

$^1$H NMR (400 MHz, Chloroform-d) δ 8.17 (d, J=2.2 Hz, 1H), 7.55 (dd, J=8.1, 2.2 Hz, 1H), 7.17 (dd, J=8.1, 0.8 Hz, 1H), 4.44 (s, 1H), 2.59 (d, J=0.6 Hz, 3H), 1.24 (s, 9H).

Step 4: Preparation of Compound A1-5

Compound A1-4 (7 g, 22.8 mmol) was dissolved in carbon tetrachloride (100 mL), and then N-bromosuccinimide (4.46 g, 25 mmol) and 2,2'-azobis(2-methylpropionitrile) (370 mg, 2.28 mmol) were added. After the addition, the reaction system was heated to 80° C. and stirred for 16 hours. The reaction mixture was cooled to room temperature (25° C.) and concentrated under vacuum to obtain the crude product. The crude product was purified by silica gel column chromatography (ethyl acetate/petroleum ether (v/v)=0-10%) to obtain compound A1-5.

$^1$H NMR (400 MHz, Chloroform-d) δ 8.20 (d, J=2.1 Hz, 1H), 7.66 (dd, J=8.2, 2.1 Hz, 1H), 7.43 (d, J=8.2 Hz, 1H), 4.92 (s, 2H), 1.29 (s, 9H).

Step 5: Preparation of Compound A1-6

Compound A1-5 (5.65 g, 14.67 mmol), potassium carbonate (4 g, 29.3 mmol), tetrabutylammonium iodide (1 g, 3 mmol) were dissolved in acetonitrile (100 mL). After the addition, the system was heated to 50° C. and stirred for 16 hours. The reaction mixture was cooled to room temperature (25° C.), to which water (200 mL) was added, extracted with ethyl acetate (100 mL×3), and the organic phases were combined, dried over anhydrous sodium sulfate, filtered, and the filtrate was concentrated to obtain the crude product. The crude product was purified by silica gel column chromatography (ethyl acetate/petroleum ether (v/v)=0-30%) to obtain compound A1-6.

MS (ESI) m/z $[(M+H)^+-56]$=248.0.

Step 6: Preparation of Compound A1-8

Compound A1-6 (4.07 g, 13.39 mmol), compound A1-7 (5.54 g, 15.40 mmol), tetrakis(triphenylphosphine)palladium (775 mg, 0.67 mmol) were dissolved in N,N-dimethylformamide (50 mL). Under nitrogen atmosphere, the system was heated to 100° C. and stirred for 4 hours. The reaction mixture was cooled to room temperature (25° C.), to which water (100 mL) was added, extracted with ethyl acetate (100 mL×2), and the organic phases were combined, dried over anhydrous sodium sulfate, filtered, and the filtrate was concentrated to obtain the crude product. The crude product was purified by silica gel column chromatography (ethyl acetate/petroleum ether (v/v)=0-20%) to obtain compound A1-8.

MS (ESI) m/z $[(M+H)^+-56]$=240.0.

Step 7: Preparation of Compound A1-9

Compound A1-8 (3.54 g, 12 mmol) was dissolved in a mixed solution of THF (50 ml) and water (20 mL). Under the condition of 0° C., to which N-bromosuccinimide (2.13 g, 12 mmol) was added, the system was stirred at 0° C. for 1 hour. The reaction mixture was concentrated to obtain the crude product, which was purified by silica gel column chromatography (ethyl acetate/petroleum ether (v/v)=0-30%) to obtain compound A1-9.

MS (ESI) m/z $[(M+H)^+-56]$=291.9.

Step 8: Preparation of Compound A1-11

Compound A1-9 (3.5 g, 10.1 mmol), compound A1-10 (1.93 g, 10.1 mmol) were dissolved in 1,4-dioxane (100 mL), to which triethylamine (2.05 g, 20.2 mmol) was added, after the addition, the system was stirred at room temperature (25° C.) for 2 hours. The reaction mixture was filtered, and the filtrate A1-11 was directly used in the next step.

MS (ESI) m/z $(M+H)^+$=455.0.

Step 9: Preparation of Compound A1-12

Compound A1-11 (the filtrate obtained in step 8) was dissolved in methanol (100 mL), to which sodium borohydride (740 mg, 20 mmol) was added in batches at 0° C., and the system was heated to 5° C. and stirred for 2 hours. Acetone (5 mL) was added to the system, and the system was concentrated under vacuum. The concentrated residue was dissolved in dichloromethane (50 mL), and washed with saturated aqueous sodium chloride solution. The organic phases were combined, dried over anhydrous sodium sulfate, filtered, and the filtrate was concentrated to obtain compound A1-12, which was used directly in the next step without further purification.

MS (ESI) m/z $(M+H)^+$=457.1.

Step 10: Preparation of Compound A1-13

Compound A1-12 (4.5 g, 9.82 mmol) was dissolved in anhydrous dichloromethane (20 mL), to which concentrated sulfuric acid (20 mL) was added dropwise at 0° C., after the addition, the system was heated to 90° C. and stirred for 1 hour. After the reaction mixture was cooled to room temperature (25° C.), it was poured into ice water (200 g), and the pH of which was adjusted to 9 with 2N aqueous sodium hydroxide solution. The reaction mixture was extracted with dichloromethane (100 mL×3), and the organic phases were combined, dried over anhydrous sodium sulfate, filtered, and the filtrate was concentrated to obtain the crude product. The crude product was separated and purified to obtain compound A1-13.

$^1$H NMR (400 MHz, Methanol-$d_4$) δ 7.55 (d, J=1.4 Hz, 1H), 7.39 (qd, J=8.0, 1.2 Hz, 2H), 7.33-7.20 (m, 1H), 6.72 (dd, J=2.1, 0.9 Hz, 1H), 4.51 (s, 1H), 4.34 (s, 2H), 3.66-3.60 (m, 2H), 2.92 (dd, J=11.8, 5.4 Hz, 1H), 2.61 (dd, J=11.7, 7.4 Hz, 1H), 2.38 (s, 3H).

Similar to the synthesis of intermediate A1-13, the following intermediate A2-13 was synthesized, as shown in Table 1 below:

TABLE 1

Structural formula and analysis data of intermediate A2-13

| Intermediate | Structural formula | Analysis data |
|---|---|---|
| A2-13 | 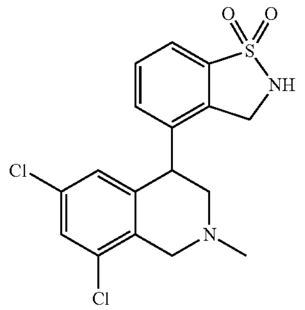 [SMILES: CN1Cc2c(Cl)cc(Cl)cc2C(c2cccc3c2CNS3(=O)=O)C1] | $^1$H NMR (400 MHz, DMSO-$d_6$) δ 7.84 (t, J = 4.5 Hz, 1H), 7.69 (dd, J = 7.8, 0.9 Hz, 1H), 7.53 (d, J = 2.1 Hz, 1H), 7.46 (t, J = 7.7 Hz, 1H), 7.17 (dd, J = 7.6, 1.0 Hz, 1H), 6.99 (d, J = 2.3 Hz, 1H), 4.71 (dd, J = 15.3, 4.4 Hz, 1H), 4.40 (d, J = 4.8 Hz, 1H), 4.31 (dd, J = 15.2, 4.4 Hz, 1H), 3.76 (d, J = 16.2 Hz, 1H), 3.43 (d, J = 16.3 Hz, 1H), 2.82 (dd, J = 11.7, 5.1 Hz, 1H), 2.63 (dd, J = 11.7, 5.1 Hz, 1H), 2.34 (s, 3H). MS (ESI) m/z $(M + H)^+$ = 382.8. |

Step 11: Preparation of Compound A1-15

Compound A1-13 (246 mg, 0.642 mmol), compound A1-14 (290 mg, 0.942 mmol), cesium carbonate (416 mg, 1.280 mmol), sodium iodide (10 mg, 0.071 mmol) were dissolved in N,N-dimethylformamide (4 mL), and the system was heated to 60° C. and stirred for 1 hour. The reaction mixture was cooled to room temperature, filtered, and the filtrate was purified by C18 reversed-phase silica gel column chromatography (acetonitrile/0.1% aqueous ammonium bicarbonate (v/v)=5-65%) to obtain compound A1-15.

MS (ESI) m/z $(M+H)^+$=614.2.

Step 12: Preparation of Compound A1-16

Compound A1-15 (240 mg, 0.390 mmol) was dissolved in anhydrous methanol (3 mL), to which concentrated hydrochloric acid (2 mL) was added, after the addition, the system was stirred at room temperature (25° C.) for 1 hour. The reaction mixture was concentrated under vacuum to obtain the crude product, dissolved with dichloromethane (20 mL), to which water (20 mL) was added, and the pH of which was adjusted to 9 with saturated aqueous sodium bicarbonate solution, and separated, and the aqueous phase was extracted with dichloromethane (20 mL×2), and the organic phases were combined, dried over anhydrous sodium sulfate, filtered, and the filtrate was concentrated to obtain compound A1-16.

MS (ESI) m/z $(M+H)^+$=514.0.

Step 13: Preparation of Compound A1

Compound A1-16 (165 mg, 0.320 mmol) was dissolved in N,N-dimethylformamide (2 mL), to which 1,4-diisocyanatobutane (20 mg, 0.128 mmol) was added, after the addition, the system was stirred at room temperature (25° C.) for 1 hour. The reaction mixture was purified by high performance preparative liquid chromatography (separation conditions: column: Agilent 10 Prep-C18 250×21.2 mm; column temperature: 25° C.; mobile phase: water (10 mM/L ammonium bicarbonate)-acetonitrile; acetonitrile: 60%-80% 12 min, flow rate: 30 mL/min) to obtain compound A1.

$^1$H NMR (400 MHz, Methanol-$d_4$) δ 7.58 (d, J=1.7 Hz, 2H), 7.44-7.35 (m, 4H), 7.24 (d, J=2.0 Hz, 2H), 6.71 (d, J=2.1 Hz, 2H), 4.45 (s, 4H), 4.32 (t, J=6.3 Hz, 2H), 3.70 (t, J=5.2 Hz, 4H), 3.60 (s, 4H), 3.58-3.50 (m, 8H), 3.38 (dt, J=15.5, 5.1 Hz, 8H), 3.15 (t, J=5.2 Hz, 4H), 3.04 (dd, J=11.8, 5.3 Hz, 2H), 3.01-2.91 (m, 4H), 2.82-2.71 (m, 2H), 2.48 (d, J=3.5 Hz, 6H), 1.40-1.27 (m, 4H).

MS (ESI) m/z $(M+H)^+$=1169.20.

HPLC 100% purity; retention time was 7.680 min.

Separation conditions: column: Waters XBridge 4.6*100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min.

Similar to the synthesis of embodiment A1, embodiments A2 was synthesized from A2-13, as shown in Table 2 below:

TABLE 2

| Structural formula and analysis data of embodiment A2 | |
|---|---|
| Structural formula | 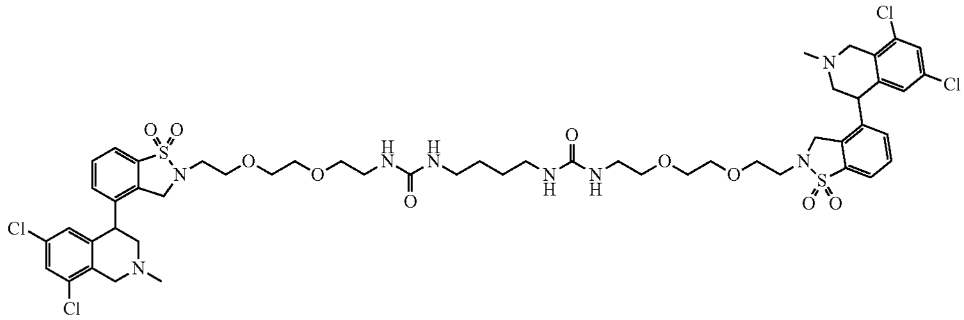 [SMILES: CN1Cc2c(Cl)cc(Cl)cc2C(c2cccc3c2CN(CCOCCOCCNC(=O)NCCCCNC(=O)NCCOCCOCCN2Cc4c(C5CN(C)Cc6c(Cl)cc(Cl)cc65)cccc4S2(=O)=O)S3(=O)=O)C1] |
| Analysis data | $^{1}$H NMR (400 MHz, Methanol-$d_4$) δ 7.61 (dd, J = 7.8, 1.0 Hz, 2H), 7.44 (t, J = 7.7 Hz, 2H), 7.30-7.22 (m, 4H), 6.73 (d, J = 2.1 Hz, 2H), 4.64 (d, J = 14.5 Hz, 2H), 4.34 (t, J = 6.6 Hz, 2H), 4.29 (d, J = 14.4 Hz, 2H), 3.73-3.69 (m, 4H), 3.65 (s, 2H), 3.59 (s, 2H), 3.57-3.51 (m, 8H), 3.42-3.37 (m, 8H), 3.15 (t, J = 5.4 Hz, 4H), 2.97 (q, J = 2.9 Hz, 4H), 2.94-2.90 (m, 2H), 2.55 (dd, J = 11.8, 7.5 Hz, 2H), 2.37 (s, 6H), 1.34 (t, J = 3.1 Hz, 4H). MS (ESI) m/z $(M + H)^+$ = 1169.20. HPLC 100% purity; retention time was 7.114 min. Separation conditions: column: Waters XBridge 4.6 * 100 mm, 3.5 um; column temperature: 40° C.; mobile phase: water (10 mM $NH_4HCO_3$)-acetonitrile; acetonitrile: 5%-95% 7 min, 95% 8 min; flow rate: 1.2 mL/min. |

Synthesis of Embodiment B1

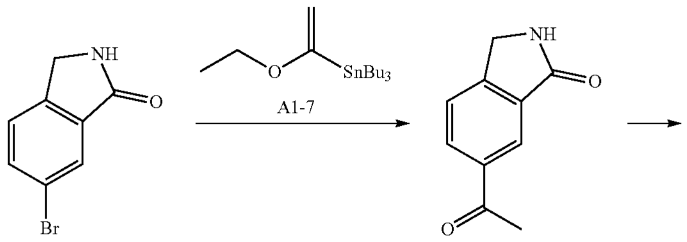

B1-1 B1-2

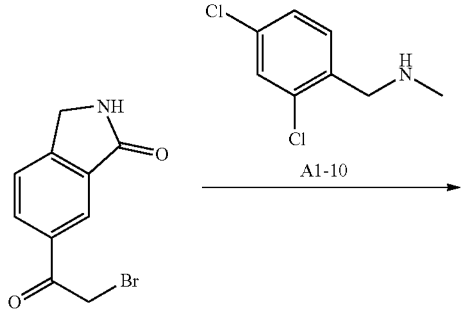

B1-3

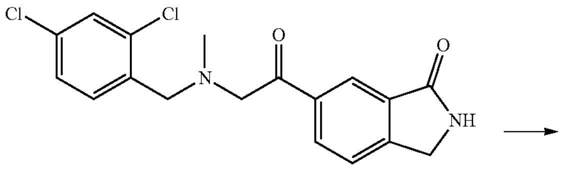

B1-4

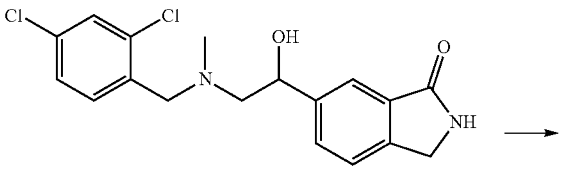

B1-5

-continued

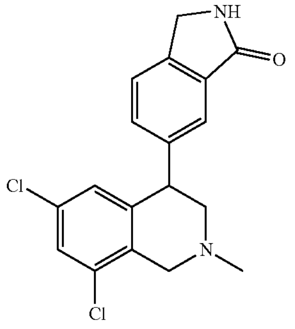

B1-6

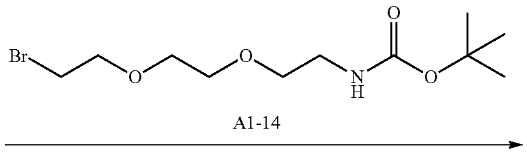

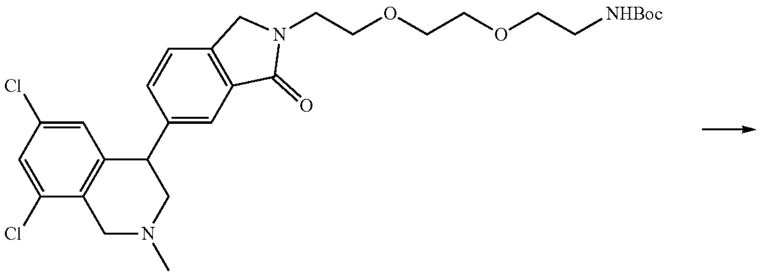

B1-7

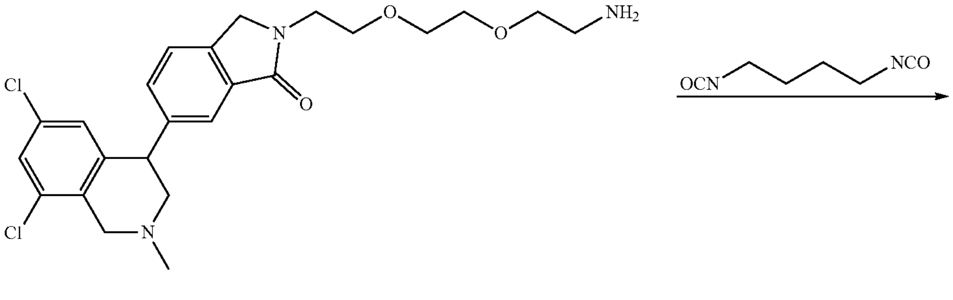

B1-8

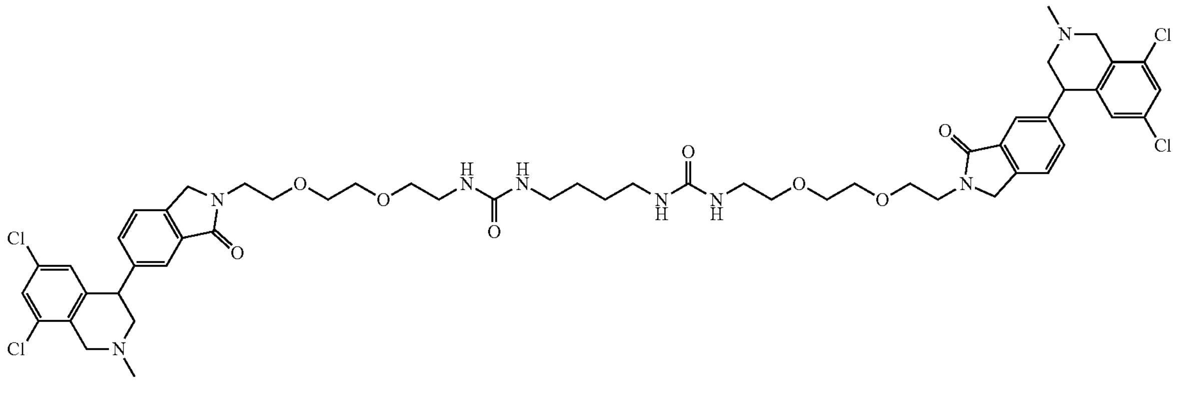

B1

Step 1: Preparation of Compound B1-2

Under nitrogen atmosphere, compound B1-1 (8.48 g, 40 mmol), compound A1-7 (17.32 g, 48.0 mmol) and tetrakis (triphenylphosphine)palladium (2.31 g, 2 mmol) were dissolved in N,N-dimethylformamide (80 mL), and system was heated to 100° C. and stirred for 4 hours. The reaction mixture was cooled to room temperature (25° C.), quenched by adding saturated aqueous ammonium chloride (200 mL) and extracted with ethyl acetate (200 mL×3), and the organic phases were combined, washed by saturated sodium chloride (200 mL×2), dried over anhydrous sodium sulfate, filtered, and the filtrate was concentrated to obtain the crude product. The crude product was dissolved in tetrahydrofuran (60 mL), to which aqueous hydrochloric acid (2 N, 8 mL) was added, and the system was stirred for 30 minutes. The system was concentrated, slurried with petroleum ether, and filtered to obtain compound B1-2, which was directly used for the next step without further purification.

MS (ESI) m/z $(M+H)^+$=175.8.

Step 2: Preparation of Compound B1-3

Compound B1-2 (200 mg, 1.14 mmol) was dissolved in chloroform (30 mL), to which liquid bromine (1.21 g, 7.66 mmol) was added dropwise, after the addition, the system was heated to 70° C. and stirred for 30 minutes. The reaction mixture was filtered to obtain compound B1-3, which was directly used in the next step without further purification.

MS (ESI) m/z $(M+H)^+$=256.0.

Step 3: Preparation of Compound B1-4

Compound B1-3 (1.4 g, 5.53 mmol), compound A1-10 (1.25 g, 5.53 mmol) and triethylamine (2.8 g, 27.65 mmol) were dissolved in 1,4-dioxane (20 mL), and the system was reacted at room temperature (25° C.) for 3 hours. The reaction mixture was concentrated, to which water (40 mL) was added, extracted by ethyl acetate (50 mL×3), and the organic phase was dried over anhydrous sodium sulfate, filtered and concentrated to obtain compound B1-4, which was used directly in the next step without further purification.

MS (ESI) m/z $(M+H)^+$=363.0.

Step 4: Preparation of Compound B1-5

Compound B1-4 (1.4 g, 3.87 mmol) was dissolved in methanol (20 mL), to which sodium borohydride (300 mg, 7.74 mmol) was added in batches at 0° C. After the addition, the system was reacted at 0° C. for 2 hours. The reaction mixture was quenched by adding acetone (5 mL), and concentrated to obtain the crude product, which was purified by silica gel column chromatography (dichloromethane/methanol (v/v)=10-1%) to obtain compound B1-5.

MS (ESI) m/z $(M+H)^+$=365.0.

Step 5: Preparation of Compound B1-6

Compound B1-5 (1.9 g, 5.2 mmol) was dissolved in dichloromethane (5 mL), to which concentrated sulfuric acid (3 mL) was added dropwise at 0° C. After the addition, the system was heated to room temperature (25° C.) and reacted for 5 hours. The reaction mixture was poured into ice water, and the pH of which was adjusted to 7-8 with 2N aqueous sodium hydroxide solution. The reaction mixture was extracted with dichloromethane (80 mL×3), and the organic phases were combined, dried over anhydrous sodium sulfate, filtered, and the filtrate was concentrated to obtain the crude product. The crude product was separated and purified to obtain compound B1-6.

$^1$H NMR (400 MHz, DMSO-$d_6$) δ 8.54 (s, 1H), 7.54-7.40 (m, 4H), 6.86 (d, J=2.1 Hz, 1H), 4.41 (t, J=5.4 Hz, 1H), 4.34 (s, 2H), 3.73 (d, J=16.2 Hz, 1H), 3.47 (d, J=16.1 Hz, 1H), 2.84 (dd, J=11.6, 5.1 Hz, 1H), 2.71-2.62 (m, 1H), 2.36 (s, 3H).

HPLC 100%. Retention time was 5.598 min.

Separation conditions: column: Waters XBridge 4.6*100 mm, 3.5 m; column temperature: 40° C.; mobile phase: water (10 mM ammonium bicarbonate)-acetonitrile; acetonitrile: 5%-95% 7 min; flow rate: 1.2 mL/min.

Similar to the synthesis of intermediate B1-6, the following intermediate B2-6-B5-6 were synthesized, as shown in Table 3 below:

TABLE 3

Structural formula and analysis data of intermediate B2-6-B5-6

| Intermediates | Structural formula | Analysis data |
|---|---|---|
| B2-6 | 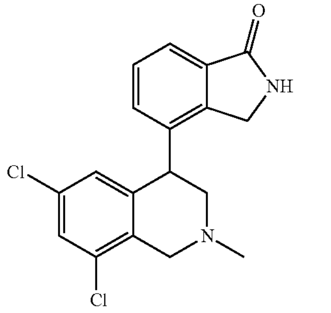 [SMILES: CN1Cc2c(Cl)cc(Cl)cc2C(c2cccc3c2CNC3=O)C1] | $^1$H NMR (400 MHz, DMSO-$d_6$) δ 8.57 (s, 1H), 7.55 (d, J = 7.3 Hz, 1H), 7.51 (d, J = 2.0 Hz, 1H), 7.38 (t, J = 7.5 Hz, 1H), 7.16 (d, J = 7.1 Hz, 1H), 6.94 (d, J = 1.7 Hz, 1H), 4.56 (d, J = 17.6 Hz, 1H), 4.40 (t, J = 5.4 Hz, 1H), 4.15 (d, J = 17.6 Hz, 1H), 3.70 (d, J = 16.2 Hz, 1H), 3.50 (d, J = 16.2 Hz, 1H), 2.87 (dd, J = 11.6, 5.2 Hz, 1H), 2.65 (dd, J = 11.6, 6.0 Hz, 1H), 2.35 (s, 3H)<br>MS (ESI) m/z $(M + H)^+$ = 346.8<br>LCMS 100%. Retention time was 0.98 min.<br>Separation conditions: column: Infinitylab Poroshell HPH-C18 3.0*30 mm, 1.9 um; column temperature: 40° C.; mobile phase: water (10 mM ammonium bicarbonate)-acetonitrile: 5%-95% 0.7 min, 95% 0.8 min, 5% 0.5 min; flow rate: 1.2 ml/min. |
| B3-6 | 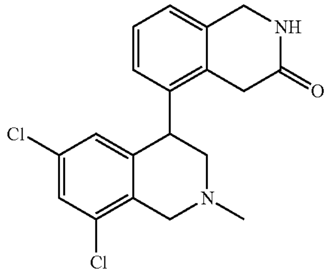 [SMILES: CN1Cc2c(Cl)cc(Cl)cc2C(c2cccc3c2CC(=O)NC3)C1] | $^1$H NMR (400 MHz, DMSO-$d_6$) δ 7.93 (d, J = 2.8 Hz, 1H), 7.63 (d, J = 1.9 Hz, 1H), 7.49 (d, J = 2.2 Hz, 1H), 7.33 (dd, J = 7.8, 2.0 Hz, 1H), 7.23 (d, J = 7.8 Hz, 1H), 6.84 (d, J = 2.1 Hz, 1H), 4.32 (t, J = 5.6 Hz, 1H), 3.72-3.46 (m, 2H), 3.36 (dd, J = 6.7, 2.8 Hz, 2H), 2.85 (dt, J = 16.2, 5.8 Hz, 3H), 2.61 (dd, J = 11.5, 6.2 Hz, 1H), 2.36 (s, 3H)<br>MS (ESI) m/z $(M + H)^+$ = 360.8<br>HPLC 100.0% purity; retention time was 6.264 min.<br>Separation conditions: column: Waters XBridge 4.6*100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min. |

TABLE 3-continued

Structural formula and analysis data of intermediate B2-6-B5-6

| Inter-mediates | Structural formula | Analysis data |
|---|---|---|
| B4-6 | 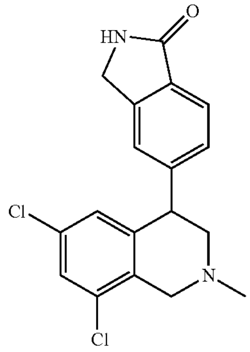 [SMILES: CN1Cc2c(Cl)cc(Cl)cc2C(c2ccc3c(c2)CNC3=O)C1] | $^1$H NMR (400 MHz, DMSO-$d_6$) δ 8.50 (s, 1H), 7.60 (d, J = 7.8 Hz, 1H), 7.50 (s, 1H), 7.40 (s, 1H), 7.35 (d, J = 8.9 Hz, 1H), 6.87 (s, 1H), 4.40 (t, J = 5.3 Hz, 1H), 4.32 (s, 2H), 3.69 (d, J = 16.2 Hz, 1H), 3.49 (d, J = 16.1 Hz, 1H), 2.86 (dd, J = 11.5, 5.2 Hz, 1H), 2.69 (dd, J = 11.5, 5.8 Hz, 1H), 2.37 (s, 3H).<br>MS (ESI) m/z (M + H)$^+$ = 346.8.<br>HPLC 100%. Retention time was 6.02 min.<br>Separation conditions: column: Waters XBridge 4.6*100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min. |
| B5-6 | 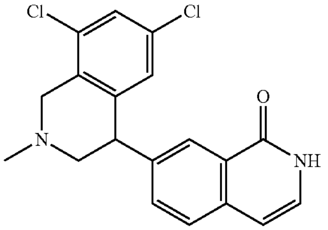 [SMILES: CN1Cc2c(Cl)cc(Cl)cc2C(c2ccc3cc[nH]c(=O)c3c2)C1] | $^1$H NMR (400 MHz, DMSO-$d_6$) δ 11.25 (d, J = 5.6 Hz, 1H), 7.96 (d, J = 1.6 Hz, 1H), 7.62-7.54 (m, 2H), 7.50 (d, J = 2.0 Hz, 1H), 7.14 (dd, J = 7.1, 5.7 Hz, 1H), 6.88 (d, J = 2.0 Hz, 1H), 6.52 (d, J = 7.0 Hz, 1H), 4.43 (t, J = 5.5 Hz, 1H), 3.71 (d, J = 16.2 Hz, 1H), 3.50 (d, J = 16.2 Hz, 1H), 2.87 (dd, J = 11.6, 5.1 Hz, 1H), 2.68 (dd, J = 11.5, 6.0 Hz, 1H), 2.36 (s, 3H).<br>MS (ESI) m/z (M + H)$^+$ = 359.0<br>HPLC retention time was 6.880 min<br>Separation conditions: column: Waters XBridge 4.6*100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min. |

Step 6: Preparation of Compound B1-7

Compound B1-6 (250 mg, 0.72 mmol), compound A1-14 (335 mg, 1.08 mmol), cesium carbonate (585 mg, 1.8 mmol), 18-crown-6 (19 mg, 0.072 mmol) were added into acetonitrile (25 ml), and the system was heated to 90° C. for 10 hours. The reaction mixture was concentrated, to which water (30 mL) was added, extracted with ethyl acetate (50 mL×3), the organic phases were combined, dried over anhydrous sodium sulfate, filtered, and the filtrate was concentrated to obtain the crude product, which was purified by reverse phase C18 column chromatography (acetonitrile/water (5% aqueous ammonium bicarbonate solution) (v/v) =30-40%) to obtain compound B1-7.

MS (ESI) m/z (M+H)$^+$=578.2.

Step 7: Preparation of Compound B1-8

Compound B1-7 (134 mg, 0.2 mmol) was dissolved in dichloromethane (2 mL) at room temperature (25° C.), to which a solution of dioxane with hydrochloric acid (2 mL) was added, and the reaction was stirred at room temperature (25° C.) for 2 hours. The reaction mixture was concentrated, and the crude product was dissolved in saturated aqueous sodium bicarbonate solution, extracted with dichloromethane, and the organic phases were combined, dried over anhydrous sodium sulfate, filtered, and the filtrate was concentrated to obtain compound B1-8.

MS (ESI) m/z (M+H)$^+$=478.0.

Step 8: Preparation of Compound B1

Compound B1-8 (120 mg, 0.25 mmol) was dissolved in N,N-dimethylformamide (1 mL), to which 1,4-diisocyanatobutane (14 mg, 0.09 mmol) was added at 0° C., and the reaction was stirred at room temperature (25° C.) for 0.5 hour. The reaction mixture was purified directly by high performance preparative liquid chromatography (separation conditions: column: Welch Xtimate C18 250×21.2 mm; column temperature: 25° C.; mobile phase: water (10 mM/L ammonium bicarbonate)-acetonitrile; acetonitrile: 50%-70% 12 min, flow rate: 30 mL/min) to obtain compound B1.

$^1$H NMR (400 MHz, Methanol-$d_4$) δ 7.48-7.40 (m, 4H), 7.37 (d, J=9.4 Hz, 2H), 7.23 (d, J=1.7 Hz, 2H), 6.76-6.64 (m, 2H), 4.51 (s, 4H), 4.35-4.28 (m, 2H), 3.75-3.61 (m, 10H), 3.54-3.50 (m, 6H), 3.48-3.44 (m, 4H), 3.33 (t, J=5.4 Hz, 4H), 3.09 (t, J=5.3 Hz, 4H), 3.03-2.89 (m, 6H), 2.55 (dd, J=11.7, 8.1 Hz, 2H), 2.37 (s, 6H), 1.35 (t, J=4.7 Hz, 4H).

MS (ESI) m/z (M+H)$^+$=1097.4.

HPLC 100% purity; retention time was 6.908 min.

Separation conditions: column: Waters XBridge 4.6*100 mm, 3.5 um; column temperature: 40° C.; mobile phase: water (10 mM ammonium bicarbonate)-acetonitrile; acetonitrile: 5%-95% 7 min; flow rate: 1.2 mL/min.

Synthesis of Embodiment B3

Step 1: Preparation of Compound B3-7

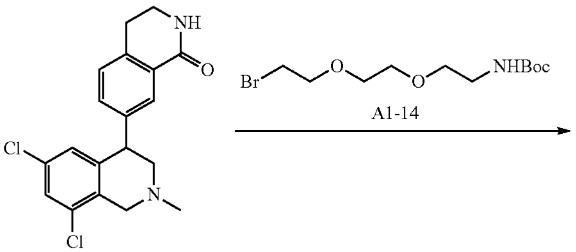

B3-6

-continued

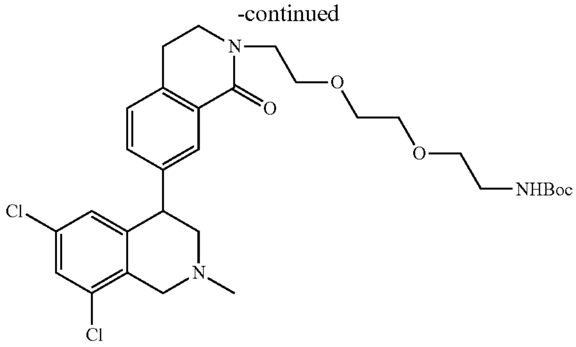

B3-7

Compound B3-6 (144 mg, 0.398 mmol) was dissolved in tetrahydrofuran (2 mL), to which sodium hydride (29.6 mg, 0.74 mmol) was added under argon protection, and the system was stirred at room temperature (25° C.) for 0.5 hour. 18-Crown ether-6 (101.6 mg, 0.39 mmol) and compound A1-14 (186 mg, 0.589 mmol) were dissolved in tetrahydrofuran (2 mL), which were slowly added into the above reaction system under argon protection, and the system was stirred at room temperature (25° C.) for 16 hours. The reaction mixture was purified by C18 reversed-phase silica gel column chromatography (acetonitrile/0.1% aqueous ammonium bicarbonate (v/v)=5-65% to obtain compound B3-7.

MS (ESI) m/z $(M+H)^+$=592.40.

Similar to the synthesis of embodiment B1, embodiments B2-B6 were synthesized from B2-6-B3-6, as shown in Table 4 below:

TABLE 4

| Structural formula and analysis data of embodiments B2-B6 | |
|---|---|
| Embodiment B2 | 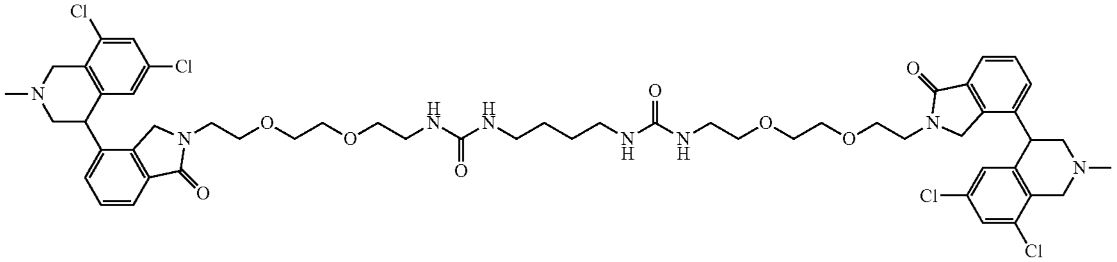<br>$^1$H NMR (400 MHz, Methanol-$d_4$) δ 7.62-7.57 (m, 2H), 7.37 (t, J = 7.6 Hz, 2H), 7.27 (d, J = 2.0 Hz, 2H), 7.22 (d, J = 7.6 Hz, 2H), 6.71 (d, J = 2.0 Hz, 2H), 4.57 (d, J = 17.9 Hz, 2H), 4.43-4.35 (m, 2H), 4.16 (d, J = 17.9 Hz, 2H), 3.80-3.59 (m, 10H), 3.56-3.43 (m, 10H), 3.35 (t, J = 5.4 Hz, 4H), 3.11 (t, J = 5.4 Hz, 4H), 2.97 (dt, J = 11.7, 5.6 Hz, 6H), 2.57 (dd, J = 11.7, 8.3 Hz, 2H), 2.38 (s, 6H), 1.41-1.32 (m, 4H).<br>MS (ESI) m/z $(M + H)^+$ = 1097.4<br>HPLC 100% purity; retention time was 6.929 min.<br>Separation conditions: column: Waters XBridge 4.6*100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min. |

TABLE 4-continued

Structural formula and analysis data of embodiments B2-B6

Embodiment B3

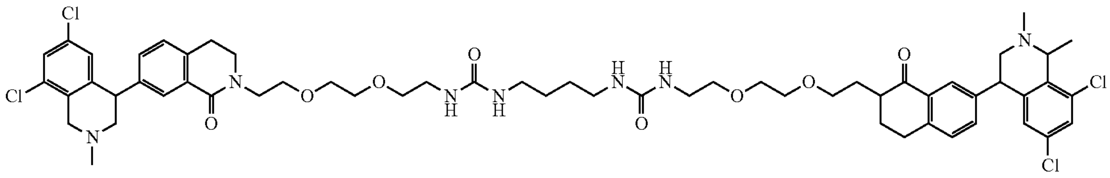 [SMILES: CC1c2c(Cl)cc(Cl)cc2C(c2ccc3c(c2)C(=O)C(CCOCCOCCNC(=O)NCCCCNC(=O)NCCOCCOCCN2CCc4ccc(C5CN(C)Cc6c(Cl)cc(Cl)cc65)cc4C2=O)CC3)CN1C]

$^1H$ NMR (400 MHz, DMSO-$d_6$) δ 7.65 (d, J = 1.9 Hz, 2H), 7.49 (d, J = 2.1 Hz, 2H), 7.31 (dd, J = 7.9, 2.0 Hz, 2H), 7.21 (d, J = 7.8 Hz, 2H), 6.86-6.80 (m, 2H), 5.92 (t, J = 5.7 Hz, 2H), 5.78 (t, J = 5.7 Hz, 2H), 4.32 (t, J = 5.3 Hz, 2H), 3.71-3.43 (m, 24H), 3.33 (d, J = 5.5 Hz, 4H), 3.09 (q, J = 5.7 Hz, 4H), 2.97-2.88 (m, 8H), 2.83 (s, 2H), 2.63 (s, 2H), 2.36 (s, 6H), 1.30 (t, J = 4.1 Hz, 4H).
MS (ESI) m/z $(M + H)^+$ = 1123.60.
HPLC 100% purity; retention time was 7.717 min.
Separation conditions: column: Waters XBridge 4.6*100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min.

Embodiment B4

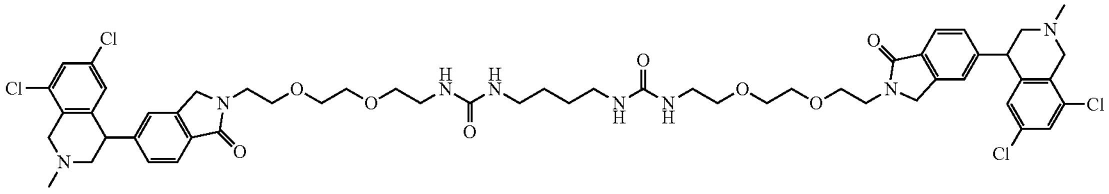 [SMILES: CN1Cc2c(Cl)cc(Cl)cc2C(c2ccc3c(c2)CN(CCOCCOCCNC(=O)NCCCCNC(=O)NCCOCCOCCN2Cc4cc(C5CN(C)Cc6c(Cl)cc(Cl)cc65)ccc4C2=O)C3=O)C1]

$^1H$ NMR (400 MHz, DMSO-$d_6$) δ 7.60 (d, J = 7.8 Hz, 2H), 7.47 (d, J = 2.1 Hz, 2H), 7.43 (s, 2H), 7.33 (dd, J = 7.9, 1.5 Hz, 2H), 6.85 (d, J = 2.0 Hz, 2H), 5.91 (t, J = 5.6 Hz, 2H), 5.77 (t, J = 5.8 Hz, 2H), 4.50 (s, 4H), 4.39 (t, J = 5.6 Hz, 2H), 3.73-3.58 (m, 10H), 3.57-3.43 (m, 10H), 3.34 (s, 2H), 3.31 (s, 2H), 3.08 (q, J = 5.7 Hz, 4H), 2.94 (q, J = 5.6, 5.2 Hz, 4H), 2.86 (dd, J = 11.6, 5.2 Hz, 2H), 2.67 (dd, J = 11.5, 6.1 Hz, 2H), 2.36 (s, 6H). 1.31 (t, J = 4.7 Hz, 4H).
MS (ESI) m/z $(M + H)^+$ = 1097.4
HPLC 100% purity; retention time was 7.228 min.
Separation conditions: column: Waters XBridge 4.6*100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min.

Embodiment B5

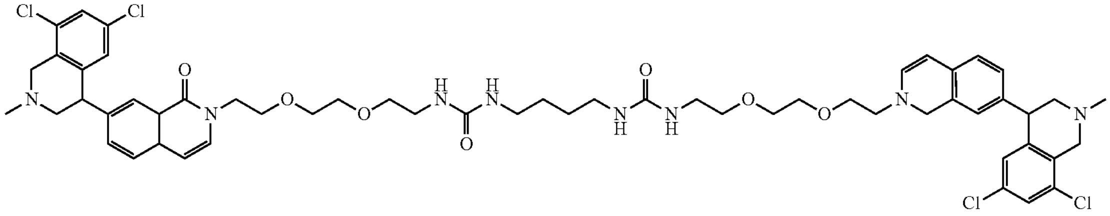

$^1H$ NMR (400 MHz, Methanol-$d_4$) δ 8.04 (d, J = 1.8 Hz, 2H), 7.53 (d, J = 8.2 Hz, 2H), 7.47-7.42 (m, 2H), 7.31-7.24 (m, 4H), 6.70 (d, J = 2.1, 1.0 Hz, 2H), 6.56 (d, J = 7.3 Hz, 2H), 4.44 (t, J = 9.1, 5.8 Hz, 2H), 4.11 (t, J = 5.2 Hz, 4H), 4.01 (d, J = 16.1 Hz, 2H), 3.78 (d, J = 16.1 Hz, 2H), 3.72 (t, J = 5.2 Hz, 4H), 3.51-3.44 (m, 4H), 3.44-3.37 (m, 4H), 3.29 (t, J = 5.3 Hz, 4H), 3.07 (t, J = 5.3 Hz, 4H), 3.01-2.94 (m, 4H), 2.85 (t, J = 11.9, 9.3 Hz, 2H), 2.57 (s, 6H), 1.37-1.30 (m, 4H).
MS (ESI) m/z $(M + H)^+$ = 1121.2.
HPLC 100% purity; retention time was 7.978 min.
Separation conditions: column: Waters XBridge 4.6*100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min.

TABLE 4-continued

| Structural formula and analysis data of embodiments B2-B6 | |
|---|---|
| Embodiment B6 | 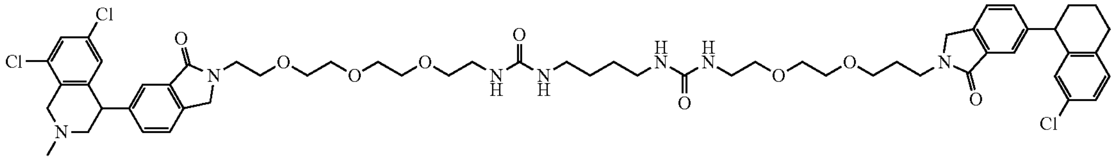 $^1$H NMR (400 MHz, DMSO-$d_6$) δ 7.52-7.45 (m, 8H), 6.85 (d, J = 2.1 Hz, 2H), 5.91 (t, J = 5.7 Hz, 2H), 5.79 (t, J = 5.8 Hz, 2H), 4.51 (s, 4H), 4.42-4.38 (m, 2H), 3.72 (d, J = 16.1 Hz, 2H), 3.67-3.59 (m, 8H), 3.54-3.47 (m, 10H), 3.47-3.45 (m, 4H), 3.43-3.41 (m, 4H), 3.31 (d, J = 5.7 Hz, 4H), 3.10 (q, J = 5.7 Hz, 4H), 2.94 (d, J = 5.6 Hz, 4H), 2.84 (dd, J = 11.5, 5.2 Hz, 2H), 2.68-2.63 (m, 2H), 2.35 (s, 6H), 1.31-1.28 (m, 4H).<br>MS (ESI) m/z $(M + 2H)^+/2$ = 593.2.<br>HPLC 100% purity; retention time was 7.099 min<br>Separation conditions: column: Waters XBridge 4.6*100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min. |

Synthesis of Embodiment C1

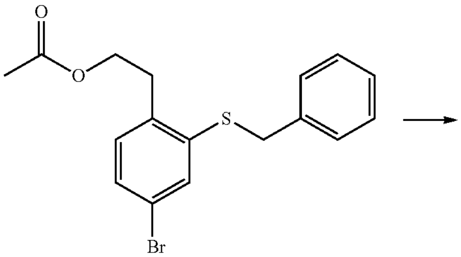

C1-1

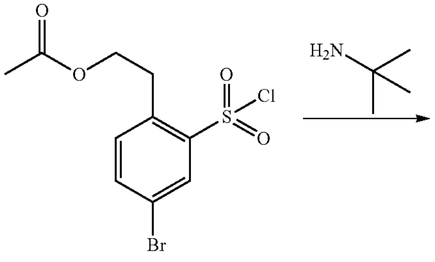

C1-2

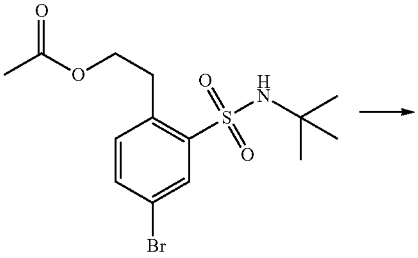

C1-3

-continued

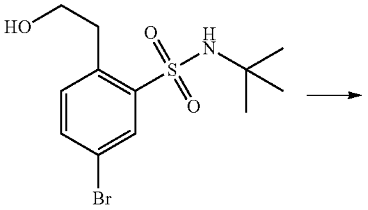

C1-4

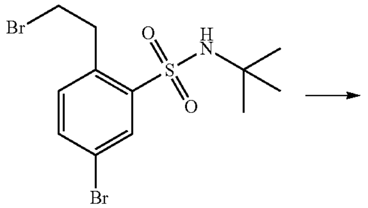

C1-5

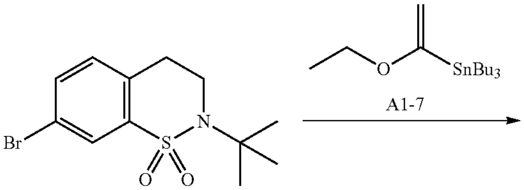

C1-6

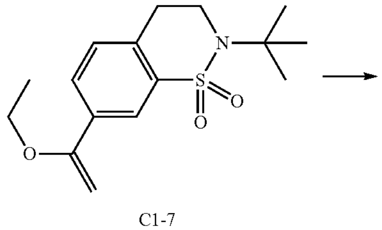

C1-7

-continued

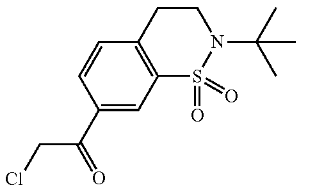

C1-8

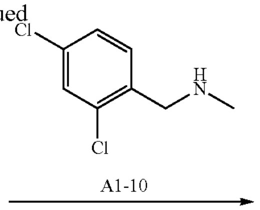

A1-10

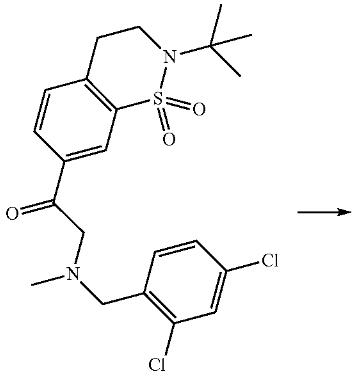

C1-9

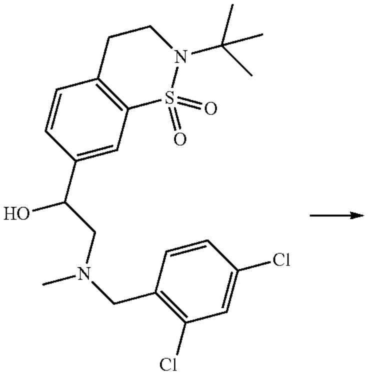

C1-10

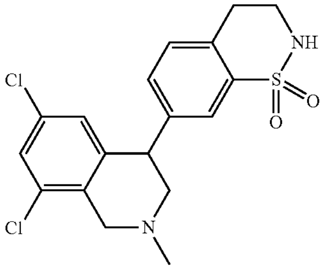

C1-11

Step 1: Preparation of Compound C1-2

Compound C1-1 (200.0 mg, 0.548 mmol) was dissolved in a mixed solvent of acetic acid (2.50 mL) and water (0.25 mL), which was placed in a water bath at 10° C. to cool down, to which N-chlorosuccinimide (220.0 mg, 1.64 mmol, 3.0 equiv) was added. The reaction was continued to stir for 1.0 hour in a water bath at 10° C. The reaction mixture was quenched by adding saturated brine (5.0 mL), then the reaction was extracted with ethyl acetate (10.0 mL×3 times), and the organic phases were combined, dried over anhydrous sodium sulfate and concentrated, and the crude product was purified by silica gel column chromatography (ethyl acetate/petroleum ether (v/v)=0-10%) to obtain compound C1-2.

$^1$H NMR (400 MHz, Chloroform-d) δ 8.24 (d, J=2.1 Hz, 1H), 7.79 (dd, J=8.3, 2.1 Hz, 1H), 7.36 (s, 1H), 4.40 (t, J=6.7 Hz, 2H), 3.44 (t, J=6.7 Hz, 2H), 2.05 (s, 3H).

Step 2: Preparation of Compound C1-3

Tert-butylamine (44.0 mg, 0.60 mmol, 1.1 equiv) and triethylamine (83.0 mg, 0.82 mmol, 1.5 equiv) were dissolved in dichloromethane (2.50 mL), which was placed in a water bath at 10° C. to cool down, then compound C1-2 (185.0 mg, 0.54 mmol) was dissolved in dichloromethane (1.0 mL) which was added dropwise to the above reaction mixture. The reaction was heated to room temperature (25° C.) and continued to stir for 2.0 hours. The reaction mixture was directly concentrated to obtain the crude product, which was purified by silica gel column chromatography (ethyl acetate/petroleum ether (v/v)=0-15%) to obtain compound C1-3.

$^1$H NMR (400 MHz, Chloroform-d) δ 8.20 (d, J=2.2 Hz, 1H), 7.60 (dd, J=8.2, 2.2 Hz, 1H), 7.22 (d, J=8.2 Hz, 1H), 4.33 (t, J=7.6 Hz, 2H), 3.33 (t, J=7.6 Hz, 2H), 2.07 (s, 3H), 1.27 (s, 9H).

Step 3: Preparation of Compound C1-4

Compound $C_{1-3}$ (150.0 mg, 0.398 mmol) was dissolved in a mixed solvent of tetrahydrofuran (0.70 mL), methanol (0.70 mL) and lithium hydroxide (34.0 mg, 1.4 mmol, 3.5 equiv) in water (0.25 mL), and the system was stirred at room temperature (25° C.) for 1.0 hour. The reaction mixture was quenched by adding saturated ammonium chloride aqueous solution (5.0 mL), then extracted by ethyl acetate (10.0 mL×3 times), and the organic phases were combined, washed with saturated brine (10.0 mL×2 times), the organic phase was dried over anhydrous sodium sulfate after and concentrated to obtain compound C1-4, which was used directly in the next step without further purification.

MS (ESI) m/z $(M+H)^+$=335.8.

Step 4: Preparation of Compound C1-5

Compound C1-4 (1.0 g, 3.0 mmol) and triphenylphosphine (787.0 mg, 3.0 mmol, 1.0 equiv) were dissolved in dichloromethane (10.0 mL) solution, to which a solution of carbon tetrabromide (1.1 g, 3.3 mmol, 1.1 equiv) in dichloromethane (5.0 mL) was added at 0° C., after the addition, the system was heated to room temperature (25° C.) and stirred for 1.0 hour. The reaction mixture was directly concentrated to obtain the crude product, which was purified by silica gel column chromatography (ethyl acetate/petroleum ether (v/v)=0-10%) to obtain compound C1-5.

$^1$H NMR (400 MHz, Chloroform-d) δ 8.11 (d, J=2.1 Hz, 1H), 7.56 (dd, J=8.2, 2.1 Hz, 1H), 7.20 (s, 1H), 3.65-3.55 (m, 2H), 3.44 (t, J=7.4 Hz, 2H), 1.20 (d, J=2.6 Hz, 9H).

Step 5: Preparation of Compound C1-6

Compound C1-5 (8.20 g, 20.65 mmol) and potassium carbonate (5.70 g, 41.3 mmol, 2.0 equiv) were added to N,N-dimethylformamide (100.0 mL) solution, and the system was stirred overnight at room temperature (25° C.). The reaction mixture was directly concentrated to obtain the crude product, which was purified by silica gel column chromatography (ethyl acetate/petroleum ether (v/v)=0-5%) to obtain compound C1-6.

$^1$H NMR (400 MHz, Chloroform-d) δ 7.97 (d, J=2.3 Hz, 1H), 7.53 (dt, J=8.3, 1.8 Hz, 1H), 7.08 (dd, J=8.4, 1.0 Hz, 1H), 3.98 (ddd, J=6.8, 5.6, 1.3 Hz, 2H), 2.90 (t, J=6.2 Hz, 2H), 1.46 (d, J=1.6 Hz, 9H).

Step 6: Preparation of Compound C1-7

Compound $C_{1-6}$ (3.17 g, 10.0 mmol), tetrakis(triphenylphosphine)palladium (3.17 g, 10.0 mmol, 0.1 equiv) and tributyl (1-ethoxyethylene) tin (5.43 g, 15.0 mmol, 1.5 equiv) were added to N,N-dimethylformamide (30.0 mL) solution, and the system was heated to 100° C. and reacted for 16.0 hours under argon atmosphere. The reaction mixture was filtered to remove the residue and washed with ethyl acetate, and the organic phase was concentrated to obtain compound C1-7, which was directly used in the next step without further purification.

MS (ESI) m/z $(M+H-56)^+$=253.8.

Step 7: Preparation of Compound C1-8

Compound $C_{1-7}$ (309.0 mg, 1.0 mmol) and N-chlorosuccinimide (134.0 mg, 1.0 mmol, 1.0 equiv) were added to a mixed solution of tetrahydrofuran (3.0 mL) and water (1.0 mL), and the system was stirred for 1.0 hour in ice bath. The reaction mixture was added with saturated aqueous ammonium chloride solution (10.0 mL), extracted with ethyl acetate (10.0 mL×3 times), and the organic phases were combined, washed with saturated brine (10.0 mL×2 times), and the organic phases were combined, dried over anhydrous sodium sulfate and concentrated, and the crude product was purified by silica gel column chromatography (ethyl acetate/petroleum ether (v/v)=0-50%) to obtain compound C1-8.

MS (ESI) m/z $(M+H-56)^+$=259.8.

Step 8: Preparation of Compound C1-9

Compound $C_{1-8}$ (3.15 g, 10.0 mmol), compound A1-10 (2.30 g, 12.0 mmol, 1.2 equiv) and potassium carbonate (4.14 g, 30.0 mmol, 3.0 equiv) were added to acetonitrile (30.0 mL) solution, and the system was heated to 80° C. and stirred for 2.0 hours. The reaction mixture was directly concentrated, and the crude product was purified by silica gel column chromatography (ethyl acetate/petroleum ether (v/v)=0-50%) to obtain compound C1-9.

MS (ESI) m/z $(M+H)^+$=469.0.

Step 9: Preparation of Compound C1-10

Compound $C_{1-9}$ (2.33 g, 5.0 mmol) was dissolved in methanol (25.0 mL) solution, after being cooled to 0° C., sodium borohydride (380.0 mg, 10.0 mmol, 2.0 equiv) was gradually added to the reaction mixture in small amounts, and the system was continued to react for 30 minutes. The reaction mixture was quenched by adding acetone (2.0 mL) and concentrated, the crude product was purified by silica gel column chromatography (methanol/dichloromethane (v/v)=0-1%) to obtain compound C1-10.

MS (ESI) m/z $(M+H)^+$=470.8.

Step 10: Preparation of Compound C1-11

Compound $C_{1-10}$ (2.0 g, 4.25 mmol) was dissolved in dichloromethane (20.0 mL) solution, after being cooled to 0° C., concentrated sulfuric acid (10.0 mL) was gradually added dropwise to the reaction mixture in small amounts. After the addition, the system was heated to room temperature (25° C.) and stirred overnight. The reaction mixture was added to ice water to be quenched, then the pH of which was adjusted to 8-9 by adding saturated aqueous sodium carbonate solution, finally the reaction mixture was extracted with dichloromethane (100.0 mL×3 times), and the organic phase was dried over anhydrous sodium sulfate and concentrated, and the crude product was separated and purified to obtain compound C1-11.

$^1$H NMR (400 MHz, Chloroform-d) δ 7.72 (d, J=1.8 Hz, 1H), 7.26-7.20 (m, 2H), 7.17 (d, J=8.0 Hz, 1H), 6.75 (d, J=2.0 Hz, 1H), 4.62 (t, J=7.9 Hz, 1H), 4.25 (t, J=6.1 Hz, 1H), 3.80 (q, J=6.5 Hz, 2H), 3.66 (t, J=14.3 Hz, 2H), 2.97 (t, J=6.1 Hz, 3H), 2.63 (dd, J=11.7, 7.2 Hz, 1H), 2.48 (s, 3H).

MS (ESI) m/z $(M+H)^+$=397.0.

Similar to the synthesis of embodiment A1, embodiment C1 was synthesized from $C_1$-11, as shown in Table 5 below:

TABLE 5

| Structural formula and analysis data of embodiment C1 | |
|---|---|
| Structural formula | 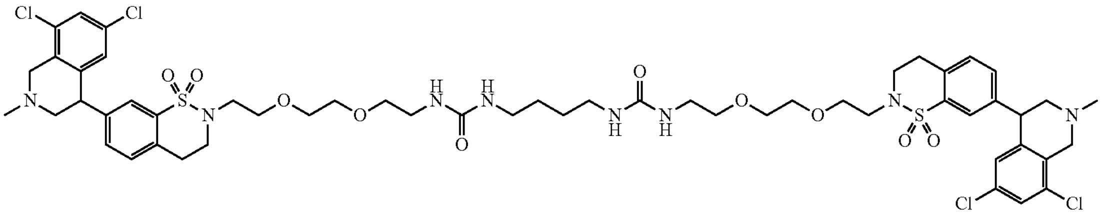 |
| Analysis data | $^1$H NMR (400 MHz, Chloroform-d) δ 7.64 (d, J = 2.0 Hz, 2H), 7.39-7.34 (m, 2H), 7.34-7.31 (m, 2H), 7.28 (d, J = 7.9 Hz, 2H), 6.74 (t, J = 1.4 Hz, 2H), 5.32-5.19 (m, 4H), 4.86 (s, 2H), 4.37 (s, 2H), 4.15 (d, J = 16.0 Hz, 2H), 3.98 (m, 4H), 3.70 (t, J = 5.2 Hz, 4H), 3.60 (dd, J = 6.1, 2.9 Hz, 4H), 3.55 (dd, J = 5.6, 2.3 Hz, 4H), 3.47 (t, J = 5.4 Hz, 4H), 3.43 (t, J = 5.2 Hz, 4H), 3.29 (q, J = 5.2 Hz, 4H), 3.24 (s, 2H), 3.05 (t, J = 6.3 Hz, 8H), 2.93 (s, 6H), 1.38 (q, J = 3.3 Hz, 4H).<br>MS (ESI) m/z $(M + H)^+$ = 1197.2. |

Synthesis of Embodiment D1

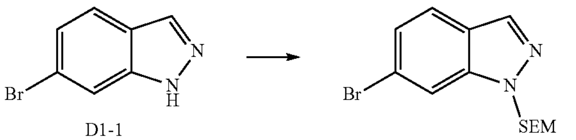

D1-1 D1-2

Compound D1-1 (1.96 g, 10 mmol) was dissolved in dichloromethane (20 mL), to which a solution of potassium hydroxide (1.4 g, 25 mmol) in water (3 mL) was added at 0° C., followed by tetrabutylammonium bromide (64 mg, 0.2 mmol) and chloromethyltrimethylsilyl ethyl ether (2.1 mL, 12 mmol) were added sequentially, and the reaction was stirred at 0° C. for 1 hour. The reaction mixture was diluted with ethyl acetate (100 mL), washed with water, and the organic phases were combined, dried over anhydrous sodium sulfate, filtered, and the filtrate was concentrated to obtain the crude product, which was purified by silica gel column chromatography (ethyl acetate/petroleum ether (v/v) =10%) to obtain compound D1-2.

MS (ESI) m/z $(M+H)^+$=326.8.

Similar to the synthesis of intermediate B1-6, intermediate D1-7 was synthesized, as shown in Table 6 below:

TABLE 6

Structural formula and analysis data of intermediate D1-7

| Inter-mediates | Structural formula | Analysis data |
|---|---|---|
| D1-7 | 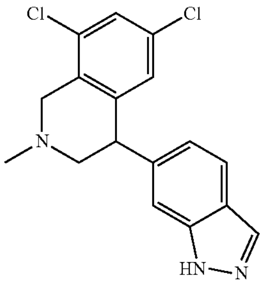 [SMILES: CN1Cc2c(Cl)cc(Cl)cc2C(c2ccc3cn[nH]c3c2)C1] | $^1H$ NMR (400 MHz, Chloroform-d) δ 10.09 (s, 1H), 8.05 (d, J = 1.0 Hz, 1H), 7.70 (dd, J = 8.3, 0.8 Hz, 1H), 7.31 (d, J = 1.2 Hz, 1H), 7.26 (s, 1H), 6.97 (dd, J = 8.4, 1.4 Hz, 1H), 6.81 (dd, J = 2.1, 1.0 Hz, 1H), 4.44 (s, 1H), 3.88 (d, J = 16.3 Hz, 1H), 3.65 (d, J = 16.1 Hz, 1H), 3.09 (d, J = 10.1 Hz, 1H), 2.80-2.68 (m, 1H), 2.55 (s, 3H).<br>MS (ESI) m/z $(M + H)^+$ = 331.8<br>HPLC retention time was 6.632 min.<br>Separation conditions: column: Waters XBridge 4.6 * 100 mm, 3.5 μm; column temperature: 40° C.; mobile phase: water (10 mM ammonium bicarbonate)-acetonitrile; acetonitrile: 5%-95% 7 min, 95% 8 min; flow rate: 1.2 mL/min. |
| D1-7-S | 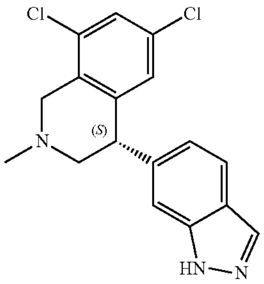 | D1-7 was split to obtain D1-7-S, and the specific splitting method was as follows:<br>Instrument: Waters UPC2 analytical SFC (SFC-H); column: ChiralPak AD, 150 x 4.6 mm I.D., 3 μm; mobile phase: A represented CO2, B represented ethanol (0.05% DEA); gradient: from 5% to 40% B within 5 minutes and hold 40% for 2.5 minutes, then hold 5% B for 2.5 minutes; flow rate: 2.5 mL/min; back pressure: 100 bar; column temperature: 35° C.; wavelength: 220 nm. Retention time: 6.095 min.<br>MS (ESI) m/z M + $H^+$ = 332.1. |

Similar to the synthesis of embodiment B3, embodiments D1-P1 and D1-P2 were synthesized from D1-7, as shown in Table 7 below:

TABLE 7

| | |
|---|---|
| Embodiment D1-P1 | 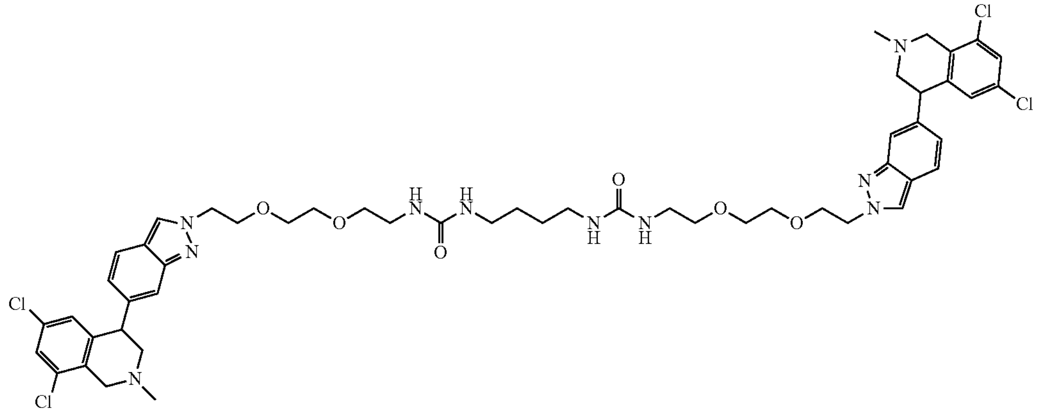 [SMILES: CN1Cc2c(Cl)cc(Cl)cc2C(c2ccc3cn(CCOCCOCCNC(=O)NCCCCNC(=O)NCCOCCOCCn4cc5ccc(C6CN(C)Cc7c(Cl)cc(Cl)cc76)cc5n4)nc3c2)C1] $^1$H NMR (400 MHz, Methanol-d4) δ 8.21 (d, J = 0.9 Hz, 2H), 7.62 (dd, J = 8.7, 0.9 Hz, 2H), 7.43 (d, J = 1.3 Hz, 2H), 7.29 (dd, J = 2.1, 0.8 Hz, 2H), 6.79 (dd, J = 8.7, 1.5 Hz, 4H), 4.57 (t, J = 5.1 Hz, 4H), 4.36 (dd, J = 9.2, 5.9 Hz, 2H), 3.98-3.86 (m, 6H), 3.57-3.51 (m, 5H), 3.51-3.46 (m, 5H), 3.36 (t, J = 5.4 Hz, 4H), 3.16 (t, J = 5.3 Hz, 4H), 3.11-3.01 (m, 6H), 2.65 (dd, J = 11.7, 9.3 Hz, 2H), 2.47 (s, 6H), 1.45-1.38 (m, 4H). MS (ESI) m/z M + H$^+$ = 1067.40 HPLC 100% purity; retention time was 7.562 min. Separation conditions: column: Waters XBridge 4.6 * 100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min. |
| Embodiment D1-P2 | 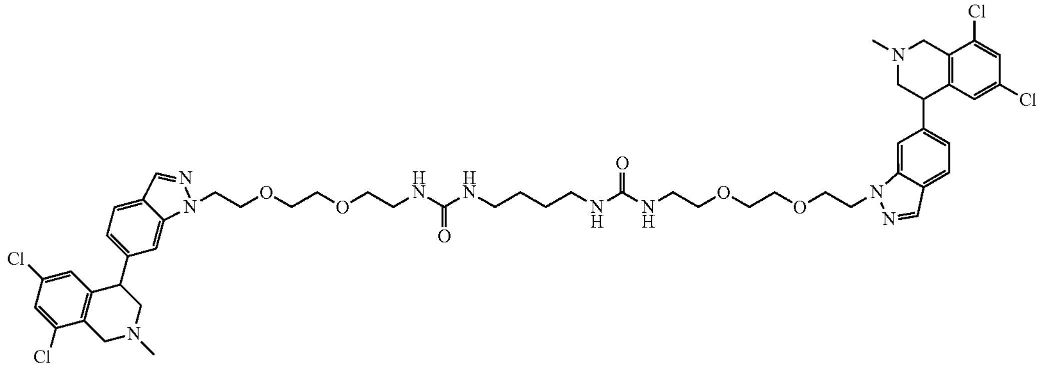 [SMILES: CN1Cc2c(Cl)cc(Cl)cc2C(c2ccc3cnn(CCOCCOCCNC(=O)NCCCCNC(=O)NCCOCCOCCn4ncc5ccc(C6CN(C)Cc7c(Cl)cc(Cl)cc76)cc54)c3c2)C1] $^1$H NMR (400 MHz, DMSO-d6) δ 8.02 (d, J = 0.8 Hz, 2H), 7.64 (d, J = 8.3 Hz, 2H), 7.58 (d, J = 1.2 Hz, 2H), 7.47 (d, J = 2.1 Hz, 2H), 6.95 (dd, J = 8.4, 1.3 Hz, 2H), 6.79 (dd, J = 2.1, 0.9 Hz, 2H), 5.90 (t, J = 5.7 Hz, 2H), 5.75 (t, J = 5.7 Hz, 2H), 4.54-4.47 (m, 4H), 4.39 (t, J = 6.5 Hz, 2H), 3.82 (t, J = 5.4 Hz, 4H), 3.62 (q, J = 16.1 Hz, 4H), 3.44 (dd, J = 5.8, 3.8 Hz, 4H), 3.38-3.35 (m, 4H), 3.24 (t, J = 5.7 Hz, 4H), 3.05 (q, J = 5.6 Hz, 4H), 2.97-2.88 (m, 6H), 2.72-2.65 (m, 2H), 2.39 (s, 6H), 1.33-1.25 (m, 4H). MS (ESI) m/z M + H$^+$ = 1067.40 HPLC 100% purity; retention time was 8.046 min. Separation conditions: column: Waters XBridge 4.6 * 100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min. |

Similar to the synthesis of embodiment B3, embodiment D1-P1-S was synthesized from D1-7-S, as shown in Table 8 below:

TABLE 8
| | |
|---|---|
| Embodiment D1-P1-S | 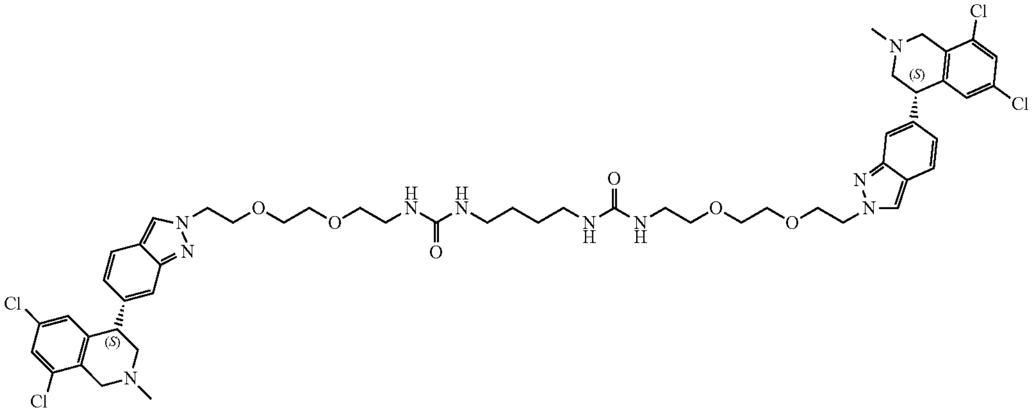 $^1H$ NMR (400 MHz, Chloroform-d) δ 8.00 (d, J = 2.0 Hz, 2H), 7.58 (dd, J = 8.7, 0.8 Hz, 2H), 7.50 (d, J = 1.3 Hz, 2H), 7.22 (dd, J = 2.1, 0.7 Hz, 2H), 6.82 (ddd, J = 5.7, 3.5, 1.4 Hz, 4H), 5.37 (d, J = 5.7 Hz, 2H), 5.23 (t, J = 5.7 Hz, 2H), 4.56 (t, J = 5.3 Hz, 4H), 4.33 (t, J = 7.0 Hz, 2H), 4.00 (t, J = 5.3 Hz, 4H), 3.85 (d, J = 16.1 Hz, 2H), 3.60-3.46 (m, 10H), 3.43 (t, J = 5.0 Hz, 4H), 3.29 (q, J = 5.3 Hz, 4H), 3.14 (d, J = 5.8 Hz, 4H), 3.04 (dd, J = 11.7, 5.5 Hz, 2H), 2.68 (dd, J = 11.6, 8.4 Hz, 2H), 2.49 (s, 6H), 1.48-1.39 (m, 4H). |
Synthesis of Embodiment D2-P1 Hydrochloride
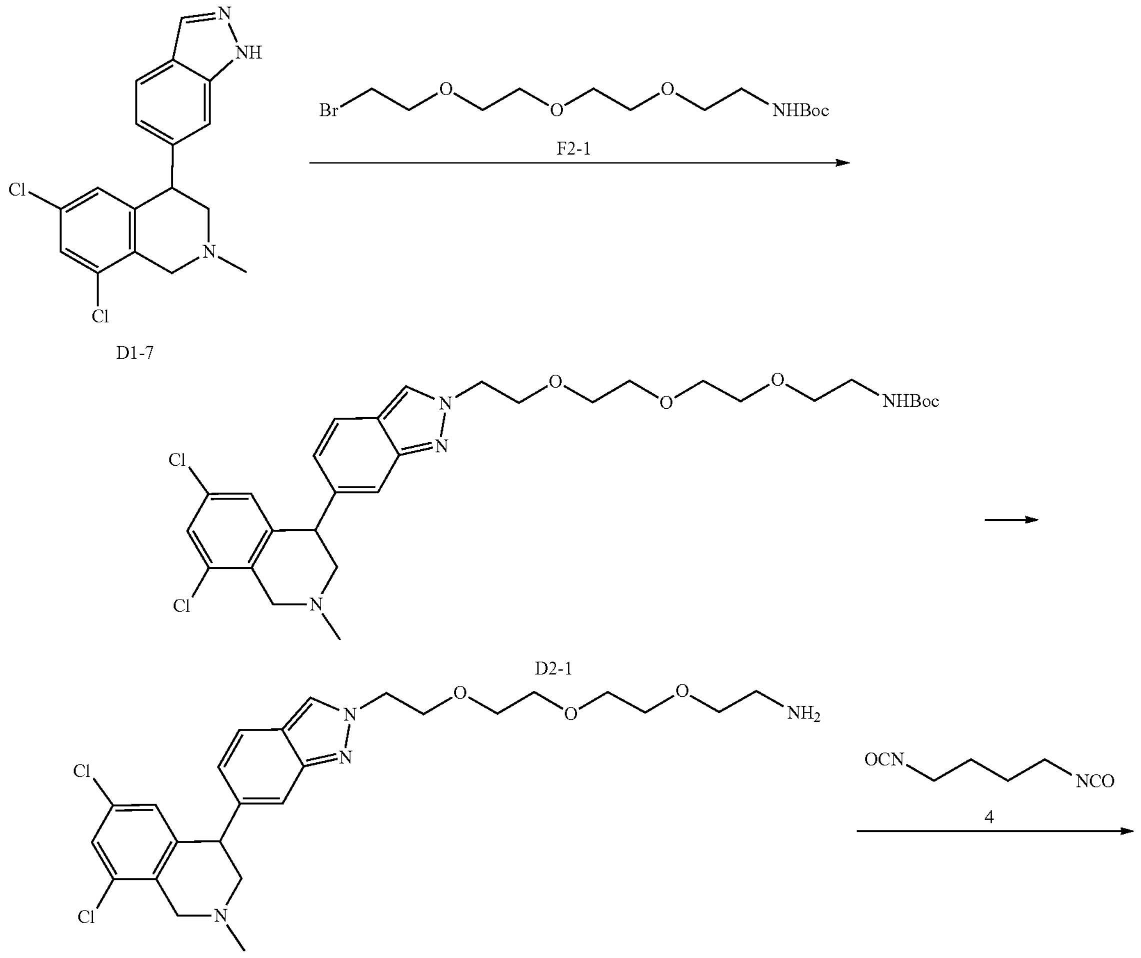
D1-7
F2-1
D2-1
4
D2-2

-continued

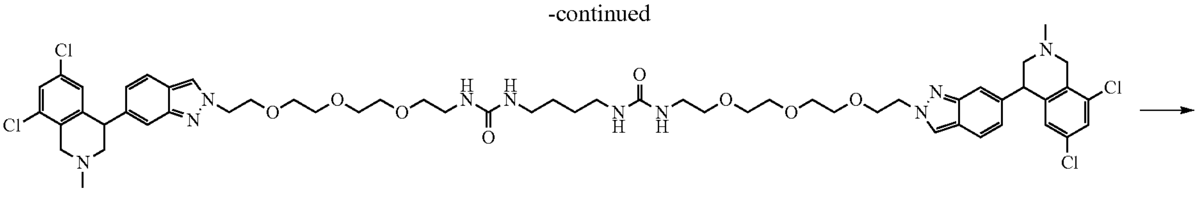

D2-P1

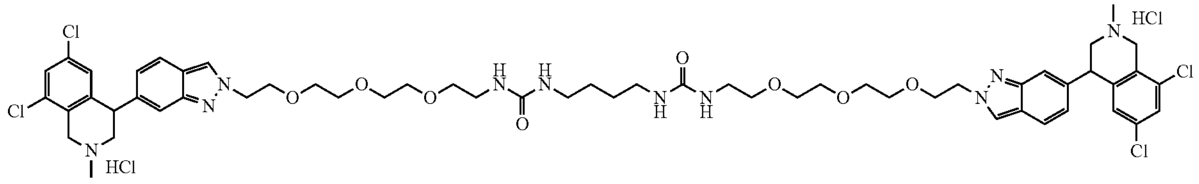

D2-P1 hydrochloride

Step 1: Preparation of Compound D2-P1

Similar to the synthesis of embodiment B3, embodiment D2-P1 was synthesized from D1-7.

Step 2: Preparation of Compound D2-P1 Hydrochloride

D2-P1 (113 mg, 0.1 mmol) was dissolved in a mixed solvent of methanol (2 mL) and water (3 mL), to which concentrated hydrochloric acid (1 mL) was added at room temperature (25° C.), and the system was ultrasonicated at room temperature for 30 minutes. The system was concentrated and freeze-dried to obtain compound D2-P1 hydrochloride.

$^1$H NMR (400 MHz, DMSO-d$_6$, T=60° C.) δ 12.13 (s, 2H), 8.38 (d, J=0.8 Hz, 2H), 7.72 (d, J=8.6 Hz, 2H), 7.58 (d, J=2.1 Hz, 4H), 6.78 (s, 4H), 4.93-4.76 (m, 2H), 4.59 (t, J=5.4 Hz, 6H), 4.50-4.36 (m, 2H), 3.93 (t, J=5.4 Hz, 4H), 3.84-3.71 (m, 2H), 3.64 (t, J=11.9 Hz, 2H), 3.54 (dd, J=5.7, 3.3 Hz, 4H), 3.51-3.47 (m, 4H), 3.47-3.42 (m, 8H), 3.35 (t, J=5.9 Hz, 4H), 3.12 (t, J=5.8 Hz, 4H), 3.03-2.90 (m, 10H), 1.37-1.30 (m, 4H).

MS (ESI) m/z (M+H)$^+$=1155.60.

HPLC retention time was 7.417 min.

Separation conditions: column: Waters XBridge 4.6*100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min.

Synthesis of Embodiment D2-P2 Hydrochloride

Similar to the synthesis of D2-P1 hydrochloride, embodiment D2-P2 hydrochloride was synthesized from D1-7.

$^1$H NMR (400 MHz, DMSO-d$_6$) δ 12.22 (d, J=57.8 Hz, 2H), 8.10 (s, 2H), 7.81-7.72 (m, 4H), 7.69-7.62 (m, 2H), 6.91 (dd, J=8.3, 1.3 Hz, 2H), 6.75-6.61 (m, 2H), 4.97-4.76 (m, 2H), 4.75-4.51 (m, 6H), 4.51-4.33 (m, 2H), 3.97-3.60 (m, 8H), 3.51-3.42 (m, 4H), 3.42-3.34 (m, 12H), 3.31 (t, J=5.8 Hz, 4H), 3.11 (t, J=5.8 Hz, 4H), 3.05-2.84 (m, 10H), 1.39-1.21 (m, 4H).

MS (ESI) m/z (M+H)$^+$=1155.6.

HPLC retention time was 7.976 min.

Separation conditions: column: Waters XBridge 4.6*100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min.

Synthesis of Embodiment E1

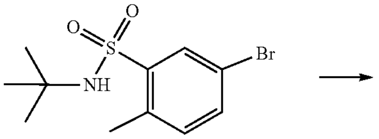

A1-4

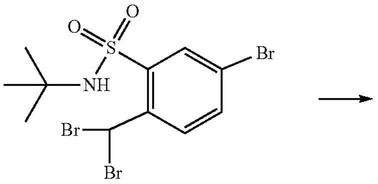

E1-1

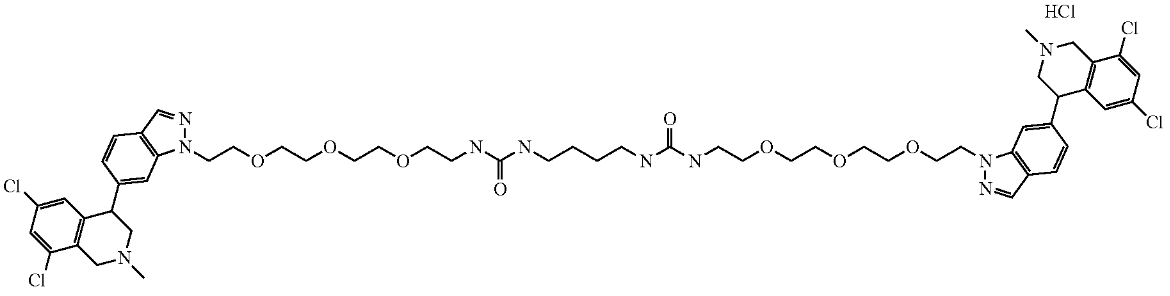 [SMILES: Cl ; CN1Cc2c(Cl)cc(Cl)cc2C(c2ccc3cnn(CCOCCOCCOCCNC(=O)NCCCCNC(=O)NCCOCCOCCOCCn4ncc5ccc(C6CN(C)Cc7c(Cl)cc(Cl)cc76)cc54)c3c2)C1]

-continued

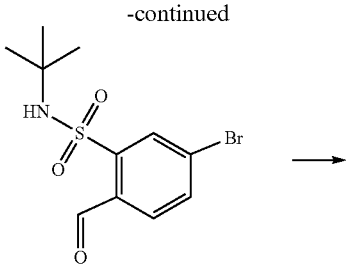

E1-2

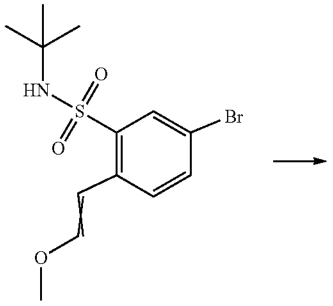

E1-3

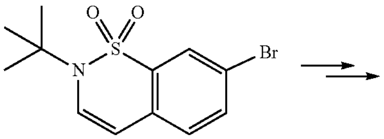

E1-4

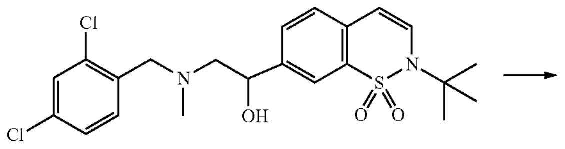

E1-8

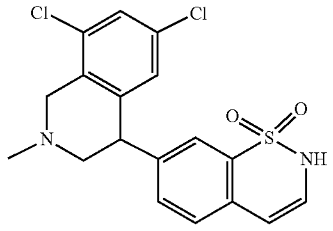

E1-9

Step 1: Preparation of Compound E1-1

Compound A1-4 (10 g, 32.8 mmol), N-bromosuccinimide (12.85 g, 72.16 mmol), azobisisobutyronitrile (1.08 g, 6.56 mmol) were dissolved in carbon tetrachloride (80 mL). The reaction was heated to 80° C. and stirred for 18 hours. After the reaction, the mixture was filtered by celite, washed with water and concentrated to obtain the crude product. The crude product was purified by silica gel column chromatography (ethyl acetate/petroleum ether (v/v)=0-10% to obtain compound E1-1.

MS (ESI) m/z $(M+Na)^+$=482.6.

$^1$H NMR (400 MHz, Chloroform-d) δ 8.08 (d, J=2.1 Hz, 1H), 8.05 (d, J=8.5 Hz, 1H), 7.77 (dd, J=8.5, 2.1 Hz, 1H), 7.58 (s, 1H), 4.67 (s, 1H), 1.27 (s, 9H).

Step 2: Preparation of Compound E1-2

Compound E1-1 (10 g, 21.7 mmol) was dissolved in a mixed solvent of tetrahydrofuran (75 mL) and water (25 mL), to which silver nitrate (11.1 g, 65.1 mmol) was added at room temperature (25° C.), and the reaction was heated to 80° C. and stirred for 2 hours. The reaction mixture was cooled to room temperature (25° C.), filtered by celite, concentrated to 1/3 volume, diluted with ethyl acetate (200 mL), washed with water, and the organic phase was dried over anhydrous sodium sulfate, filtered, and the filtrate was concentrated to obtain the crude product. The crude product was purified by silica gel column chromatography (ethyl acetate/petroleum ether (v/v)=0-10% to obtain compound E1-2.

MS (ESI) m/z (M−55)=264.

Step 3: Preparation of Compound E1-3

(Methoxymethyl) triphenylphosphonium chloride (8.17 g, 23.9 mmol) was dissolved in tetrahydrofuran (50 mL), to which sodium bis(trimethylsilyl)amide (12 mL, 23.9 mmol, 2 M) was added under argon atmosphere at 0° C. After the addition, the system was stirred at 0° C. for 1 hour. The reaction mixture was cooled to −78° C., to which a tetrahydrofuran solution (10 mL) of the compound E1-2 in step 2 was added dropwise, and the system was slowly heated to room temperature (25° C.) and stirred for 16 hours. The reaction mixture was concentrated to obtain the crude product, which was purified by silica gel column chromatography (ethyl acetate/petroleum ether (v/v)=0-20%) to obtain compound E1-3.

$^1$H NMR (400 MHz, Chloroform-d) δ 8.16 (d, J=2.2 Hz, 1H), 7.55 (ddd, J=8.3, 2.1, 0.6 Hz, 1H), 7.24 (d, J=0.6 Hz, 1H), 6.96 (d, J=12.8 Hz, 1H), 6.43 (d, J=12.8 Hz, 1H), 4.46 (s, 1H), 3.74 (s, 3H), 1.17 (s, 9H).

Step 4: Preparation of Compound E1-4

Compound E1-3 (2.2 g, 6.3 mmol) was dissolved in tetrahydrofuran (30 mL), to which 2 N HCl (31 mL, 63 mmol) was added at room temperature (25° C.). After the addition, the reaction was heated to 50° C. and stirred for 1 hour. The reaction mixture was concentrated to remove tetrahydrofuran, extracted with ethyl acetate (100 mL), and the organic phases were combined, dried over anhydrous sodium sulfate, filtered, and the filtrate was concentrated to obtain the crude product, which was purified by silica gel column chromatography (ethyl acetate/petroleum ether (v/v)=0-20%) to obtain compound E1-4.

$^1$H NMR (400 MHz, Chloroform-d) δ 8.02 (dt, J=2.0, 0.5 Hz, 1H), 7.66 (dd, J=8.4, 2.0 Hz, 1H), 7.23 (d, J=8.3 Hz, 1H), 6.85 (d, J=8.2 Hz, 1H), 6.29-6.24 (m, 1H), 1.62 (s, 9H).

Step 5: Preparation of Compound E1-8

Similar to the synthesis of compound B1-5, compound E1-8 was synthesized.

MS (ESI) m/z $(M+H)^+$=469.2.

Step 6: Preparation of Compound E1-9

Compound E1-8 (1.3 g, 2.8 mmol) was dissolved in 1,2-dichloroethane (10 mL), to which aluminum trichloride (1.85 g, 14 mmol) was added under nitrogen atmosphere, and the reaction was heated to 80° C. and continued to stir for 0.5 hour. The system was cooled to room temperature (25° C.), diluted with ethyl acetate (200 mL), the pH of which was adjusted to alkaline with saturated aqueous sodium bicarbonate solution, filtered with celite, washed with water, and the organic phases were combined, dried over anhydrous sodium sulfate, filtered, and the filtrate was concentrated to obtain the crude product, which was purified by silica gel column chromatography (ethyl acetate/petroleum ether (v/v)=0-60%) to obtain compound E1-9.

MS (ESI) m/z $(M+H)^+$=395.2.

$^1H$ NMR (400 MHz, DMSO-$d_6$) δ 11.12 (s, 1H), 7.65 (d, J=1.7 Hz, 1H), 7.51 (d, J=2.1 Hz, 1H), 7.46 (dd, J=8.2, 1.8 Hz, 1H), 7.41 (d, J=8.1 Hz, 1H), 6.92 (d, J=2.1 Hz, 1H), 6.80 (d, J=7.6 Hz, 1H), 6.19 (d, J=7.6 Hz, 1H), 4.42 (t, J=5.3 Hz, 1H), 3.75 (d, J=16.2 Hz, 1H), 3.45 (d, J=16.2 Hz, 1H), 2.84 (dd, J=11.6, 5.0 Hz, 1H), 2.74-2.68 (m, 1H), 2.37 (s, 3H).

Similar to the synthesis of embodiment C1, embodiment E1 was synthesized from E1-9, as shown in Table 9 below:

TABLE 9

| | |
|---|---|
| Structural formula | 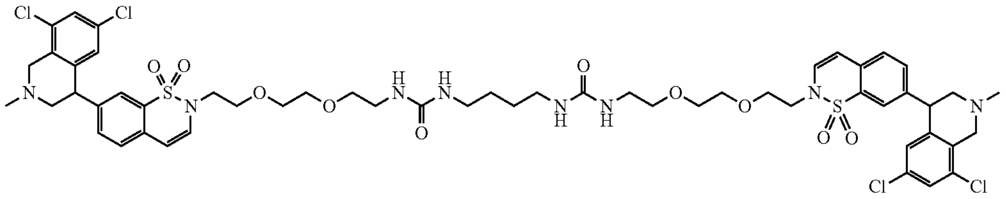 |
| Analysis data | $^1H$ NMR (400 MHz, DMSO-$d_6$) δ 7.73 (d, J = 1.6 Hz, 2H), 7.57-7.41 (m, 6H), 6.97-6.90 (m, 4H), 6.35 (d, J = 7.9 Hz, 2H), 5.92 (t, J = 5.7 Hz, 2H), 5.79 (t, J = 5.8 Hz, 2H), 4.45 (t, J = 5.1 Hz, 2H), 3.84 (t, J = 5.5 Hz, 4H), 3.76 (d, J = 16.2 Hz, 2H), 3.61 (t, J = 5.4 Hz, 4H), 3.51-3.46 (m, 4H), 3.45-3.38 (m, 6H), 3.30 (t, J = 5.7 Hz, 4H), 3.09 (q, J = 5.7 Hz, 4H), 2.94 (q, J = 5.8 Hz, 4H), 2.81 (dd, J = 11.7, 5.0 Hz, 2H), 2.71 (dd, J = 11.7, 5.2 Hz, 2H), 2.36 (s, 6H), 1.35-1.25 (m, 4H).<br>MS (ESI) m/z M + $H^+$ = 1193.4.<br>HPLC 100% purity; retention time was 8.051 min.<br>Separation conditions: column: Waters XBridge 4.6 * 100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min. |

Synthesis of Embodiment F1

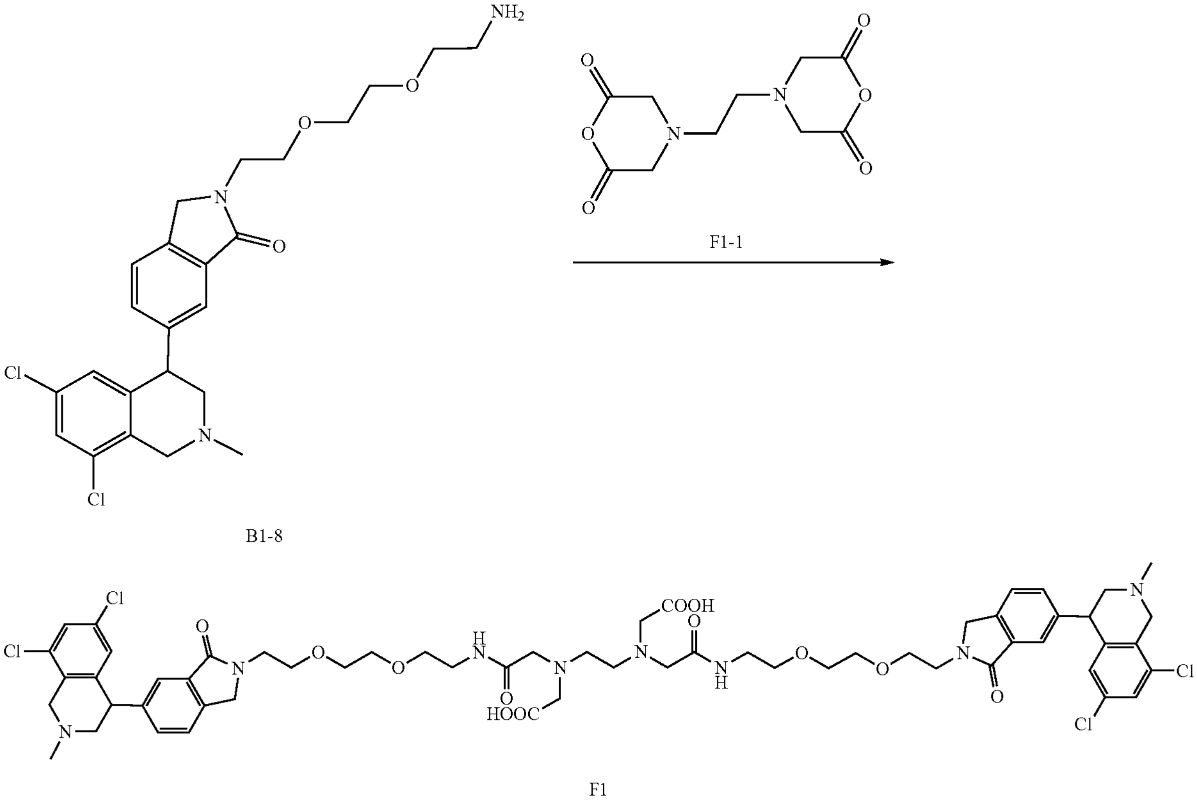

B1-8

F1-1

F1

Step 1: Preparation of Compound F1

Compound B1-8 (91 mg, 0.19 mmol) was dissolved in N,N-dimethylformamide (2 mL), to which ethylenediaminetetraacetic dianhydride (19 mg, 0.07 mmol) and triethylamine were added (57 mg, 0.57 mmol). After the addition, the system was reacted at room temperature (25° C.) for 2 hours. The reaction mixture was purified by high performance preparative liquid chromatography (separation conditions: column: Agilent 10 Prep-C18 250×21.2 mm; column temperature: 25° C.; mobile phase: water (10 mM/L ammonium bicarbonate)-acetonitrile; acetonitrile: 60%-80% 12 min, flow rate: 30 mL/min) to obtain compound F1.

$^1$H NMR (400 MHz, Methanol-$d_4$) δ 7.50 (d, J=1.5 Hz, 2H), 7.46 (d, J=7.9 Hz, 2H), 7.36 (dd, J=7.9, 1.6 Hz, 2H), 7.26 (d, J=2.3 Hz, 2H), 6.69 (dd, J=2.2, 1.0 Hz, 2H), 4.51 (s, 4H), 4.45-4.39 (m, 2H), 3.92 (d, J=16.1 Hz, 2H), 3.76-3.63 (m, 10H), 3.57 (d, J=1.5 Hz, 4H), 3.52-3.33 (m, 18H), 3.15 (q, J=5.7 Hz, 6H), 3.03 (s, 4H), 2.77 (dd, J=11.9, 8.9 Hz, 2H), 2.52 (s, 6H).

MS (ESI) m/z M+H$^+$=1211.20.

HPLC 100% purity; retention time was 6.180 min.

Separation conditions: column: Waters XBridge 4.6*100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min.

Synthesis of Embodiment F2

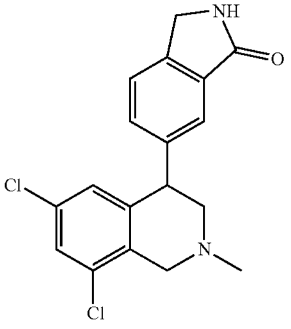

B1-6

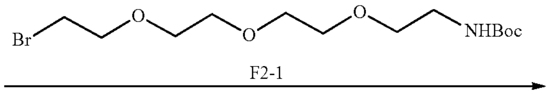

F2-1

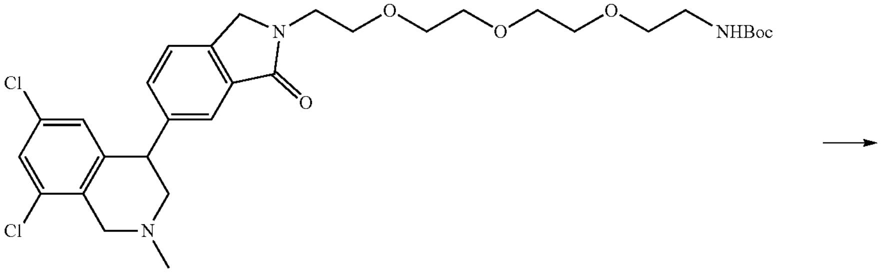

F2-2

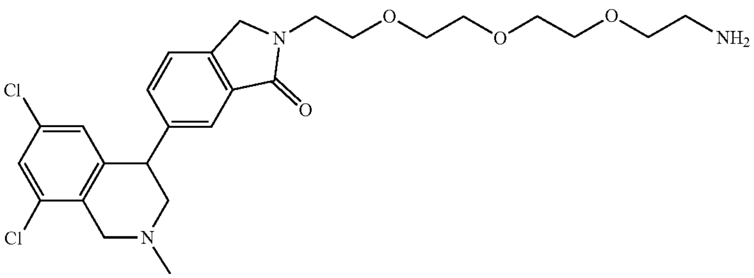

F2-3

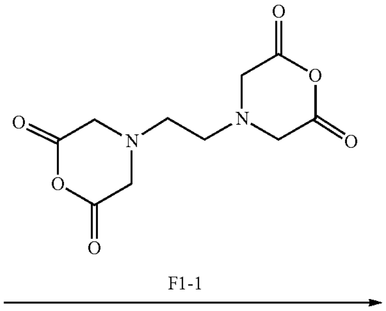

F1-1

-continued

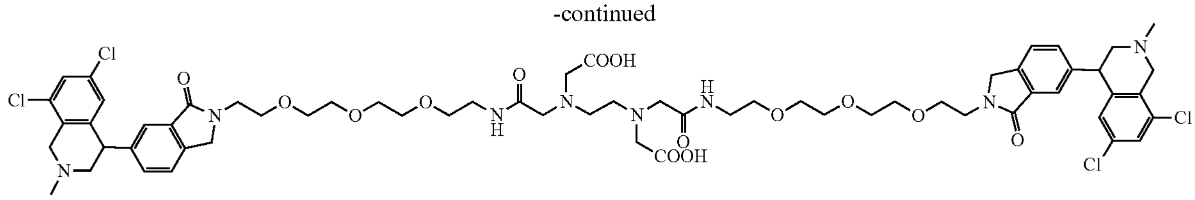

F2

Step 1: Preparation of Compound F2-2

Compound B1-6 (200 mg, 0.58 mmol), F2-1 (410 mg, 1.15 mmol), cesium carbonate (563 mg, 1.73 mmol), 18-crown-6 (15.2 mg, 0.06 mmol) were dissolved in acetonitrile (1.5 mL), and the system was replaced with a nitrogen stream, and heated to 90° C. and stirred for 16 hours under nitrogen protection. The reaction mixture was cooled to room temperature, filtered, and the filtrate was purified by C18 reversed-phase silica gel column chromatography (acetonitrile/0.1% aqueous ammonium bicarbonate (v/v)=5-75%) to obtain compound F2-2.

MS (ESI) m/z $(M+H)^+$=622.0.

Step 2: Preparation of Compound F2-3

Compound F2-2 (260 mg, 0.42 mmol) was dissolved in anhydrous dichloromethane (4 mL), to which trifluoroacetic acid (1 mL) was added under ice bath, and the system was heated to room temperature (25° C.) and stirred for 3 hours. The reaction mixture was concentrated under vacuum to obtain the crude product, dissolved with dichloromethane (20 mL), to which water (20 mL) was added, and the pH of which was adjusted to 9 with saturated aqueous sodium bicarbonate solution, and separated, and the aqueous phase was extracted with dichloromethane (20 mL×2), and the organic phases were combined, dried over anhydrous sodium sulfate, filtered, and the filtrate was concentrated to obtain compound F2-3.

MS (ESI) m/z $(M+H)^+$=522.0.

Similar to the synthesis of embodiment F1, embodiment F2 was synthesized from F2-3, as shown in Table 10 below:

TABLE 10

| Structural formula and analysis data of embodiments F2 | |
|---|---|
| Structural formula | 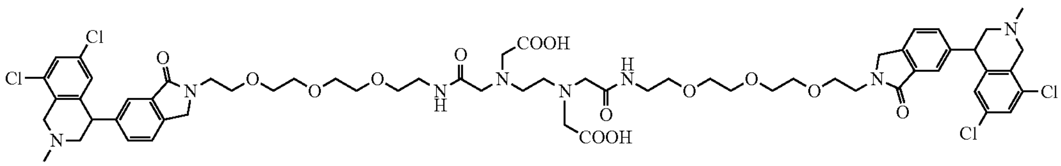 [SMILES: CN1Cc2c(Cl)cc(Cl)cc2C(c2ccc3c(c2)C(=O)N(CCOCCOCCOCCNC(=O)CN(CCN(CC(=O)O)CC(=O)NCCOCCOCCOCCN2Cc4ccc(C5CN(C)Cc6c(Cl)cc(Cl)cc65)cc4C2=O)CC(=O)O)C3)C1] |
| Analysis data | $^1$H NMR (400 MHz, DMSO-d6) δ 7.95 (t, J = 5.8 Hz, 2H), 7.53-7.45 (m, 8H), 6.85 (d, J = 2.1 Hz, 2H), 4.50 (s, 4H), 4.40 (t, J = 5.2 Hz, 2H), 3.72 (d, J = 16.1 Hz, 2H), 3.63 (dq, J = 8.8, 4.2 Hz, 8H), 3.53-3.45 (m, 12H), 3.39-3.36 (m, 12H), 3.24-3.19 (m, 8H), 2.84 (dd, J = 11.5, 5.1 Hz, 2H), 2.68-2.64 (m, 6H), 2.36 (s, 6H).<br>MS (ESI) m/z $(M + H)^+/2$ = 651.3.<br>HPLC 91.13% purity; retention time was 3.392 min.<br>Separation conditions: column: Agilent 10 Prep-C18 250 * 21.2 mm, 3.5 um; column temperature: 25° C.; mobile phase: water (0.1% formic acid)-acetonitrile; acetonitrile: 12%-32% 9 min, flow rate: 30 mL/min) |

Synthesis of Embodiment G1

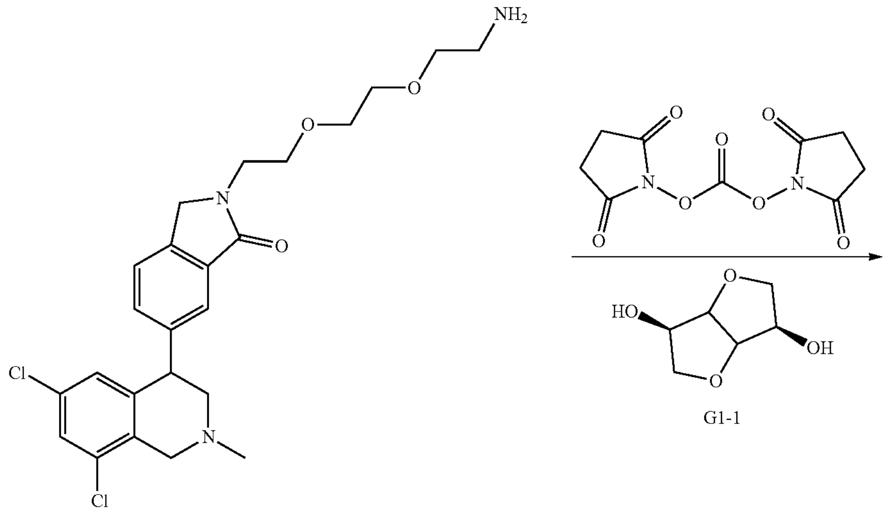

G1-1

B1-8

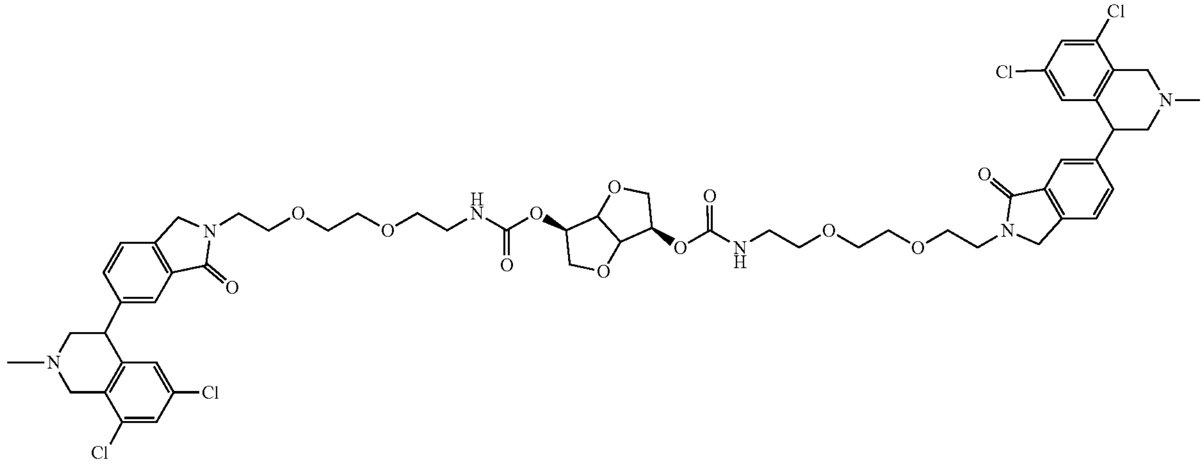

G1

1,4:3,6-bis-anhydromannitol (15 mg, 0.102 mmol) was dissolved in N,N-dimethylformamide (2 mL), to which N,N'-disuccinimidyl carbonate (52.2 mg, 0.204 mmol) was added, and the system was stirred at room temperature (25° C.) for 1 hour. Compound B1-8 (108 mg, 0.226 mmol) and triethylamine (30.9 mg, 0.306 mmol) were added to the above reaction mixture, and after the addition was complete, the system was reacted at 60° C. for 16 hours, the reaction mixture was purified by high performance preparative liquid chromatography (separation conditions: column: Agilent 10 Prep-C18 250×21.2 mm; column temperature: 25° C.; mobile phase: water (10 mM/L $NH_4HCO_3$)-acetonitrile; acetonitrile: 60%-90% 12 min, flow rate: 30 mL/min) to obtain compound G1.

$^1$H NMR (400 MHz, Methanol-$d_4$) δ 7.48-7.41 (m, 4H), 7.36 (dd, J=7.9, 1.6 Hz, 2H), 7.22 (d, J=2.0 Hz, 2H), 6.68 (d, J=1.9 Hz, 2H), 4.50 (s, 6H), 4.34-4.27 (m, 2H), 3.85-3.60 (m, 14H), 3.59-3.43 (m, 12H), 3.35 (t, J=5.5 Hz, 4H), 3.08 (t, J=5.4 Hz, 4H), 2.95 (dd, J=11.7, 5.6 Hz, 2H), 2.56 (dd, J=11.7, 8.2 Hz, 2H), 2.37 (s, 6H).

MS (ESI) m/z $M+H^+$=1155.40.

HPLC 100% purity; retention time was 7.593 min.

Separation conditions: column: Waters XBridge 4.6*100 mm, 3.5 um; column temperature: 40° C.; mobile phase: water (10 mM $NH_4HCO_3$)-acetonitrile; acetonitrile: 5%-95% 7 min, 95% 8 min; flow rate: 1.2 mL/min.

Synthesis of Embodiment H1

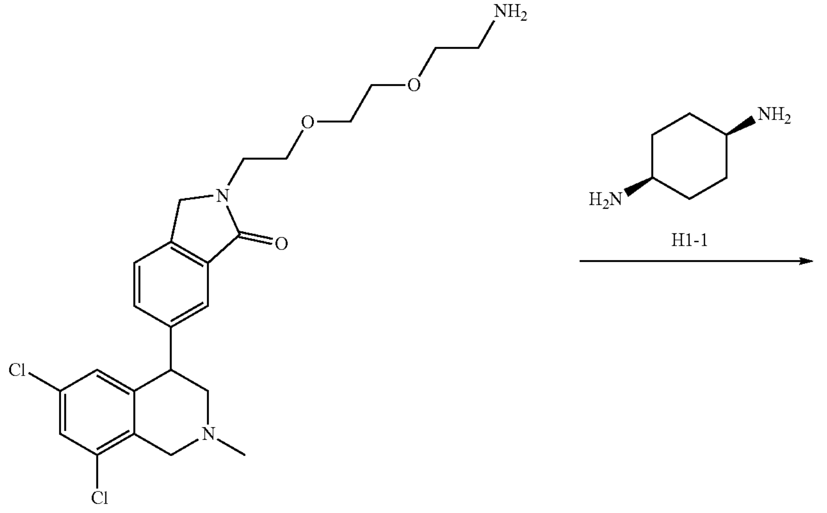

H1-1

B1-8

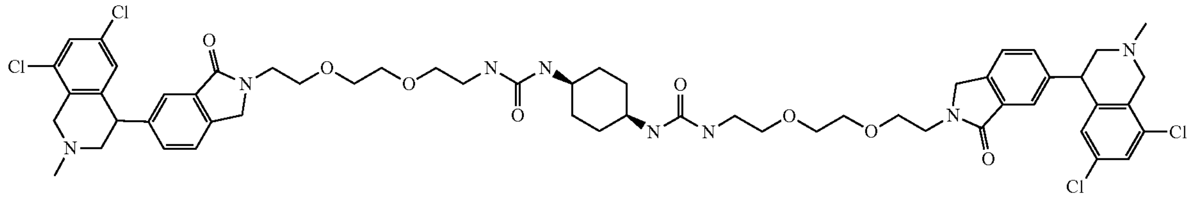

H1

Compound B1-8 (110 mg, 0.23 mmol) was dissolved in N,N-dimethylformamide (2 mL), to which N,N'-carbonyldiimidazole (44.8 mg, 0.27 mmol) was added, after the addition, the system was stirred at room temperature (25° C.) for 1 hour. After the complete conversion into active intermediate was monitored through sampling, cis-1,4-cyclohexanediamine (10.5 mg, 0.092 mmol) and triethylamine (81.8 mg, 0.81 mmol) were added to the reaction mixture, and the system was reacted at 80° C. for 16 hours, the reaction mixture was purified by high performance preparative liquid chromatography (separation conditions: column: Agilent 10 Prep-C18 250×21.2 mm; column temperature: 25° C.; mobile phase: water (10 mM/L $NH_4HCO_3$)-acetonitrile; acetonitrile: 60%-80% 12 min, flow rate: 30 mL/min) to obtain compound H1.

$^1$H NMR (400 MHz, Methanol-$d_4$) δ 7.45-7.37 (m, 6H), 7.22 (d, J=2.1 Hz, 2H), 6.69-6.65 (d, 2H), 4.48 (s, 4H), 4.32-4.27 (t, 2H), 3.71-3.62 (m, 10H), 3.54-3.42 (m, 12H), 3.30 (t, J=5.2 Hz, 4H), 3.08 (dd, J=6.5, 4.8 Hz, 4H), 2.96-2.89 (m, 2H), 2.53 (dd, J=11.7, 8.1 Hz, 2H), 2.36 (s, 6H), 1.56-1.36 (m, 8H).

MS (ESI) m/z $(M+H)^+$=1123.40.

HPLC 100% purity; retention time was 7.249 min.

Separation conditions: column: Waters XBridge 4.6*100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min.

Similar to the synthesis of embodiment H1, embodiment H2 was synthesized, as shown in Table 11 below:

TABLE 11

| Structural formula and analysis data of embodiments H2 | |
|---|---|
| Embodiment H2 | 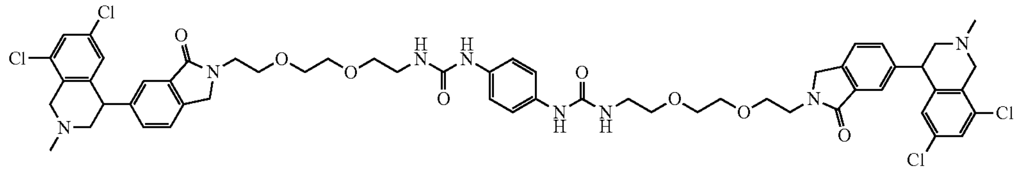 [SMILES: CN1Cc2c(Cl)cc(Cl)cc2C(c2ccc3c(c2)C(=O)N(CCOCCOCCNC(=O)Nc2ccc(NC(=O)NCCOCCOCCN4Cc5ccc(C6CN(C)Cc7c(Cl)cc(Cl)cc76)cc5C4=O)cc2)C3)C1] $^1$H NMR (400 MHz, DMSO-d6) δ 8.32 (s, 2H), 7.51-7.43 (m, 8H), 7.20 (s, 4H), 6.84 (d, J = 2.0 Hz, 2H), 6.03 (t, J = 5.6 Hz, 2H), 4.51 (s, 4H), 4.39 (t, J = 5.4 Hz, 2H), 3.75-3.61 (m, 10H), 3.53 (ddt, J = 10.2, 7.5, 3.5 Hz, 10H), 3.40 (t, J = 5.5 Hz, 4H), 3.17 (q, J = 5.5 Hz, 4H), 2.84 (dd, J = 11.6, 5.1 Hz, 2H), 2.66 (dd, J = 11.5, 6.6 Hz, 2H), 2.36 (s, 6H). |

Synthesis of Embodiment I1

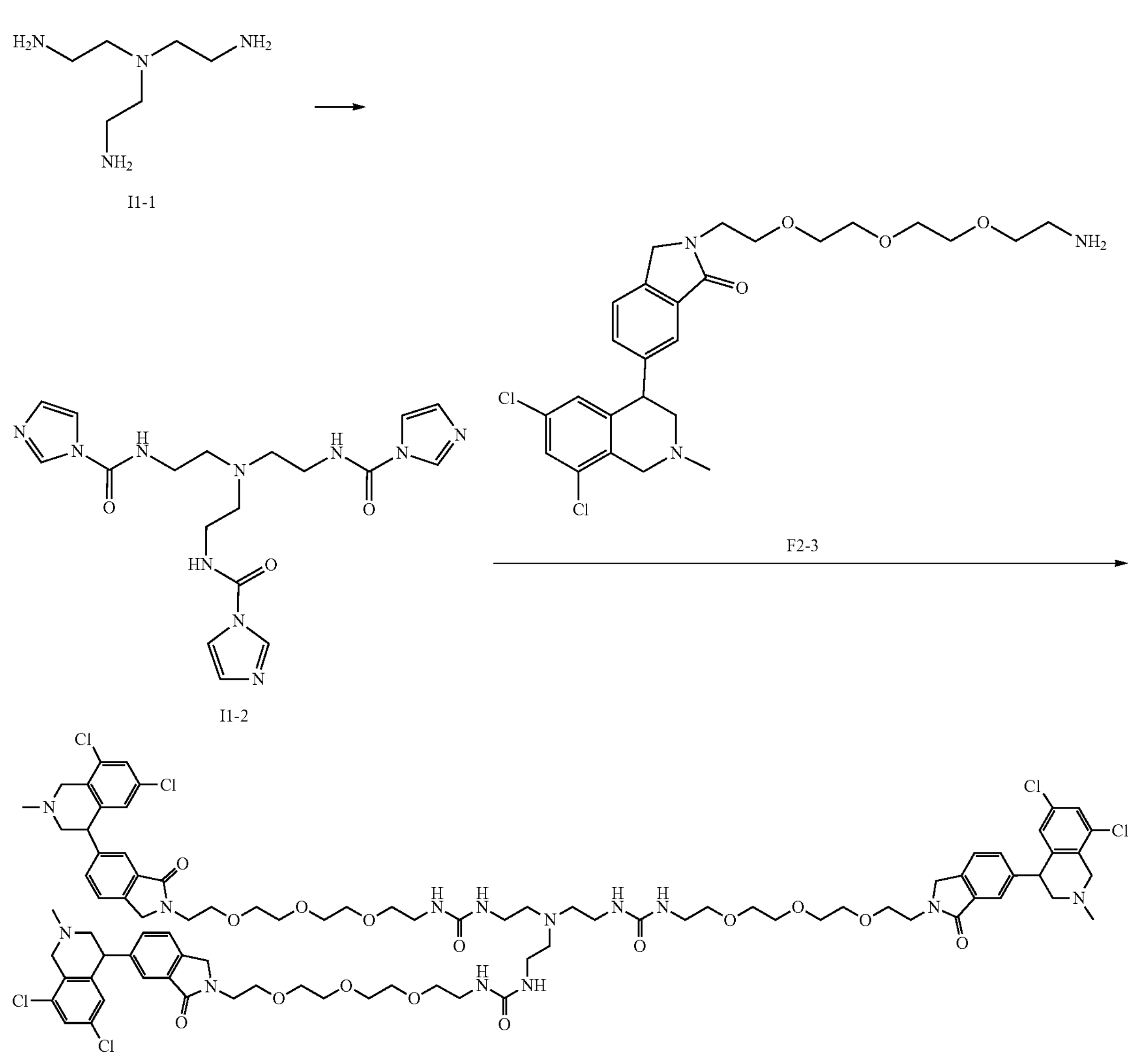

I1-1

I1-2

F2-3

I1

Step 1: Preparation of Compound I1-2

N,N'-carbonyl diimidazole (487 mg, 3.00 mmol) was dissolved in N,N-dimethylformamide (1.5 ml), to which compound I1-1 (146 mg, 1.00 mmol) was added in batches at 0° C., after the addition, the system was slowly heated to room temperature (25° C.) and stirred for 2 h. The system was directly used in the next step without further purification.

MS (ESI) m/z $(M+H)^+$=429.00

Step 2: Preparation of Compound I1

Compound F2-3 (80 mg, 0.15 mmol) was dissolved in N,N-dimethylformamide (2 mL), after the addition, the system was heated to 75° C., to which the reaction solution of compound I1-2 (0.05 mL, 0.05 mmol) was added dropwise, after the addition, the system was stirred at 75° C. for 17 hours. The reaction mixture was purified by high performance preparative liquid chromatography (separation conditions: column: Welch Xtimate® C18 21.2×250 mm; column temperature: 25° C.; mobile phase: water (10 mM/L ammonium bicarbonate)-acetonitrile; acetonitrile: 65%-95% 9 min; flow rate 30 mL/min) to obtain compound I1.

$^1$H NMR (400 MHz, DMSO-$d_6$) δ 7.51-7.44 (m, 12H), 6.84 (d, J=2.2 Hz, 3H), 5.95 (s, 6H), 4.50 (s, 6H), 4.39 (t, J=5.3 Hz, 3H), 3.73-3.69 (m, 3H), 3.64-3.59 (m, 12H), 3.52-3.46 (m, 15H), 3.46-3.44 (m, 6H), 3.43-3.40 (m, 6H), 3.32-3.31 (m, 6H), 3.14-3.09 (m, 6H), 3.02-3.98 (m, 6H), 2.85-2.82 (m, 3H), 2.68-2.64 (m, 3H), 2.36 (s, 9H).

MS (ESI) m/z $(M+2H)^+/2$=897.0.

HPLC 100% purity; retention time was 3.350 min.

Separation conditions: column: Waters Xselect CSH C18 4.6*100 mm, 3.5 um; column temperature: 60° C.; mobile phase: water (0.01% trifluoroacetic acid)-acetonitrile (0.01% trifluoroacetic acid); acetonitrile: 5%-95% 7 min; flow rate: 1.2 mL/min.

Synthesis of Embodiment 12
Step 1: Preparation of Compound I2-3
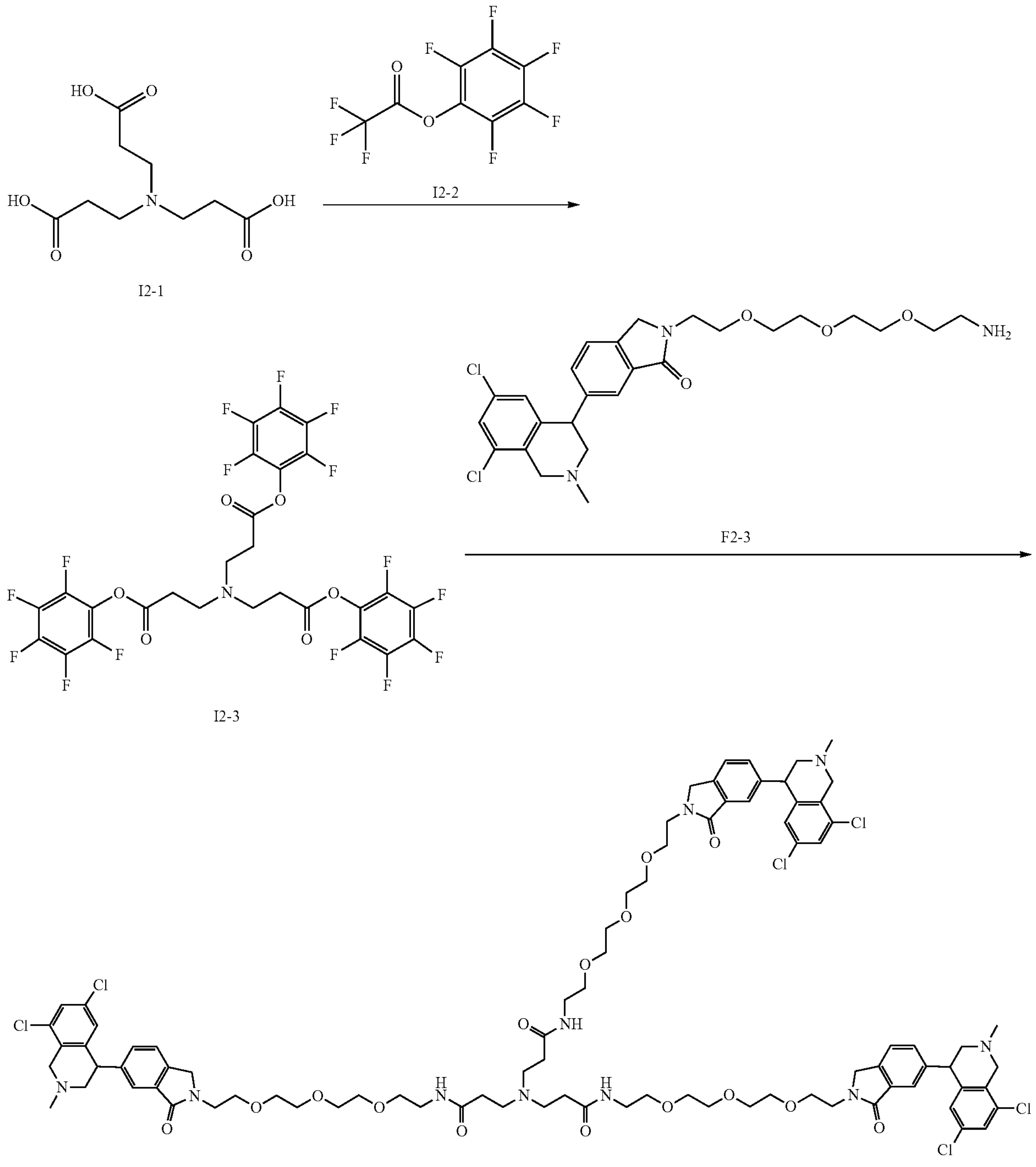
I2

Compound I2-1 (300 mg, 1.29 mmol) was dissolved in dichloromethane (3 mL), to which compound I2-2 (1.26 g, 4.5 mmol) and triethylamine (911 mg, 9.0 mmol) were added sequentially at 0° C., after the addition, the system was slowly heated to room temperature (25° C.) and stirred for 1 hour. The system was the reaction mixture of compound I2-3, which was directly used in the next step without further purification.

MS (ESI) m/z $(M+H)^+=732.00$

Step 2: Preparation of Compound I2

Compound F2-3 (80 mg, 0.15 mmol) and triethylamine (31 mg, 0.31 mmol) were dissolved in N,N-dimethylformamide (2 mL), to which the reaction mixture of compound I2-3 (0.12 mL, 0.05 mmol) was added dropwise at room temperature (25° C.), after the addition, the system was stirred at room temperature (25° C.) for 3 hours. The reaction mixture was purified by high performance preparative liquid chromatography (separation conditions: column: Welch Xtimate® C18 21.2×250 mm; column temperature: 25° C.; mobile phase: water (10 mM/L ammonium bicarbonate)-acetonitrile; acetonitrile: 65%-95% 9 min; flow rate 30 mL/min) to obtain compound 12.

$^1H$ NMR (400 MHz, DMSO-$d_6$) δ 7.91 (s, 3H), 7.50-7.45 (m, 12H), 6.84 (d, J=2.0 Hz, 3H), 4.49 (s, 6H), 4.39 (t, J=5.5 Hz, 3H), 3.71 (d, J=16.2 Hz, 3H), 3.66-3.59 (m, 12H), 3.52-3.48 (m, 15H), 3.45-3.40 (m, 12H), 3.35-3.43 (m, 6H), 3.17-3.13 (m, 6H), 2.85-2.81 (m, 3H), 2.67-2.58 (m, 9H), 2.35 (s, 9H), 2.18 (s, 6H).

MS (ESI) m/z $(M+2H)^+/2=873.4$.

HPLC 100% purity; retention time was 9.618 min.

Separation conditions: column: Waters XBridge 4.6*100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min.

Synthesis of Embodiment 13

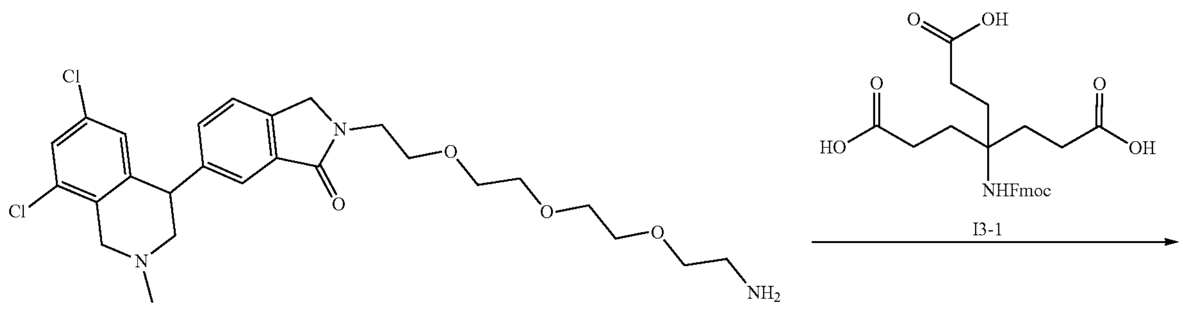

F2-3

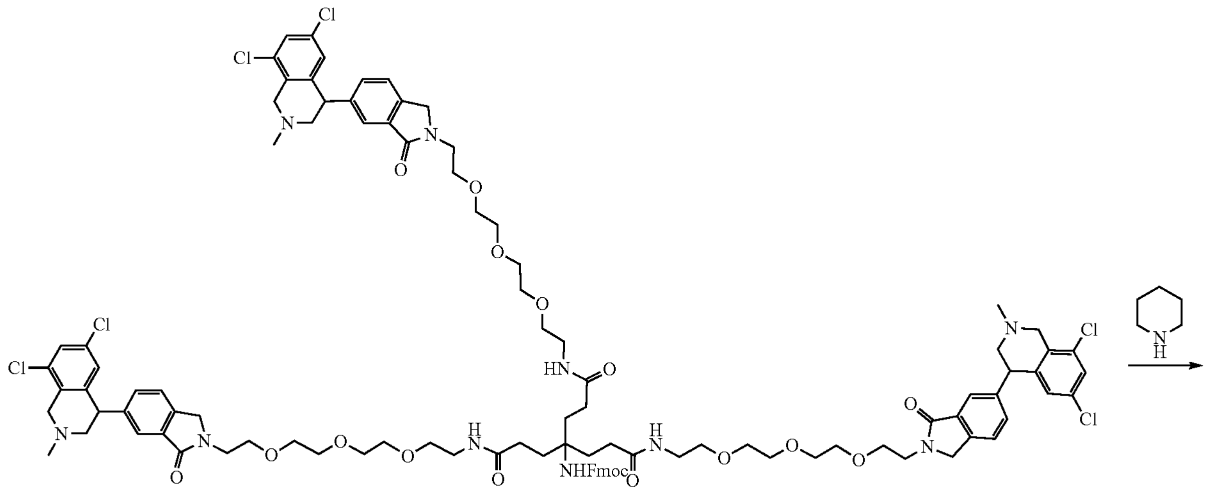

I3-2

-continued

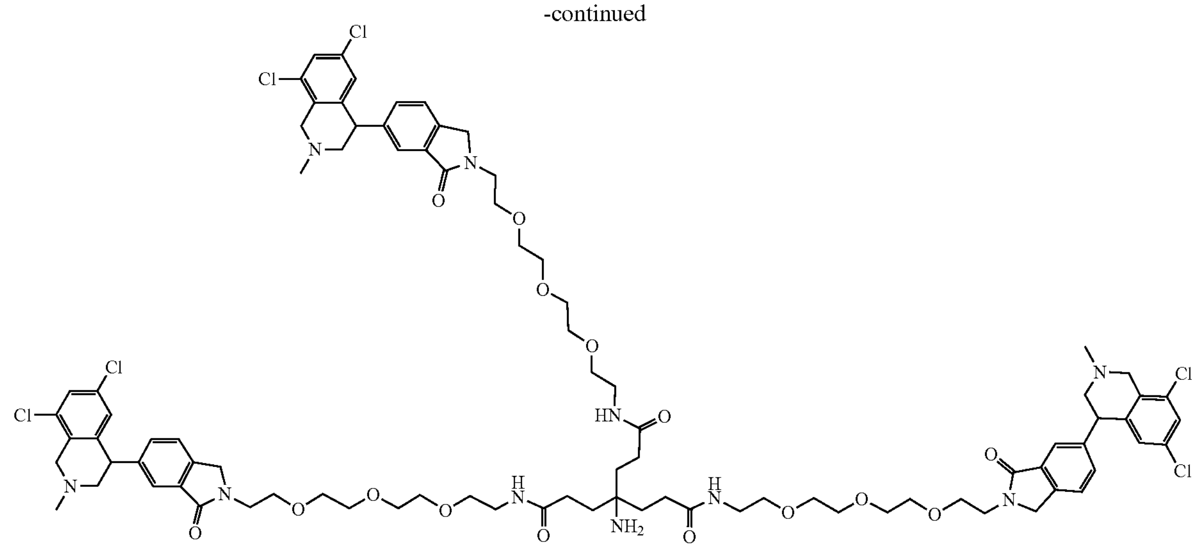

I3

Step 1: Preparation of Compound I3-2

4-(2-Carboxyethyl)-4-[[(9H-fluoren-9-methoxy)carbonyl]amino]heptanedioic acid (94 mg, 0.2 mmol) was dissolved in N,N-dimethylformamide (5 mL), to which N,N-diisopropylethylamine (170 mg, 1.32 mmol), 2-(7-azobenzotriazole)-N,N,N',N'-tetramethyluroniumhexafluorophosphate (384 mg, 1.0 mmol) were added sequentially. After the addition, the system was stirred at room temperature (25° C.) for 10 minutes, to which compound F2-3 (410 mg, 0.785 mmol) was added, after the addition, the system was stirred at room temperature (25° C.) for 18 hours. The system was filtered, and the filtrate was purified by C18 reversed-phase silica gel column chromatography (acetonitrile/0.1% aqueous ammonium bicarbonate (v/v)=5-95%) to obtain compound I3-2.

(ESI) m/z $(M/2+H)^+$=992.0.

Step 2: Preparation of Compound I3

Compound I3-2 (280 mg, 0.141 mmol) was dissolved in N,N-dimethylformamide (3 mL), to which piperidine (120 mg, 1.41 mmol) was added, after the addition, the system was stirred at room temperature (25° C.) for 1 hour. The reaction mixture was purified by high performance preparative liquid chromatography (separation conditions: column: Agilent 10 Prep-C18 250×21.2 mm; column temperature: 25° C.; mobile phase: water (10 mM/L trifluoroacetic acid)-acetonitrile; acetonitrile: 10%-30% 12 min, flow rate: 30 mL/min) to obtain compound 13.

$^1$H NMR (400 MHz, DMSO-$d_6$) δ 7.97 (t, J=5.7 Hz, 3H), 7.55-7.42 (m, 12H), 6.84 (d, J=2.0 Hz, 3H), 4.50 (s, 6H), 4.39 (t, J=5.5 Hz, 3H), 3.71 (d, J=16.1 Hz, 3H), 3.65-3.56 (m, 12H), 3.54-3.39 (m, 27H), 3.38-3.27 (m, 6H), 3.15 (q, J=5.8 Hz, 6H), 2.83 (dd, J=11.6, 5.1 Hz, 3H), 2.73-2.61 (m, 3H), 2.35 (s, 9H), 2.12 (t, J=8.1 Hz, 6H), 1.67-1.51 (m, 6H).

MS (ESI) m/z $(M/2+H)^+$=881.3.

HPLC 98.9% purity; retention time was 5.747 min.

Separation conditions: column: ZORBAX Extend-C18 4.6*150 mm, 3.5 um; column temperature: 30° C.; mobile phase: water (10 mM/L TFA)-acetonitrile; acetonitrile: 5%-5% 0-8 min, 5-95% 8-15 min; flow rate: 1.0 mL/min.

Synthesis of Embodiment I4

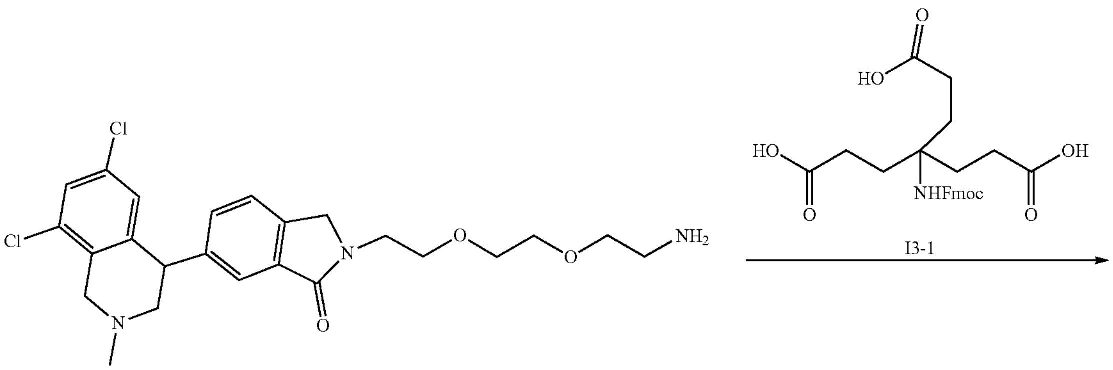

B1-8

I3-1

-continued
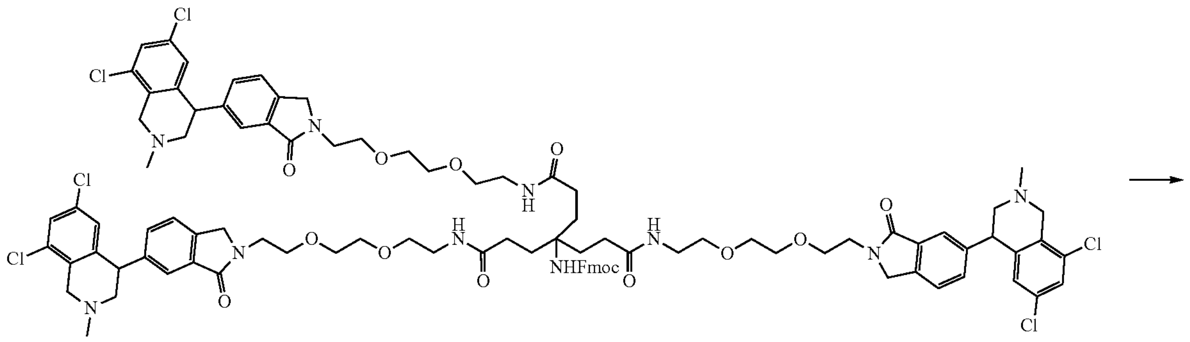
I4-1
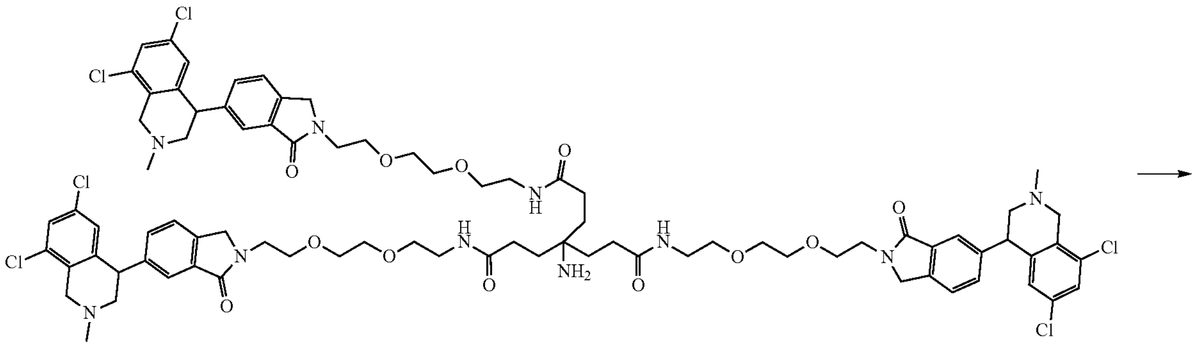
I4-2
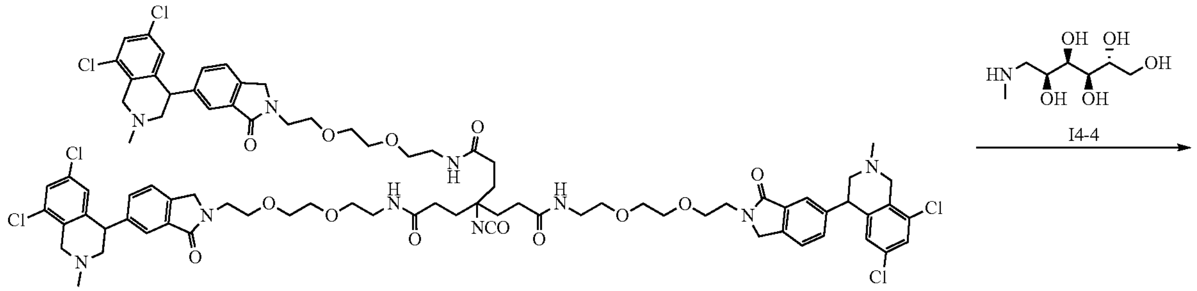
I4-3
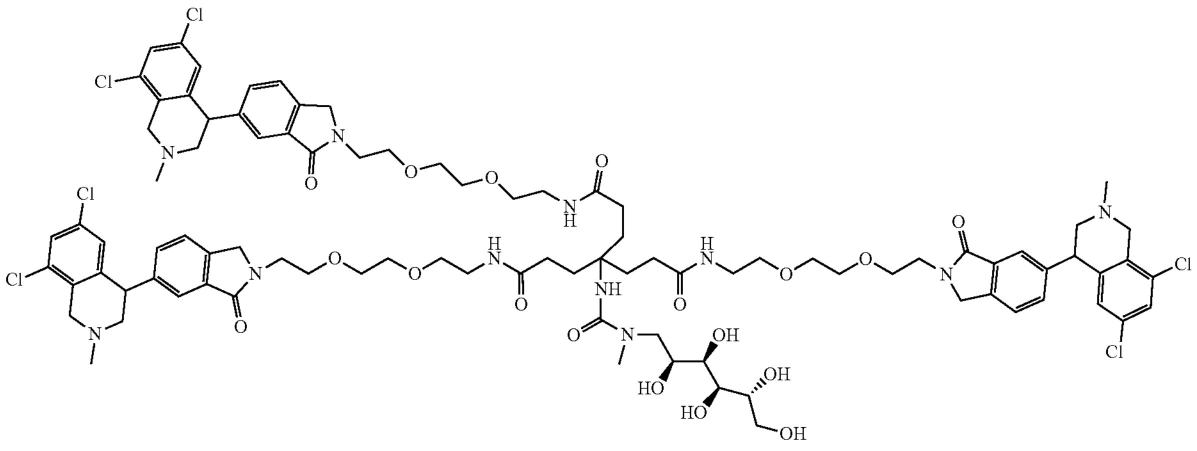
I4

Step 1: Preparation of Compound I4-2

Similar to the synthesis of compound I3, intermediate I4-3 was synthesized.

(ESI) m/z $(M/2+H)^+$=814.5.

Step 2: Preparation of Compound I4-3

Compound I4-2 (90 mg, 0.055 mmol) and triethylamine (33 mg, 0.33 mmol) were dissolved in a mixed solvent of tetrahydrofuran (2 mL) and dichloromethane (2 mL), and the system was cooled to 0° C. under nitrogen atmosphere, to which triphosgene (49 mg, 0.165 mmol) was added. The system was diluted by adding ethyl acetate (100 mL), washed with saturated aqueous sodium bicarbonate solution and saturated aqueous sodium chloride solution sequentially, and the organic phases were combined, dried over anhydrous sodium sulfate, filtered, and the filtrate was concentrated to obtain compound 14-3, which was directly used in the next reaction step without further purification.

(ESI) m/z $(M/2+H)^+$=827.5.

Step 3: Preparation of Compound I4

Compound I4-3 (91 mg, 0.055 mmol) was dissolved in N,N-dimethylformamide (2 mL), to which compound I4-4 (32 mg, 0.165 mmol) was added at room temperature (25° C.), after the addition, the system was stirred at room temperature (25° C.) for 1 hour. The reaction mixture was purified by high performance preparative liquid chromatography (separation conditions: column: Agilent 10 Prep-C18 250×21.2 mm; column temperature: 25° C.; mobile phase: water (10 mM/L ammonium bicarbonate)-acetonitrile; acetonitrile: 65%-95% 12 min, flow rate: 30 mL/min) to obtain compound 14.

$^1$H NMR (400 MHz, DMSO-$d_6$) δ 7.79 (t, J=5.6 Hz, 3H), 7.54-7.37 (m, 13H), 6.85 (d, J=2.1 Hz, 3H), 5.75 (s, 1H), 5.13 (d, J=4.4 Hz, 1H), 4.55 (dd, J=14.2, 5.9 Hz, 2H), 4.51-4.46 (m, 7H), 4.41-4.35 (m, 4H), 3.76-3.55 (m, 19H), 3.54-3.43 (m, 18H), 3.37-3.34 (m, 5H), 3.17-3.08 (m, 7H), 2.83 (dd, J=11.6, 5.1 Hz, 3H), 2.76 (s, 3H), 2.67-2.62 (m, 3H), 2.35 (s, 9H), 2.05-1.95 (m, 6H), 1.83-1.71 (m, 6H).

(ESI) m/z $(M/2+H)^+$=924.8.

HPLC 100% purity; retention time was 8.367 min.

Separation conditions: column: Waters XBridge 4.6*100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min.

Synthesis of Embodiment J1

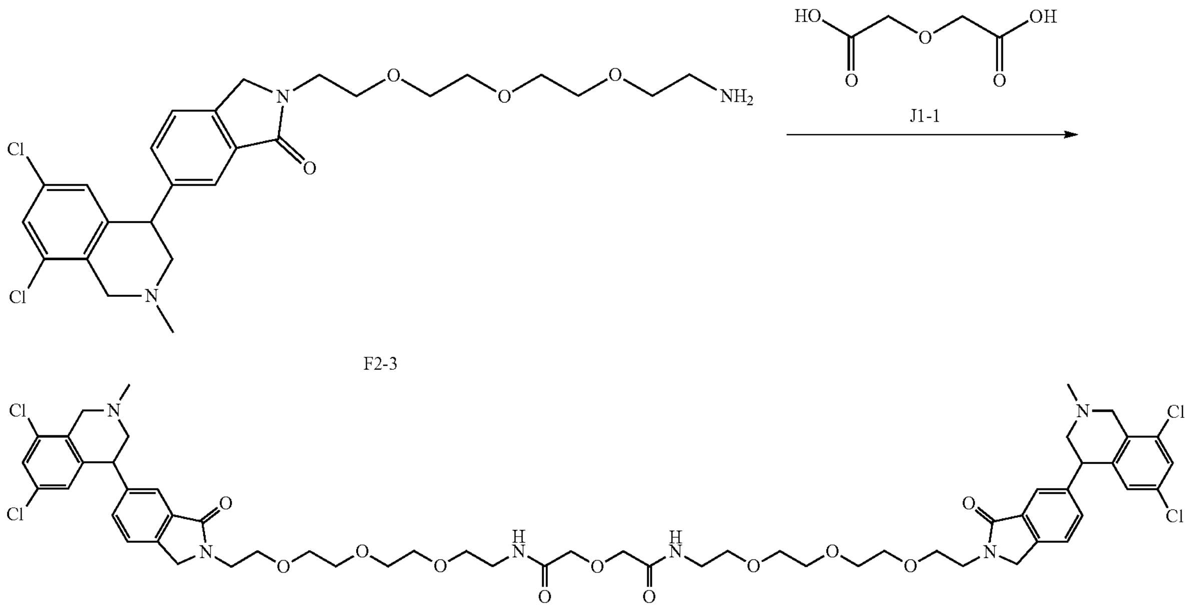

F2-3

J1-1

J1

Step 1: Preparation of Compound J1

Compound F2-3 (90 mg, 0.17 mmol) and compound J1-1 (7.7 mg, 0.06 mmol) were dissolved in N,N-dimethylformamide (2 mL), to which 2-(7-azobenzotriazole)-N,N,N',N'-tetramethyluronium hexafluorophosphate (66 mg, 0.17 mmol) and N,N-diisopropylethylamine (45 mg, 0.34 mmol) were added at room temperature (25° C.), after the addition, the system was stirred at room temperature (25° C.) for 2 hours. The reaction mixture was purified by high performance preparative liquid chromatography (separation conditions: column: Welch Xtimate® C18 21.2×250 mm; column temperature: 25° C.; mobile phase: water (10 mM/L ammonium bicarbonate)-acetonitrile; acetonitrile: 65%-95% 9 min; flow rate 30 mL/min) to obtain compound J1.

$^1$H NMR (400 MHz, DMSO-$d_6$) δ 8.04 (t, J=5.8 Hz, 2H), 7.51-7.45 (m, 8H), 6.85 (d, J=2.0 Hz, 2H), 4.50 (s, 4H), 4.40 (t, J=5.4 Hz, 2H), 3.92 (s, 4H), 3.72 (d, J=16.2 Hz, 2H), 3.66-3.59 (m, 8H), 3.53-3.48 (m, 8H), 3.47-3.42 (m, 10H), 3.41-3.38 (m, 4H), 3.27-2.22 (m, 4H), 2.87-2.82 (m, 2H), 2.69-2.64 (m, 2H), 2.36 (s, 6H).

MS (ESI) m/z $(M+H)^+$=1143.4.

HPLC 100% purity; retention time was 7.582 min.

Separation conditions: column: Waters XBridge 4.6*100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min.

Similar to the synthesis of embodiment J1, embodiments J2-J3 were synthesized, as shown in Table 12 below:

TABLE 12

| Structural formula and analysis data of embodiments J2-J3 | |
|---|---|
| Embodiment J2 | 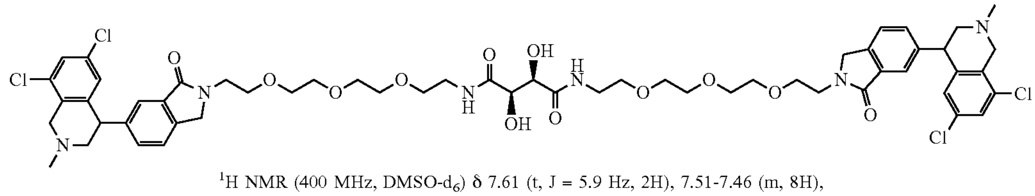<br>$^1H$ NMR (400 MHz, DMSO-$d_6$) δ 7.61 (t, J = 5.9 Hz, 2H), 7.51-7.46 (m, 8H), 6.85 (d, J = 2.1 Hz, 2H), 5.60 (d, J = 7.2 Hz, 2H), 4.51 (s, 4H), 4.40 (t, J = 5.4 Hz, 2H), 4.23 (d, J = 7.0 Hz, 2H), 3.72 (d, J = 16.2 Hz, 2H), 3.67-3.61 (m, 8H), 3.54-3.50 (m, 8H), 3.47-3.43 (m, 10H), 3.40 (t, J = 6.0 Hz, 4H), 3.28-3.18 (m, 4H), 2.86-2.82 (m, 2H), 2.68-2.64 (m, 2H), 2.36 (s, 6H).<br>MS (ESI) m/z $(M + H)^+$ = 1159.4.<br>HPLC 100% purity; retention time was 7.243 min.<br>Separation conditions: column: Waters XBridge 4.6 * 100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min. |
| Embodiment J3 | 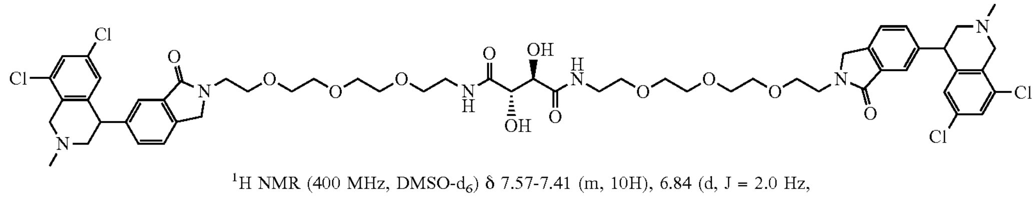<br>$^1H$ NMR (400 MHz, DMSO-$d_6$) δ 7.57-7.41 (m, 10H), 6.84 (d, J = 2.0 Hz, 2H), 5.86 (d, J = 5.3 Hz, 2H), 4.51 (s, 4H), 4.44 (s, 2H), 4.13 (d, J = 5.0 Hz, 2H), 3.79 (s, 2H), 3.69-3.61 (m, 8H), 3.54-3.42 (m, 18H), 3.39-3.37 (m, 4H), 3.28-3.11 (m, 4H), 2.94-2.76 m, 4H), 2.43 (s, 3H).<br>MS (ESI) m/z $(M + H)^+$ = 1159.4.<br>HPLC 100% purity; retention time was 7.328 min.<br>Separation conditions: column: Waters XBridge 4.6 * 100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min. |

Synthesis of Embodiment J4

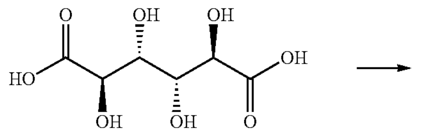

J4-1

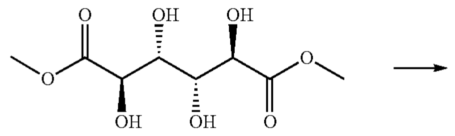

J4-2

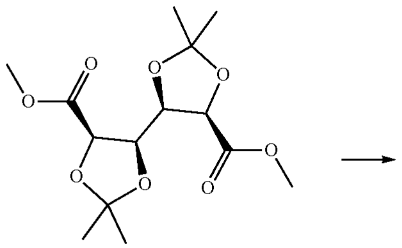

J4-3

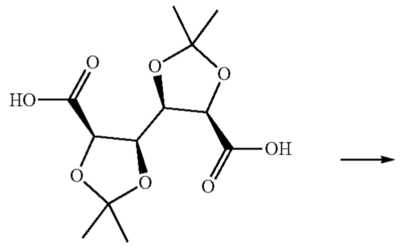

J4-4

-continued

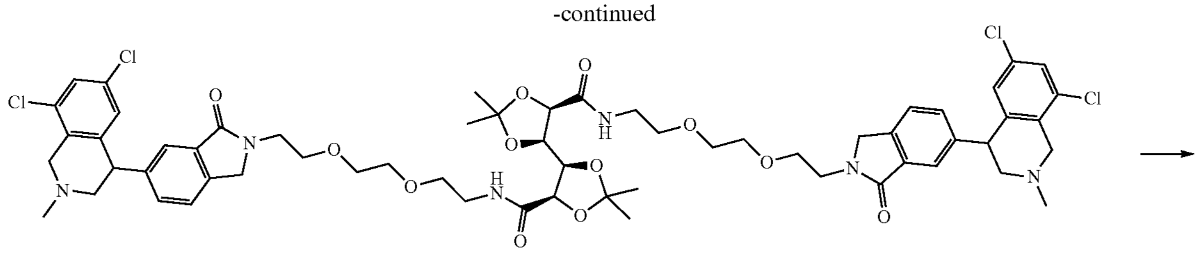

J4-5

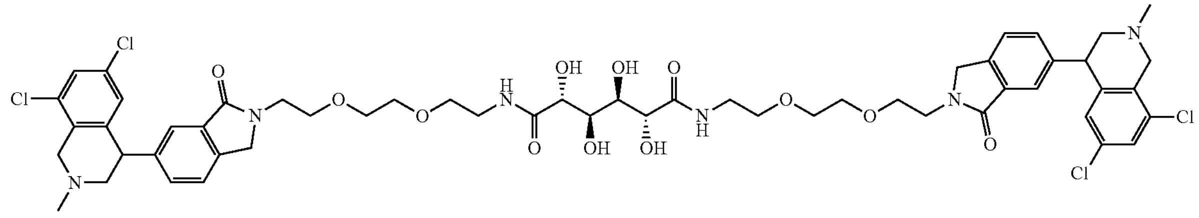

J4

Step 1: Preparation of Compound J4-2

Compound J4-1 (10 g, 47 mmol) was dissolved in methanol (200 mL), to which concentrated sulfuric acid (2.5 mL, 47 mmol) was added, after the addition, the system was stirred at 80° C. for 3 days. The system was cooled to room temperature, continued to stir for 2 days, and a large amount of solids were precipitated. The reaction mixture was filtered, and the resulting solid was washed with methanol for three times, dried to obtain compound J4-2, which was directly used in the next step without further purification.

$^1H$ NMR (400 MHz, DMSO-$d_6$) δ 4.92 (d, J=8.0 Hz, 2H), 4.85-4.78 (m, 2H), 4.31 (dd, J=8.0, 1.1 Hz, 2H), 3.81-3.74 (m, 2H), 3.64 (s, 6H).

Step 2: Preparation of Compound J4-3

Compound J4-2 (500 mg, 2.1 mmol) was dissolved in acetone (5 mL), to which 2,2-dimethoxypropane (2.6 mL, 47 mmol) and p-toluenesulfonic acid (79 mg, 0.415 mmol) were added, after the addition, the system was stirred at 65° C. for 3 hours. The reaction mixture was cooled to room temperature and spin-dried to obtain solids, to which methanol was added, then the reaction mixture was filtered, and the resulting solid was washed with methanol for three times, dried to obtain compound J4-3, which was directly used in the next step without further purification.

$^1H$ NMR (400 MHz,) δ 4.57-4.53 (m, 2H), 4.44-4.39 (m, 2H), 3.71 (s, 6H), 1.38 (s, 6H), 1.33 (s, 6H).

Step 3: Preparation of Compound J4-4

Compound J4-3 (500 mg, 1.57 mmol) was dissolved in a mixed solvent of tetrahydrofuran (4 mL) and water (1 mL), to which sodium hydroxide (100 mg, 2.5 mmol) was added, after the addition, the system was stirred at room temperature (25° C.) for 16 hours. The pH of the reaction mixture was adjusted to 5 with 3M hydrochloric acid solution, then the reaction mixture was extracted with ethyl acetate, and the organic phase was dried, filtered and concentrated to obtain solids, to which methanol was added for slurry, then the reaction mixture was filtered, and the resulting solid was washed with methanol for three times, dried to obtain compound J4-4, which was directly used in the next step without further purification.

$^1H$ NMR (400 MHz, DMSO-$d_6$) δ 13.18 (s, 2H), 4.46-4.43 (m, 2H), 4.41-4.37 (m, 2H), 1.38 (s, 6H), 1.33 (s, 6H).

Step 4: Preparation of Compound J4-5

Similar to the synthesis of embodiment J1, compound J4-5 was synthesized.

MS (ESI) m/z $(M+H)^+$=1211.60

Step 5: Preparation of Compound J4

Compound J4-5 (52 mg, 0.042 mmol) was dissolved in methanol (2 mL), to which concentrated hydrochloric acid (0.5 mL) was added, after the addition, the system was stirred at room temperature for 5 hours. The reaction mixture was concentrated, dissolved by adding methanol, and the pH of which was adjusted to 8 by adding sodium bicarbonate solution, then the reaction mixture was filtered, and the filtrate was purified by high performance preparative liquid chromatography (separation conditions: column: Agilent 10 Prep-C18 250×21.2 mm; column temperature: 25° C.; mobile phase: water (10 mM/L ammonium bicarbonate)-acetonitrile; acetonitrile: 65%-95% 9 min, flow rate: 30 mL/min) to obtain compound J4.

$^1H$ NMR (400 MHz, DMSO-$d_6$) δ 7.47 (dd, J=14.8, 7.0 Hz, 4H), 7.40 (q, J=3.5, 2.9 Hz, 6H), 6.78 (d, J=2.0 Hz, 2H), 5.20 (d, J=7.0 Hz, 2H), 4.45 (s, 4H), 4.35-4.28 (m, 4H), 4.07 (d, J=7.0 Hz, 2H), 3.73 (dd, J=5.8, 2.5 Hz, 2H), 3.68-3.54 (m, 10H), 3.47-3.32 (m, 14H), 3.22-3.18 (m, 2H), 3.12 (dd, J=13.3, 6.2 Hz, 2H), 2.77 (dd, J=11.6, 5.1 Hz, 2H), 2.59 (dd, J=11.6, 5.7 Hz, 2H), 2.29 (s, 6H).

MS (ESI) m/z $(M+H)^+$=1131.40

HPLC 100% purity; retention time was 6.968 min

Separation conditions: column: Waters XBridge 4.6*100 mm, 3.5 um; column temperature: 40° C.; mobile phase: water (10 mM ammonium bicarbonate)-acetonitrile; acetonitrile: 5%-95% 7 min, 95% 8 min; flow rate: 1.2 mL/min.

Experimental Example 1 Cell-Based NHE3 Activity Analysis Under Transient and Persistent Conditions Opossum kidney (OK) cells were obtained from ATCC and cultured and expanded according to its instructions. OK monoclonal stable cell lines expressing the Rat NHE3 (Gene Bank registration number: M85300) protein and OK monoclonal stable cell lines expressing the Human NHE3 (Gene Bank registration number: NM_004174.1) protein were constructed by lentivirus infection.

The general procedure of the cell-based NHE3 activity experiments under transient conditions (transient inhibition) was based on an adaptation method of the pH-sensitive dye method originally reported by Tisen (Proc. Natl. Acad. Sci. USA) (1984) 81(23):7436-7440) to measure rat NHE3-mediated Na+-dependent reverse H+ transport, and was optimized according to the instructions "Measuring Intracellular pH With the FLIPR and FLIPR 384 Fluorometric Imaging Plate Reader Systems" published by Molecular Devices. The specific method was: Rat NHE3 OK monoclonal cells or Human NHE3 OK monoclonal cells were inoculated into 384-well plates and grew overnight. The medium was aspirated from the wells and the cells were washed twice with FLIPR buffer (Hank's BSS 1×, 20 mM HEPES, 1% BSA) followed by incubation with FLIPR buffer (Hank's BSS 1×, 20 mM HEPES, 1% BSA) containing 5 mM BCECF-AM (Invitrogen) for 45 min at room temperature. Subsequently, 5 mL of 200 mM NH4Cl-HEPES buffer (Hank's BSS 1×, 20 mM HEPES, 200 mM $NH_4Cl$) was added and the cells were incubated for 15-20 minutes at room temperature. Cells were washed twice with 20 mM $NH_4Cl$-HEPES buffer (Hank's BSS 1×, 20 mM HEPES, 20 mM $NH_4Cl$). NHE3-mediated pH sensitization in cells was normalized by addition of containing 0.4 mM amiloride (EIPA) and 0-30 mM test compound or Na-HEPES buffer (100 mM NaCl, 50 mM HEPES, 10 mM glucose, 5 mM KCl, 2 mM $CaCl_2$), 1 mM $MgCl_2$, pH 7.4) and monitoring of BCECF-AM fluorescence at λem 535 nm excitated by λex 440 nm and λex 490 nm respectively. Ratio=fluorescence value (λex 490 nm)/fluorescence value (λex 440 nm) was set, the average value of the Ratio difference between the end time and the start time between the duplicate wells was calculated, the average value and the concentration value of the compound were drawn, and Graphpad Prism software was used to estimate IC50 value. The results were shown in Table 13:

The general procedure of the cell-based NHE3 activity assay under persistent conditions (persistent inhibition) was: Rat NHE3 OK monoclonal cells or Human NHE3 OK monoclonal cells were inoculated into 384-well plates and grew overnight. The medium was aspirated from the wells and the cells were washed twice with FLIPR buffer (Hank's BSS 1×, 20 mM HEPES, 1% BSA) followed by the addition of Na-HEPES buffer containing 0-30 mM test compound (100 mM NaCl, 50 mM HEPES, 10 mM glucose, 5 mM KCl, 2 mM $CaCl_2$, 1 mM $MgCl_2$, pH 7.4) and incubated for 60 minutes at room temperature. The compounds were aspirated from the wells and incubated with FLIPR buffer (Hank's BSS 1×, 20 mM HEPES, 1% BSA) containing 5 mM BCECF-AM (Invitrogen) for 45 minutes at room temperature. Subsequently, 5 mL of 200 mM $NH_4Cl$-HEPES buffer (Hank's BSS 1×, 20 mM HEPES, 200 mM $NH_4Cl$) was added and incubated for 15-20 minutes at room temperature. The cells were washed twice with 20 mM $NH_4Cl$-HEPES buffer (Hank's BSS 1×, 20 mM HEPES, 20 mM $NH_4CC$). NHE3-mediated pH sensitization in cells was normalized by addition of Na-HEPES buffer (100 mM NaCl, 50 mM HEPES, 10 mM glucose, 5 mM KCl, 2 mM $CaCl_2$, 1 mM $MgCl_2$, pH 7.4) containing 0.4 mM amiloride (EIPA, a selective antagonist of NHE-1 activity that does not inhibit NHE3) and monitoring of BCECF fluorescence at λem 535 nm excitated by λex 440 nm and λex 490 nm respectively. Ratio=fluorescence value (λex 490 nm)/fluorescence value (λex 440 nm) was set, the average value of the Ratio difference between the end time and the start time between the duplicate wells was calculated, the average value and the concentration value of the compound were drawn, and the dose-response-inhibition (four parameters) equation was used to estimate EC50 value by GraphpadPrism. The results were shown in Tables 13 and Table 14:

TABLE 13

NHE3 inhibitory activity of intermediates based on opossum kidney cells under transient conditions

| Intermediates number | Cell-based NHE3 inhibition $IC_{50}$ (uM) under transient conditions |
|---|---|
| A1-13 | 0.60 |
| A2-13 | 1.63 |
| B1-6 | 0.53 |
| B2-6 | 0.17 |
| B3-6 | 0.62 |
| B4-6 | 0.79 |
| B5-6 | 1.69 |
| C1-11 | 1.24 |
| D1-7 | 1.44 |
| E1-9 | 3.17 |

TABLE 14

NHE3 inhibitory activity of compounds based on opossum kidney cells under transient and persistent conditions

| Embodiment compound No. | Cell-based NHE3 inhibition $IC_{50}$ (uM) under transient conditions | Cell-based NHE3 inhibition $IC_{50}$ (uM) under persistent conditions |
|---|---|---|
| Tenapanor | 0.74 | 0.56 |
| A1 | 0.43 | 0.50 |
| A2 | 3.14 | ND |
| B1 | 0.52 | 0.02 |
| B2 | 2.05 | ND |
| B3 | 0.77 | 0.41 |
| B4 | 0.93 | 0.45 |
| B5 | 0.23 | 0.57 |
| B6 | 1.05 | 0.04 |
| C1 | 0.22 | 0.59 |
| D1-P1 | 0.28 | 0.02 |
| D1-P2 | 2.33 | 3.61 |
| D2-P1 hydrochloride salt | 0.16 | 0.02 |
| D2-P2 hydrochloride salt | 0.27 | 0.12 |
| E1 | 0.06 | 0.05 |
| F1 | 0.91 | 0.64 |
| F2 | 0.62 | 0.08 |
| G1 | 0.93 | 0.10 |
| H1 | 0.91 | 0.04 |
| H2 | 0.48 | 0.06 |
| I1 | 0.35 | 0.09 |
| I2 | 0.17 | 0.07 |
| I3 | 0.19 | 0.13 |
| I4 | 0.20 | 0.31 |
| J1 | 0.43 | 0.03 |
| J2 | 0.32 | 0.05 |
| J3 | 0.26 | 0.08 |
| J4 | 0.25 | 0.05 |

Experimental Example 2 Inhibition of Phosphate and Sodium Absorption in the Intestine of Rats by a Single Dose Compound D1-P1-S was evaluated by measuring urinary phosphorus, urinary sodium concentration and fecal form.

Six-week-old Sprague-Dawley rats were purchased from Beijing Vital River Laboratory Animal Technology Co., Ltd. Two animals per cage were placed in SPF class animal rooms for acclimatization for about a week. Throughout the study period, animals were fed feed and water freely and the light cycle was 12 h light/12 h dark. Animal groups: vehicle group, n=5; tenapanor 0.3 mg/kg group, n=5; D1-P1-S 0.03 mg/kg group, n=5; D1-P1-S 0.1 mg/kg, n=5; D1-P1-S 0.3 mg/kg, n=5; D1-P1-S1.0 mg/kg, n=5.

On the day of the experiment, after 8 hours of fasting, the animals were administered the test compound or solvent (0.5% Tween 80+99.5% distilled water) by gavage. The animals were then transferred into metabolic cages for single-cage feeding, and the feed was restored. After 16 hours of administration, urine samples were collected and food consumption was recorded, and the fecal form in the collection funnel was evaluated by two independent observations. Standard for fecal form score: 1, normal pellets; 2, slightly soft feces (pellets adhered to the side wall of the collector due to moisture); 3, soft feces (loss the normal shape of the pellets); 4, loose and amorphous (completely loss shape, with blot pattern); 5, diarrhea (watery feces). Fecal form score (FFS) in rats was determined by averaging two independent observation scores for all rats within the same group (n=5); the vehicle group mean was 1.

The urine was centrifuged at 3220 g for 5 minutes at 4° C., and the urinary phosphorus concentration (phosphomolybdic acid UV endpoint colorimetric method) and urinary sodium concentration (ion selective electrode method) were measured.

Results were indicated as mean±standard error (Means±SEM). Urinary phosphorus excretion amount (or urinary sodium excretion amount) in rats was standardized corrected against respective dietary phosphorus (or sodium) intake, and the formula was: standardized correction value of urinary phosphorus excretion amount (indicated as nP)=urinary phosphorus excretion amount÷dietary phosphorus intake amount; standardized correction value of urinary sodium excretion amount (indicated as nNa)=urinary sodium excretion amount÷dietary sodium intake amount; fecal form score was analyzed by monofactorial variance, and verified by non-parametric test. *, $p<0.05$; **, $p<0.01$; * $p<0.001$; ****, $p<0.0001$.

Figure 2:
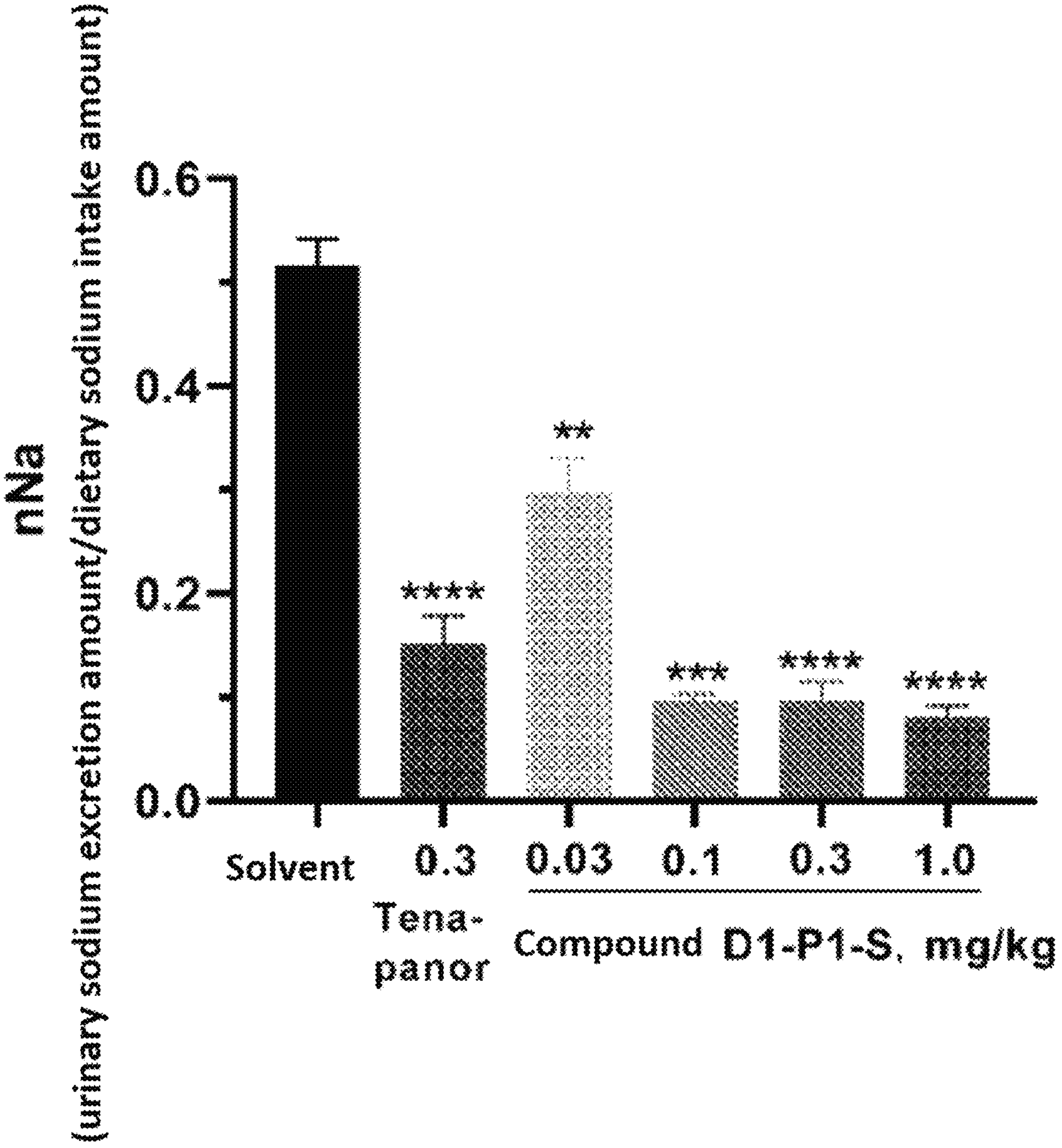
FIG. 2 is a standardized correction value (nNa) of urinary sodium excretion amount against dietary sodium intake amount according to embodiments of the present disclosure.
Figure 3:
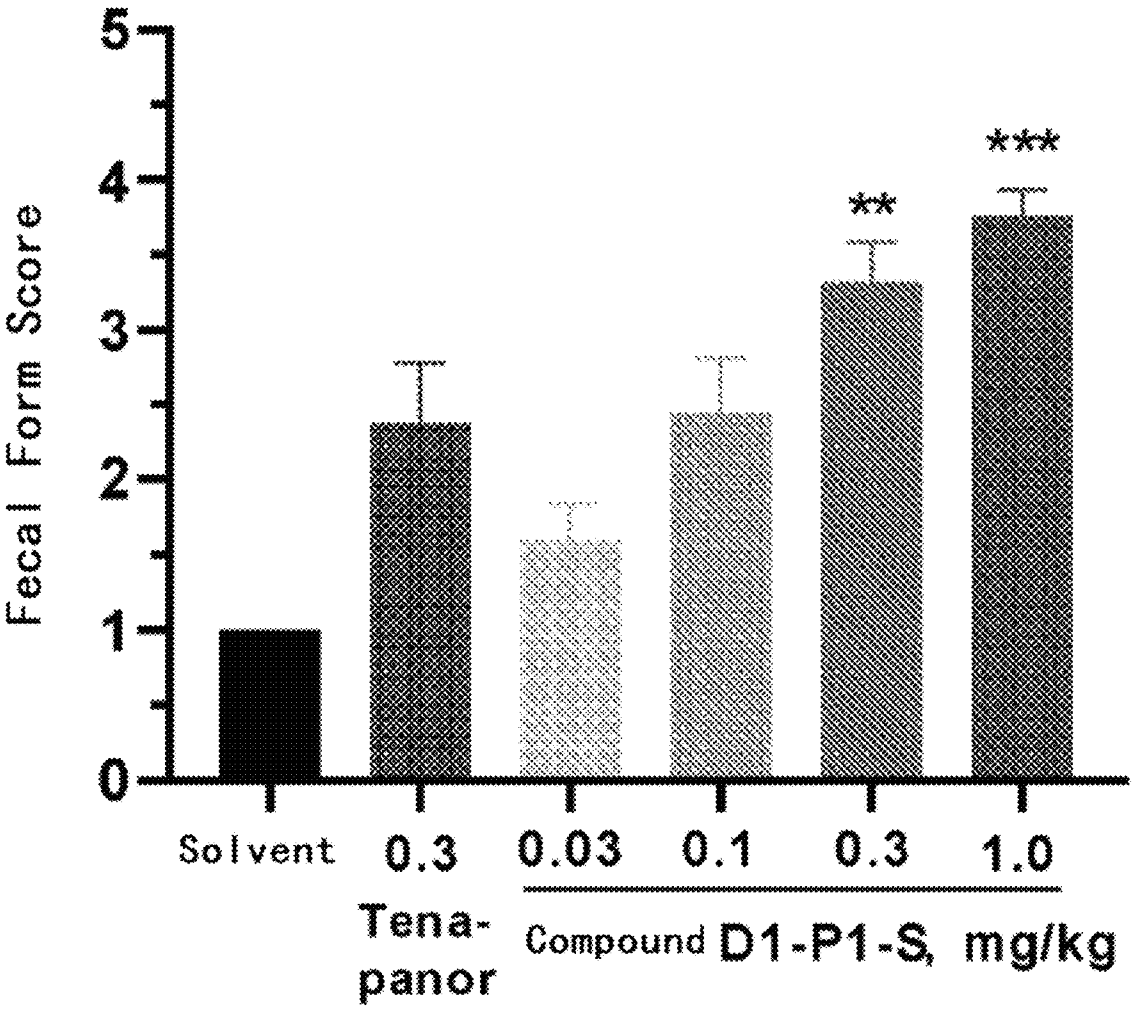
FIG. 3 is fecal form score according to embodiments of the present disclosure.

FIGS. 1 to 3 showed the effects of compound D1-P1-S on urinary phosphorus, urinary sodium excretion and fecal form in normal rats after a single administration. These results showed that compound D1-P1-S had dose-effect relationship in reducing urinary phosphorus excretion amount, and could significantly reduce urinary phosphorus excretion amount at doses of 0.3 mg/kg and 1.0 mg/kg. The effect of D1-P1-S was better than Tenapanor in reducing urinary phosphorus excretion amount at the same dose (0.3 mg/kg). Compound D1-P1-S could significantly reduce urinary sodium excretion amount. The water content in rat feces has the tendency of increasing with the increase of the dose of compound D1-P1-S.

Experimental Example 3 Effects of Multiple Administrations on Serum Phosphorus Concentration in Rats Compound D1-P1-S was evaluated by measuring serum phosphorus concentration, urinary phosphorus, urinary sodium concentration and fecal form in rats.

Six-week-old Sprague-Dawley rats were purchased from Beijing Vital River Laboratory Animal Technology Co., Ltd. Two animals per cage were placed in SPF class animal rooms for acclimatization for about a week. Throughout the study period, animals were fed feed and water freely and the light cycle was 12 h light/12 h dark. Animal groups: vehicle group, n=5; Tenapanor 0.05 mg/kg, n=5; D1-P1-S 0.01 mg/kg, n=5; D1-P1-S 0.05 mg/kg, n=5; D1-P1-S 0.5 mg/kg, n=5; D1-P1-S 1.0 mg/kg, n=5.

After the start of the experiment, the feeding rhythm of the rats was adjusted to diurnal feeding by fasting overnight for 16 hours and recovering feed for 8 hours during the day. After the administration started, the test compound or the solvent (0.5% Tween 80+99.5% distilled water) was gavaged twice a day during the feeding period, with an interval of 4 hours, for 14 consecutive days. Animal body weight and food consumption were measured every day, serum phosphorus concentration (including baseline value before administration), 24-hour urinary phosphorus excretion amount, and 24-hour urinary sodium excretion amount were measured 1-2 times a week, and feces form in the collection funnel was scored (through two independent observations to assess fecal form). Standard for fecal form score: 1, normal pellets; 2, slightly soft feces (pellets adhered to the side wall of the collector due to moisture); 3, soft feces (loss the normal shape of the pellets); 4, loose and amorphous (completely loss shape, with blot pattern); 5, diarrhea (watery feces). Fecal form score (FFS) in rats was determined by averaging two independent observation scores for all rats within the same group (n=5); the vehicle group mean was 1.

Figure 4:
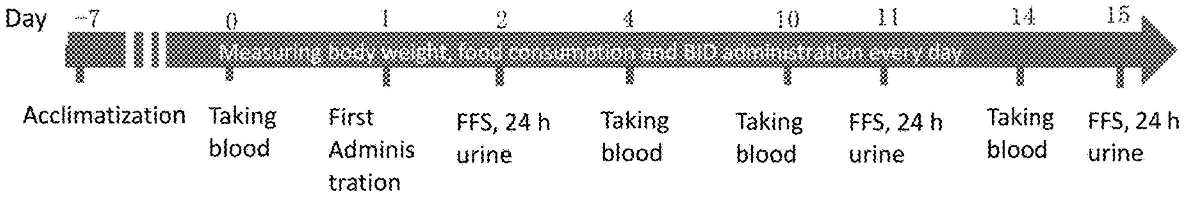
FIG. 4 is a diagram of an experimental procedure according to embodiments of the present disclosure.

The experimental procedure was shown in FIG. 4 below.

After standing at room temperature for 2 hours, the blood was centrifuged at 4500 g for 10 minutes at 4° C.; and the urine was centrifuged at 3220 g for 5 minutes at 4° C., and the serum phosphorus concentration and urinary phosphorus concentration (phosphomolybdic acid UV endpoint colorimetric method), urinary sodium concentration (indirect ion electrode method) were measured.

Results were indicated as mean±standard error (Means±SEM), n=5 animals/group. Urinary phosphorus excretion amount (or urinary sodium excretion amount) in rats was standardized corrected against respective dietary phosphorus (or sodium) intake, and the formula was: standardized correction value of urinary phosphorus excretion amount (indicated as nP)=urinary phosphorus excretion amount÷dietary phosphorus intake amount; standardized correction value of urinary sodium excretion amount (indicated as nNa)=urinary sodium excretion amount÷dietary sodium intake amount; fecal form score was analyzed by two-way variance, and verified by non-parametric test. *, $p<0.05$; , $p<0.01$; *, $p<0.001$; ****, $p<0.000^1$.

Experimental Results

Serum Phosphorus Concentration

Figure 5:
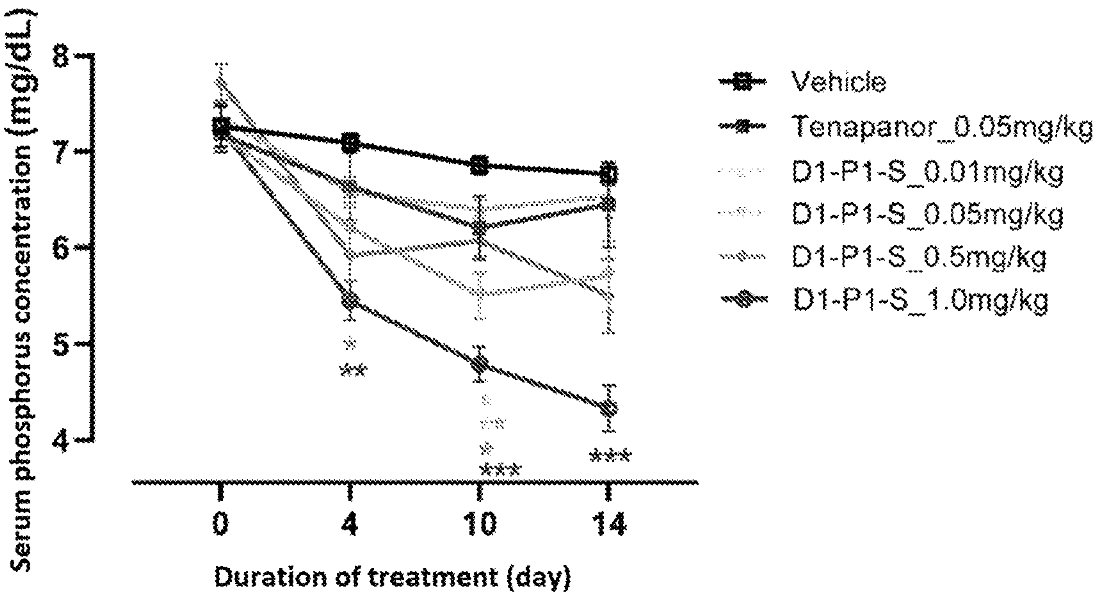
FIG. 5 is a serum phosphorus concentration in rats according to embodiments of the present disclosure.

Compared with the serum phosphorus concentration of rats in the solvent control group, compound D1-P1-S significantly decreased the serum phosphorus concentration of rats after treatment at doses of 0.5 mg/kg or 1.0 mg/kg for 4 days; after 10 days of treatment at the dose of 0.01 mg/kg, 0.05 mg/kg, 0.5 mg/kg, 1.0 mg/kg doses, the serum phosphorus concentration of rats decreased significantly; except for the highest dose group of 1.0 mg/kg, the serum phosphorus of the other groups tended to be stable. The effect of D1-P1-S at the dose of 0.01 mg/kg to reduce serum phosphorus concentration was similar to that of Tenapanor at the dose of 0.05 mg/kg. See FIG. 5 below for details.

Urinary Phosphorus Excretion

Figure 6:
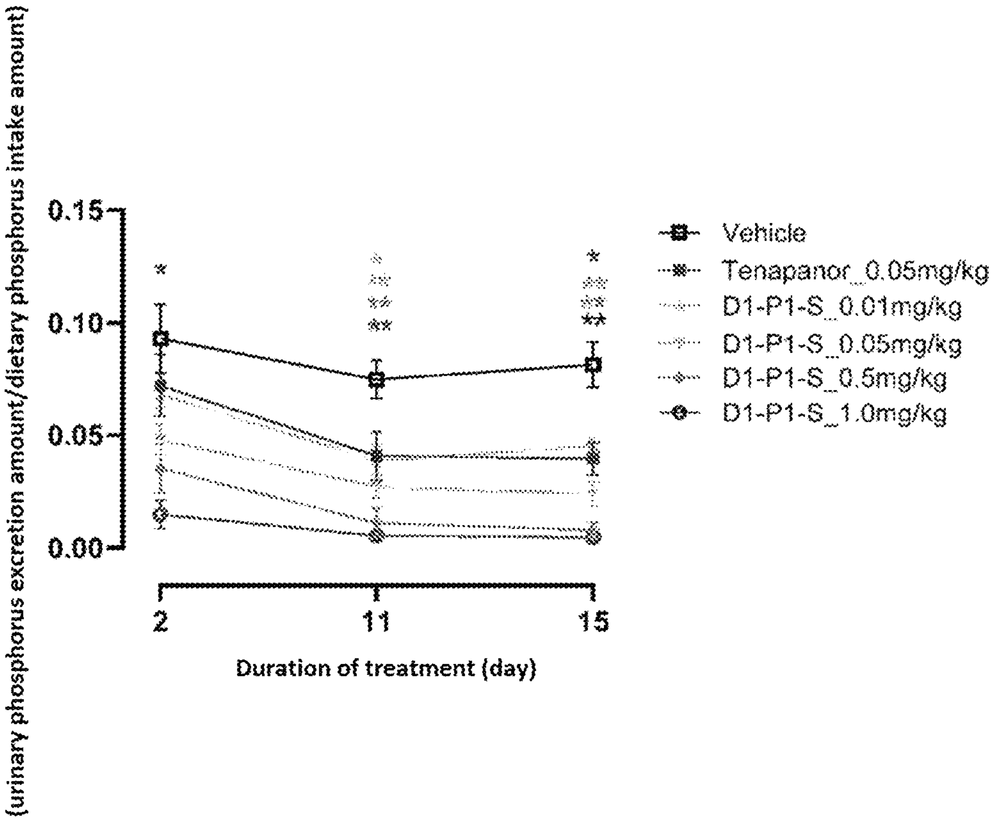
FIG. 6 is a standardized correction value (nP) for 24 h urinary phosphorus excretion amount and dietary phosphorus intake amount according to embodiments of the present disclosure.

The 24 h nP of the rats in each group was compared with that of the rats in the solvent group; after 1 day of treatment with compound D1-P1-S at the doses of 0.01 mg/kg, 0.05 mg/kg, 0.5 mg/kg and 1.0 mg/kg, the nP of rats tended to decrease, the higher the dose, the lower the nP, and nP significantly decreased at the dose of 1.0 mg/kg. After 10 days of treatment, at the doses of 0.01 mg/kg, 0.05 mg/kg, 0.5 mg/kg and 1.0 mg/kg, the nP all decreased significantly; and the nP of rats tended to be stable after 15 days, but the nP of rats in low dose group (0.01 mg/kg) tended to increase. The effect of D1-P1-S at the dose of 0.01 mg/kg to reduce nP in rats was similar to that of Tenapanor at the dose of 0.05 mg/kg. See FIG. 6 below for details.

Urinary Sodium Excretion

Figure 7:
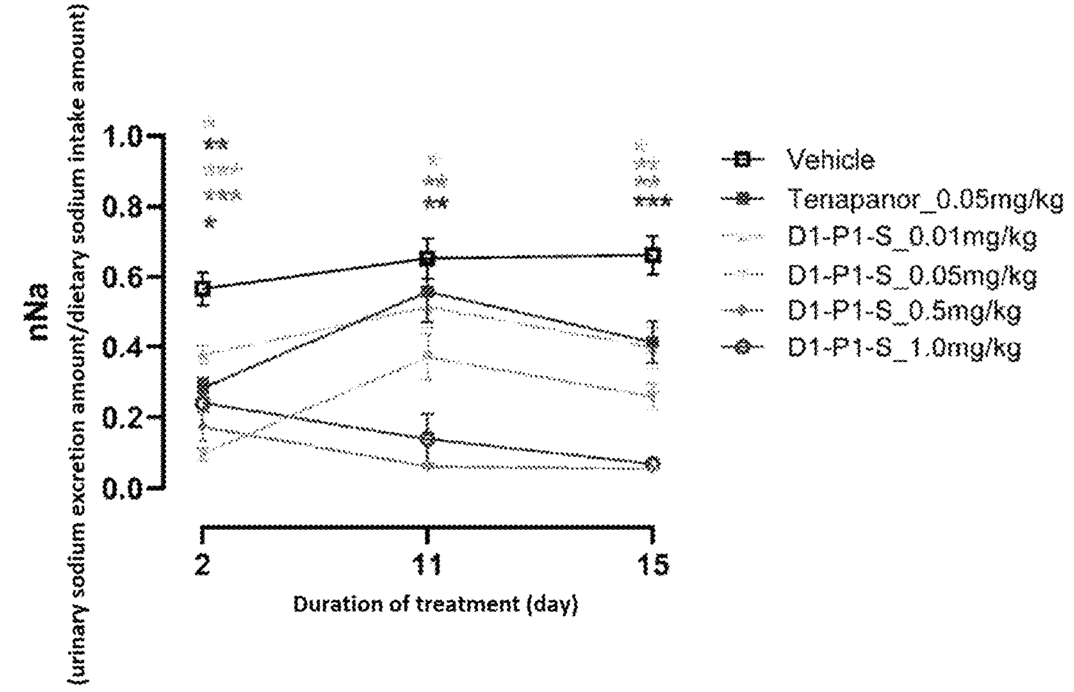
FIG. 7 is a standardized correction value (nNa) for 24 h urinary sodium excretion amount and dietary sodium intake amount according to embodiments of the present disclosure.

The 24 h nNa of the rats in each group was compared with that of the rats in the solvent group; after 1 day of treatment with compound D1-P1-S at the doses of 0.01 mg/kg, 0.05 mg/kg, 0.5 mg/kg and 1.0 mg/kg, the nNa of rats decreased significantly. However, after 10 days of treatment, the nNa in rats showed an increasing trend at the doses of 0.01 mg/kg and 0.05 mg/kg. See FIG. 7 below for details.

Fecal Form Score

Figure 8:
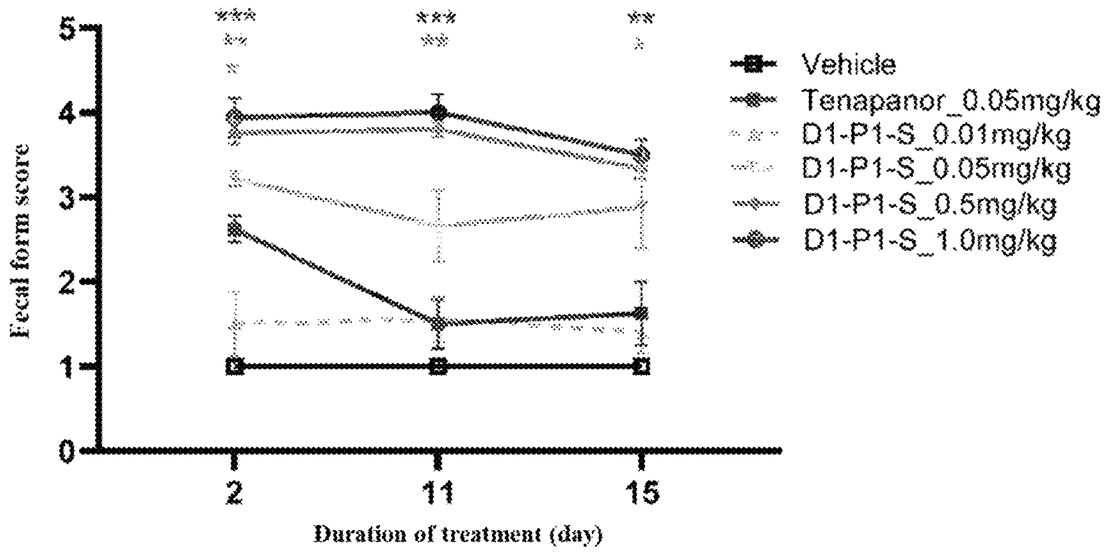
FIG. 8 is fecal form score according to embodiments of the present disclosure.

Compared with the rats in the solvent control group, the fecal form score of rats was significantly increased after 1 day of treatment with compound D1-P1-S at the doses of 0.05 mg/kg, 0.5 mg/kg and 1.0 mg/kg. Rats with high doses of 0.5 mg/kg and 1.0 mg/kg had more severe loose feces, but as the administration continued, the number of times of loose feces observed decreased. After treatment at a low dose of 0.01 mg/kg, no rats had loose feces. See FIG. 8 below details.

What is claimed is:

1. A compound as shown in formula (I), an optical isomer thereof and a pharmaceutically acceptable salt thereof, (I)

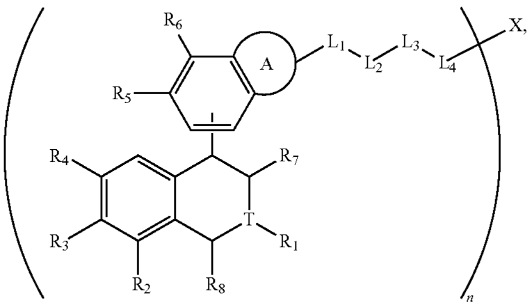

wherein, $R_1$ is selected from H, $C_{1-6}$ alkyl, $C_{3-6}$ cycloalkyl and 4-6 membered heterocycloalkyl, and the $C_{1-6}$ alkyl, $C_{3-6}$ cycloalkyl or 4-6 membered heterocycloalkyl is optionally substituted with 1, 2 or 3 R;

$R_2$, $R_3$, $R_4$, $R_5$, Re are each independently selected from H, halogen, OH, NH2, CN, $C_{1-6}$ alkyl and $C_{1-6}$ heteroalkyl, and the $C_{1-6}$ alkyl or $C_{1-6}$ heteroalkyl is optionally substituted with 1, 2 or 3 R;

$R_7$, $R_8$ are each independently selected from H;

T is selected from N;

ring A is selected from 5-6 membered heterocycloalkyl, 5-6 membered heterocycloalkenyl and 5-6 membered heteroaryl, and the 5-6 membered heterocycloalkyl, 5-6 membered heterocycloalkenyl or 5-6 membered heteroaryl is optionally substituted with 1, 2 or 3 R;

n is selected from 2 and 3;

$L_1$ is selected from

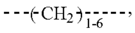, and the

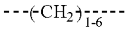

is optionally substituted with 1, 2 or 3 R;

$L_2$ is selected from

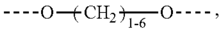, and the

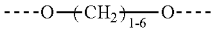

is optionally substituted with 1, 2 or 3 R;

$L_3$ is selected from a single bond,

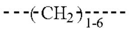 and 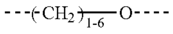, and the

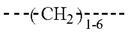 or 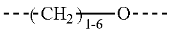

is optionally substituted with 1, 2 or 3 R;

$L_4$ is selected from

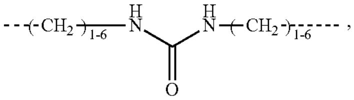,

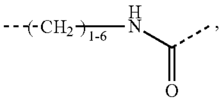, 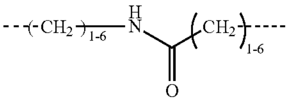,

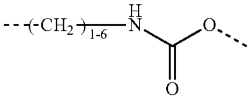, 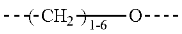 and

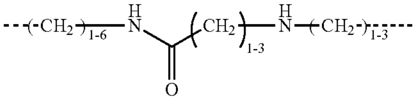, and the

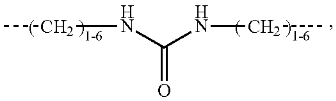, 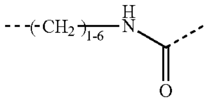,

-continued

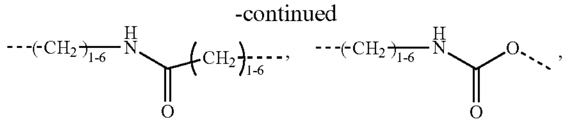

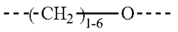

or

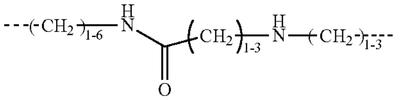

is optionally substituted with 1, 2 or O or 1-6 3 R;

X is selected from a single bond, O, N, NH, $C_{3-10}$ cycloalkyl, 5-10 membered heterocycloalkyl, $C_{1-6}$ alkyl, $C_{5-10}$ aryl and 5-12 membered heteroaryl, and the $C_{3-10}$ cycloalkyl, 5-10 membered heterocycloalkyl, $C_{1-6}$ alkyl, $C_{5-10}$ aryl or 5-12 membered heteroaryl is optionally substituted with 1, 2 or 3 Rx;

$R_X$ is each independently selected from OH, $NH_2$, $C_{1-6}$ alkyl, $C_{1-6}$ alkoxy, $C_{1-6}$ alkylthio, $C_{1-6}$ alkylamino, 5-6 membered heterocycloalkyl, —NHC(=O)N($C_{1-6}$ alkyl)$_2$, —NHC(=O)NH$C_{1-6}$ alkyl and —NHC(=O)$C_{1-6}$ alkyl-O—$C_{1-6}$ alkyl, and the $C_{1-6}$ alkyl, $C_{1-6}$ alkoxy, $C_{1-6}$ alkylthio, $C_{1-6}$ alkylamino, 5-6 membered heterocycloalkyl, —NHC(=O)N($C_{1-6}$ alkyl)$_2$, —NHC(=O)NH$C_{1-6}$ alkyl or —NHC(=O)$C_{1-6}$ alkyl-O—$C_{1-3}$ alkyl is optionally substituted with 1, 2, 3, 4 or 5 R;

R is each independently selected from H, halogen, OH, $NH_2$, CN,

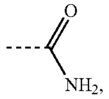

$C_{1-6}$ alkyl, $C_{1-6}$ alkoxy, $C_{1-6}$ alkylthio, $C_{1-6}$ alkylamino and 5-6 membered heterocycloalkyl, and the $NH_2$, $C_{1-6}$ alkyl, $C_{1-6}$ alkoxy, $C_{1-6}$ alkylthio, $C_{1-6}$ alkylamino or 5-6 membered heterocycloalkyl is optionally substituted with 1, 2 or 3 R';

R' is selected from F, Cl, Br, I, OH, $NH_2$, $CH_3$ and COOH;

the 4-6 membered heterocycloalkyl, $C_{1-6}$ heteroalkyl, 5-6 membered heterocycloalkyl, 5-6 membered heterocycloalkenyl, 5-6 membered heteroaryl, 6-12 membered heteroaromatic ring and 5-10 membered heterocycloalkyl contains 1, 2 or 3 heteroatoms or heteroatomic groups independently selected from O, NH, S, C(=O), C(=O)O, S(=O), S(=O)$_2$ and N.

2. The compound, the optical isomer thereof and the pharmaceutically acceptable salt thereof according to claim 1, wherein, R is selected from H, F, Cl, Br, I, OH, $NH_2$, COOH,

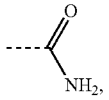

Me, $CF_3$,

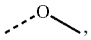, 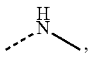, 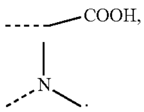, 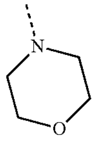 and

3. The compound, the optical isomer thereof and the pharmaceutically acceptable salt thereof according to claim 1, wherein, $R_1$ is selected from H, $CH_3$,

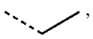, 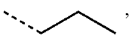, 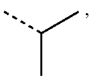, piperidinyl and tetrahydropyrrolyl, and the $CH_3$,

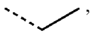, 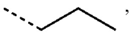, 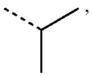, piperidinyl or tetrahydropyrrolyl is optionally substituted with 1, 2 or 3 R.

4. The compound according to claim 3, the optical isomer thereof and the pharmaceutically acceptable salt thereof, wherein, $R_1$ is selected from H, $CH_3$,

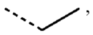, 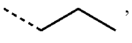, 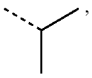,

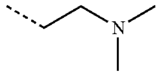, 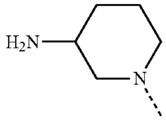 and 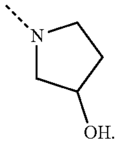

5. The compound, the optical isomer thereof and the pharmaceutically acceptable salt thereof according to claim 1, wherein, $R_2$, $R_3$, $R_4$, $R_5$, $R_6$ are independently selected from H, F, Cl, Br, OH, $NH_2$, CN, $CH_3$,

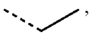, 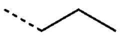 and 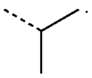.

6. The compound, the optical isomer thereof and the pharmaceutically acceptable salt thereof according to claim 1, wherein, ring A is selected from pyrrolidin-2-one group, isothiazolidine-1,1-dioxide group, 1,2-thiazine-1,1-dioxide group, piperidin-2-one group, 3,4-dihydropyridin-2 (1H)-one group, 5,6-dihydro-2H-1,2-thiazine-1,1-dioxide group, pyridinyl group and pyrazolyl group, and the pyrrolidin-2-one group, isothiazolidine-1,1-dioxide group, 1,2-thiazine-1,1-dioxide group, piperidin-2-one group, 3,4-dihydropyridin-2 (1H)-one group, 5,6-dihydro-2H-1,2-thiazine-1,1-dioxide group, pyridinyl group or pyrazolyl group is optionally substituted with 1, 2 or 3 R.

7. The compound, the optical isomer thereof and the pharmaceutically salt thereof according to claim 6, wherein, the structural moiety

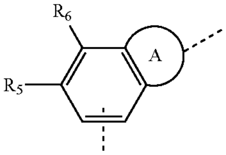

is selected from

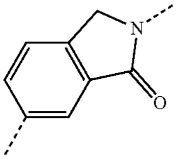,
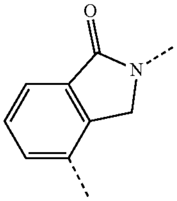,
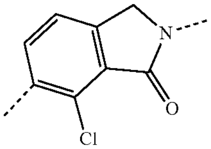,
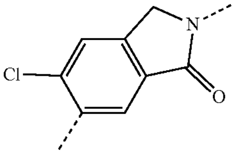,
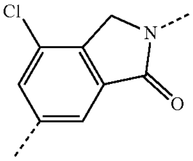,
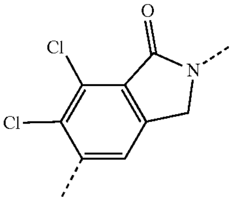,
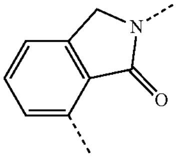,
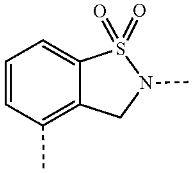,
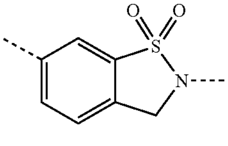,
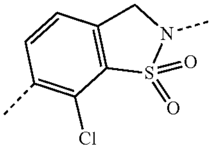,
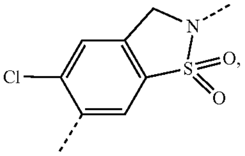,
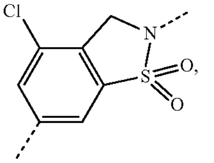
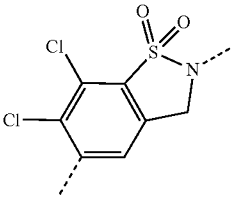,
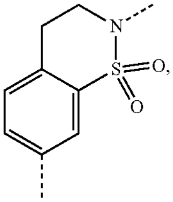

-continued

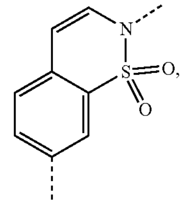
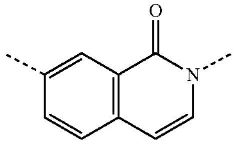,
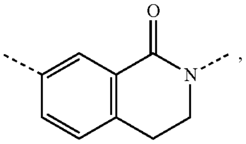,
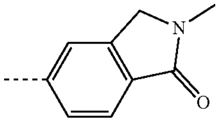,
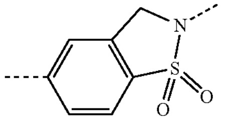,
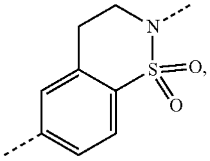
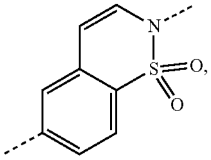
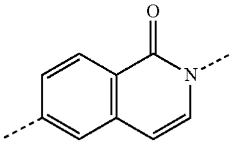,
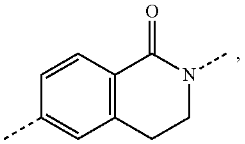,
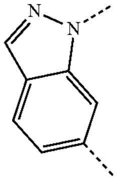 and
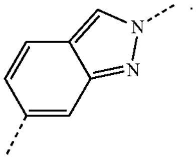.

8. The compound, the optical isomer thereof, and the pharmaceutically acceptable salt thereof according to claim 1, wherein, $L_1$ is selected from

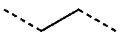 and 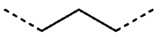.

9. The compound, the optical isomer thereof, and the pharmaceutically acceptable salt thereof according to claim 1, wherein, $L_2$ is selected from

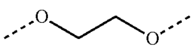 and 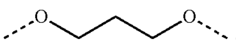.

10. The compound, the optical isomer thereof, and the pharmaceutically acceptable salt thereof according to claim 1, wherein, $L_3$ is selected from a single bond,

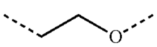 and 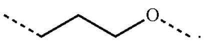.

11. The compound, the optical isomer thereof, and the pharmaceutically acceptable salt thereof according to claim 1, wherein, $L_4$ is selected from

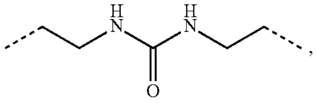

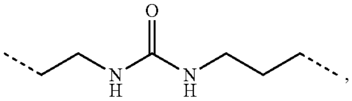

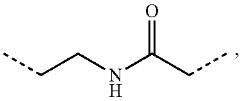 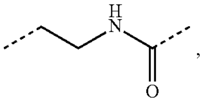

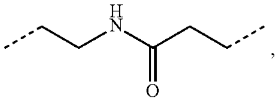 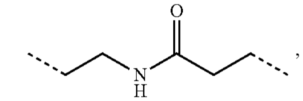

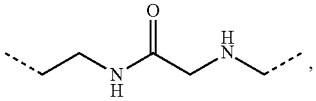

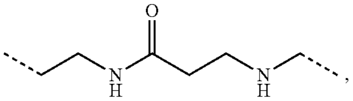

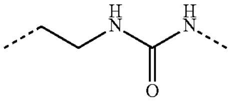 and 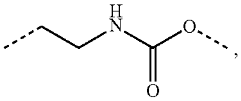

the

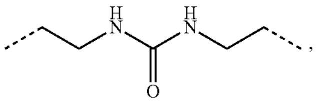

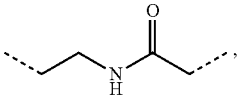 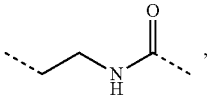

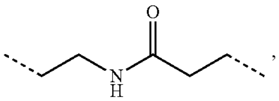

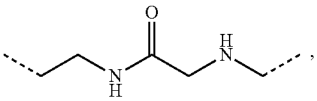

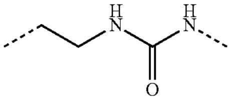 or 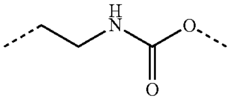

or is optionally substituted with 1, 2 or 3 R.

12. The compound, the optical isomer thereof, and the pharmaceutically acceptable salt thereof according to claim 11, wherein, $L_4$ is selected from

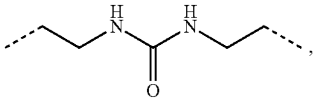

-continued

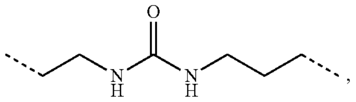

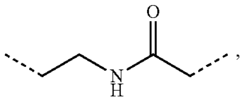 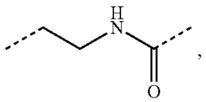

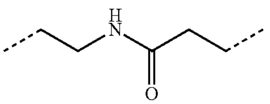 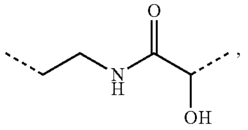

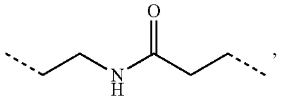

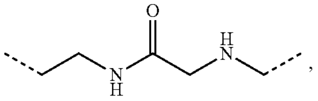

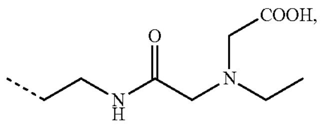 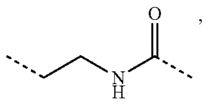

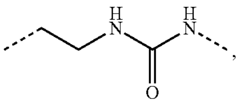 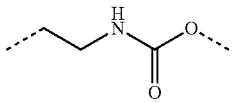 and

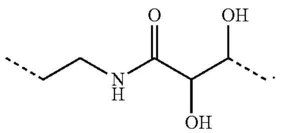

13. The compound, the optical isomer thereof, and the pharmaceutically acceptable salt thereof according to claim 1, wherein, the structural unit

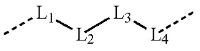

is selected from

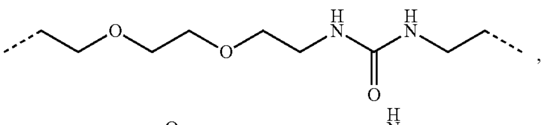

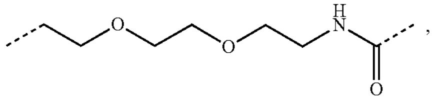

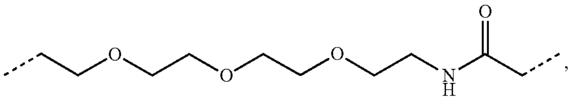

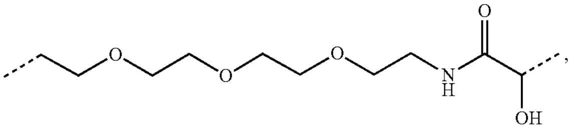

-continued

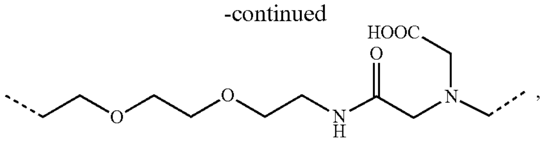

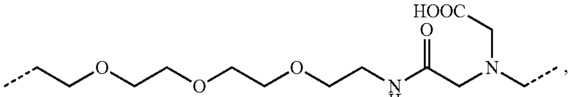

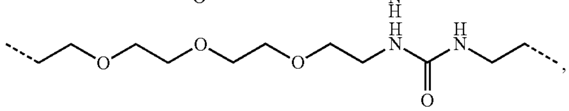

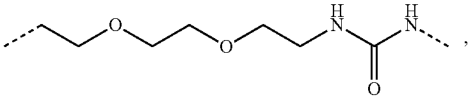

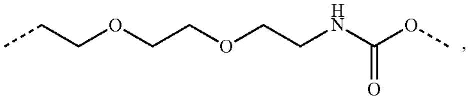

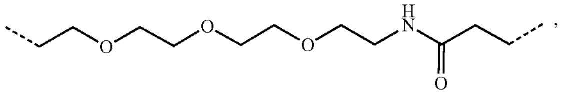

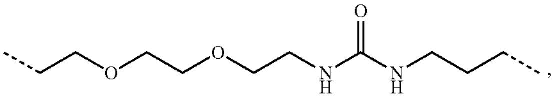

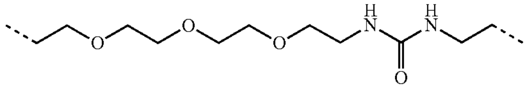 and

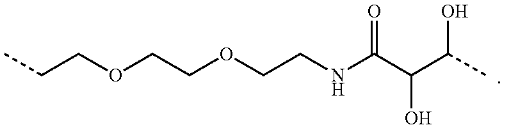

14. The compound, the optical isomer thereof, and the pharmaceutically acceptable salt thereof according to claim 1, wherein, X is selected from a single bond, N, NH, O, $C_{1-6}$ alkyl, $C_{3-8}$ cycloalkyl, 5-8 membered heterocycloalkyl, phenyl and 5-6 membered heteroaryl, and the $C_{1-6}$ alkyl, $C_3$-s cycloalkyl, 5-8 membered heterocycloalkyl, phenyl or 5-6 membered heteroaryl is optionally substituted with 1, 2 or 3 $R_X$x.

15. The compound, the optical isomer thereof and the pharmaceutically acceptable salt thereof according to claim 1, wherein, $R_X$ is selected from OH, $NH_2$,

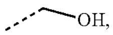

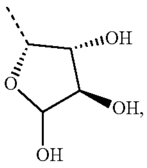

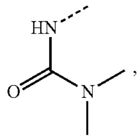

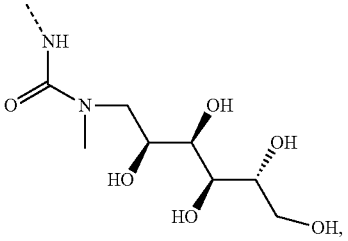

-continued

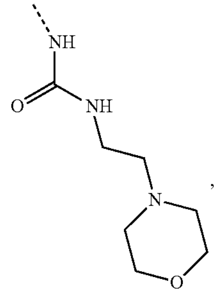

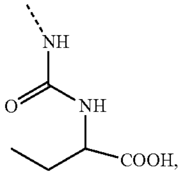

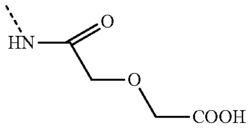 and 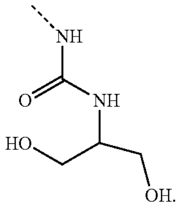

16. The compound, the optical isomer thereof and the pharmaceutically acceptable salt thereof according to claim 1, wherein, X is selected from a single bond, N, NH, O,

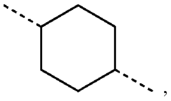

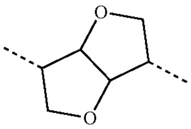

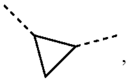

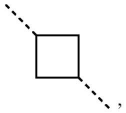

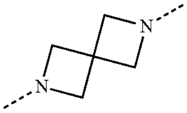

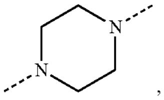

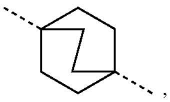

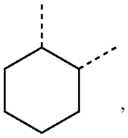

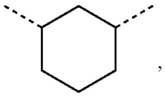

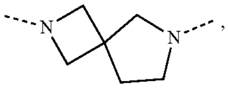

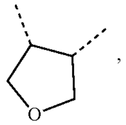

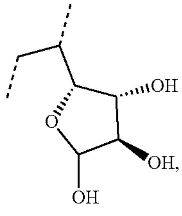

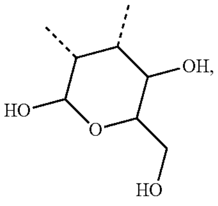

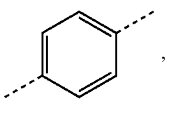

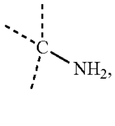

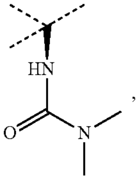

-continued
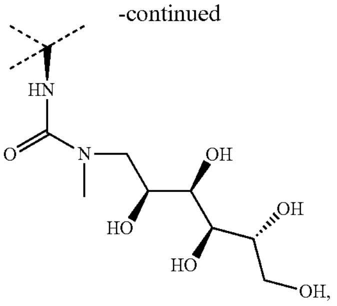
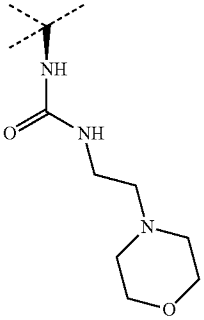
,
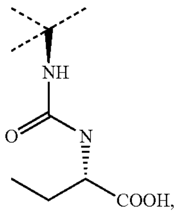
-continued
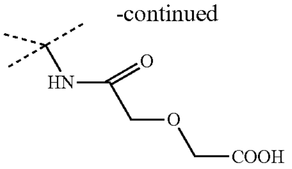
and
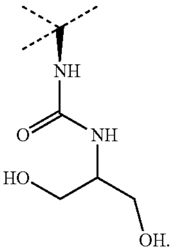
17. A compound represented by the following formula, an optical isomer thereof and a pharmaceutically acceptable salt thereof, selected from:
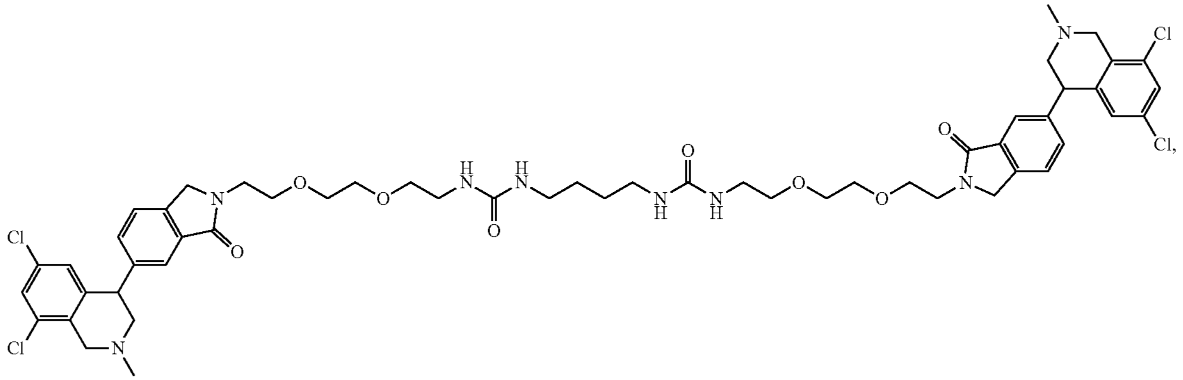
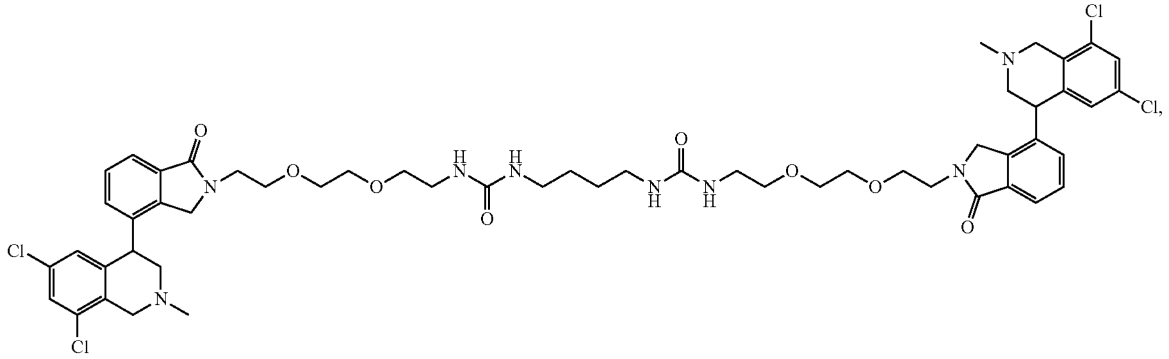

-continued
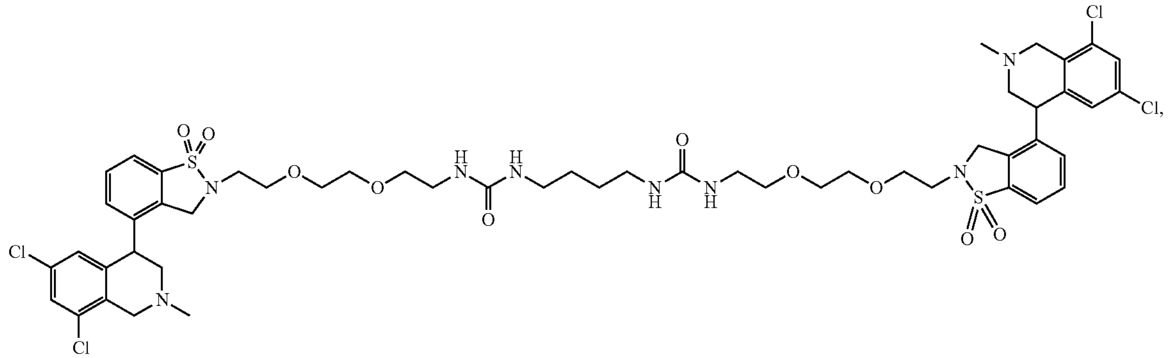
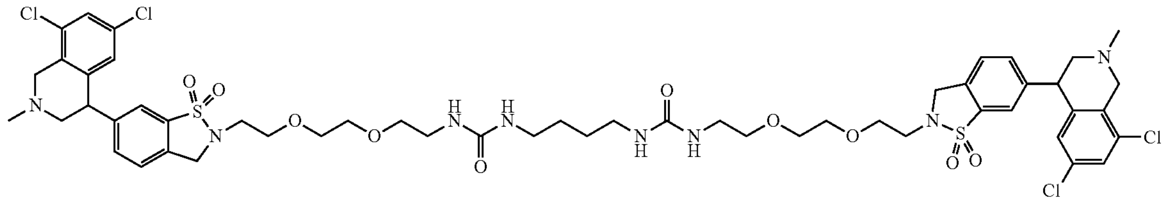
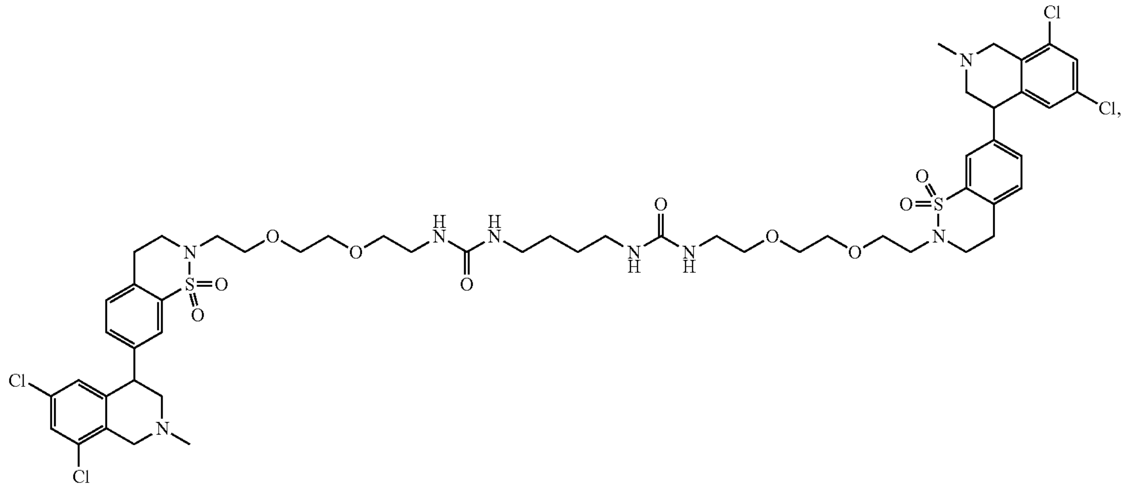
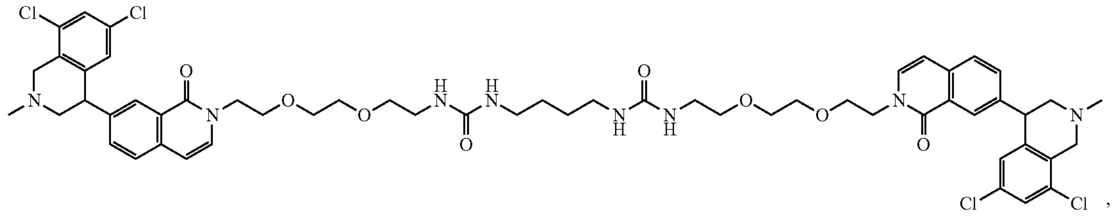
,
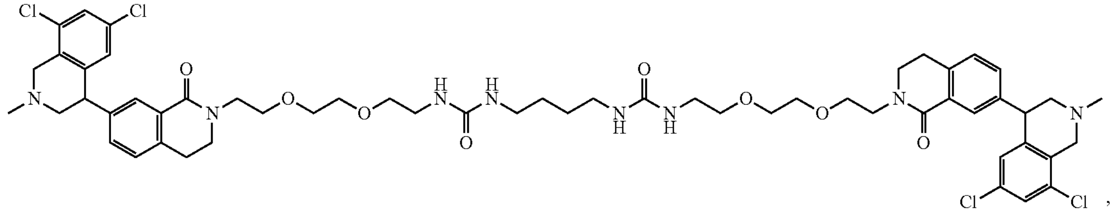
,
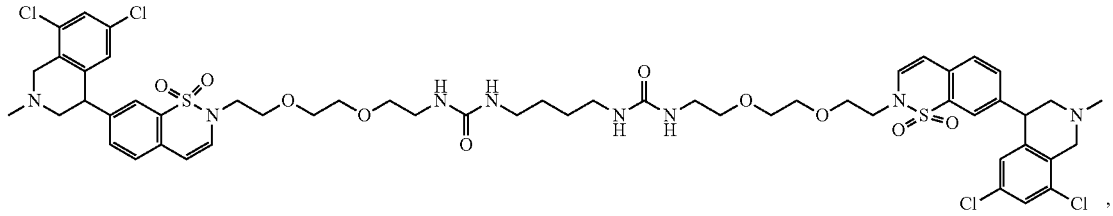
, -continued
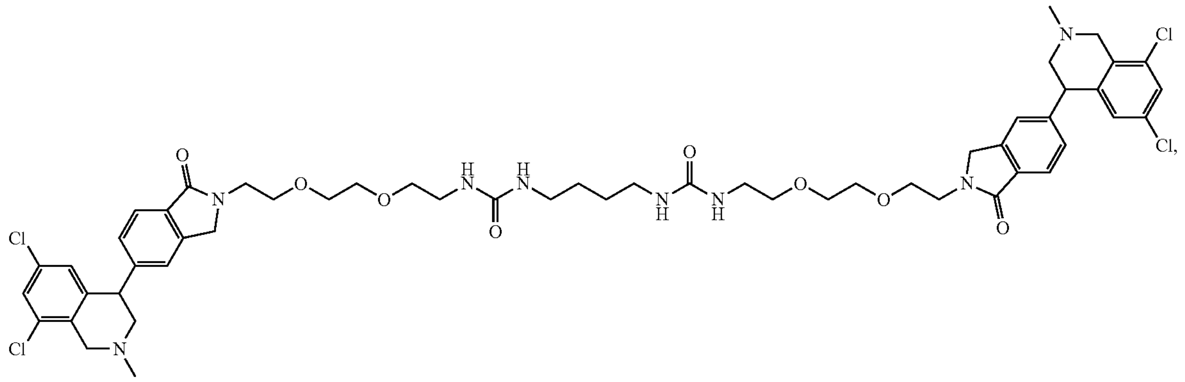
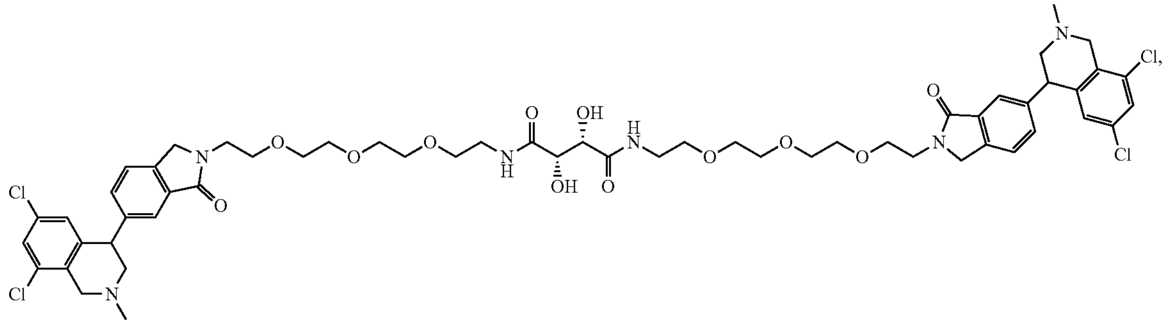
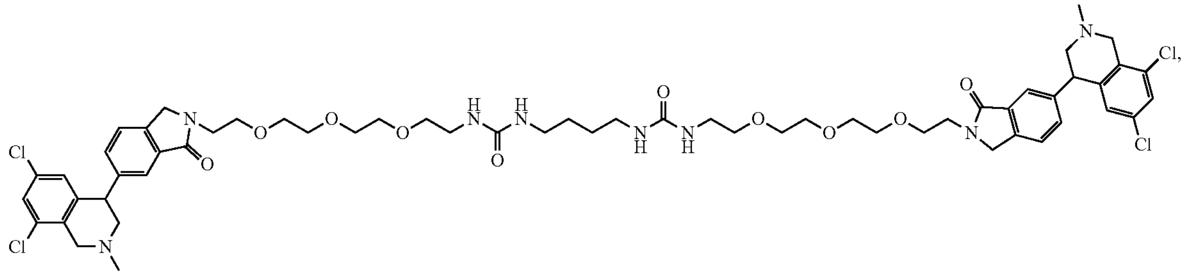
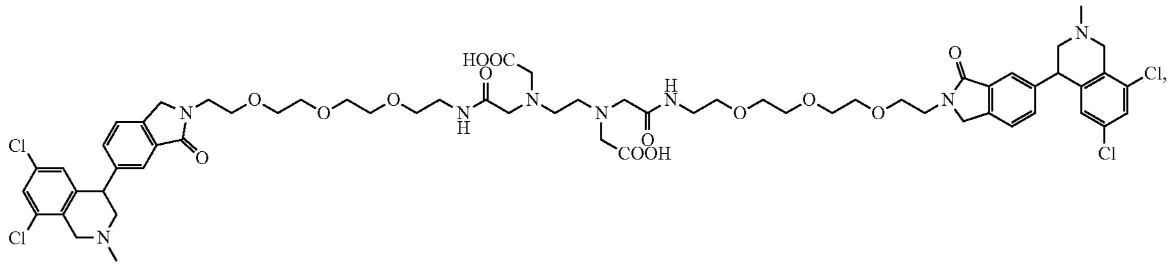
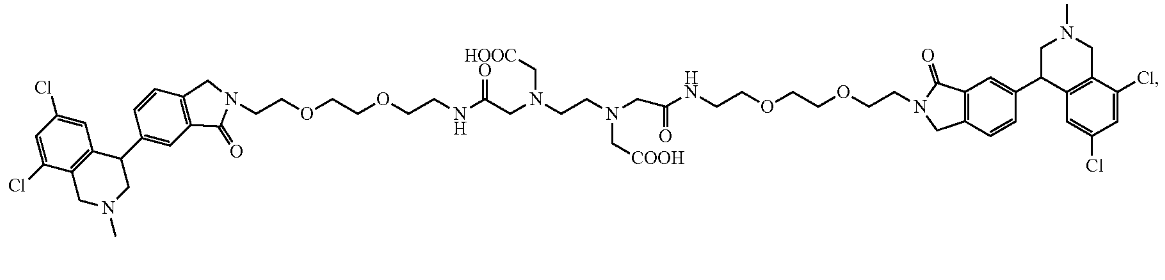

-continued
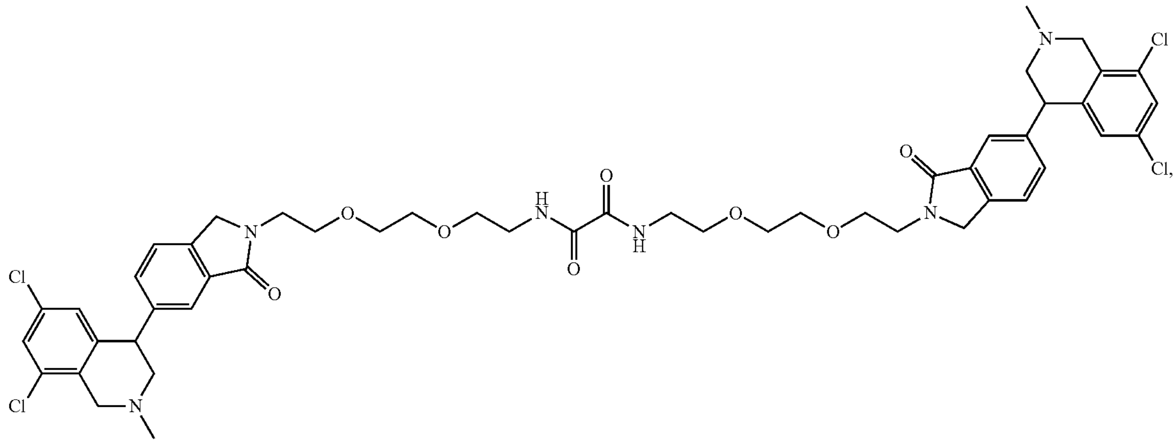
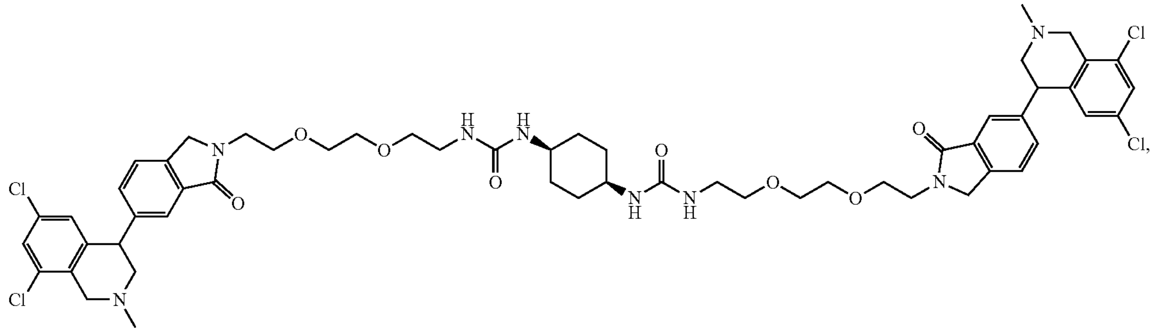
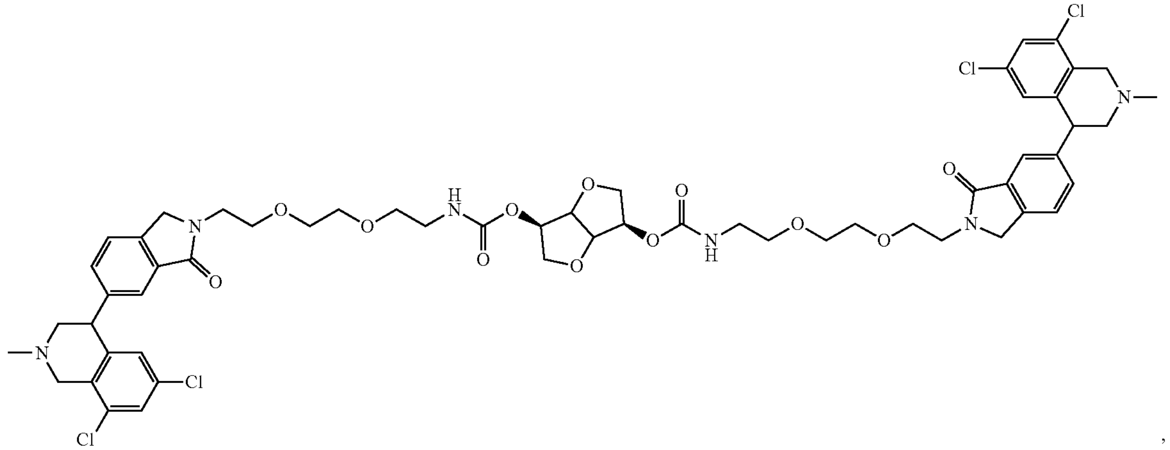
,
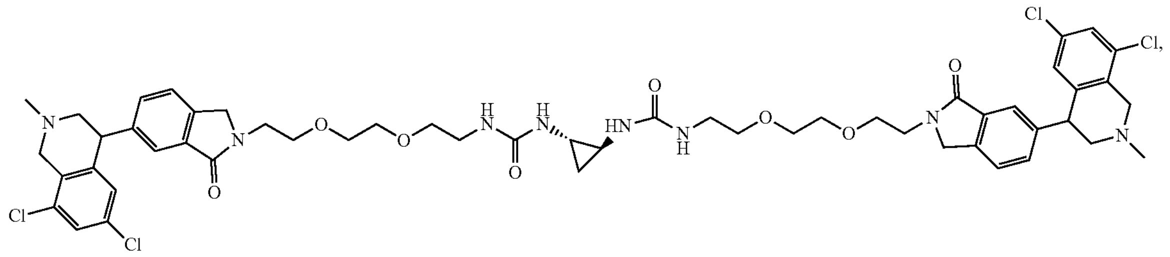
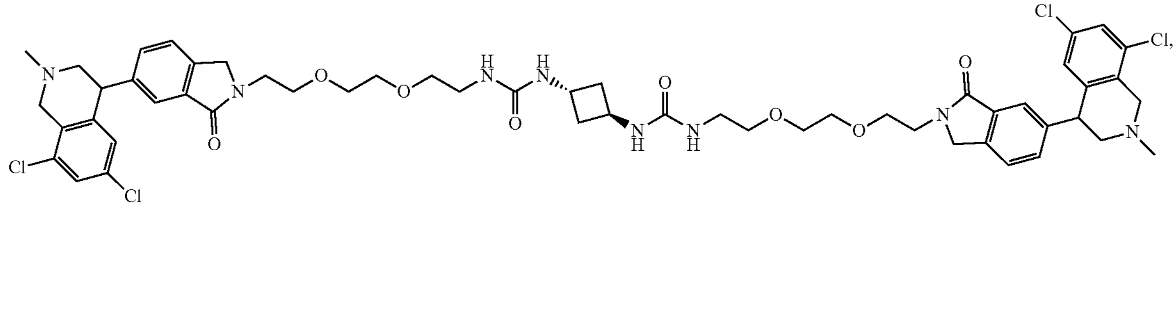

-continued
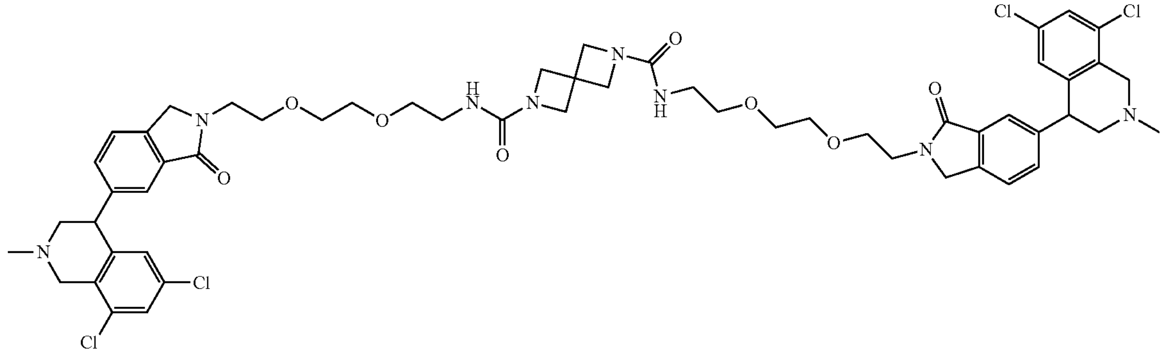
,
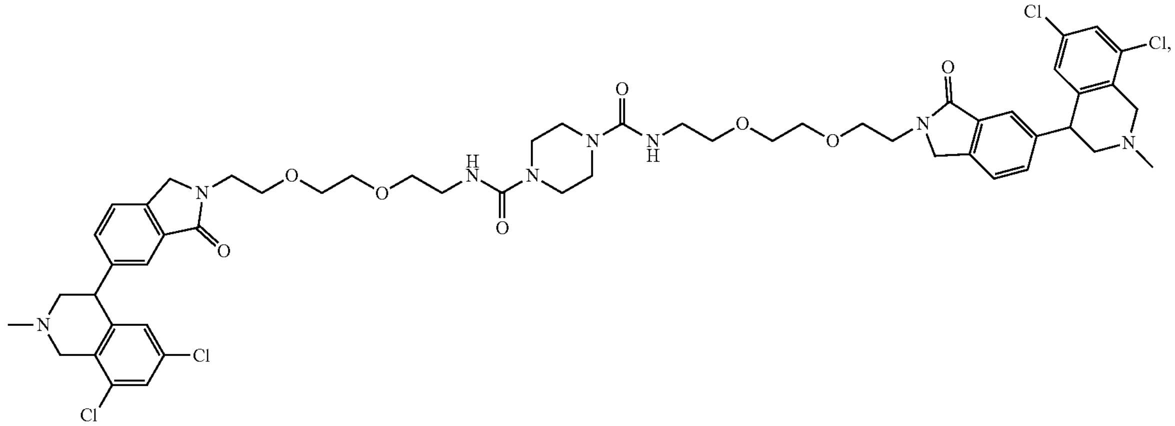
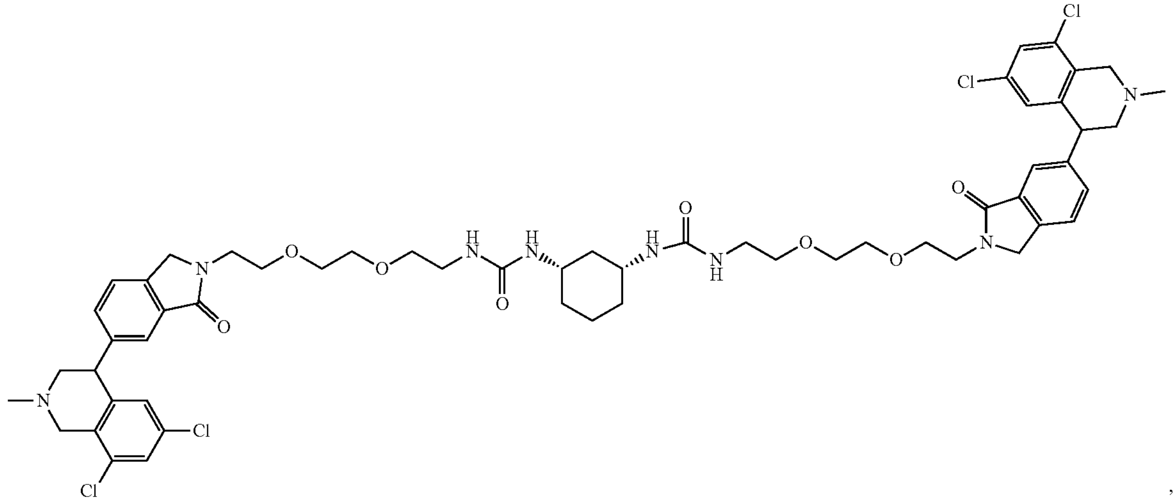
,
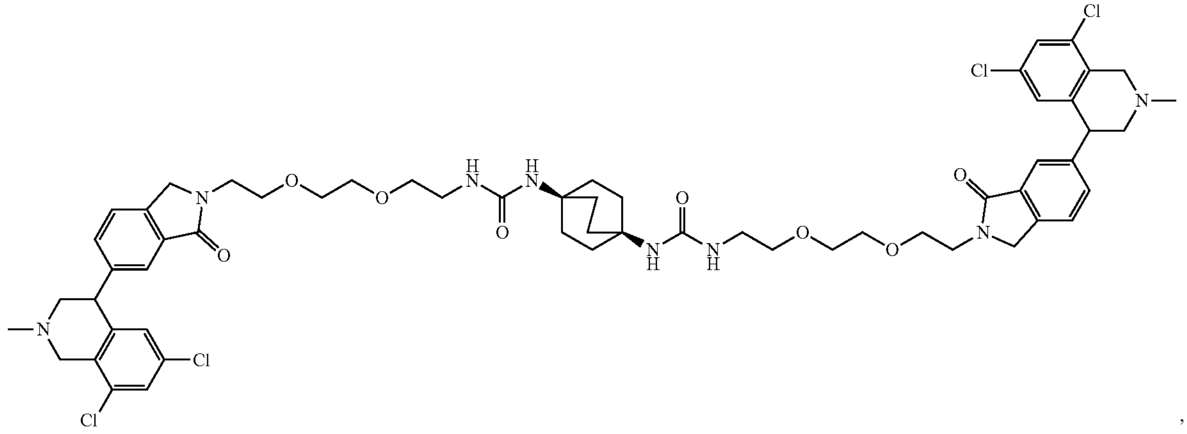
,

-continued
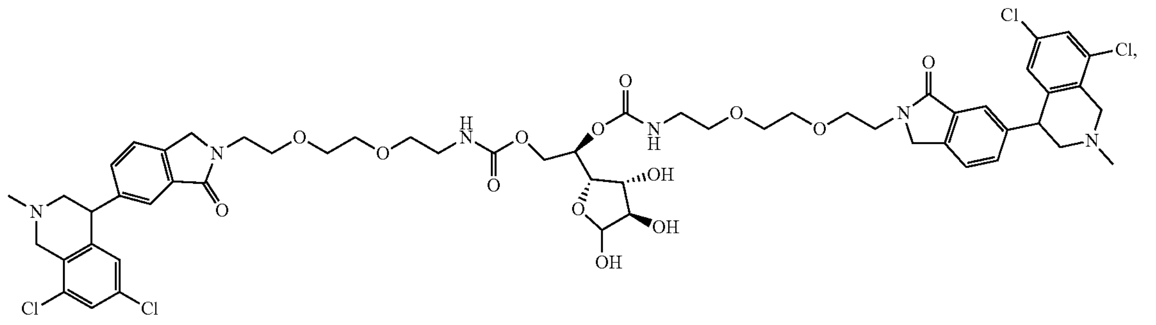
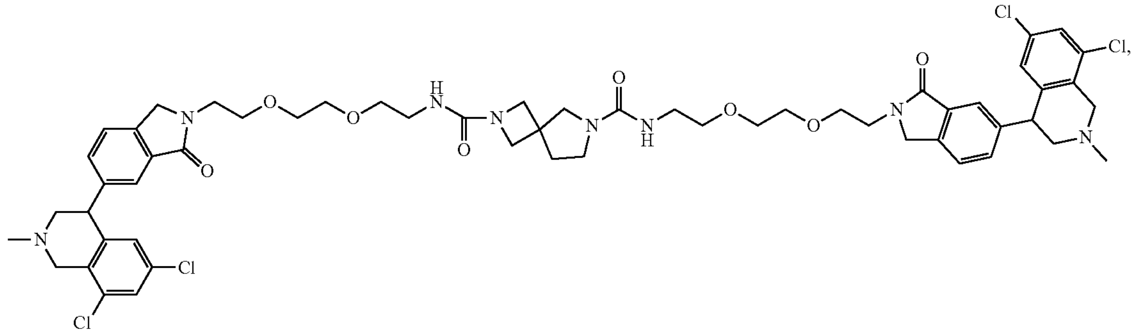
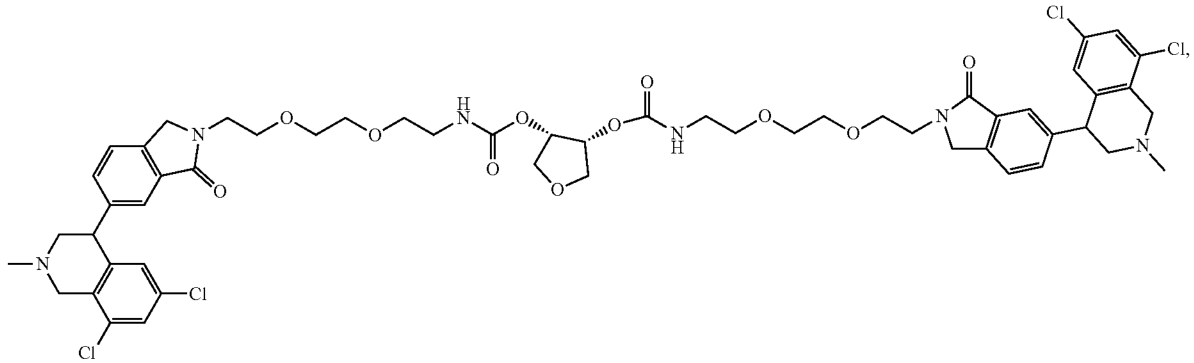
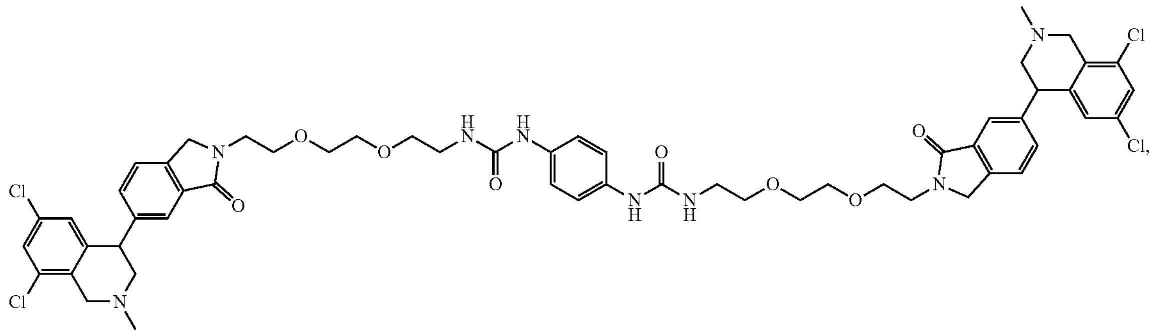
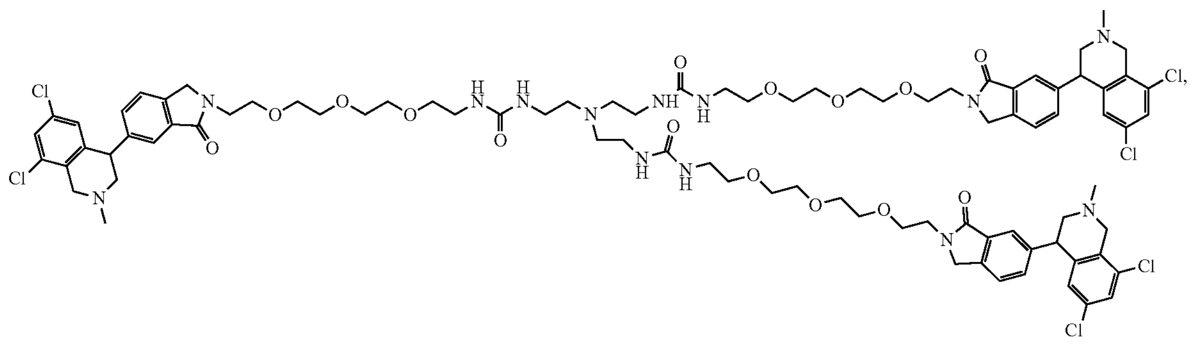

-continued
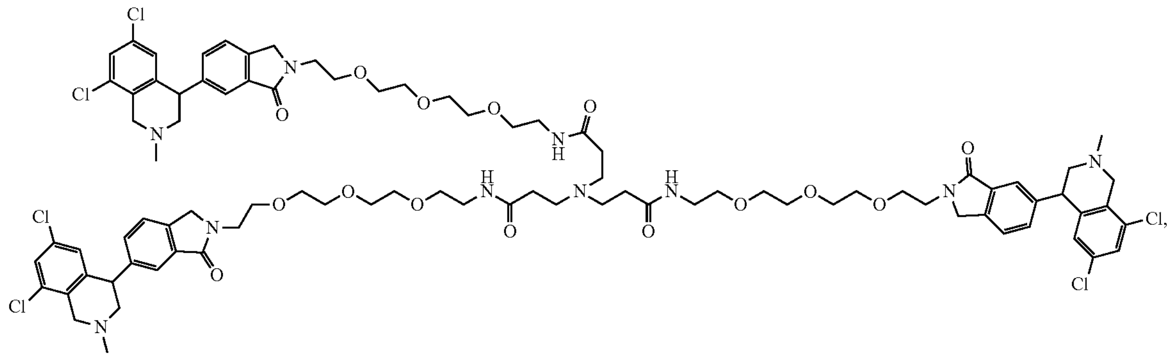
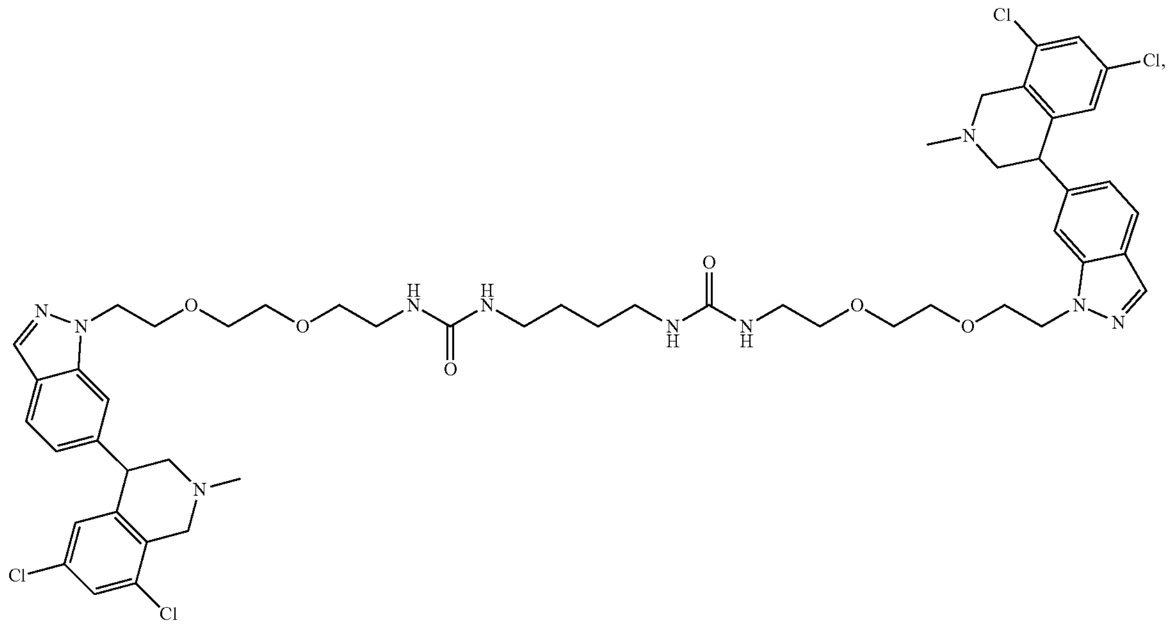
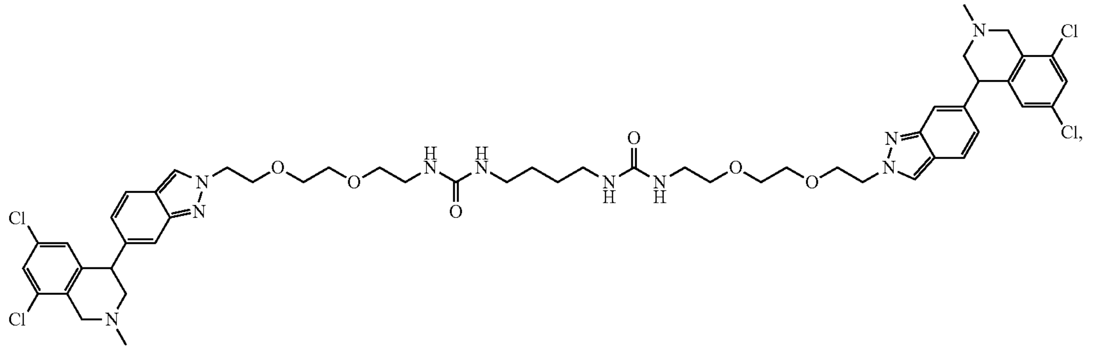
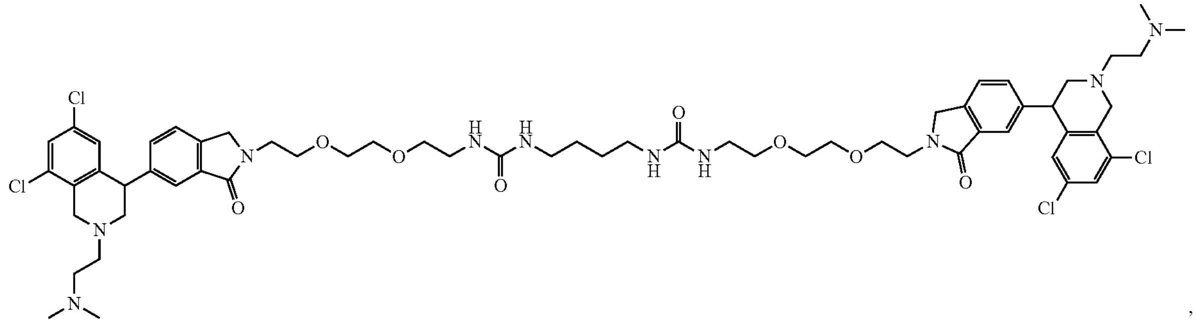
,

-continued
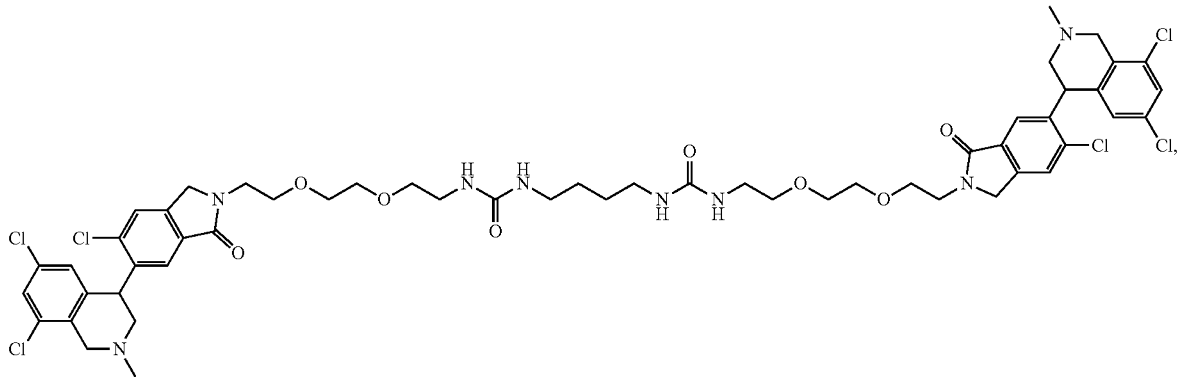
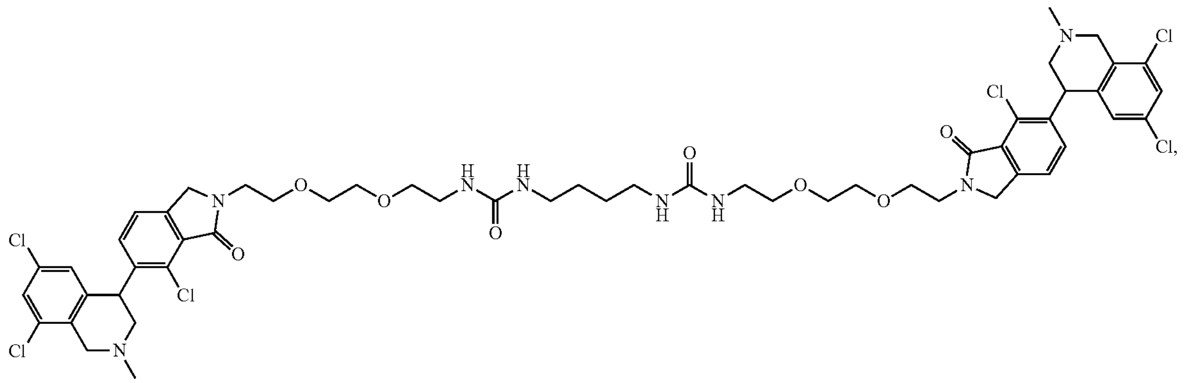
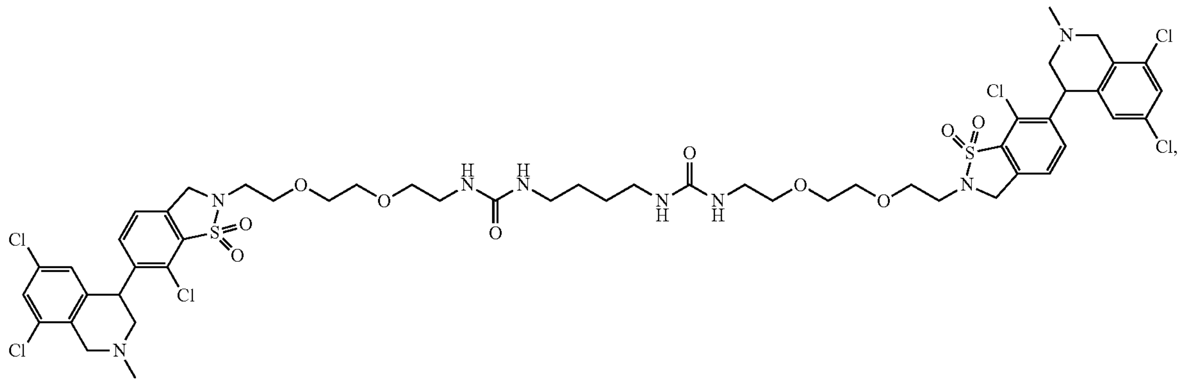
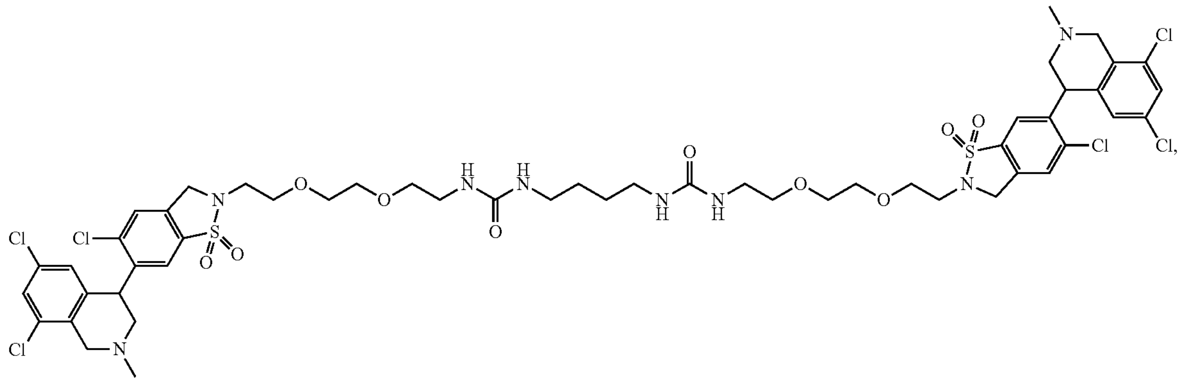

-continued
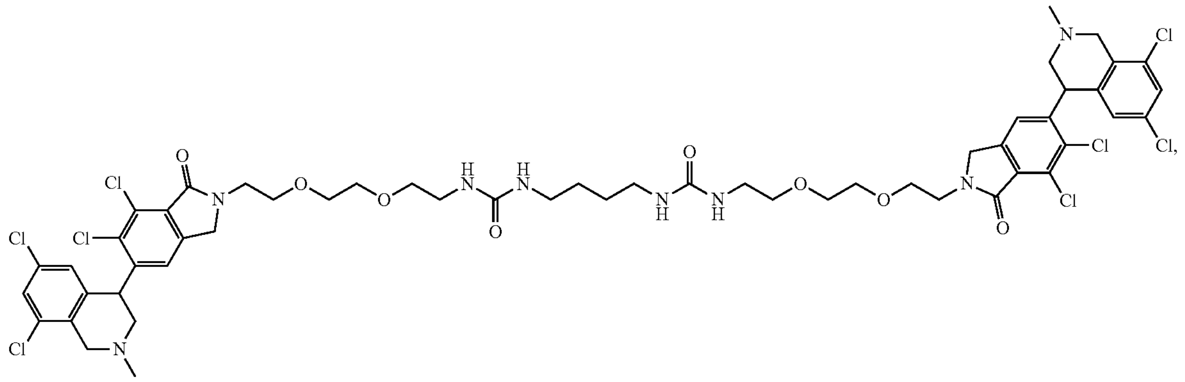
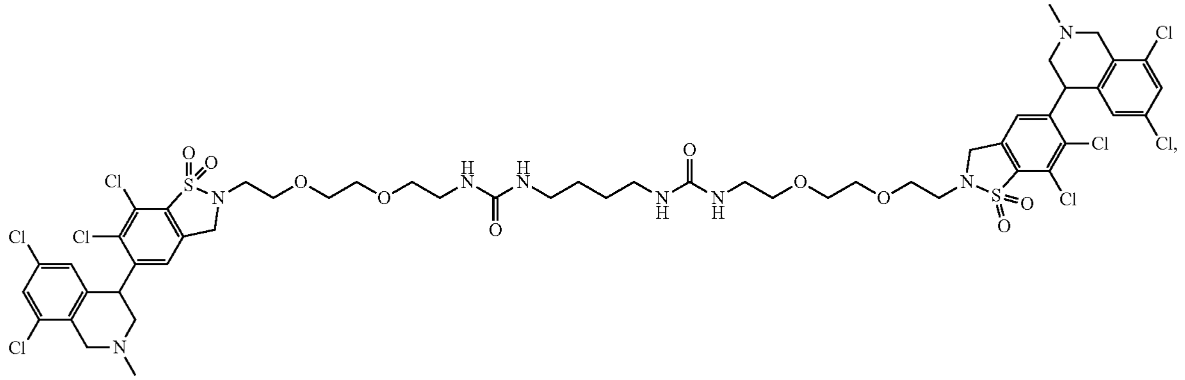
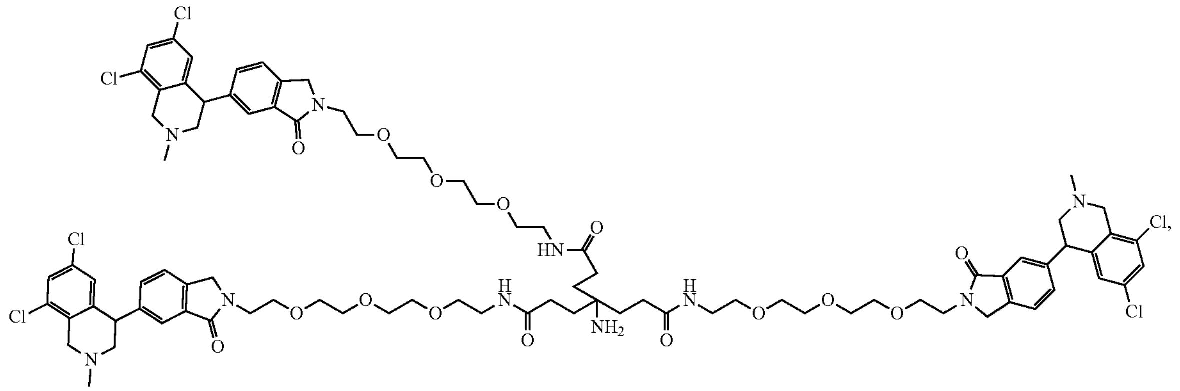
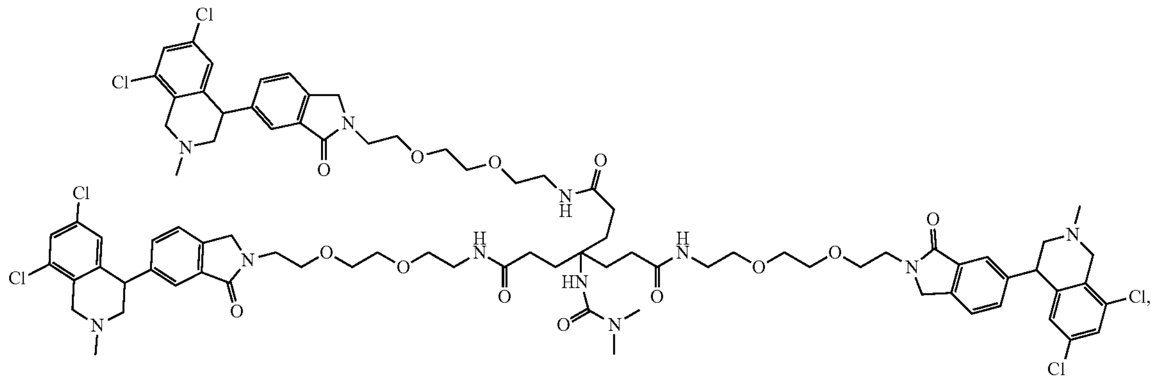

-continued
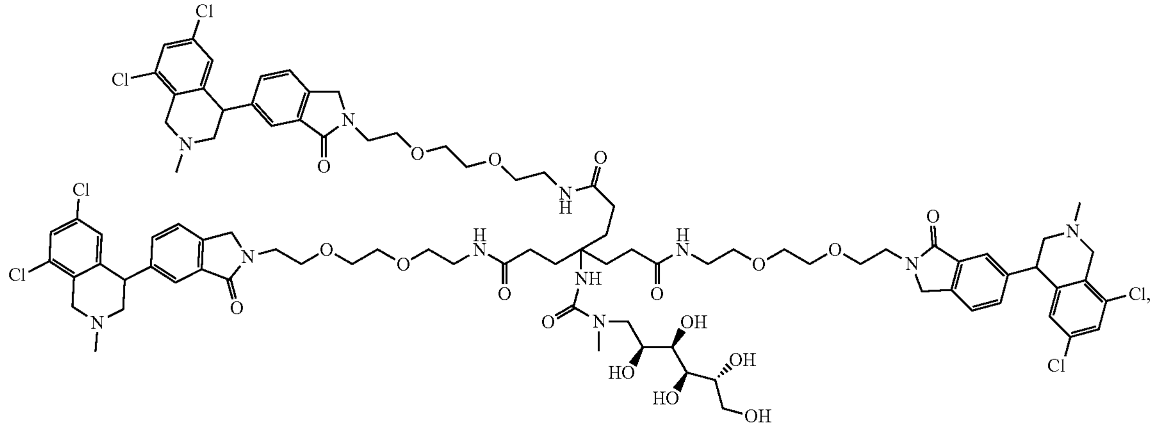
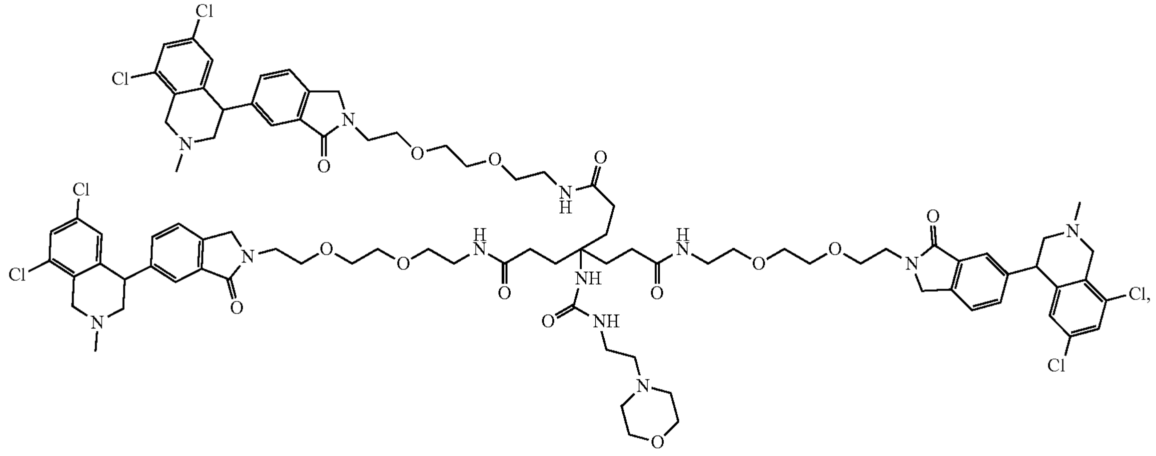
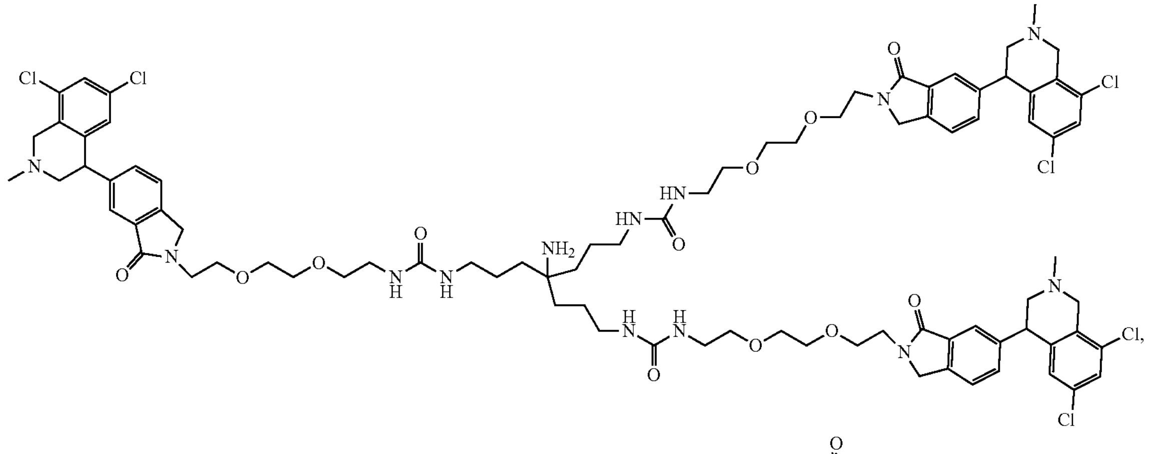
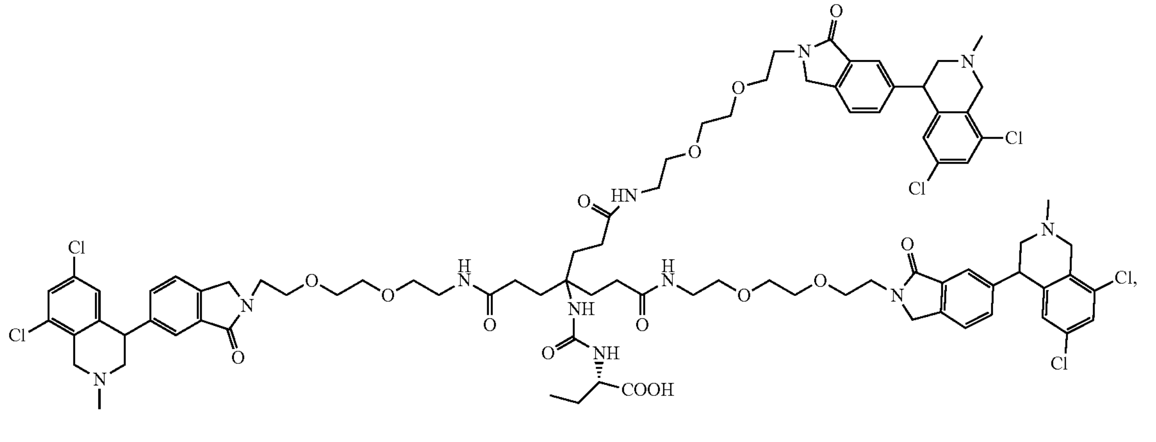

-continued
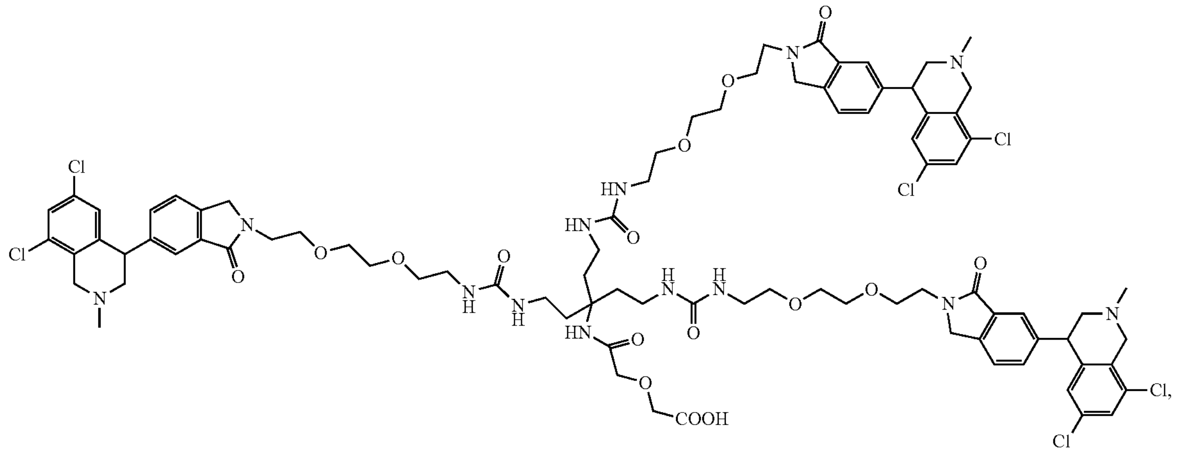
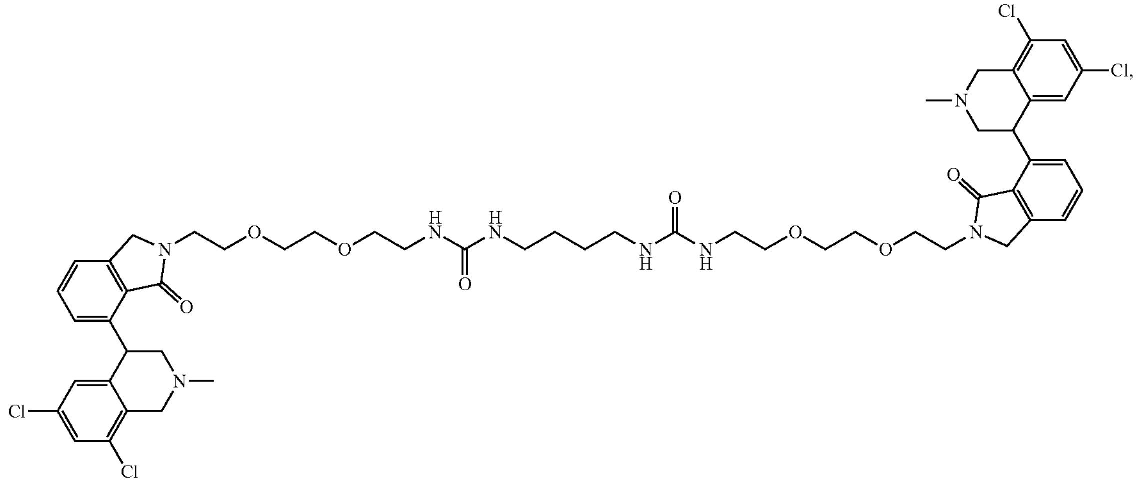
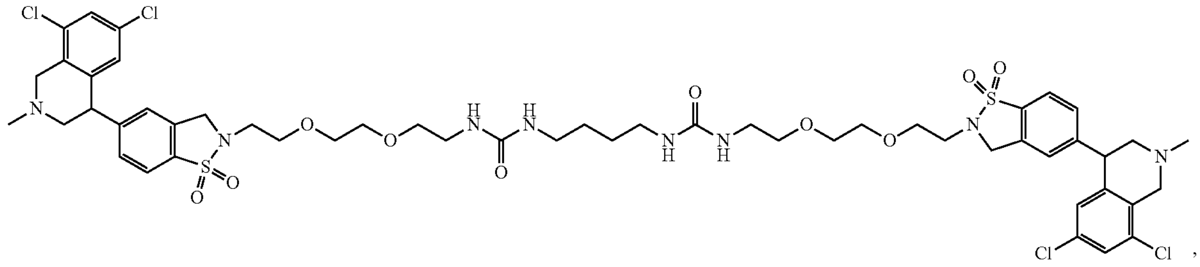
,
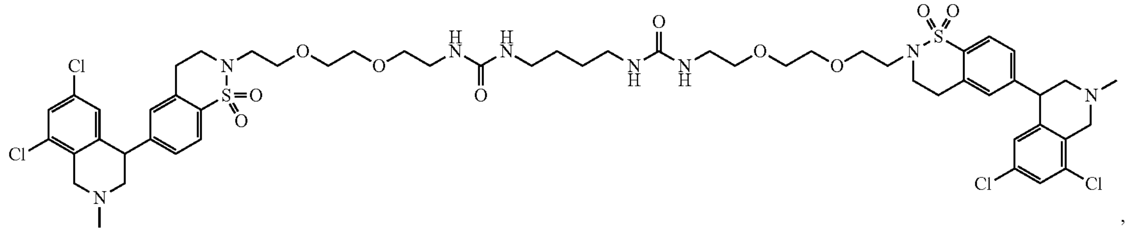
,
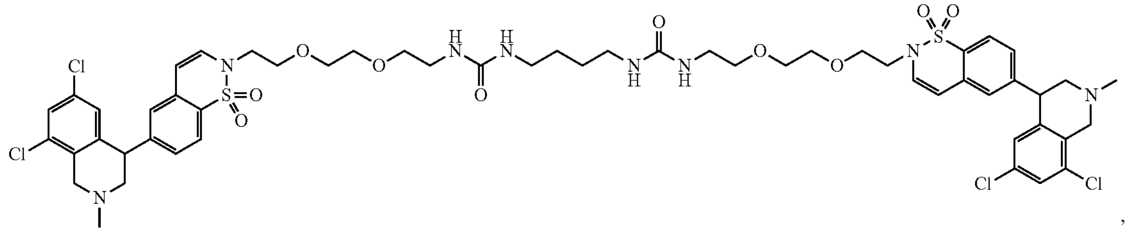
,

-continued
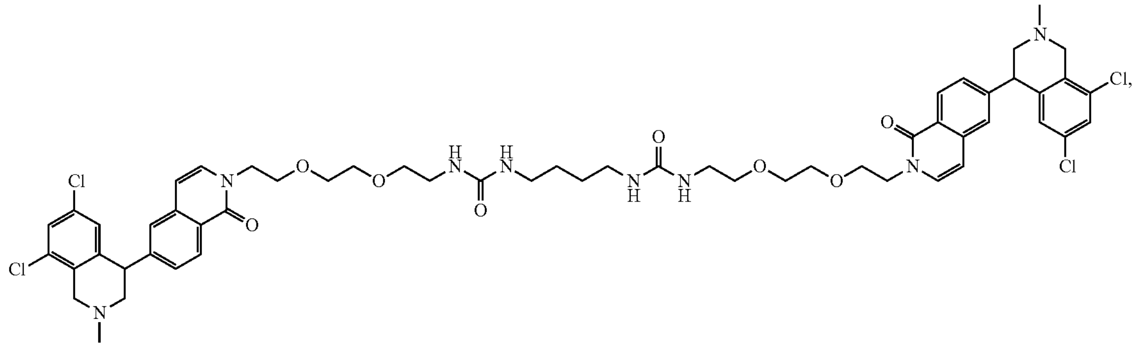
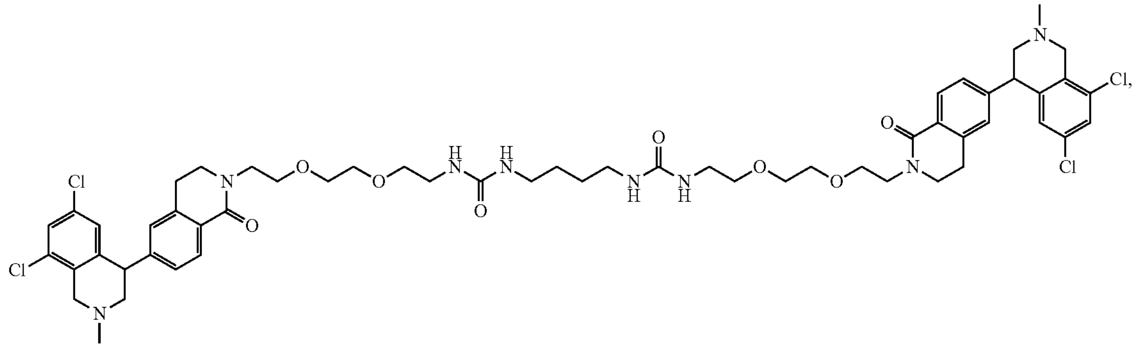
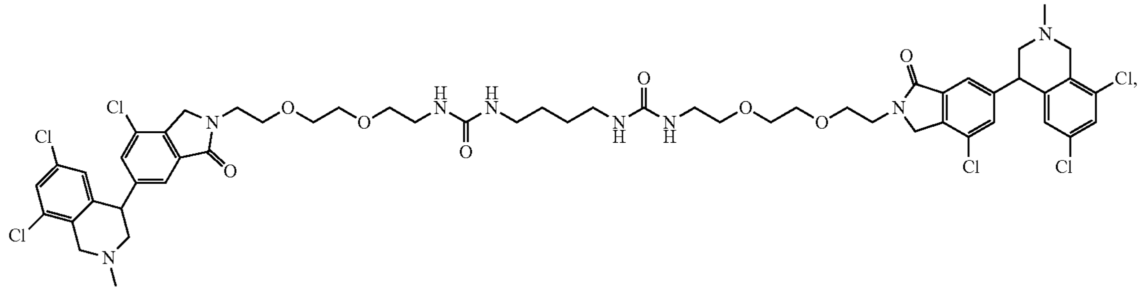
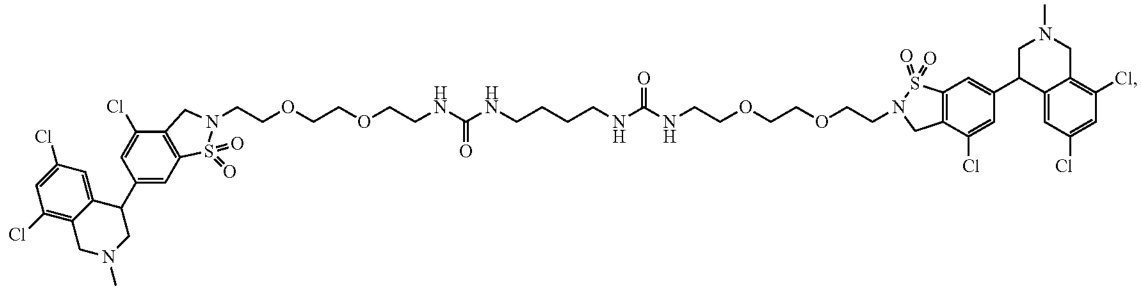
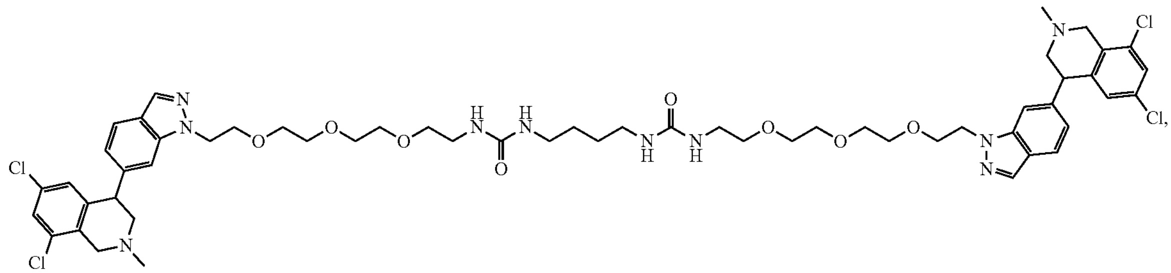

-continued

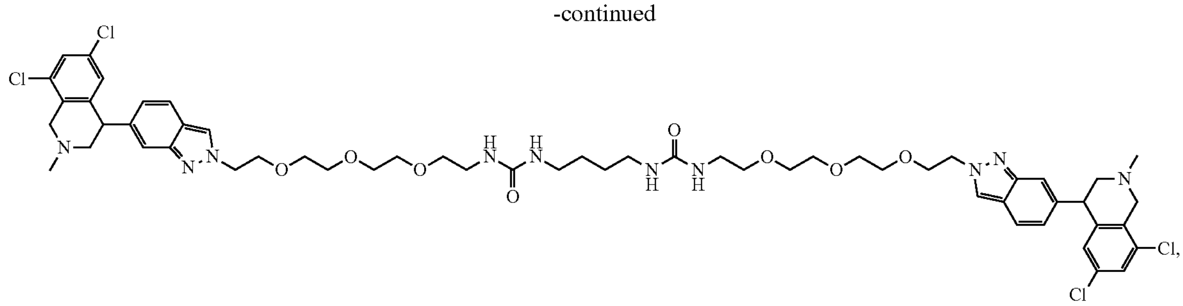

,

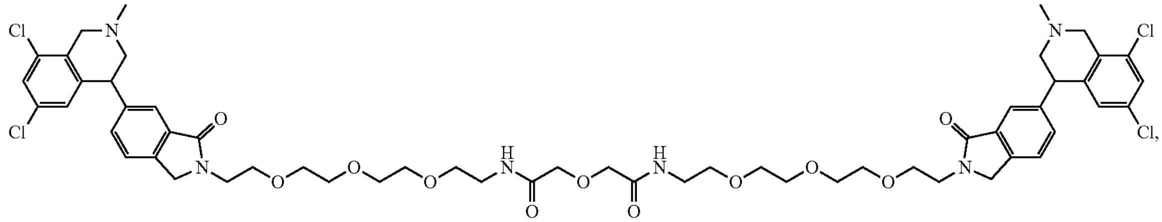

,

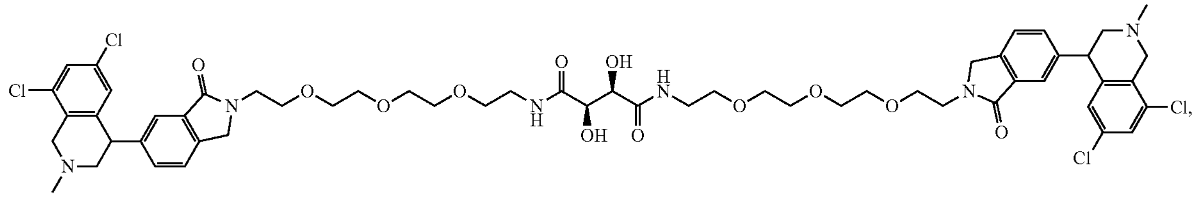

,

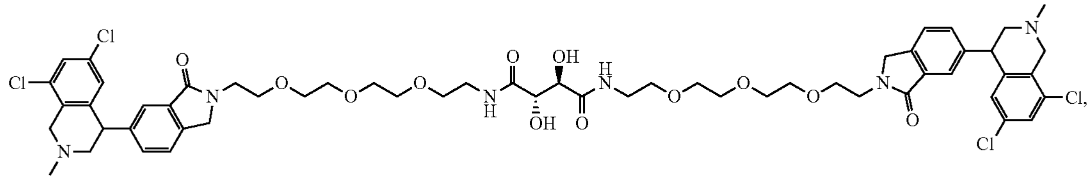 [SMILES: CN1Cc2c(Cl)cc(Cl)cc2C(c2ccc3c(c2)C(=O)N(CCOCCOCCOCCNC(=O)[C@H](O)[C@@H](O)C(=O)NCCOCCOCCOCCN2Cc4ccc(C5CN(C)Cc6c(Cl)cc(Cl)cc65)cc4C2=O)C3)C1]

, and

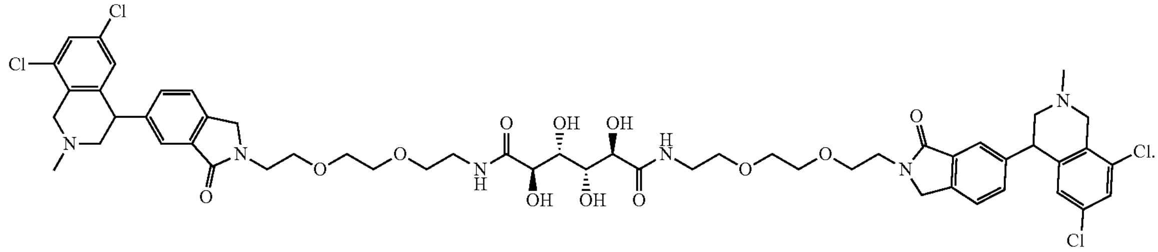

.

18. A method for inhibiting NHE-mediated reverse transport of sodium or hydrogen ions in a subject in need thereof, comprising: administering the compound, the optical isomer thereof or the pharmaceutically acceptable salt thereof according to claim 1 to the subject.

19. A method for treating irritable bowel syndrome, heart failure, chronic kidney disease, end-stage renal disease or liver disease in a subject in need thereof, comprising: administering the compound, the optical isomer thereof or the pharmaceutically acceptable salt thereof according to claim 1 to the subject.

* * * * *